(12) United States Patent
Jeon et al.

(10) Patent No.: US 11,508,915 B2
(45) Date of Patent: Nov. 22, 2022

(54) CONDENSED CYCLIC COMPOUND AND ORGANIC LIGHT-EMITTING DEVICE INCLUDING THE SAME

(71) Applicant: Samsung Electronics Co., Ltd., Gyeonggi-do (KR)

(72) Inventors: Soonok Jeon, Suwon-si (KR); Yeonsook Chung, Seoul (KR); Hasup Lee, Seoul (KR); Sooghang Ihn, Hwaseong-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 432 days.

(21) Appl. No.: 16/587,429

(22) Filed: Sep. 30, 2019

(65) Prior Publication Data
US 2020/0266360 A1 Aug. 20, 2020

(30) Foreign Application Priority Data
Feb. 15, 2019 (KR) .................... 10-2019-0017964

(51) Int. Cl.
*H01L 51/00* (2006.01)
*C07D 487/04* (2006.01)
*C09K 11/06* (2006.01)
*H01L 51/50* (2006.01)

(52) U.S. Cl.
CPC ........ *H01L 51/0072* (2013.01); *C07D 487/04* (2013.01); *C09K 11/06* (2013.01); *H01L 51/0067* (2013.01); *C09K 2211/1018* (2013.01); *H01L 51/5012* (2013.01); *H01L 51/5016* (2013.01); *H01L 51/5024* (2013.01); *H01L 51/5056* (2013.01); *H01L 51/5072* (2013.01); *H01L 51/5088* (2013.01); *H01L 51/5092* (2013.01); *H01L 51/5096* (2013.01); *H01L 2251/552* (2013.01)

(58) Field of Classification Search
CPC ............ H01L 51/0072; H01L 51/0067; H01L 51/5012; H01L 51/5016; H01L 51/5024; H01L 51/5056; H01L 51/5072; H01L 51/5088; H01L 51/5092; H01L 51/5096; H01L 2251/552; H01L 51/0071; H01L 51/5048; C07D 487/04; C07D 491/04; C07D 513/04; C09K 11/06; C09K 2211/1018
USPC ...................................................... 428/690
See application file for complete search history.

(56) References Cited

U.S. PATENT DOCUMENTS

| | | | | |
|---|---|---|---|---|
| 9,502,664 | B2 * | 11/2016 | Schaefer | ................ C09B 57/00 |
| 10,689,385 | B2 * | 6/2020 | Raimann | ............. H01L 51/0072 |
| 11,174,258 | B2 * | 11/2021 | Schaefer | .............. C07D 235/26 |
| 2014/0252280 | A1 * | 9/2014 | Schaefer | ................ H05B 33/14 |
| | | | | 544/212 |
| 2016/0072077 | A1 | 3/2016 | Ito et al. | |
| 2018/0086763 | A1 * | 3/2018 | Raimann | ............. H01L 51/5016 |
| 2018/0269407 | A1 * | 9/2018 | Schaefer | .............. C07D 487/04 |
| 2018/0291028 | A1 * | 10/2018 | Schaefer | ............. H01L 51/0067 |
| 2019/0002469 | A1 * | 1/2019 | Schafer | ................ C07D 235/26 |
| 2021/0020850 | A1 * | 1/2021 | Stengel | ............... H01L 51/0072 |
| 2022/0112215 | A1 * | 4/2022 | Thompson | .......... H01L 51/0091 |

FOREIGN PATENT DOCUMENTS

| | | | | |
|---|---|---|---|---|
| KR | 20150058083 | A | 5/2015 | |
| KR | 1020150075169 | A | 7/2015 | |
| KR | 20160029187 | A | 3/2016 | |
| WO | WO-2016157113 | A1 * | 10/2016 | .......... C07D 487/04 |
| WO | WO-2017093958 | A1 * | 6/2017 | .......... C07D 235/26 |

* cited by examiner

*Primary Examiner* — Douglas J McGinty
(74) *Attorney, Agent, or Firm* — Cantor Colburn LLP

(57) ABSTRACT

A condensed cyclic compound represented by Formula 1 and an organic light-emitting device including the same:

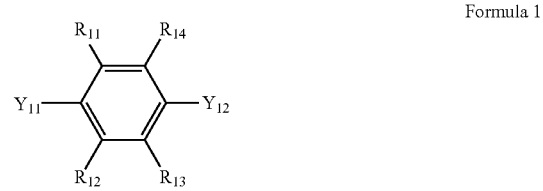

Formula 1 wherein, in Formulae 1, $Y_{11}$ is a group represented by Formulae 2-1 to 2-3 and $Y_{12}$ is a group represented by Formulae 3-1 to 3-5, 4-1, or 4-2 as described herein.

20 Claims, 1 Drawing Sheet

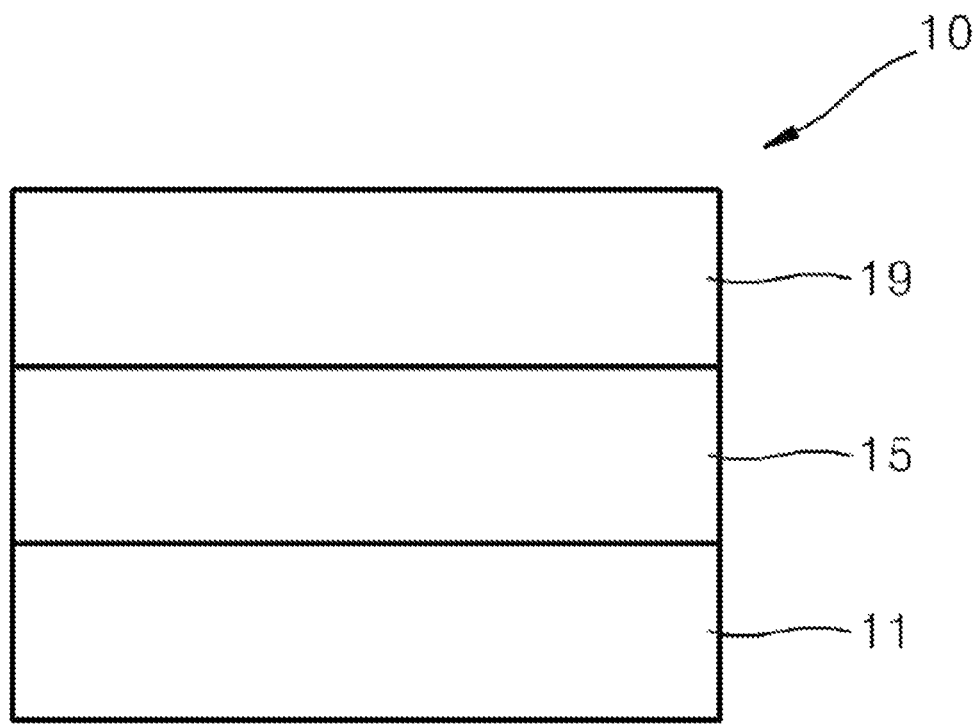

CONDENSED CYCLIC COMPOUND AND ORGANIC LIGHT-EMITTING DEVICE INCLUDING THE SAME

CROSS-REFERENCE TO RELATED APPLICATION

This application claims priority to and the benefit of Korean Patent Application No. 10-2019-0017964, filed on Feb. 15, 2019, in the Korean Intellectual Property Office, and all the benefits accruing therefrom under 35 U.S.C. § 119, the contents of which in their entirety are herein incorporated by reference.

BACKGROUND

1. Field

One or more embodiments relate to a condensed cyclic compound and an organic light-emitting device including the same.

2. Description of the Related Art

Organic light-emitting devices are self-emission devices that produce full-color images, and also have wide viewing angles, high contrast ratios, short response times, and excellent characteristics in terms of brightness, driving voltage, and response speed, compared to devices in the art.

In an example, an organic light-emitting device includes an anode, a cathode, and an organic layer that is disposed between the anode and the cathode and includes an emission layer. A hole transport region may be between the anode and the emission layer, and an electron transport region may be between the emission layer and the cathode. Holes provided from the anode may move toward the emission layer through the hole transport region, and electrons provided from the cathode may move toward the emission layer through the electron transport region. Carriers, such as holes and electrons, recombine in the emission layer to produce excitons. These excitons transit from an excited state to a ground state, thereby generating light.

SUMMARY

One or more embodiments include a condensed cyclic compound having excellent delayed fluorescence characteristics and an organic light-emitting device having high efficiency and/or long lifespan by including the condensed cyclic compound.

Additional aspects will be set forth in part in the description which follows and, in part, will be apparent from the description, or may be learned by practice of the presented embodiments.

An aspect of the present disclosure provides a condensed cyclic compound represented by Formula 1:

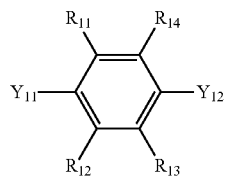

Formula 1

-continued

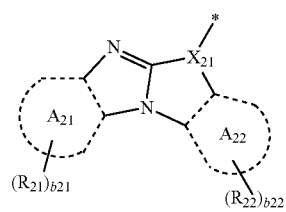

Formula 2-1

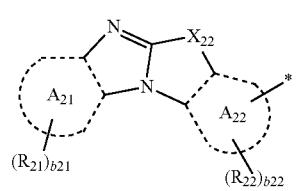

Formula 2-2

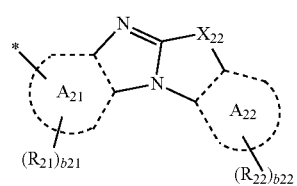

Formula 2-3

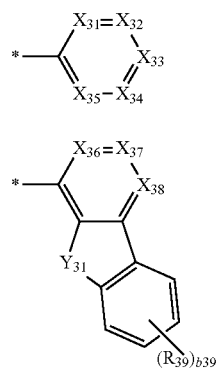

Formula 3-1

Formula 3-2

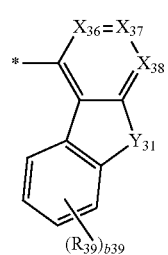

Formula 3-3

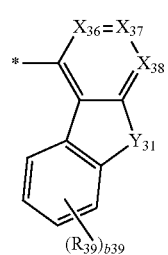

Formula 3-4

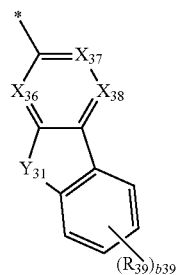

-continued

Formula 3-5

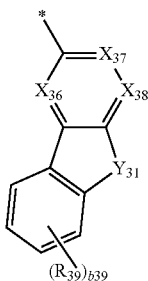

Formula 4-1

[structure with N, A41, A42, (R41)b41, (R42)b42]

Formula 4-2

[structure with X41, A41, A42, (R41)b41, (R42)b42]

In Formulae 1, 2-1 to 2-3, 3-1 to 3-5, 4-1, and 4-2, $Y_{11}$ may be a group represented by Formulae 2-1 to 2-3, $Y_{12}$ may be a group represented by Formulae 3-1 to 3-5, 4-1, or 4-2, $X_{21}$ may be N or $C(R_{23})$, $X_{22}$ may be $N(R_{24})$, $C(R_{24})(R_{25})$, O, or S, $X_{31}$ may be N or $C(R_{31})$, $X_{32}$ may be N or $C(R_{32})$, $X_{33}$ may be N or $C(R_{33})$, $X_{34}$ may be N or $C(R_{34})$, $X_{35}$ may be N or $C(R_{35})$, $X_{36}$ may be N or $C(R_{36})$, and $X_{37}$ may be N or $C(R_{37})$, $X_{38}$ may be N or $C(R_{38})$, wherein $X_{31}$ to $X_{35}$ in Formula 3-1 may be N, and $X_{36}$ to $X_{38}$ in Formulae 3-2 to 3-5 may be N, $Y_{31}$ may be O or S, $X_{41}$ may be O, S, $S(=O)_{43}$, $N(R_{21})$, or $Si(R_{43})(R_{44})$, ring $A_{21}$, ring $A_{22}$, ring $A_{41}$, and ring $A_{42}$ may each independently be a $C_5$-$C_{60}$ carbocyclic group or a $C_2$-$C_{60}$ heterocyclic group, $R_{11}$ to $R_{14}$ may each independently be hydrogen, deuterium, —F, —Cl, —Br, —I, a hydroxyl group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_7$-$C_{60}$ alkylaryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_2$-$C_{60}$ alkylheteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, a substituted or unsubstituted monovalent non-aromatic condensed heteropolycyclic group, —$Si(Q_1)(Q_2)(Q_3)$, —$B(Q_1)(Q_2)$, —$N(Q_1)(Q_2)$, —$P(Q_1)(Q_2)$, —$C(=O)(Q_1)$, —$S(=O)(Q_1)$, —$S(=O)_2(Q_1)$, —$P(=O)(Q_1)(Q_2)$, or —$P(=S)(Q_1)(Q_2)$, $R_{21}$ to $R_{25}$, $R_{31}$ to $R_{39}$, and $R_{41}$ to $R_{44}$ may each independently be hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_7$-$C_{60}$ alkylaryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_2$-$C_{60}$ alkylheteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, a substituted or unsubstituted monovalent non-aromatic condensed heteropolycyclic group, —$Si(Q_1)(Q_2)(Q_3)$, —$B(Q_1)(Q_2)$, —$N(Q_1)(Q_2)$, —$P(Q_1)(Q_2)$, —$C(=O)(Q_1)$, —$S(=O)(Q_1)$, —$S(=O)_2(Q_1)$, —$P(=O)(Q_1)(Q_2)$, or —$P(=S)(Q_1)(Q_2)$, b21, b22, b39, b41, and b42 may each independently be 1, 2, 3, 4, 5, 6, 7, 8, 9, or 10, $Q_1$ to $Q_3$ may each independently be hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_7$-$C_{60}$ alkylaryl group, a $C_6$-$C_{60}$ aryloxy group, a $C_6$-$C_{60}$ arylthio group, a $C_1$-$C_{60}$ heteroaryl group, a $C_2$-$C_{60}$ alkylheteroaryl group, a $C_1$-$C_{60}$ heteroaryloxy group, a $C_1$-$C_{60}$ heteroarylthio group, a monovalent non-aromatic condensed polycyclic group, a monovalent non-aromatic condensed heteropolycyclic group, a $C_1$-$C_{60}$ alkyl group substituted with deuterium, —F, a cyano group, a $C_1$-$C_{60}$ alkyl group, a $C_6$-$C_{60}$ aryl group, or any combination thereof, or a $C_6$-$C_{60}$ aryl group substituted with deuterium, —F, a cyano group, a $C_1$-$C_{60}$ alkyl group, a $C_6$-$C_{60}$ aryl group, or any combination thereof, and

* indicates a binding site to a neighboring atom.

Another aspect of the present disclosure provides an organic light-emitting device including: a first electrode; a second electrode; and an organic layer between the first electrode and the second electrode and including an emission layer and a condensed cyclic compound.

BRIEF DESCRIPTION OF THE DRAWING

These and/or other aspects will become apparent and more readily appreciated from the following description of the embodiments, taken in conjunction with FIGURE which is a schematic view of an organic light-emitting device according to an embodiment.

DETAILED DESCRIPTION

The invention now will be described more fully hereinafter with reference to the accompanying drawings, in which various embodiments are shown. This invention may, however, be embodied in many different forms, and should not be construed as limited to the embodiments set forth herein. Rather, these embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present.

It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer, or section from another element, component, region, layer, or section. Thus, "a first element," "component," "region," "layer," or "section" discussed below could be termed a second element, component, region, layer, or section without departing from the teachings herein.

The terminology used herein is for the purpose of describing particular embodiments only and is not intended to be limiting. As used herein, the singular forms "a," "an," and "the" are intended to include the plural forms, including "at least one," unless the content clearly indicates otherwise. "At least one" is not to be construed as limiting "a" or "an." "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the FIGURES. It will be understood that relative terms are intended to encompass different orientations of the device in addition to the orientation depicted in the FIGURES. For example, if the device in one of the FIGURES is turned over, elements described as being on the "lower" side of other elements would then be oriented on "upper" sides of the other elements. The exemplary term "lower," can therefore, encompasses both an orientation of "lower" and "upper," depending on the particular orientation of the FIGURE. Similarly, if the device in one of the FIGURES is turned over, elements described as "below" or "beneath" other elements would then be oriented "above" the other elements. The exemplary terms "below" or "beneath" can, therefore, encompass both an orientation of above and below.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, or 5% of the stated value.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

An aspect of the present disclosure provides a condensed cyclic compound represented by Formula 1, wherein, in Formula 1, $Y_{11}$ may be a group represented by Formulae 2-1 to 2-3, and $Y_{12}$ may be a group represented by Formulae 3-1 to 3-5, 4-1, or 4-2:

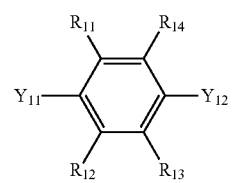

Formula 1

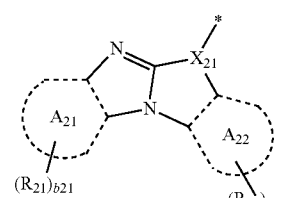

Formula 2-1

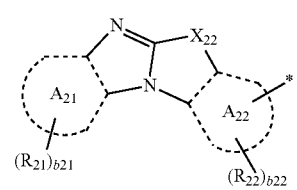

Formula 2-2

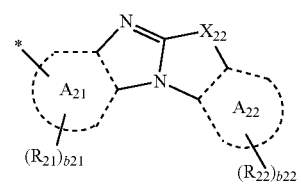

Formula 2-3

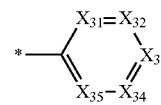

Formula 3-1

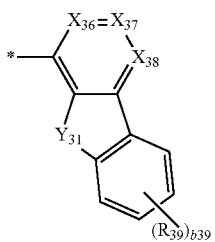

Formula 3-2

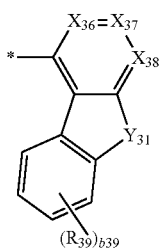

Formula 3-3

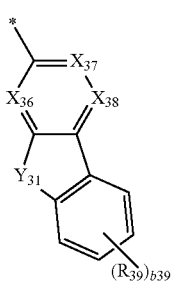

Formula 3-4

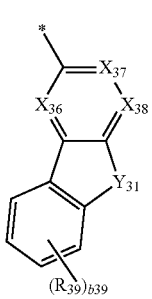

Formula 3-5

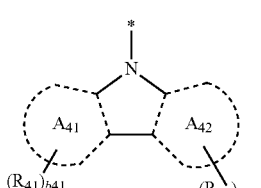

Formula 4-1

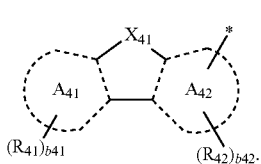

Formula 4-2

Hereinafter, Formulae 1, 2-1 to 2-3, 3-1 to 3-5, 4-1, and 4-2 will be described.

In Formula 2, $X_{21}$ may be N or $C(R_{23})$, and $X_{22}$ may be $N(R_{24})$, $C(R_{24})(R_{25})$, O or S.

$R_{23}$ to $R_{25}$ may be understood by referring to corresponding description presented herein.

For example, in Formula 2, $X_{21}$ may be N, and $X_{22}$ may be $N(R_{24})$, O, or S, but embodiments of the present disclosure are not limited thereto.

In Formulae 3-1 to 3-5, $X_{31}$ may be N or $C(R_{31})$, $X_{32}$ may be N or $C(R_{32})$, $X_{33}$ may be N or $C(R_{33})$, $X_{34}$ may be N or $C(R_{34})$, $X_{35}$ may be N or $C(R_{35})$, $X_{36}$ may be N or $C(R_{36})$, $X_{37}$ may be N or $C(R_{37})$, and $X_{38}$ may be N or $C(R_{38})$, wherein $X_{31}$ to $X_{35}$ in Formula 3-1 may be N, and $X_{36}$ to $X_{38}$ in Formulae 3-2 to 3-5 may be N. $R_{31}$ to $R_{38}$ may be understood by referring to corresponding description presented herein.

In one embodiment, two or three of $X_{31}$ to $X_{35}$ in Formula 3-1 may each independently be N, and two of $X_{36}$ to $X_{38}$ in Formulae 3-2 to 3-5 may each independently be N, but embodiments of the present disclosure are not limited thereto.

In Formulae 3-2 to 3-5, $Y_{31}$ may be O or S.

In Formula 4-2, $X_{41}$ may be O, S, $N(R_{43})$, or $C(R_{43})(R_{44})$. $R_{43}$ and $R_{44}$ may be understood by referring to corresponding description presented herein.

For example, $X_{41}$ in Formula 4-2 may be $N(R_{43})$, but embodiments of the present disclosure are not limited thereto.

In Formulae 2-1 to 2-3, 4-1, and 4-2, ring $A_{21}$, ring $A_{22}$, ring $A_{41}$, and ring $A_{42}$ may each independently be a $C_5$-$C_{60}$ carbocyclic group or a $C_2$-$C_{60}$ heterocyclic group.

For example, in Formulae 2-1 to 2-3, 4-1, and 4-2, ring $A_{21}$, ring $A_{22}$, ring $A_{41}$, and ring $A_{42}$ may each independently be a benzene group, a naphthalene group, an anthracene group, a phenanthrene group, a phenalene group, a triphenylene group, a pyridine group, a pyrimidine group, a pyrazine group, a pyridazine group, a triazine group, a quinoline group, an isoquinoline group, a 2,6-naphthyridine group, a 1,8-naphthyridine group, a 1,5-naphthyridine group, a 1,6-naphthyridine group, a 1,7-naphthyridine group, a 2,7-naphthyridine group, a quinoxaline group, a phthalazine group, a quinazoline group, a phenanthroline group, a benzoquinoline group, a benzoisoquinoline group, a benzoquinoxaline group, a benzoquinazoline group, a furan group, a thiophene group, a silole group, an indene group, a fluorene group, an indole group, a carbazole group, a benzofuran group, a dibenzofuran group, a benzothiophene group, a dibenzothiophene group, a benzosilole group, a dibenzosilole group, an indenopyridine group, an indolopyridine group, a benzofuropyridine group, a benzothienopyridine group, a benzosilolopyridine group, an indenopyrimidine group, an indolopyrimidine group, a benzofuropyrimidine group, a benzothienopyrimidine group, or a benzosilolopyrimidine group, but embodiments of the present disclosure are not limited thereto.

In one embodiment, in Formulae 2-1 to 2-3, 4-1, and 4-2,
ring $A_{21}$ and ring $A_{22}$ may each independently be a benzene group or a naphthalene group, and
ring $A_{41}$ and ring $A_{42}$ may each independently be a benzene group, a naphthalene group, a fluorene group, a carbazole group, a dibenzofuran group, or a dibenzothiophene group, but embodiments of the present disclosure are not limited thereto.

In one embodiment, in Formulae 2-1 to 2-3, 4-1, and 4-2,
ring $A_{21}$ and ring $A_{22}$ may each independently be a benzene group or a naphthalene group,
ring $A_{41}$ may be a benzene group or a naphthalene group,
ring $A_{42}$ may be a benzene group, a naphthalene group, a fluorene group, a carbazole group, a dibenzofuran group, or a dibenzothiophene group, but embodiments of the present disclosure are not limited thereto.

In one embodiment, in Formulae 2-1 to 2-3, 4-1, and 4-2,
ring $A_{21}$ and ring $A_{22}$ may each independently be a benzene group, ring $A_{41}$ may be a benzene group, and ring $A_{42}$ may be a benzene group, a naphthalene group, a fluorene group, a carbazole group, a dibenzofuran group, or a dibenzothiophene group, but embodiments of the present disclosure are not limited thereto.

In Formula 1, $R_{11}$ to $R_{14}$ may each independently be hydrogen, deuterium, —F, —Cl, —Br, —I, a hydroxyl group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_7$-$C_{60}$ alkylaryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_2$-$C_{60}$ alkylheteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —B($Q_1$)($Q_2$), —N($Q_1$)($Q_2$), —P($Q_1$)($Q_2$), —C(=O)($Q_1$), —S(=O)($Q_1$), —S(=O)$_2$($Q_1$), —P(=O)($Q_1$)($Q_2$), or —P(=S)($Q_1$)($Q_2$), and $Q_1$ to $Q_3$ may each independently be hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_7$-$C_{60}$ alkylaryl group, a $C_6$-$C_{60}$ aryloxy group, a $C_6$-$C_{60}$ arylthio group, a $C_1$-$C_{60}$ heteroaryl group, a $C_2$-$C_{60}$ alkylheteroaryl group, a $C_1$-$C_{60}$ heteroaryloxy group, a $C_1$-$C_{60}$ heteroarylthio group, a monovalent non-aromatic condensed polycyclic group, a monovalent non-aromatic condensed heteropolycyclic group, a $C_1$-$C_{60}$ alkyl group substituted with deuterium, —F, a cyano group, a $C_1$-$C_{60}$ alkyl group, a $C_6$-$C_{60}$ aryl group, or any combination thereof, or a $C_6$-$C_{60}$ aryl group substituted with deuterium, —F, a cyano group, a $C_1$-$C_{60}$ alkyl group, a $C_6$-$C_{60}$ aryl group, or any combination thereof.

In Formulae 2-1 to 2-3, 3-1 to 3-5, 4-1, and 4-2, $R_{21}$ to $R_{25}$, $R_{31}$ to $R_{39}$, and $R_{41}$ to $R_{44}$ may each independently be hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_7$-$C_{60}$ alkylaryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_2$-$C_{60}$ alkylheteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —B($Q_1$)($Q_2$), —N($Q_1$)($Q_2$), —P($Q_1$)($Q_2$), —C(=O)($Q_1$), —S(=O)($Q_1$), —S(=O)$_2$($Q_1$), —P(=O)($Q_1$)($Q_2$), or —P(=S)($Q_1$)($Q_2$), and $Q_1$ to $Q_3$ may each independently be hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_7$-$C_{60}$ alkylaryl group, a $C_6$-$C_{60}$ aryloxy group, a $C_6$-$C_{60}$ arylthio group, a $C_1$-$C_{60}$ heteroaryl group, a $C_2$-$C_{60}$ alkylheteroaryl group, a $C_1$-$C_{60}$ heteroaryloxy group, a $C_1$-$C_{60}$ heteroarylthio group, a monovalent non-aromatic condensed polycyclic group, a monovalent non-aromatic condensed heteropolycyclic group, a $C_1$-$C_{60}$ alkyl group substituted with deuterium, —F, a cyano group, a $C_1$-$C_{60}$ alkyl group, a $C_6$-$C_{60}$ aryl group, or any combination thereof, or a $C_6$-$C_{60}$ aryl group substituted with deuterium, —F, a cyano group, a $C_1$-$C_{60}$ alkyl group, a $C_6$-$C_{60}$ aryl group, or any combination thereof.

For example, in Formulae 1, 2-1 to 2-3, 3-1 to 3-5, 4-1, and 4-2, $R_{11}$ to $R_{14}$, $R_{21}$ to $R_{25}$, $R_{31}$ to $R_{39}$, and $R_{41}$ to $R_{44}$ may each independently be hydrogen, deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, or a $C_1$-$C_{20}$ alkoxy group;

a $C_1$-$C_{20}$ alkyl group and a $C_1$-$C_{20}$ alkoxy group, each substituted with deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a cyclopentyl group, a cyclohexyl group, a cycloheptyl group, a cyclooctyl group, an adamantyl group, a norbornyl group, a norbornenyl group, a cyclopentenyl group, a cyclohexenyl group, a cycloheptenyl group, a phenyl group, a biphenyl group, a $C_1$-$C_{20}$ alkylphenyl group, a naphthyl group, a pyridinyl group, a pyrimidinyl group, or any combination thereof, a cyclopentyl group, a cyclohexyl group, a cycloheptyl group, a cyclooctyl group, an adamantyl group, a norbornyl group, a norbornenyl group, a cyclopentenyl group, a cyclohexenyl group, a cycloheptenyl group, a phenyl group, a biphenyl group, a phenyl($C_1$-$C_{20}$ alkyl) group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, an imidazopyridinyl group, or an imidazopyrimidinyl group;

a cyclopentyl group, a cyclohexyl group, a cycloheptyl group, a cycloctyl group, a an adamantyl group, a norbornyl group, a norbornenyl group, a cyclopentenyl group, a cyclohexenyl group, a cycloheptenyl group, a phenyl group, a biphenyl group, a $C_1$-$C_{20}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, an imidazopyridinyl group, or an imidazopyrimidinyl group, each substituted with deuterium, —F, —Cl, —Br, —I, —$CD_3$, —$CD_2H$, —$CDH_2$, —$CF_3$, —$CF_2H$, —$CFH_2$, a hydroxyl group, a nitro group, a cyano group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cycloctyl group, an adamantyl group, a norbornyl group, a norbornenyl group, a cyclopentenyl group, a cyclohexenyl group, a cycloheptenyl group, a phenyl group, a biphenyl group, a phenyl($C_1$-$C_{20}$ alkyl) group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyridinyl group substituted with a phenyl group, a pyrazinyl group, a pyrazinyl group substituted with a phenyl group, a pyrimidinyl group, a pyrimidinyl group substituted with a phenyl group, a pyridazinyl group, a pyridazinyl group substituted with a phenyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a triazinyl group substituted with a phenyl group, a dibenzofuranyl group, a dibenzothiophenyl group, a dibenzosilolyl group, a benzocarbazolyl group, a dibenzocarbazolyl group, an imidazopyridinyl group, an imidazopyrimidinyl group, —Si($Q_{11}$)($Q_{12}$)($Q_{13}$), —B($Q_{11}$)($Q_{12}$), or —N($Q_{11}$)($Q_{12}$); or —Si($Q_1$)($Q_2$)($Q_3$), —B($Q_1$)($Q_2$), or —N($Q_1$)($Q_2$), $Q_1$ to $Q_3$ and $Q_{11}$ to $Q_{13}$ may each independently be:

a methyl group, an ethyl group, an n-propyl group, an isopropyl group, an n-butyl group, an isobutyl group, a sec-butyl group, a tert-butyl group, an n-pentyl group, an isopentyl group, a 2-methylbutyl group, a sec-pentyl group, a tert-pentyl group, a neo-pentyl group, a 3-pentyl group, a 3-methyl-2-butyl group, a phenyl group, a biphenyl group, a phenyl($C_1$-$C_{20}$ alkyl) group, or a naphthyl group; and a methyl group, an ethyl group, an n-propyl group, an isopropyl group, an n-butyl group, an isobutyl group, a sec-butyl group, a tert-butyl group, an n-pentyl group, an isopentyl group, a 2-methylbutyl group, a sec-pentyl group, a tert-pentyl group, a neo-pentyl group, a 3-pentyl group, a 3-methyl-2-butyl group, a phenyl group, or a naphthyl group, each substituted with deuterium, a phenyl group, or any combination thereof, but embodiments of the present disclosure are not limited thereto.

In one embodiment, in Formulae 1, 2-1 to 2-3, 3-1 to 3-5, 4-1, and 4-2, $R_{11}$ to $R_{14}$, $R_{21}$ to $R_{25}$, $R_{31}$ to $R_{39}$, and $R_{41}$ to $R_{44}$ may each independently be hydrogen, deuterium, —F, a nitro group, —$CH_3$, —$CD_3$, —$CD_2H$, —$CDH_2$, —$CF_3$, —$CF_2H$, —$CFH_2$, groups represented by Formulae 9-1 to 9-27, groups represented by Formulae 9-1 to 9-27 in which a hydrogen may be substituted with deuterium, groups represented by Formulae 10-1 to 10-231, —Si($Q_1$)($Q_2$)($Q_3$), —B($Q_1$)($Q_2$), or —N($Q_1$)($Q_2$), but embodiments of the present disclosure are not limited thereto:

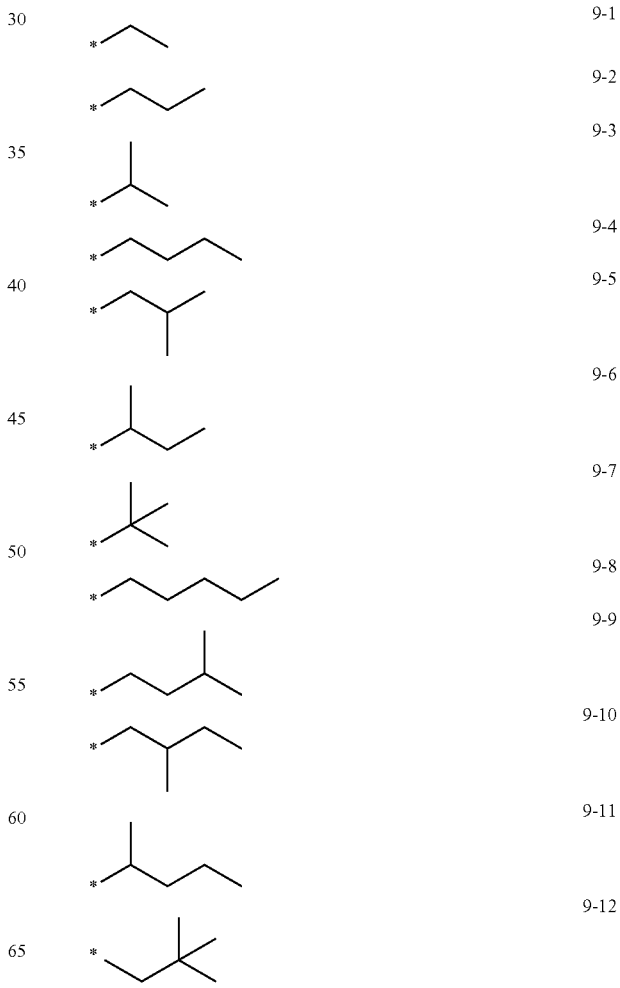

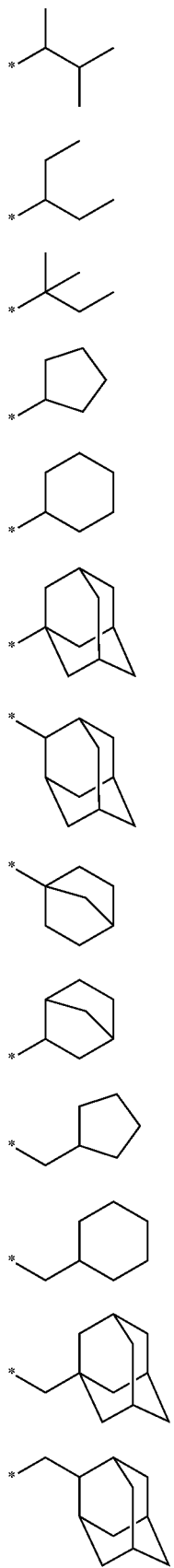
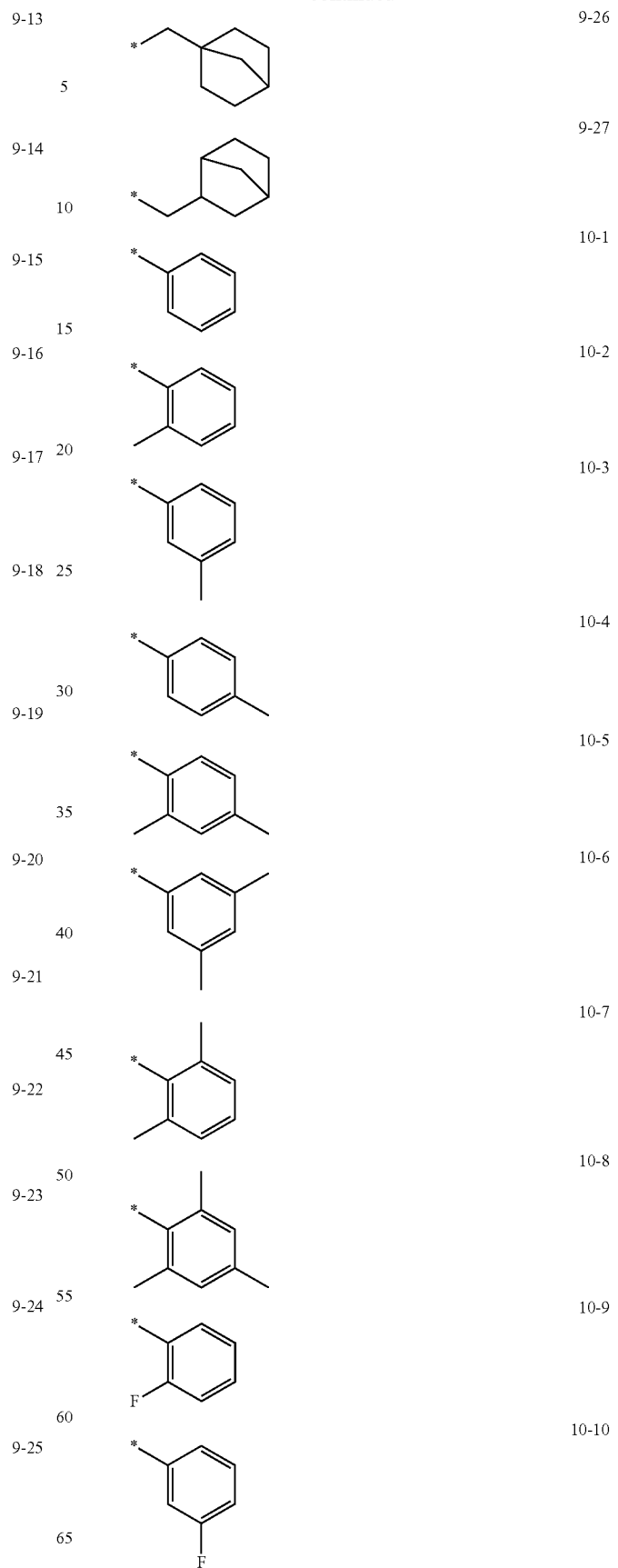

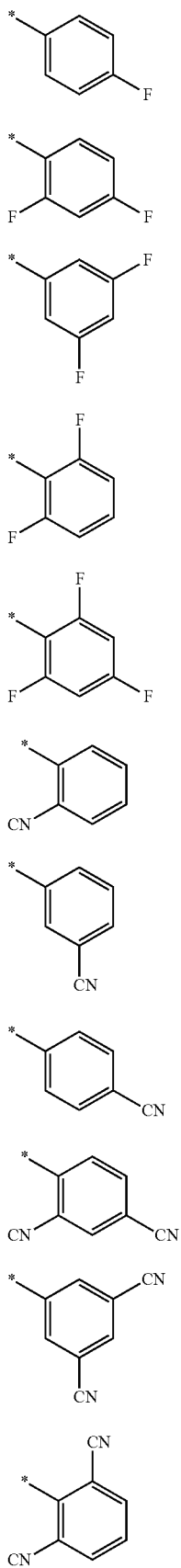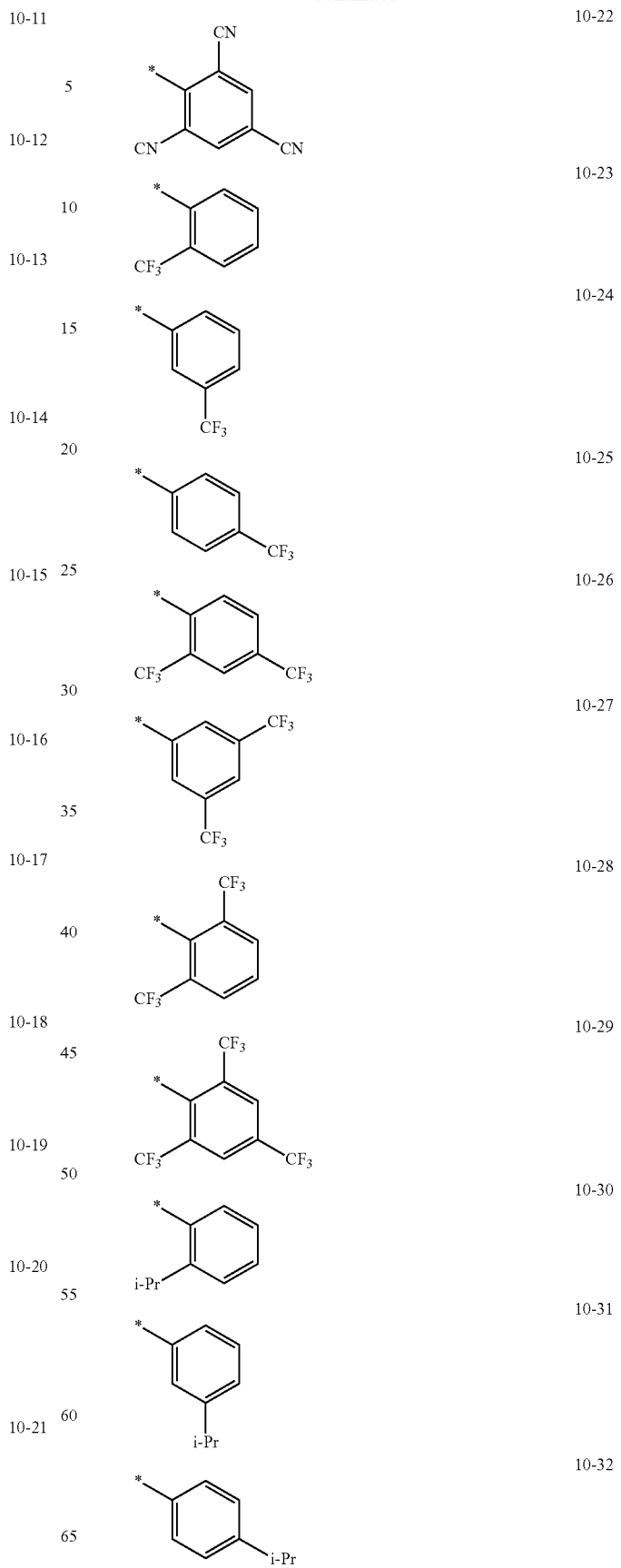

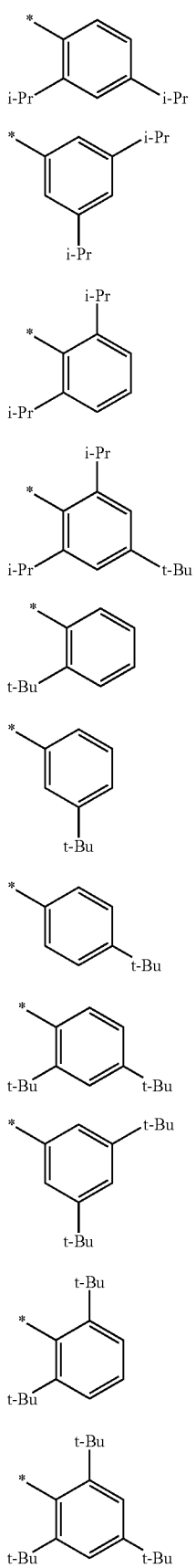
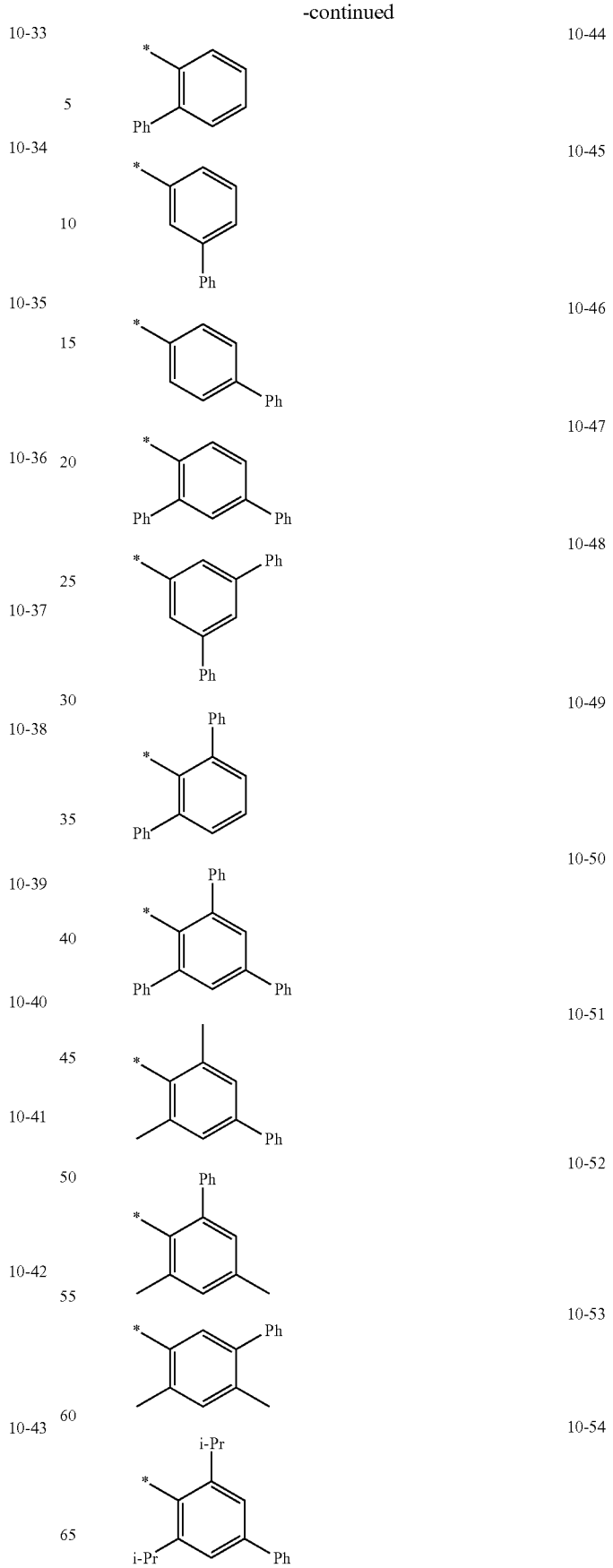

-continued
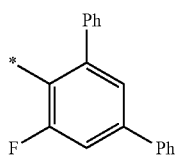 
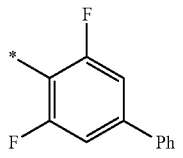
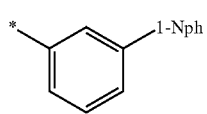
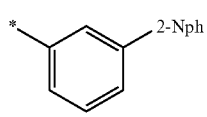
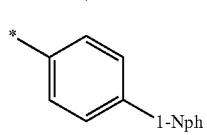
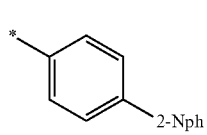
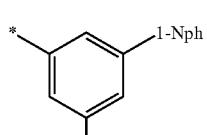
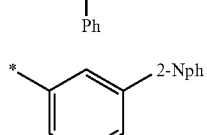
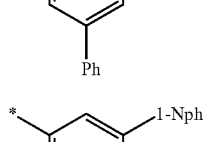
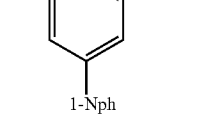
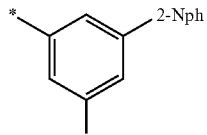
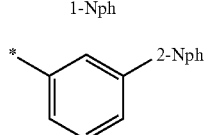
-continued
10-55
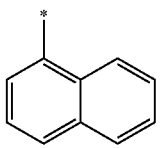
10-56
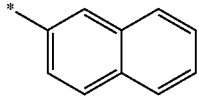
10-57
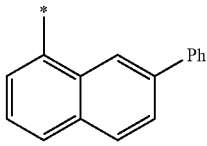
10-58
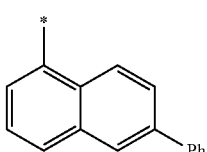
10-59
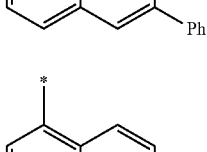
10-60
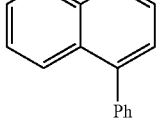
10-61
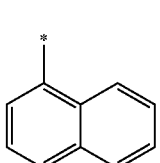
10-62
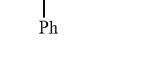
10-63
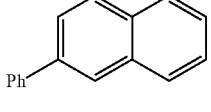
10-64
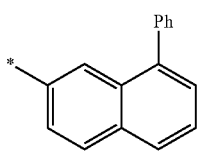
10-65
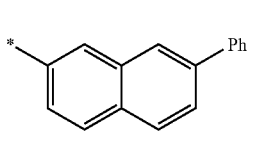
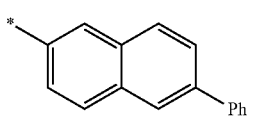
10-66
10-67
10-68
10-69
10-70
10-71
10-72
10-73
10-74
10-75

-continued
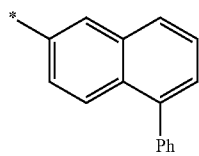
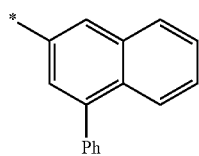
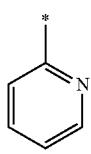
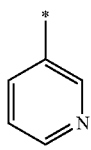
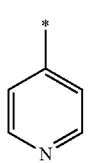
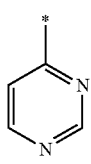
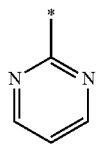
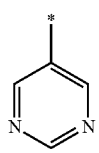
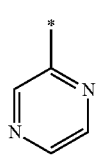
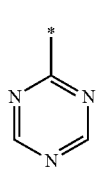
-continued
10-76
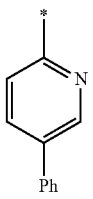
10-77
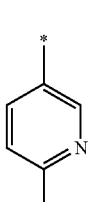
10-78
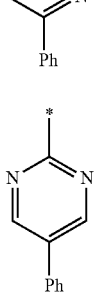
10-79
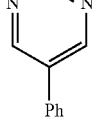
10-80
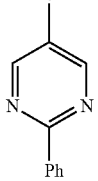
10-81
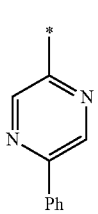
10-82
10-83
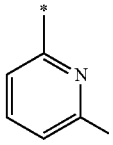
10-84
10-85
10-86
10-87
10-88
10-89
10-90
10-91
10-92
10-93

-continued
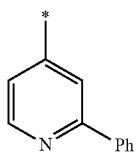 10-94
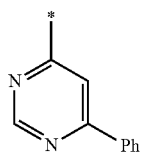 10-95
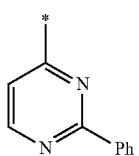 10-96
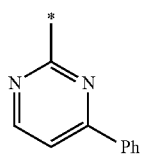 10-97
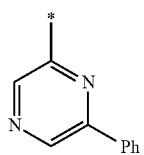 10-98
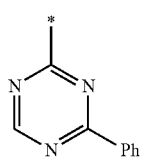 10-99
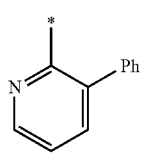 10-100
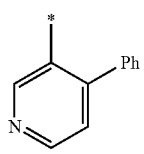 10-101
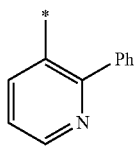 10-102
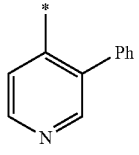 10-103
-continued
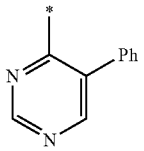 10-104
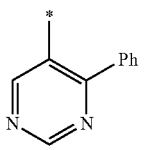 10-105
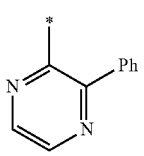 10-106
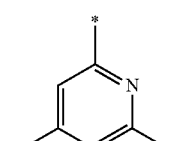 10-107
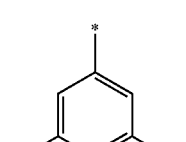 10-108
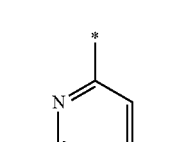 10-109
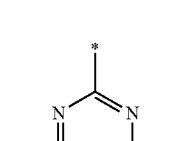 10-110
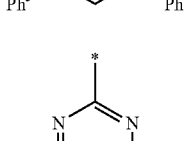 10-111
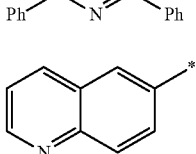 10-112
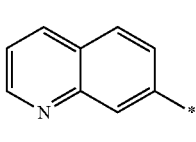 10-113

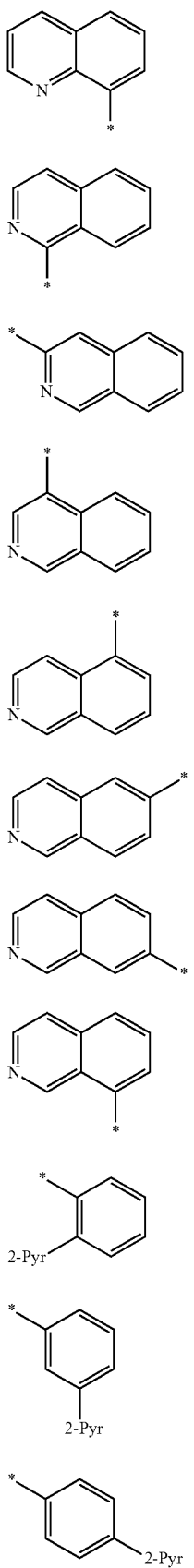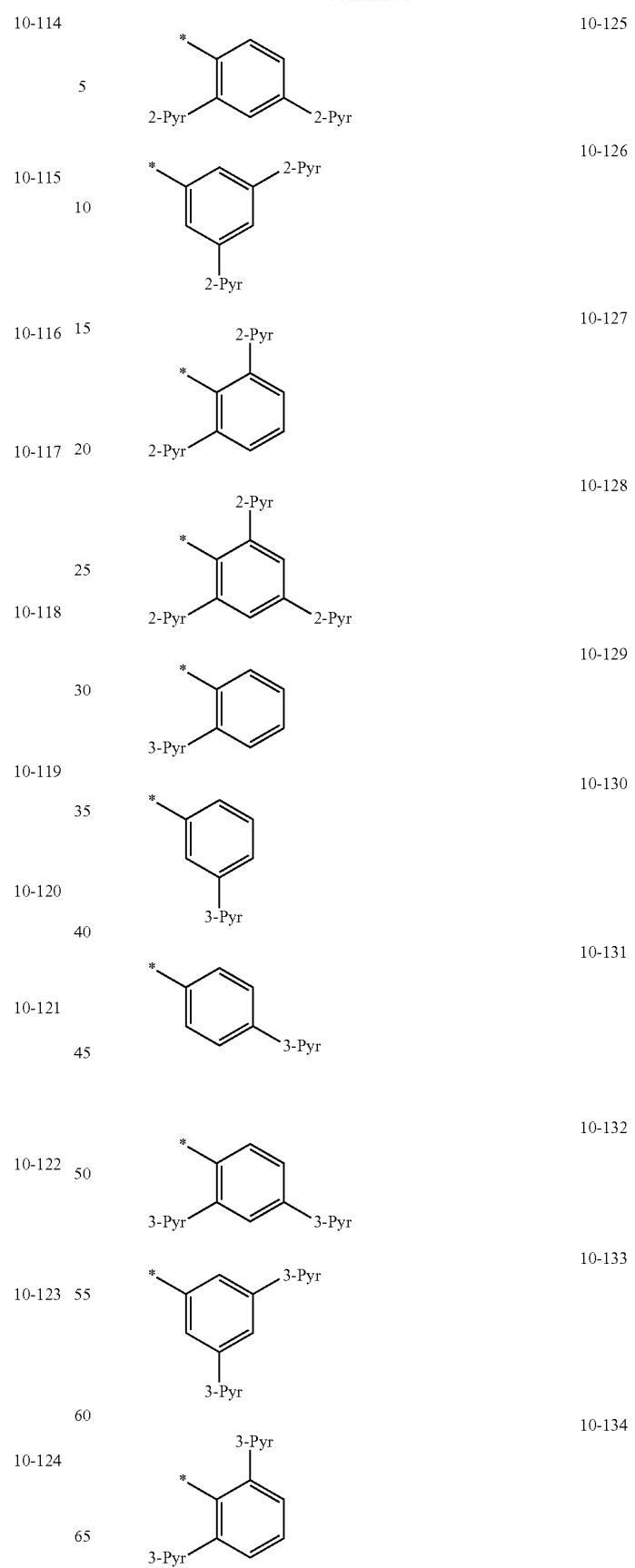

10-135 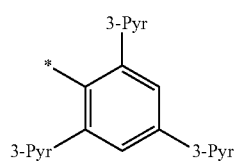
10-136 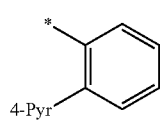
10-137 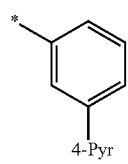
10-138 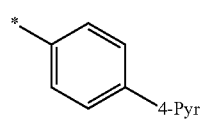
10-139 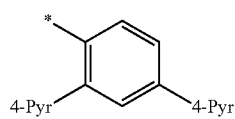
10-140 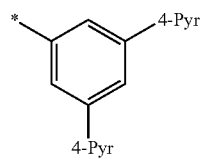
10-141 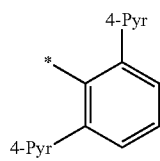
10-142 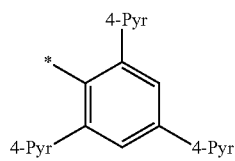
10-143 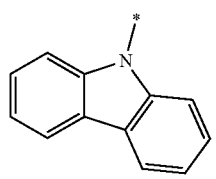
10-144 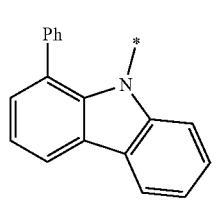
10-145 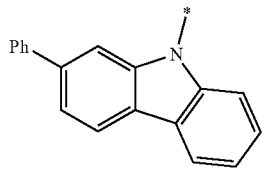
10-146 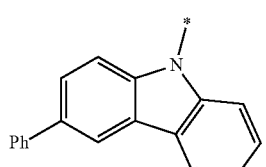
10-147 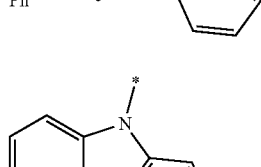
10-148 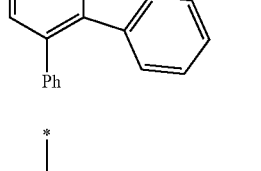
10-149 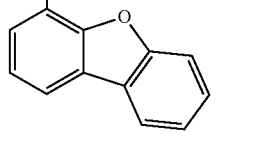
10-150 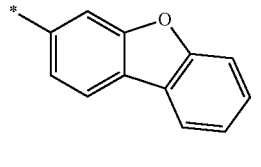
10-151 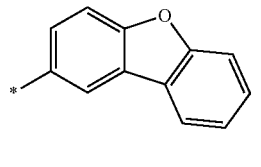
10-152 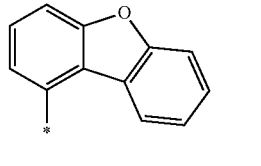
10-153 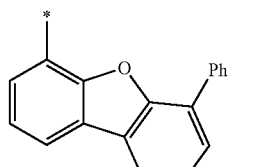
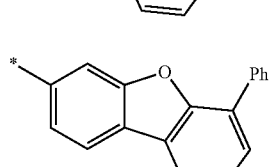

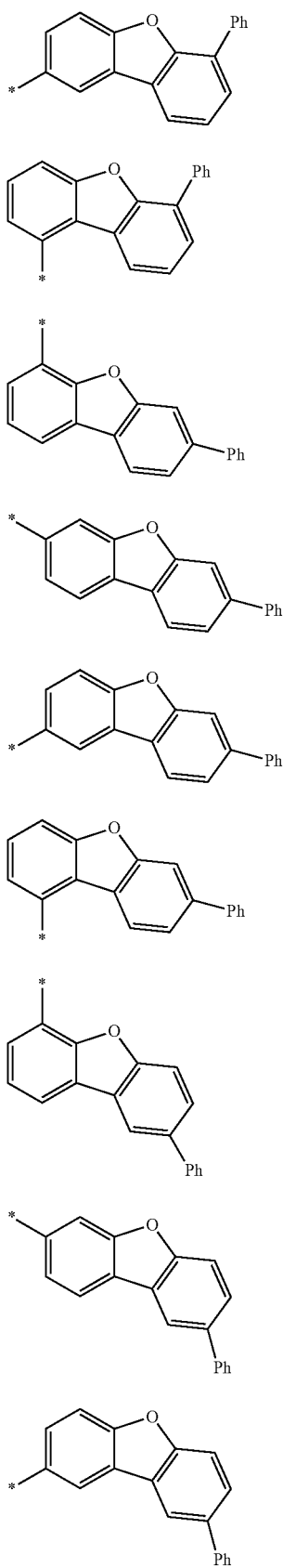
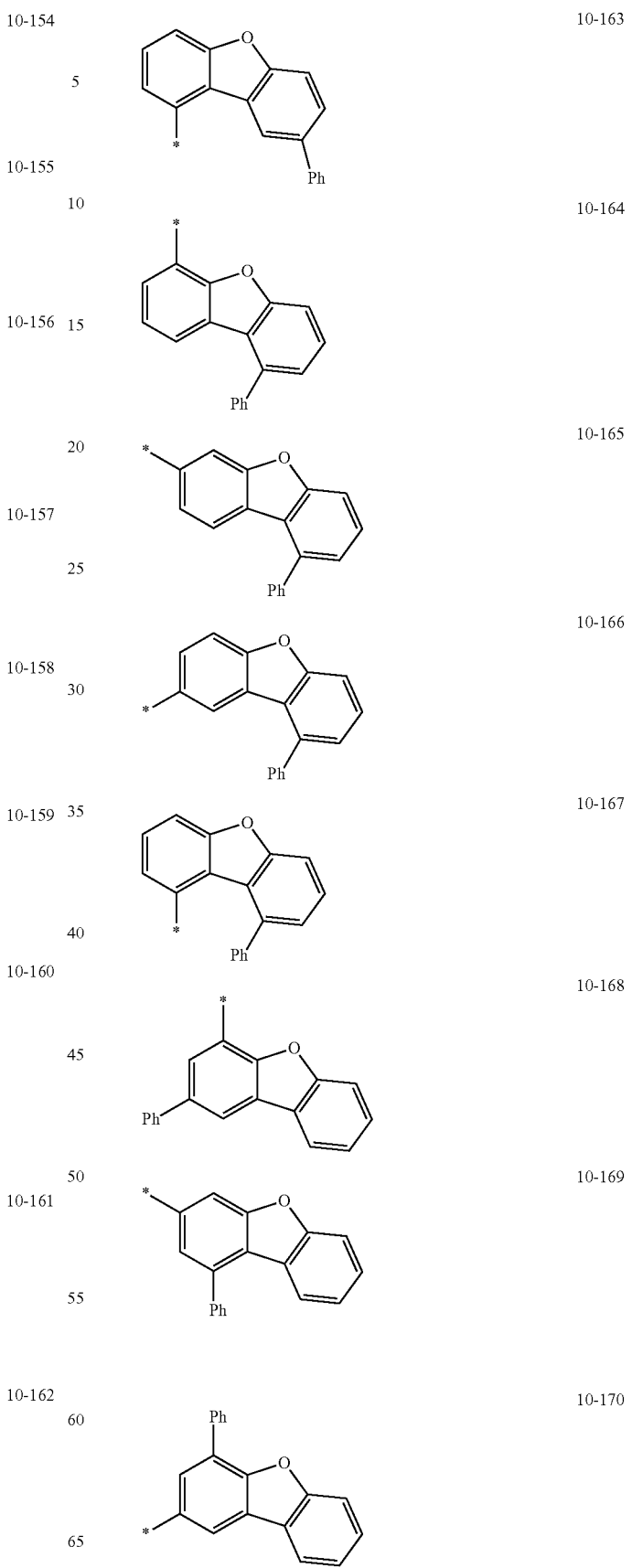

-continued
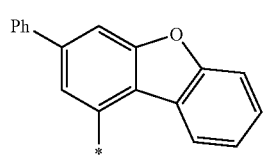
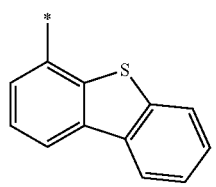
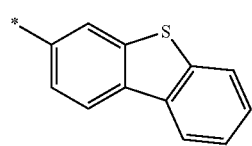
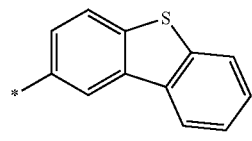
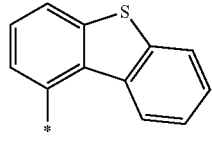
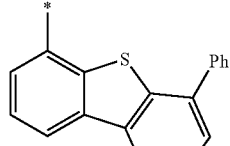
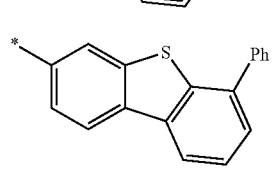
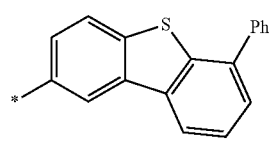
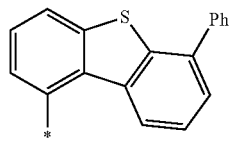
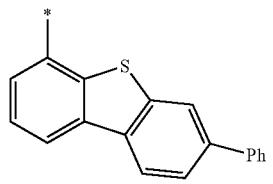
-continued
10-171
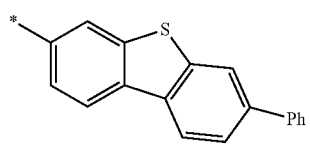
10-172
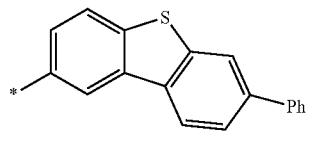
10-173
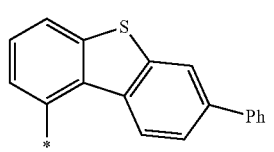
10-174
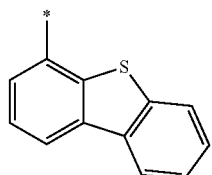
10-175
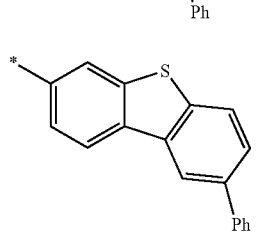
10-176
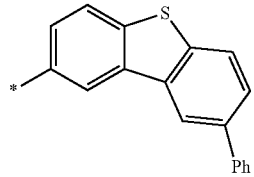
10-177
10-178
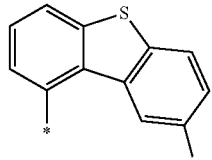
10-179
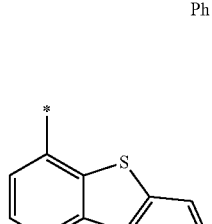
10-180
10-181
10-182
10-183
10-184
10-185
10-186
10-187
10-188
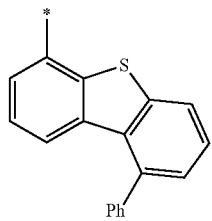

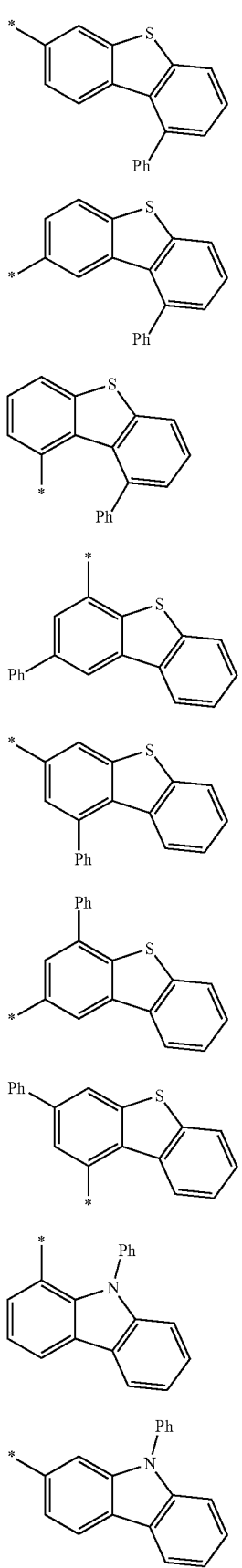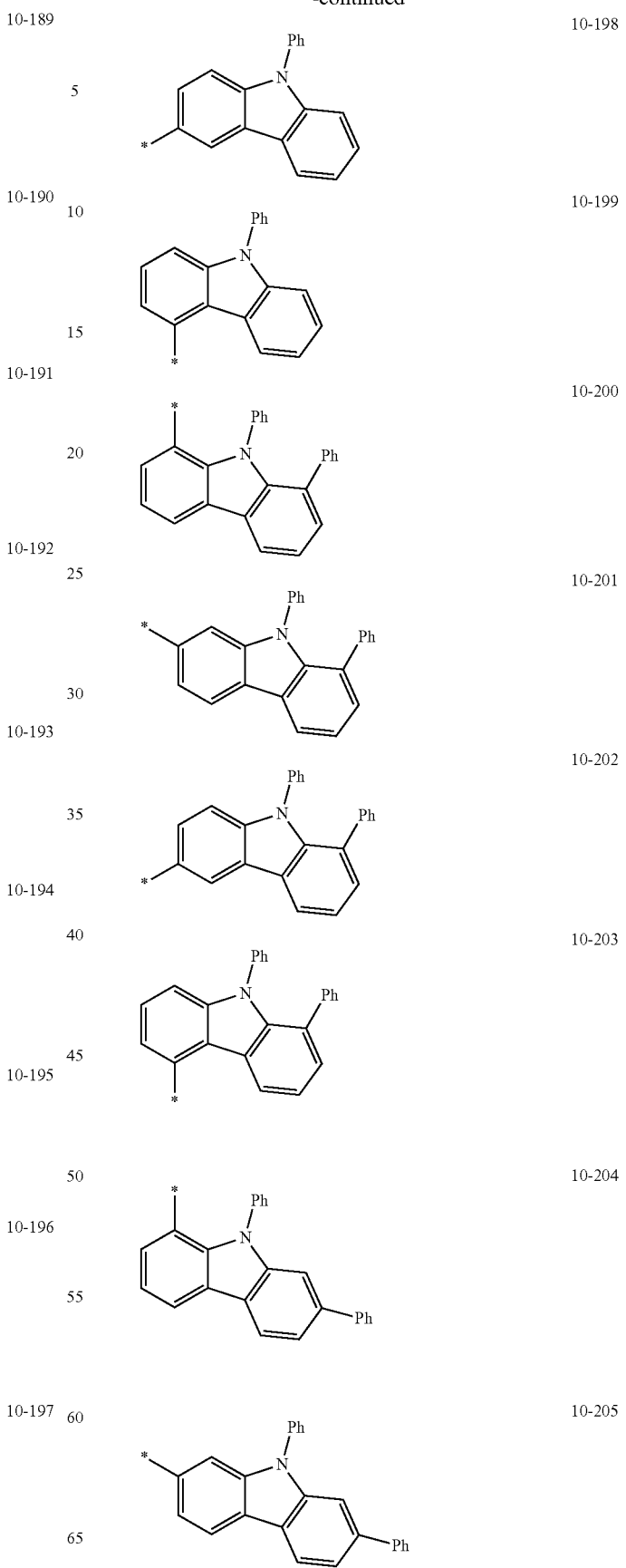

-continued
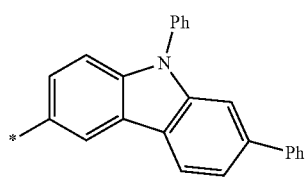
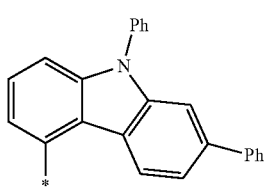
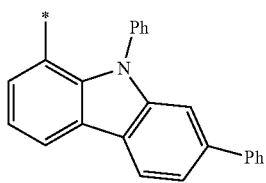
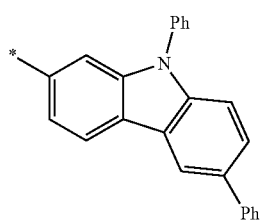
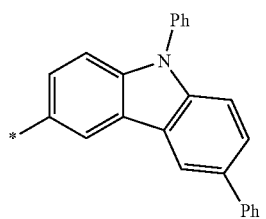
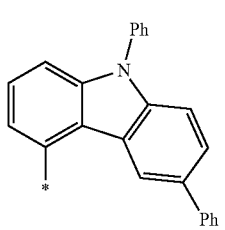
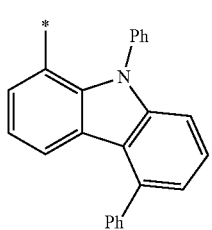
-continued
10-206
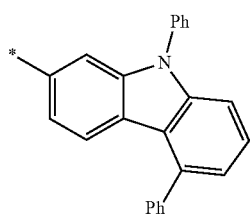
10-213
10-207
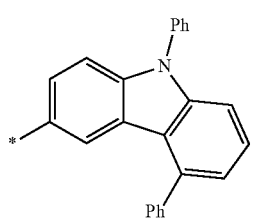
10-214
10-208
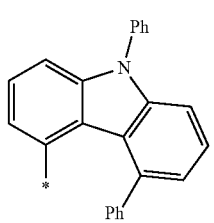
10-215
10-209
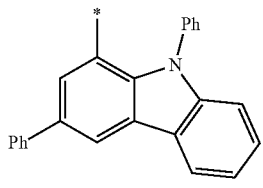
10-216
10-210
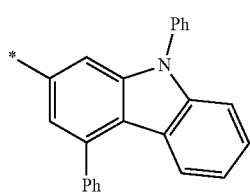
10-217
10-211
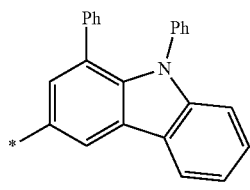
10-218
10-212
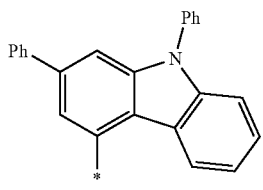
10-219
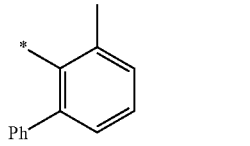
10-220

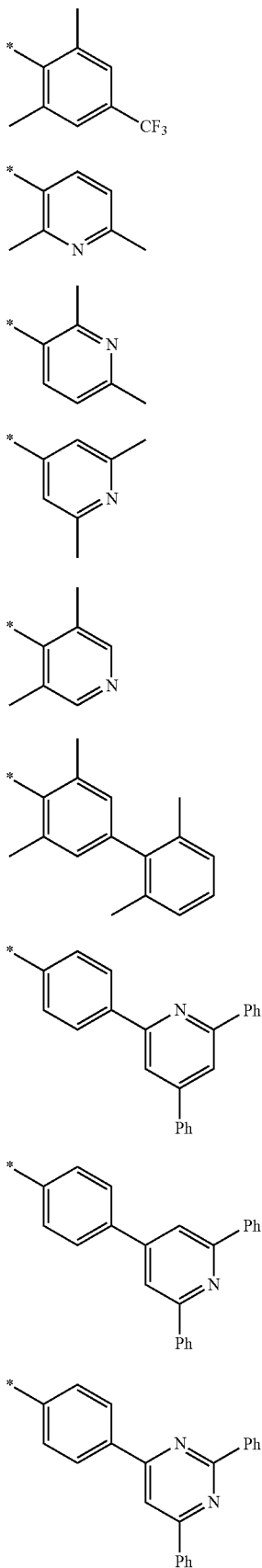

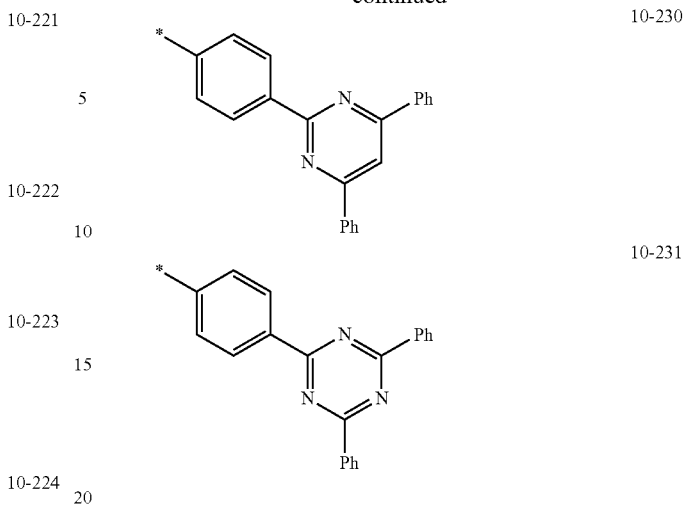

In Formulae 9-1 to 9-27 and 10-1 to 10-231,
* indicates a binding site to a neighboring atom,
i-Pr indicates an isopropyl group,
t-Bu indicates a tert-butyl group,
Ph indicates a phenyl group,
1-Nph indicates a 1-naphthyl group and 2-Nph indicates a 2-naphthyl group,
2-Pyr indicates a 2-pyridyl group, a 3-Pyr indicates a 3-pyridyl group, and 4-Pyr indicates a 4-pyridyl group,
$Q_1$ to $Q_3$ may each independently be:
a methyl group, an ethyl group, an n-propyl group, an isopropyl group, an n-butyl group, an isobutyl group, a sec-butyl group, a tert-butyl group, an n-pentyl group, an isopentyl group, a 2-methylbutyl group, a sec-pentyl group, a tert-pentyl group, a neo-pentyl group, a 3-pentyl group, a 3-methyl-2-butyl group, a phenyl group, a biphenyl group, a phenyl($C_1$-$C_{20}$ alkyl) group, or a naphthyl group; or
a methyl group, an ethyl group, an n-propyl group, an isopropyl group, an n-butyl group, an isobutyl group, a sec-butyl group, a tert-butyl group, an n-pentyl group, an isopentyl group, a 2-methylbutyl group, a sec-pentyl group, a tert-pentyl group, a neo-pentyl group, a 3-pentyl group, a 3-methyl-2-butyl group, a phenyl group, or a naphthyl group, each substituted with deuterium, a phenyl group, or a combination thereof.

In one embodiment, in Formulae 1, 2-1 to 2-3, 3-1 to 3-5, 4-1, and 4-2, $R_{11}$ to $R_{14}$ may each independently be hydrogen, —F, —$CH_3$, —$CF_3$, —$CF_2H$, —$CFH_2$, or groups represented by Formulae 9-1 to 9-15 and 10-1 to 10-56, 10-220, or 10-221, $R_{21}$ to $R_{25}$ may each independently be hydrogen or groups represented by Formulae 10-1 to 10-56, 10-78 to 10-111, 10-122 to 10-142, or 10-220 to 10-231, $R_{31}$ to $R_{39}$ may each independently be hydrogen or groups represented by Formulae 10-1 to 10-56, 10-78 to 10-111, 10-122 to 10-142, or 10-220 to 10-231, $R_{41}$ to $R_{44}$ may each independently be hydrogen or groups represented by Formulae 10-1 to 10-8, 10-30 to 10-54, 10-220, or 10-226, but embodiments of the present disclosure are not limited thereto.

In Formulae 2-1 to 2-3, 3-2 to 3-5, 4-1, and 4-2, b21, b22, b39, b41, and b42 may each independently be 1, 2, 3, 4, 5, 6, 7, 8, 9, or 10.

In one embodiment, $Y_{11}$ in Formula 1 may be a group represented by Formulae 2-11 to 2-13, but embodiments of the present disclosure are not limited thereto:

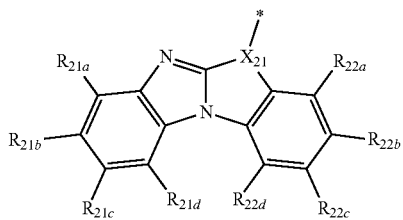

2-11

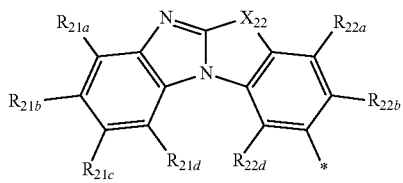

2-12

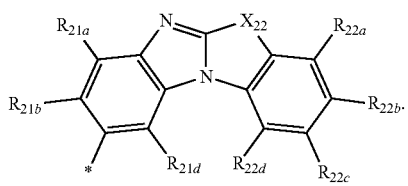

2-13

In Formulae 2-11 to 2-13, $X_{21}$ and $X_{22}$ may each independently be the same as defined in connection with those in Formulae 2-1 to 2-3, $R_{21a}$ to $R_{21d}$ may each independently be the same as defined in connection with $R_{21}$ in Formula 2-1, $R_{22a}$ to $R_{22d}$ may each independently be the same as defined in connection with $R_{22}$ in Formula 2-1, and

* indicates a binding site to a neighboring atom.

For example, in Formulae 2-11 to 2-13, $X_{21}$ may be N, and $X_{22}$ may be $N(R_{24})$, O, or S, but embodiments of the present disclosure are not limited thereto.

In one embodiment, $Y_{12}$ in Formula 1 may be a group represented by Formulae 3-11 to 3-35 or 4-11 to 4-17, but embodiments of the present disclosure are not limited thereto:

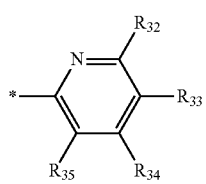

3-11

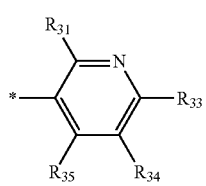

3-12

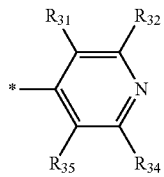

3-13

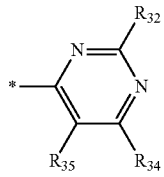

3-14

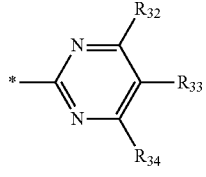

3-15

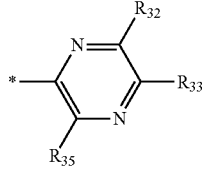

3-16

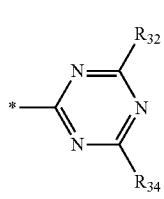

3-17

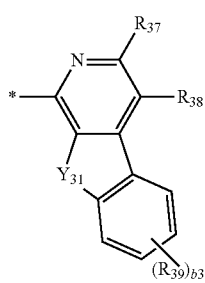

3-18

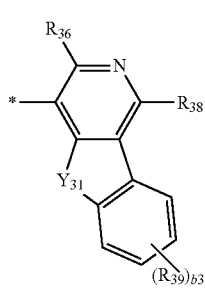

3-19

3-20 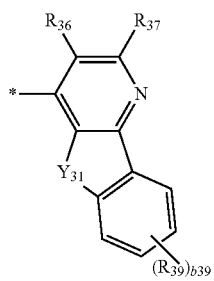
3-21 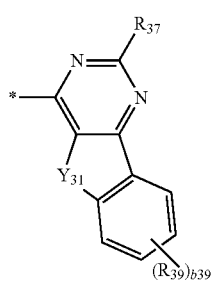
3-22 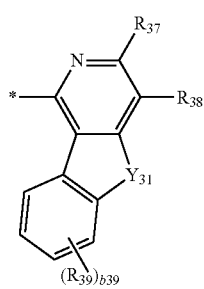
3-23 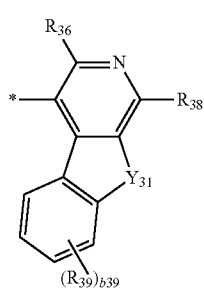
3-24 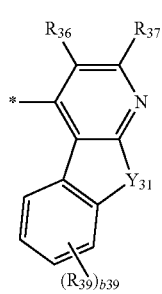
3-25 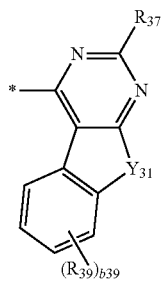
3-26 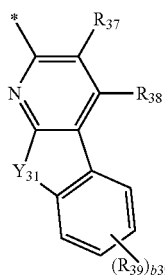
3-27 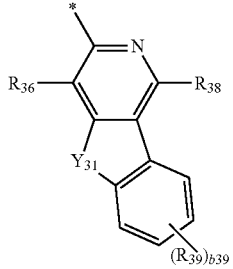
3-28 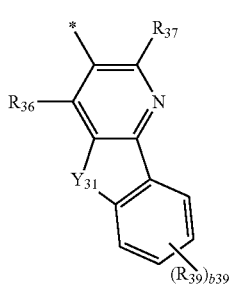
3-29 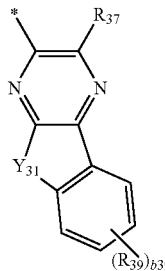

-continued
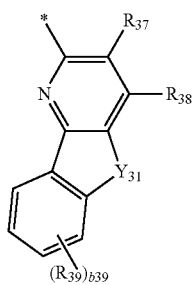
3-30
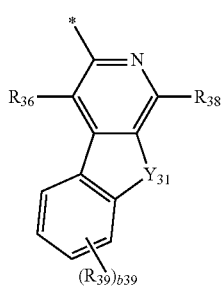
3-31
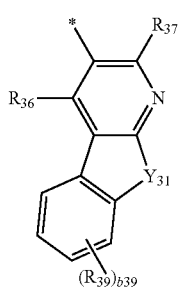
3-32
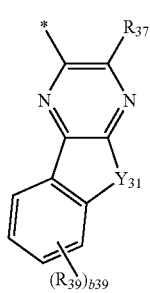
3-33
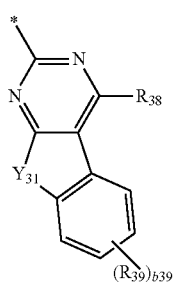
3-34
-continued
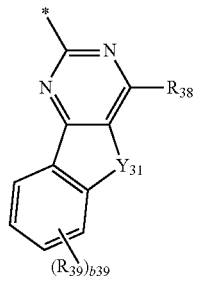
3-35
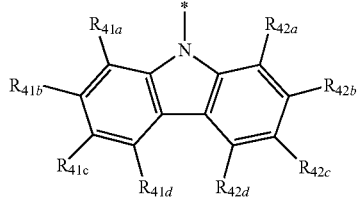
4-11
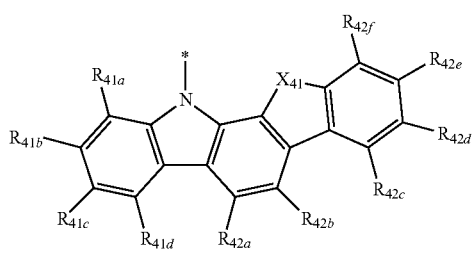
4-12
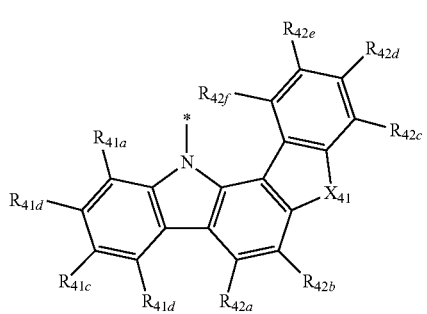
4-13
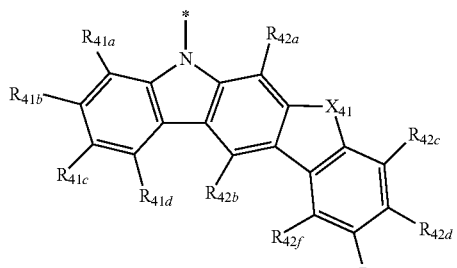
4-14
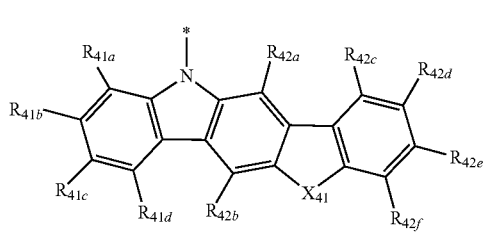
4-15

4-16

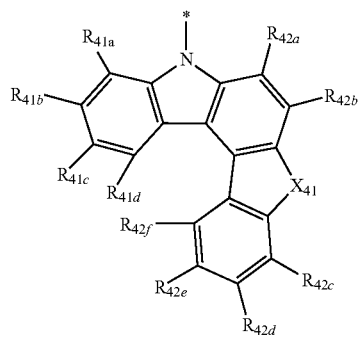

4-17

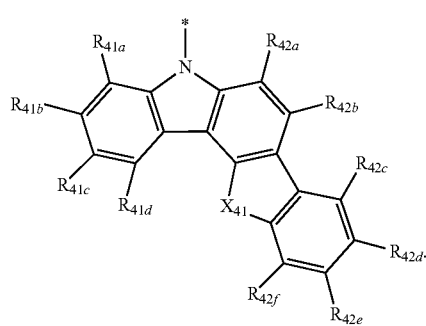

In Formulae 3-11 to 3-35 and 4-11 to 4-17, $Y_{31}$, $R_{36}$ to $R_{39}$, and b39 may each independently be the same as defined in connection with those in Formulae 3-1 to 3-5, $X_{41}$ may be O, S, $N(R_{42g})$, or $C(R_{42g})(R_{42h})$, $R_{41a}$ to $R_{41d}$ may each independently be the same as defined in connection with $R_{41}$ in Formula 4-1, $R_{42a}$ to $R_{42h}$ may each independently be the same as defined in connection with $R_{42}$ in Formula 4-1, and

* indicates a binding site to a neighboring atom.

In one or more embodiments, $Y_{11}$ in Formula 1 may be a group represented by Formulae 2-11 to 2-13, and $Y_{12}$ may be a group represented by Formulae 3-11 to 3-35 or 4-11 to 4-17, but embodiments of the present disclosure are not limited thereto.

In one or more embodiments, the condensed cyclic compound may be of Compounds 1 to 117 below, but are not limited thereto:

1

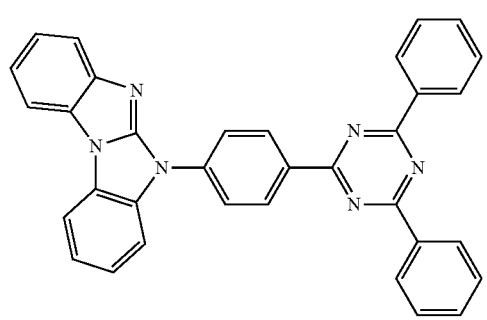

2

3

4

5

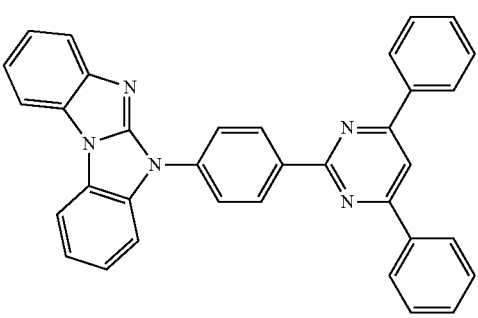

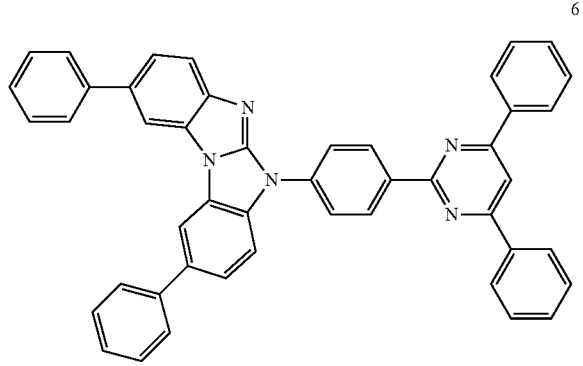
6
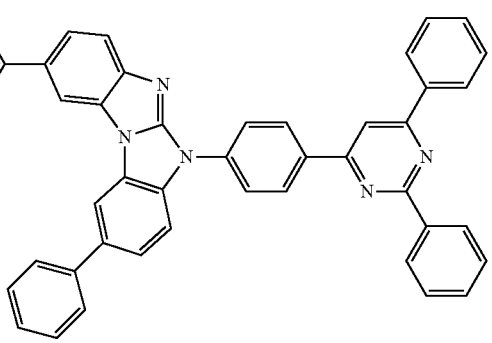
10
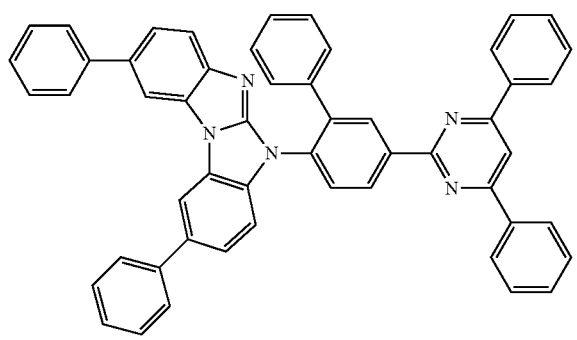
7
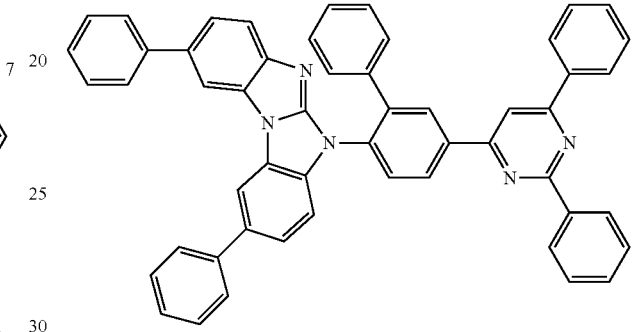
11
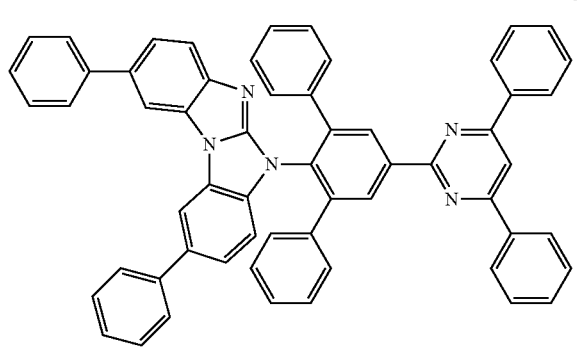
8
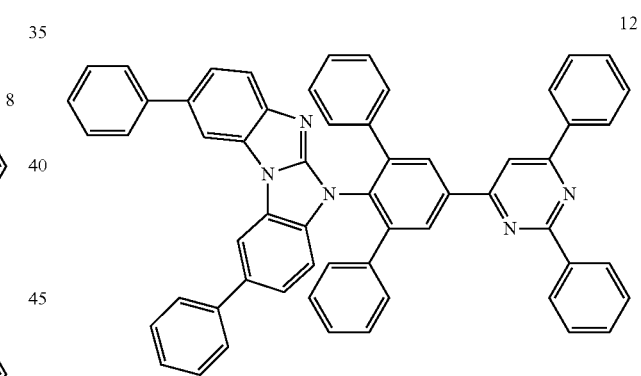
12
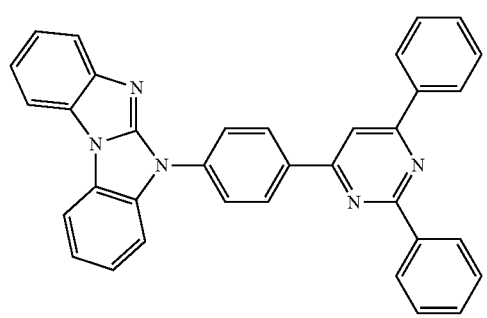
9
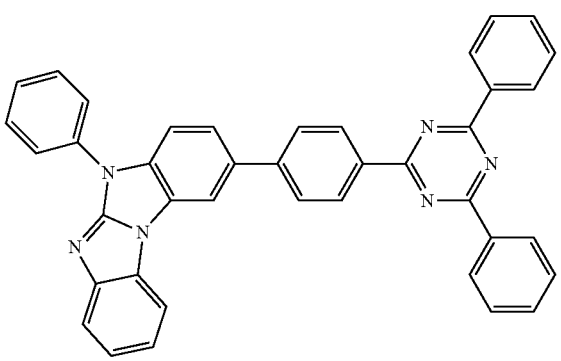
13

14
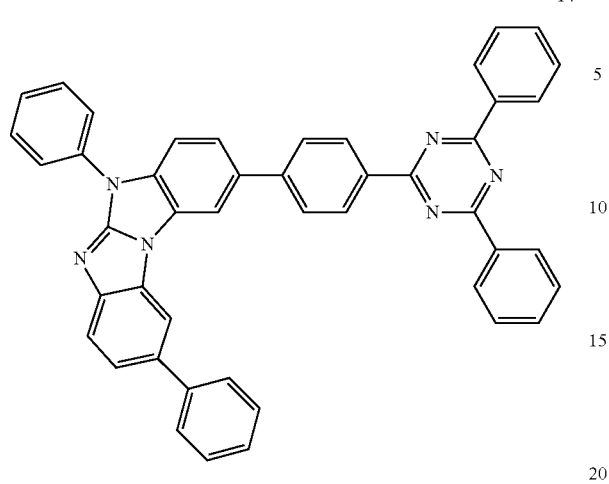
15
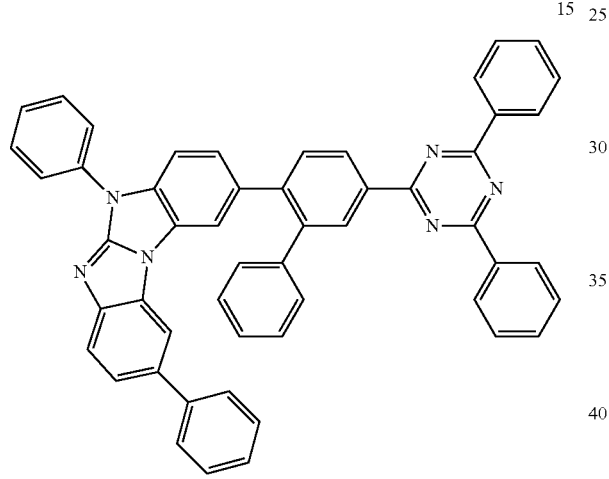
16
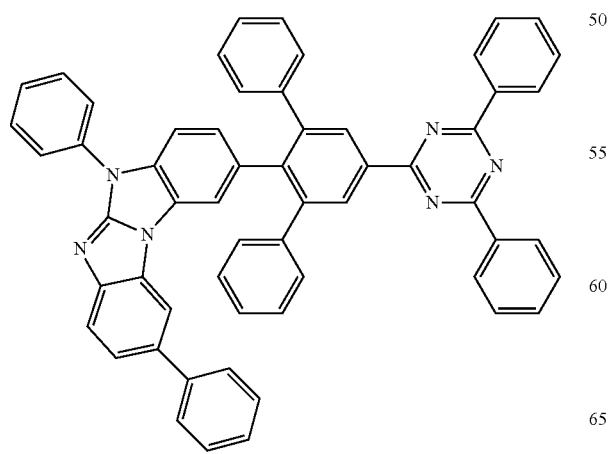
17
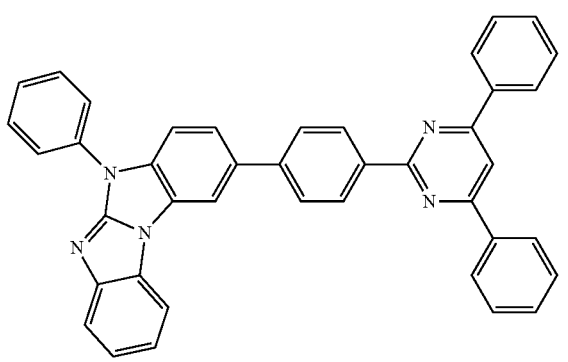
18
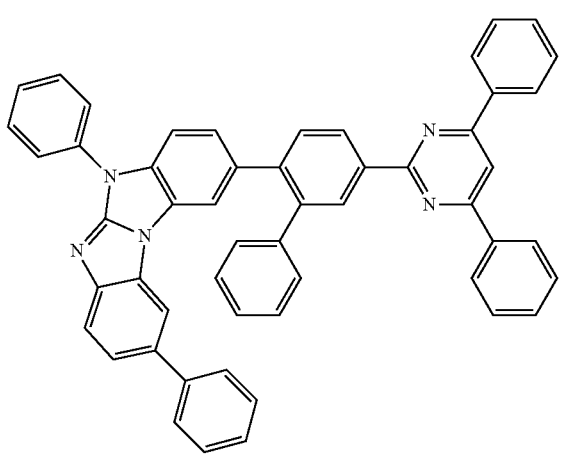
19

20
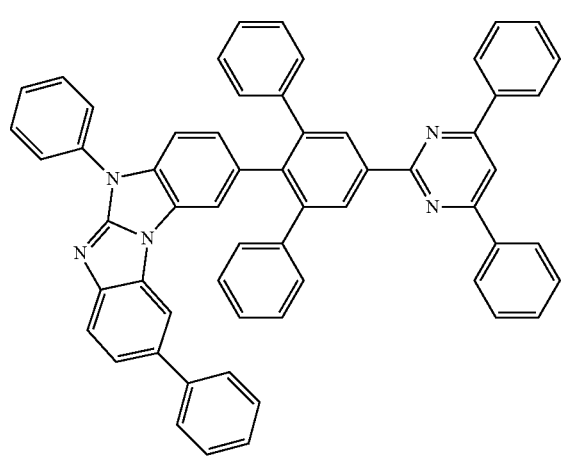
21
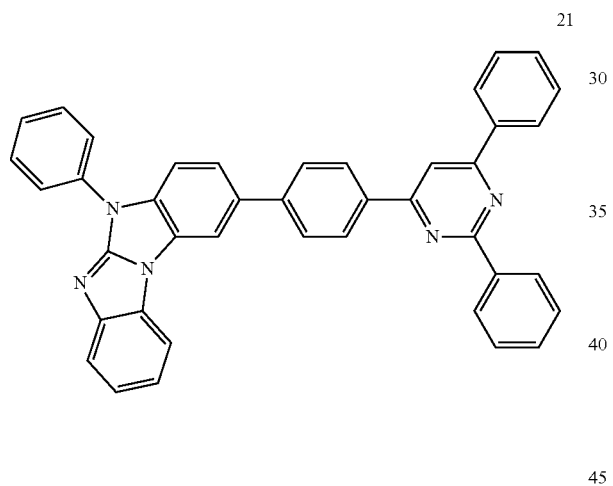
22
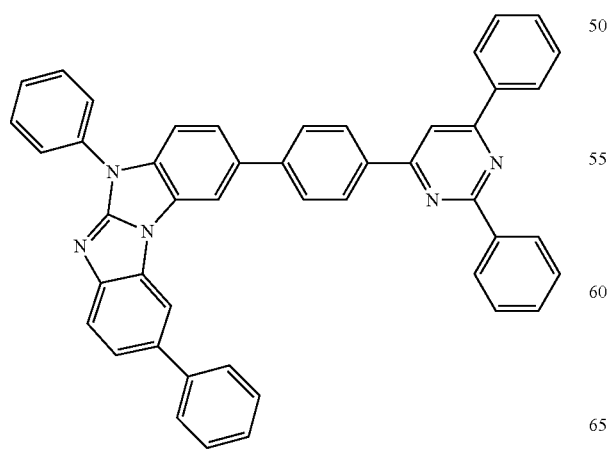
23
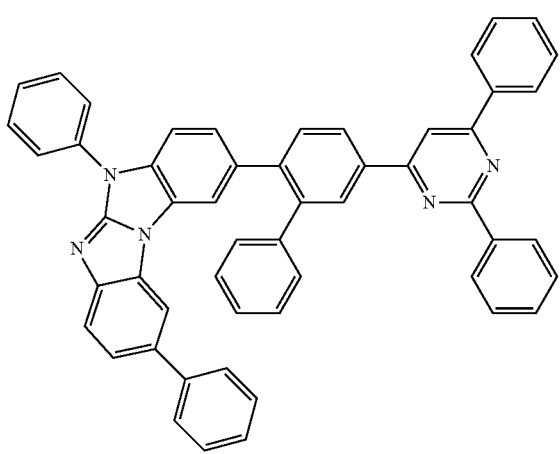
24
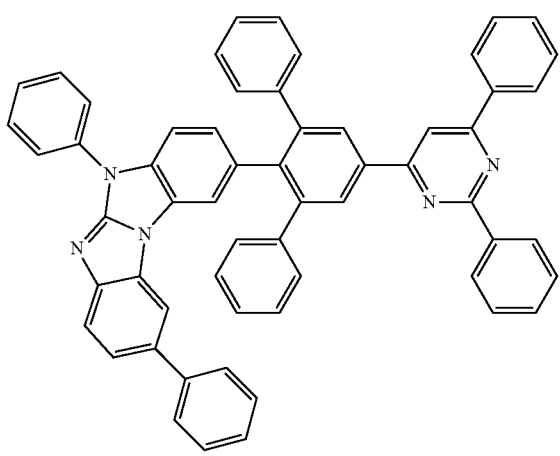
25
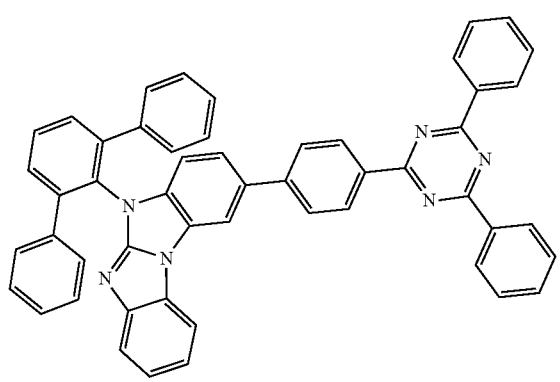

26
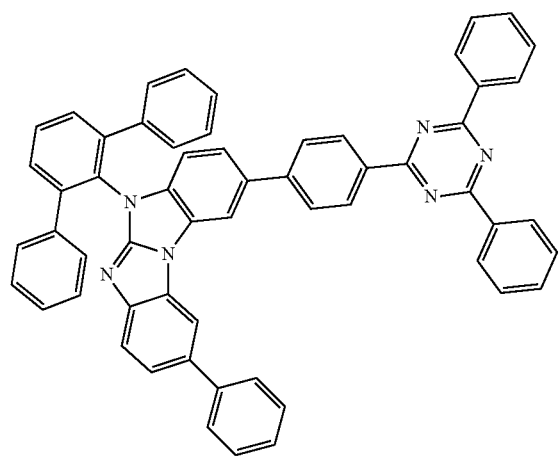
27
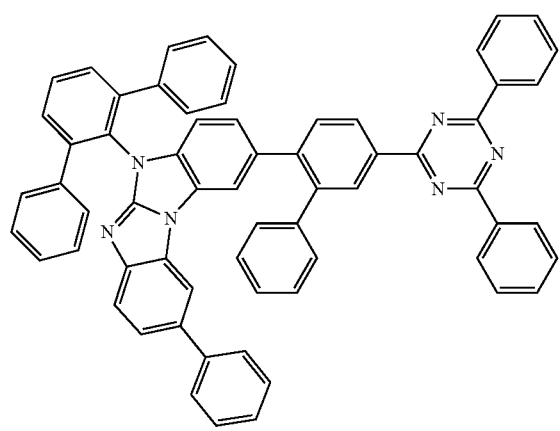
28
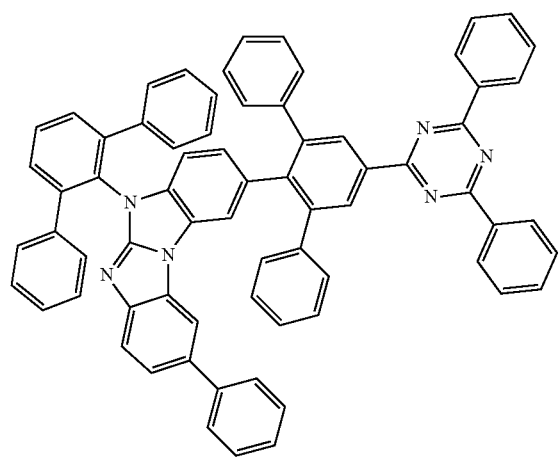
29
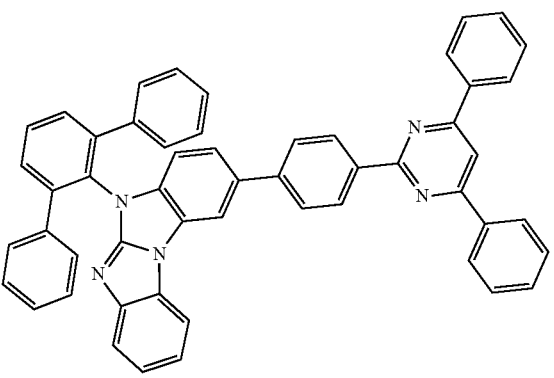
30
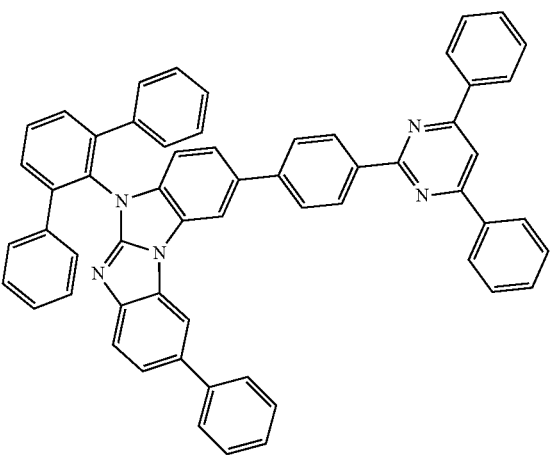
31
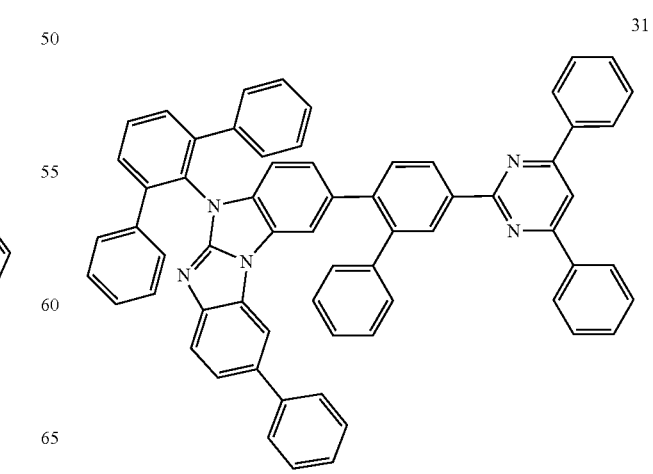

32
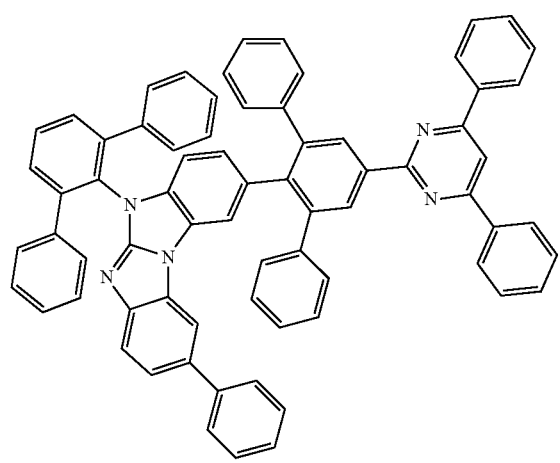
33
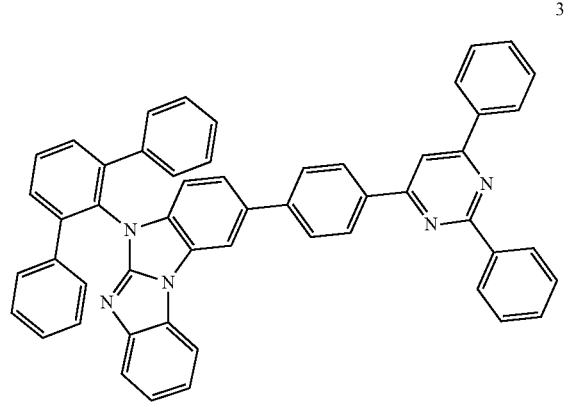
34
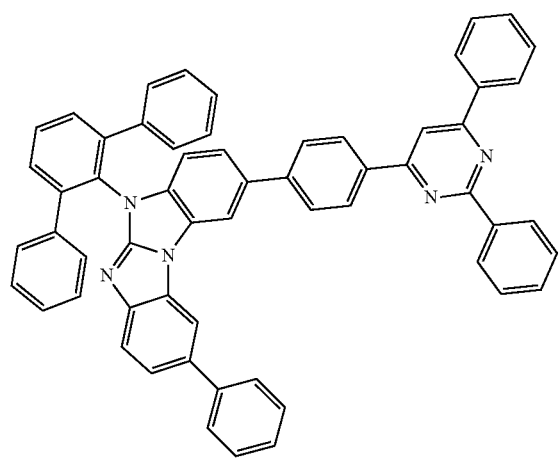
35
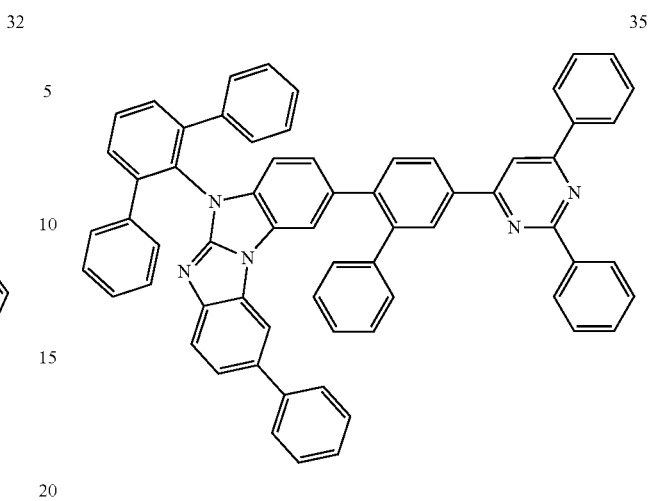
36
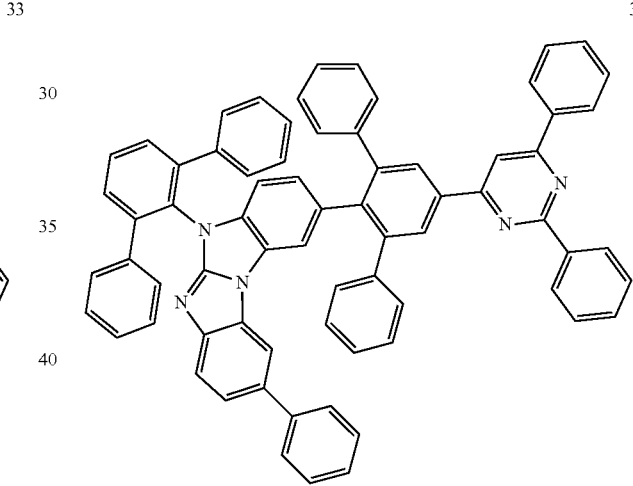
37
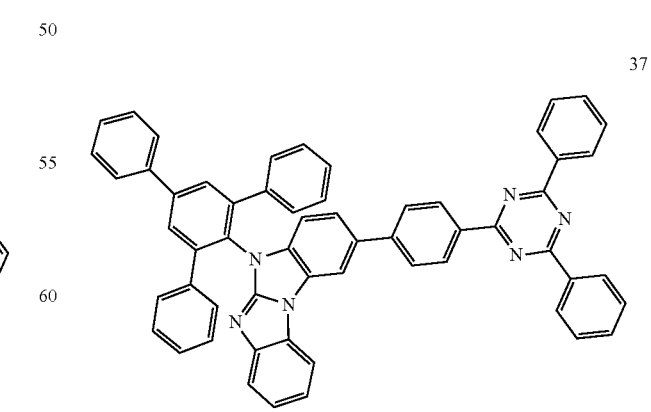

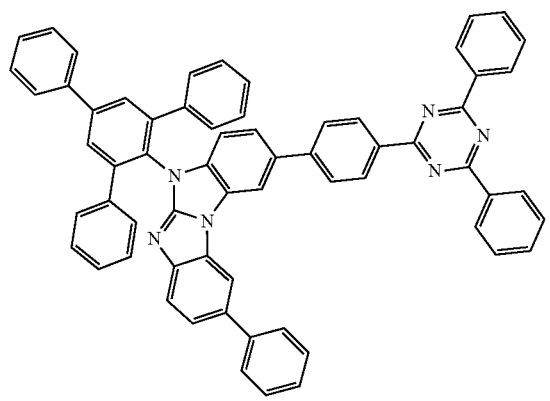
38
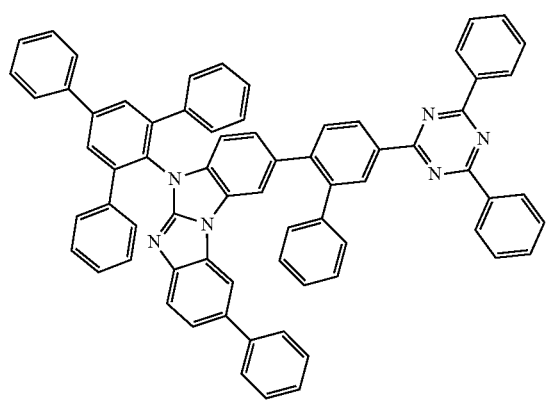
39
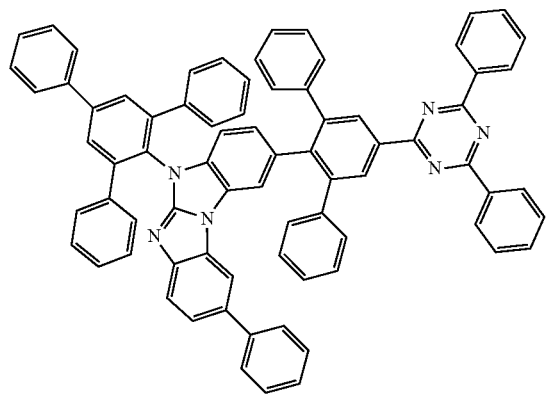
40
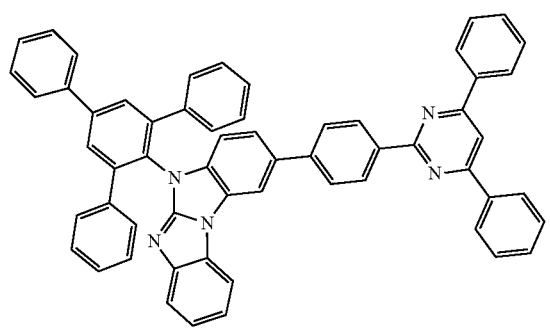
41
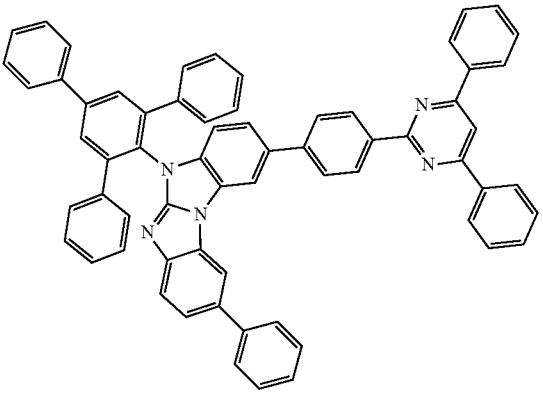
42

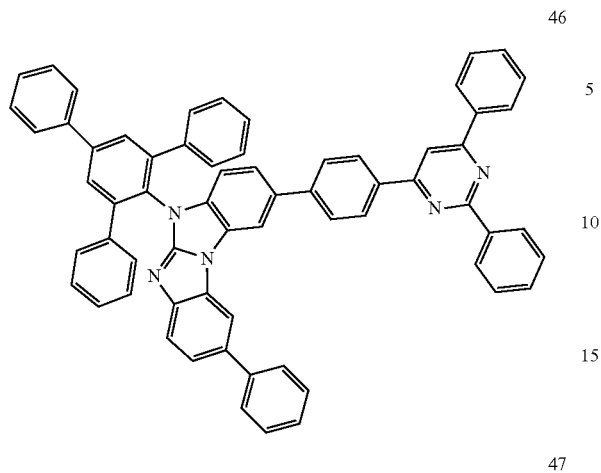
46
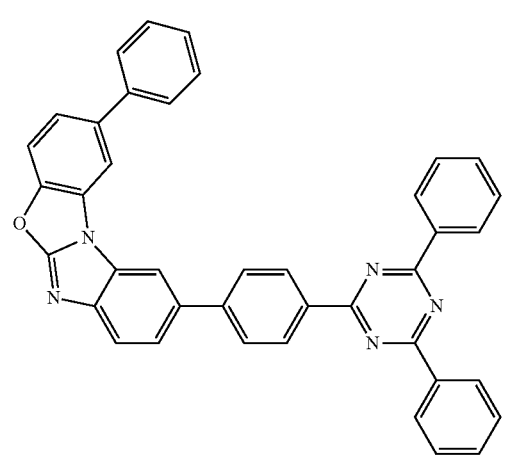
50
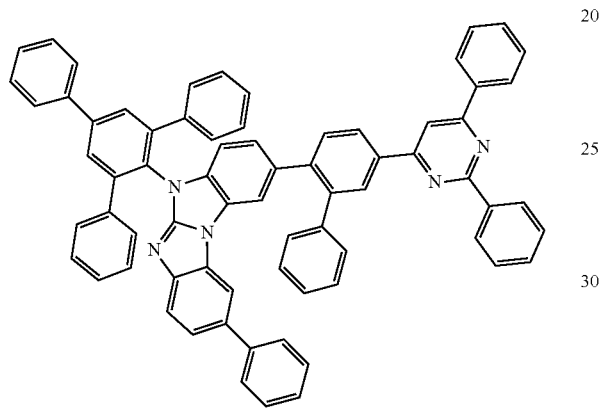
47
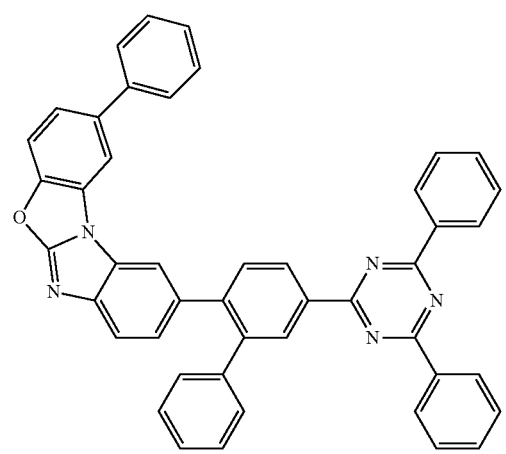
51
48
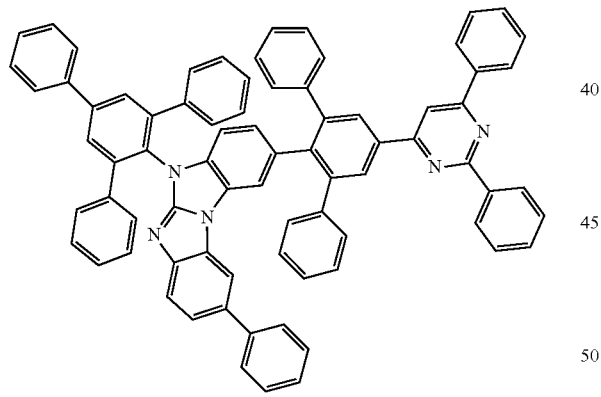
49
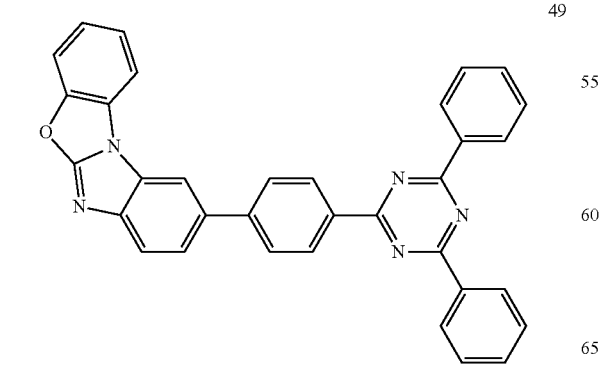
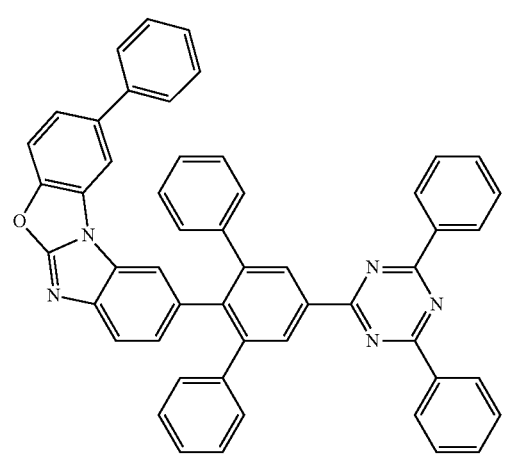
52

53
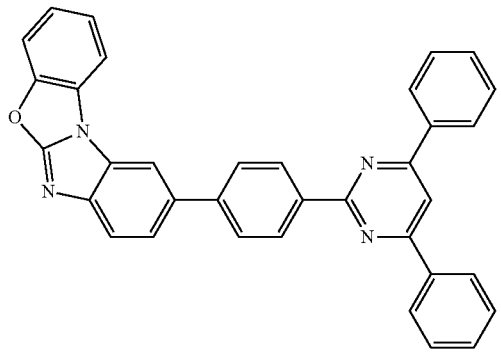
54
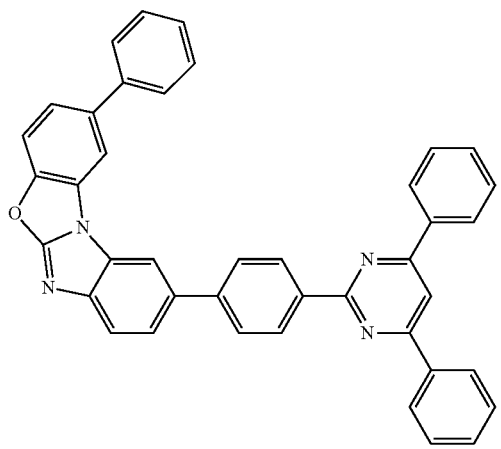
55
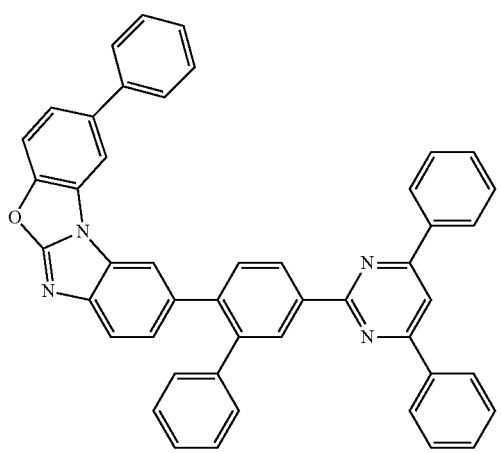
56
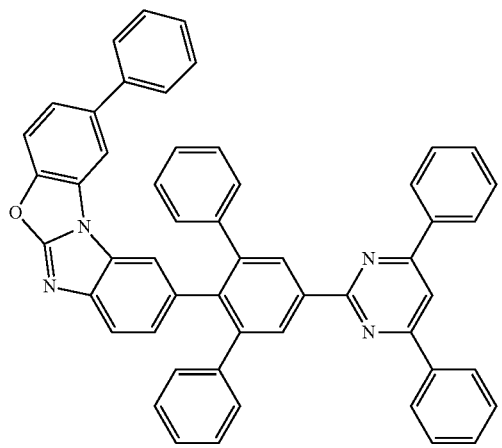
57
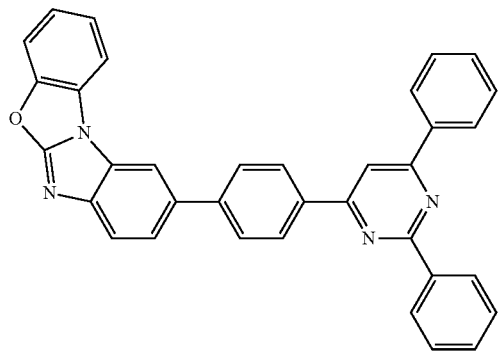
58
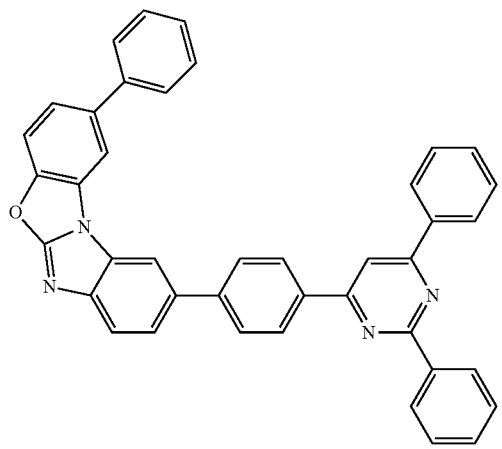

59
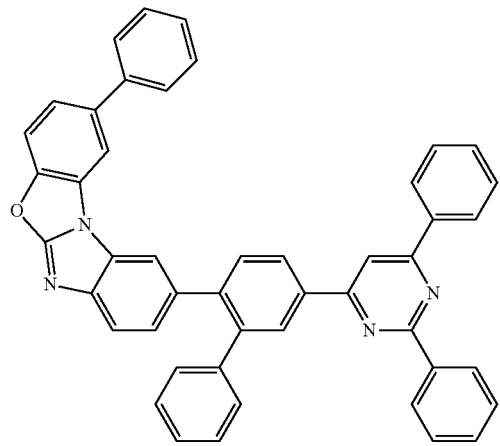
60
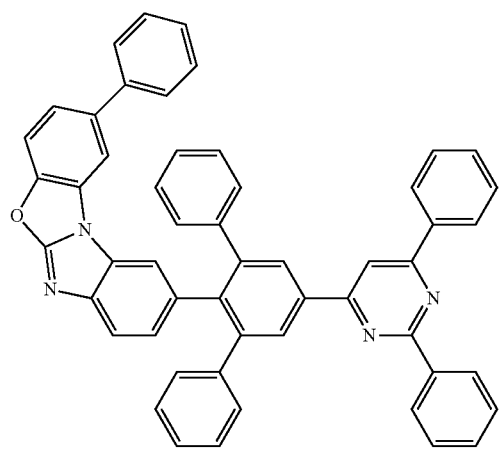
61
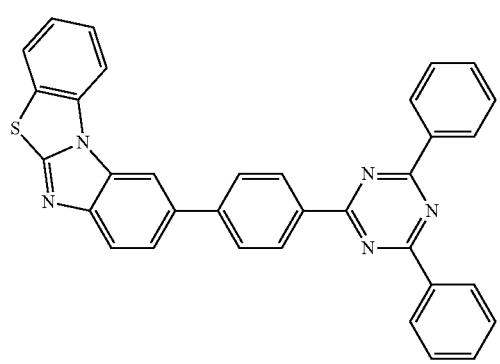
62
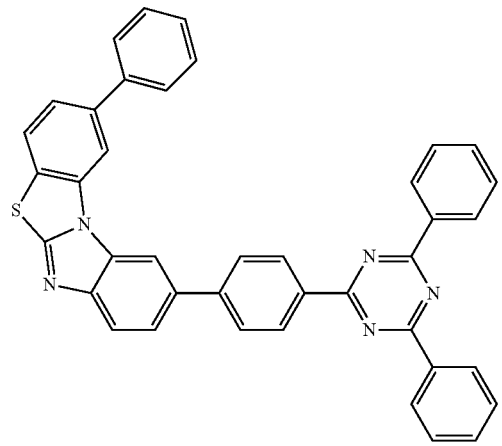
63
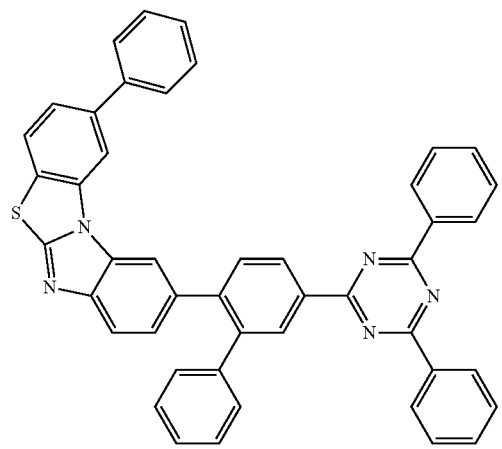
64
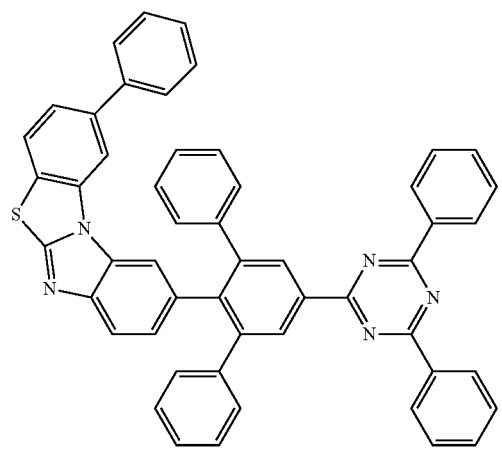

-continued
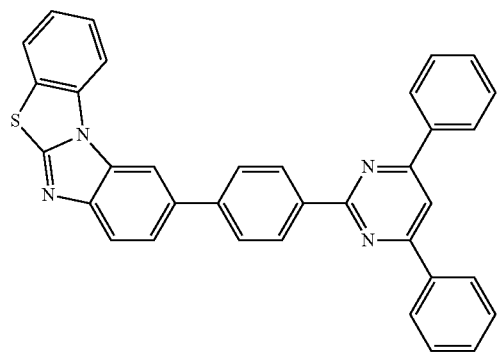
65
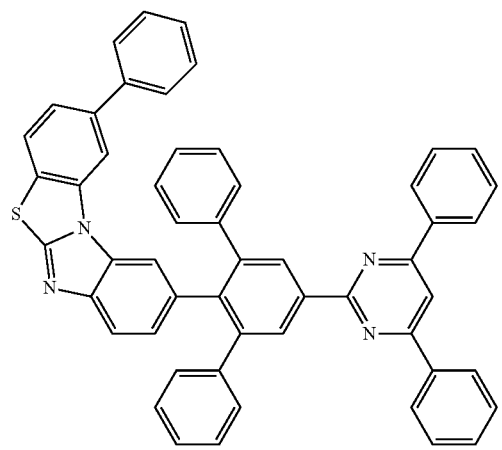
68
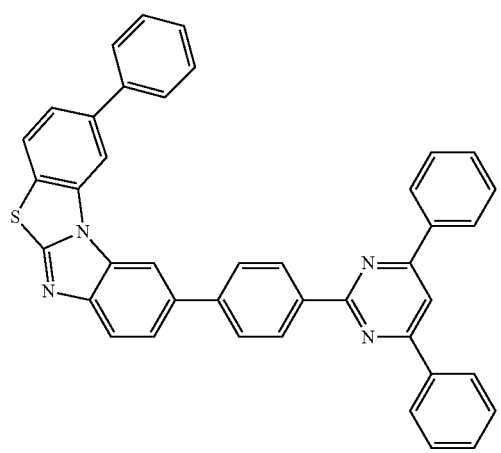
66
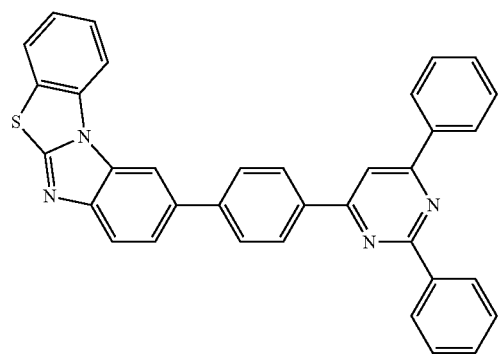
69
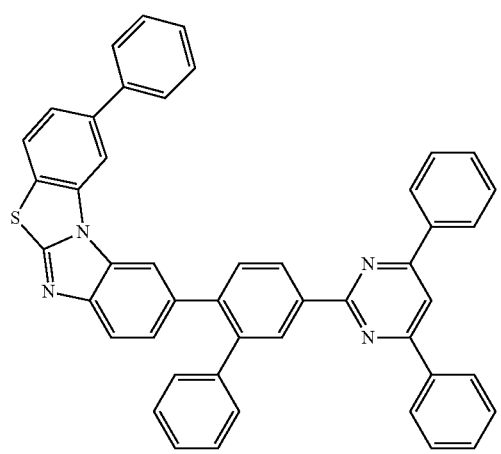
67
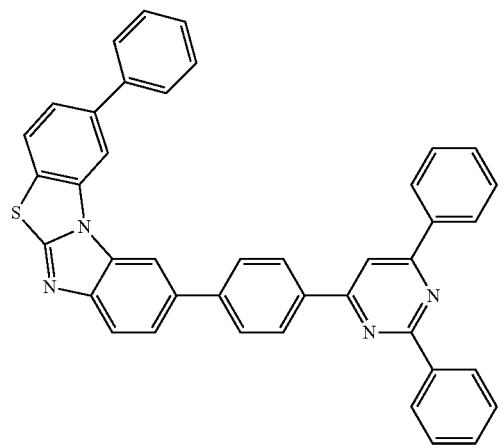
70

-continued
71
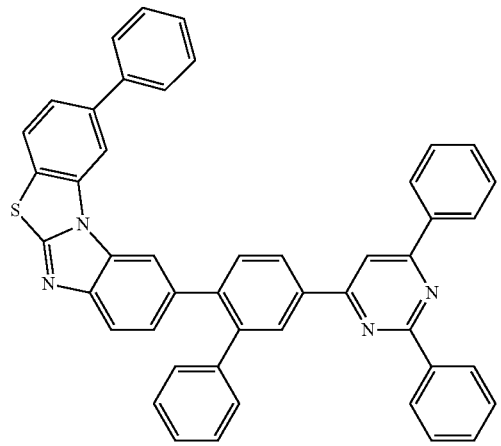
72
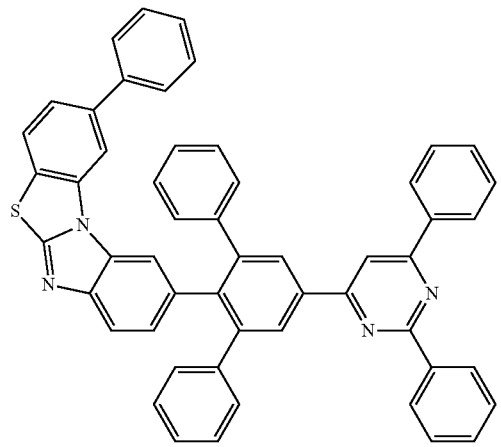
73
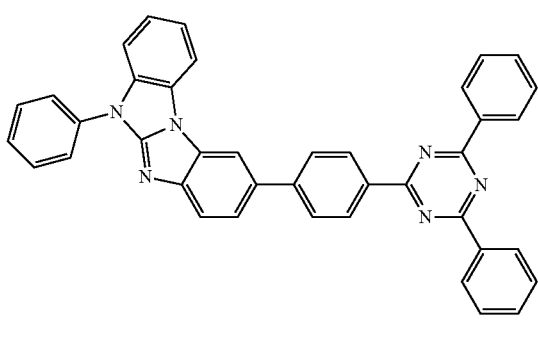
74
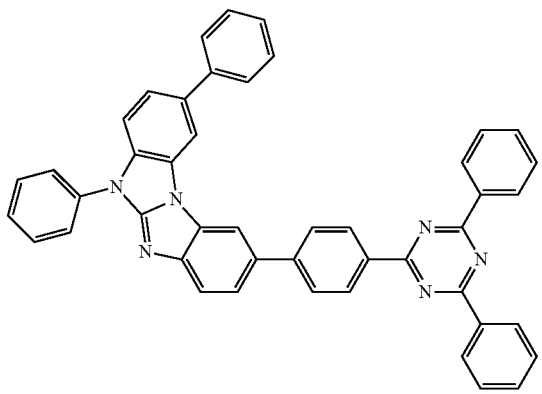
-continued
75
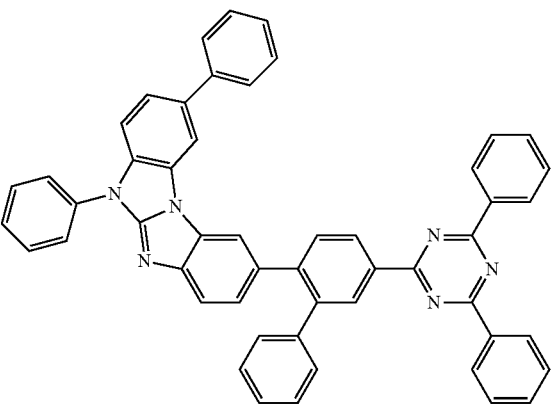
76
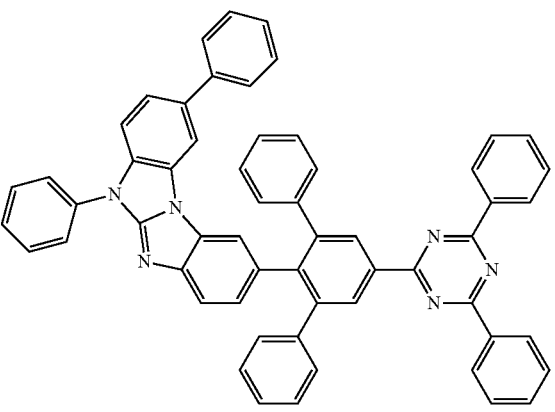
77
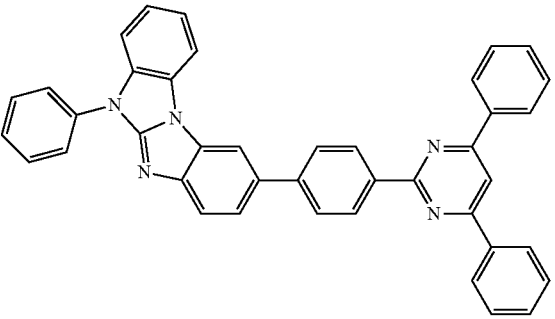
78
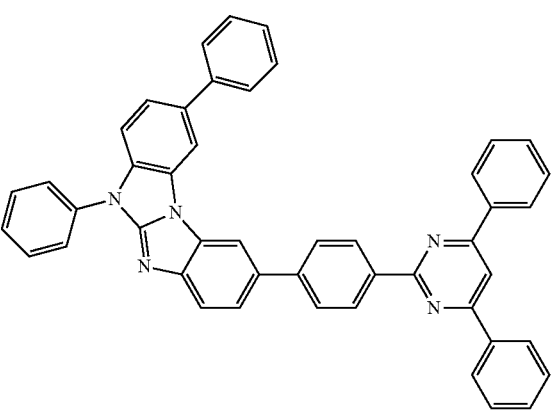

79
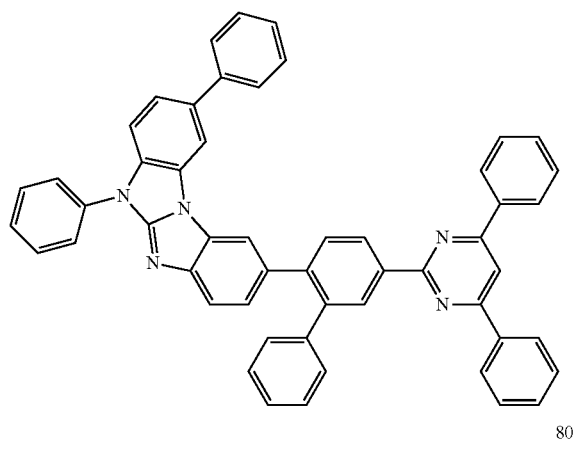
80
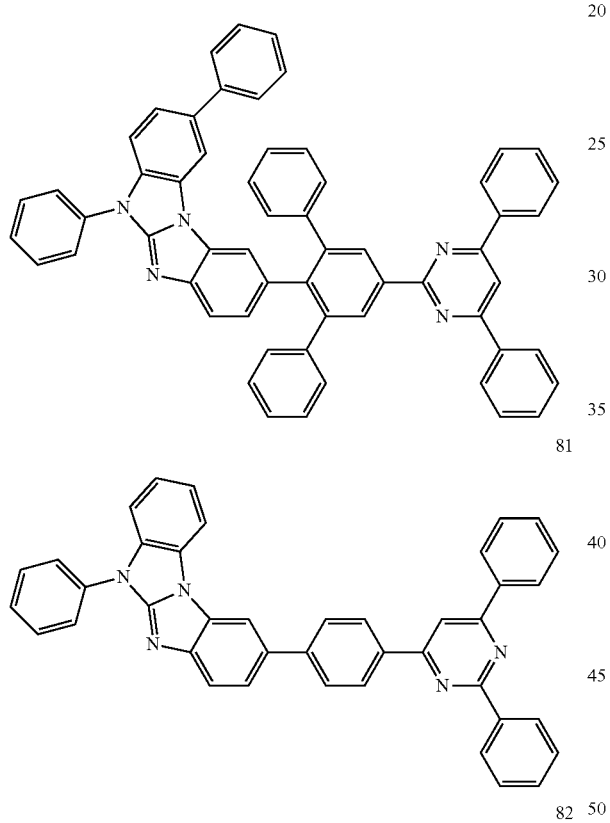
81
82
83
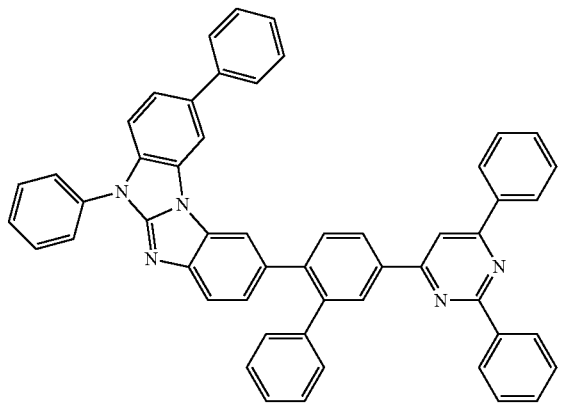
84
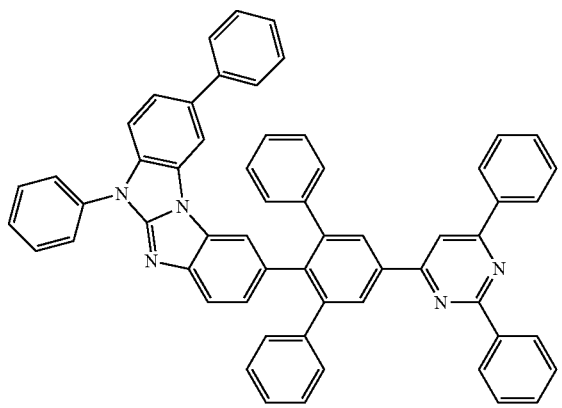
85
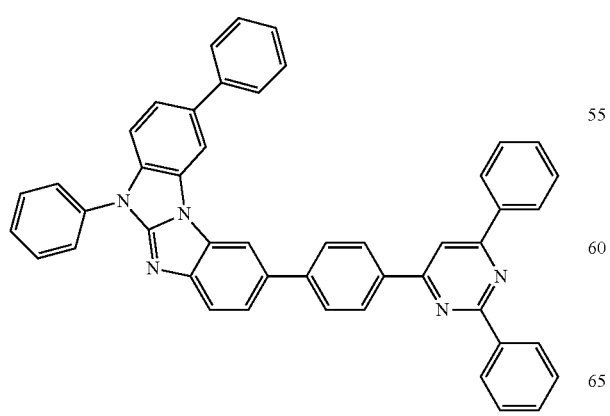
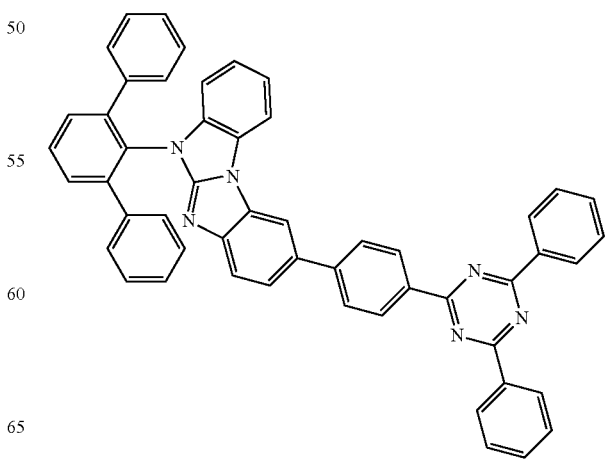

86
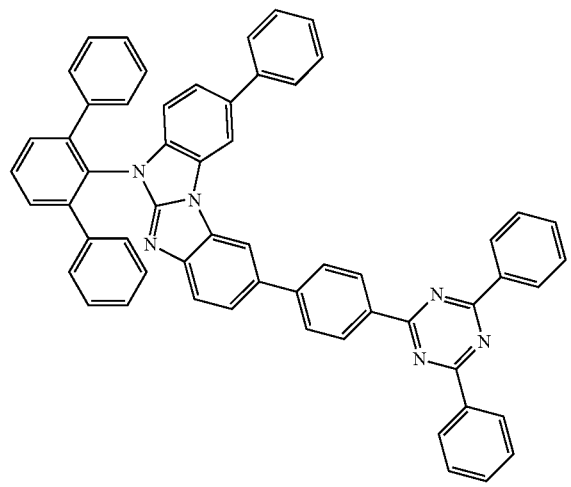
87
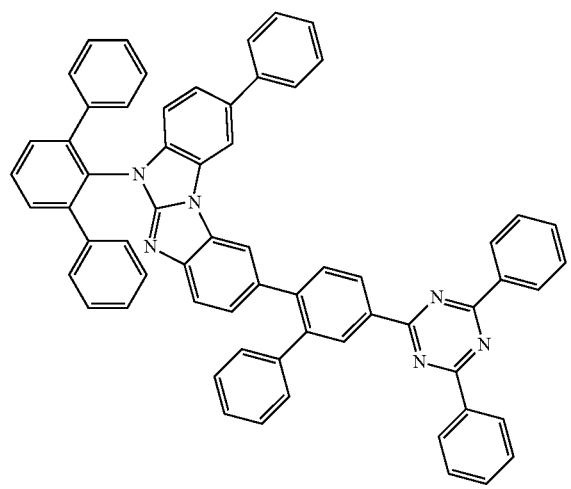
88
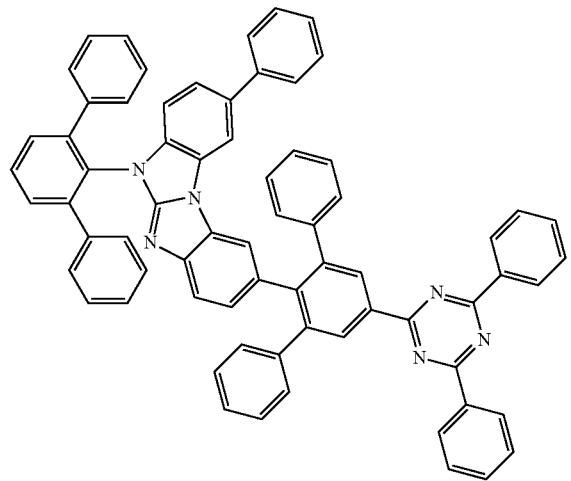
89
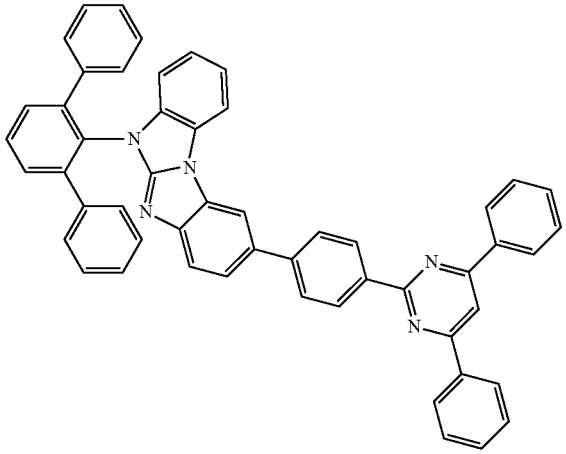
90
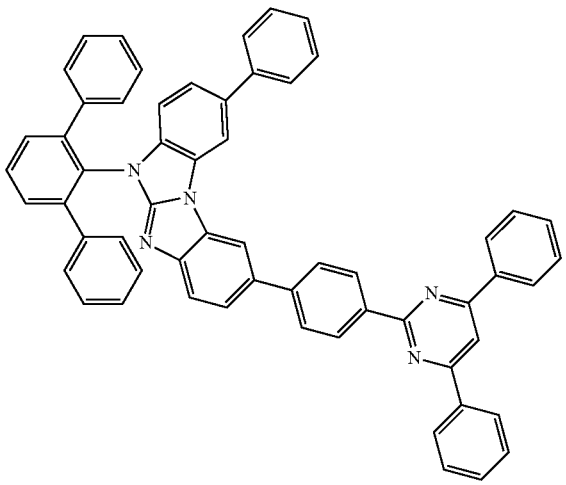
91
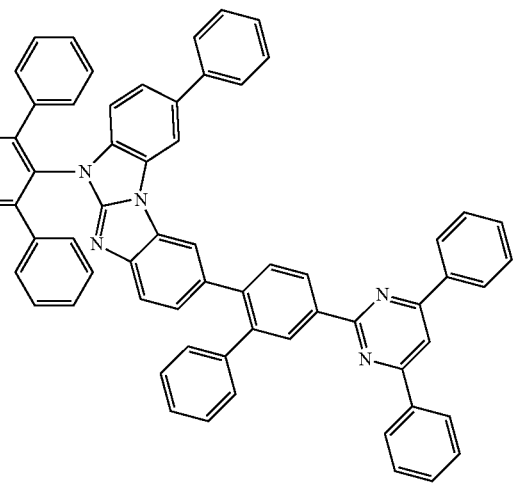

92
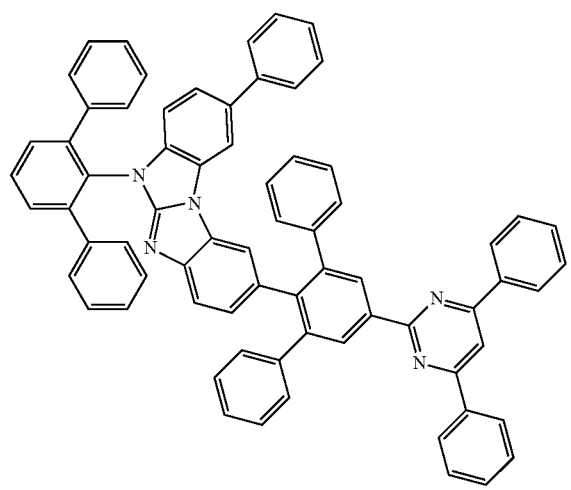
93
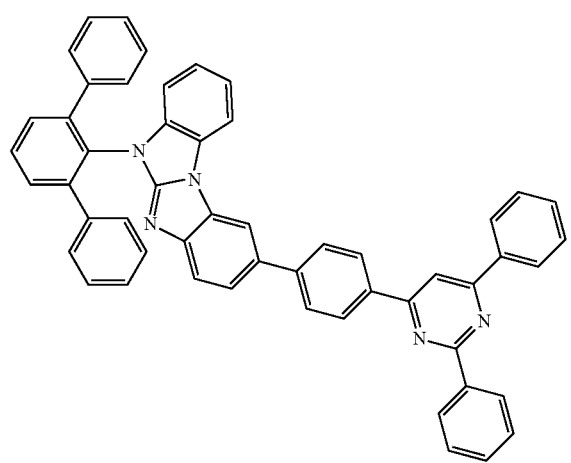
94
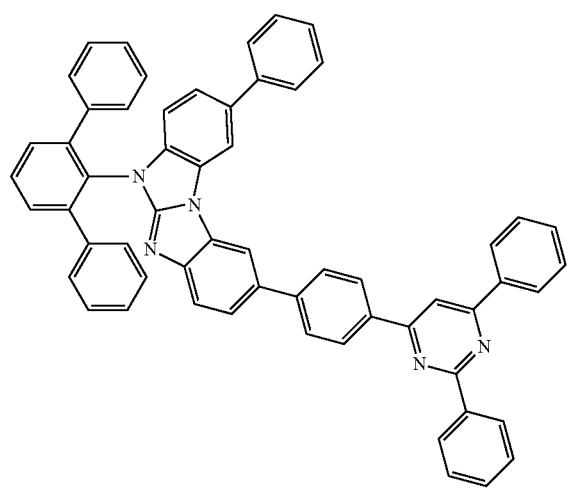
95
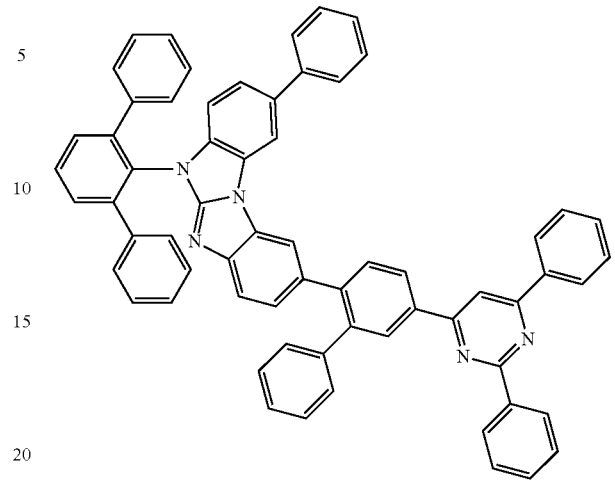
96
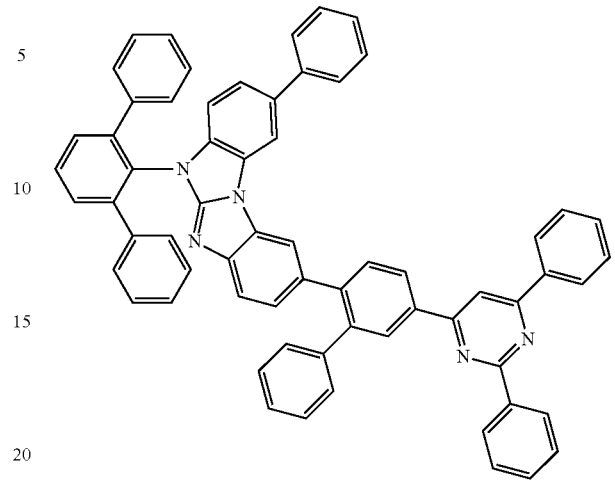
97
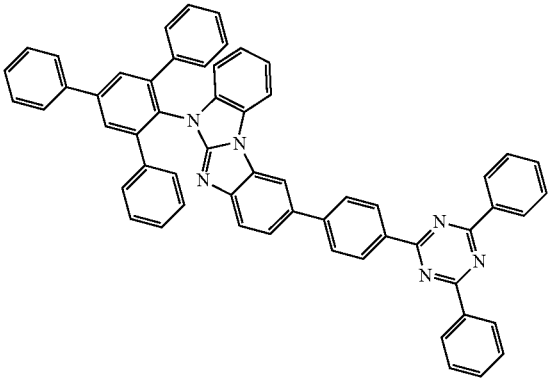

98
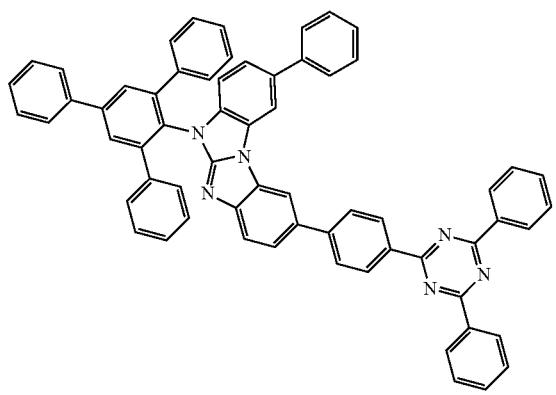
99
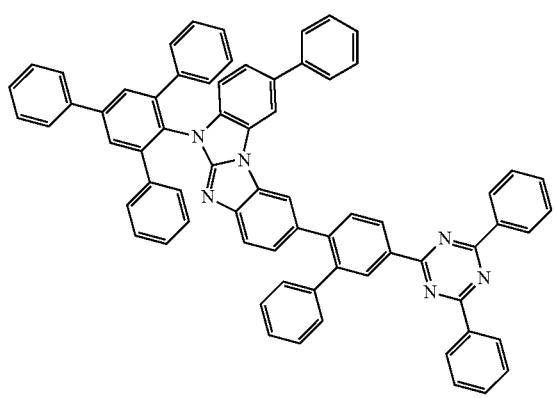
100
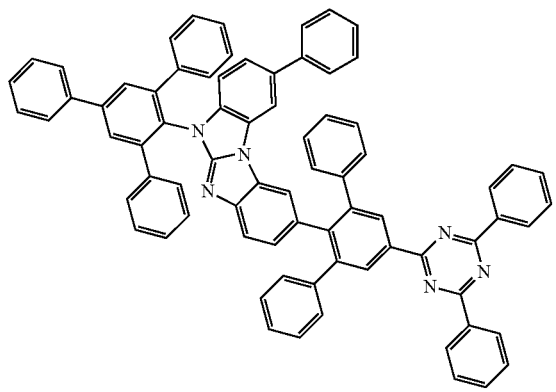
101
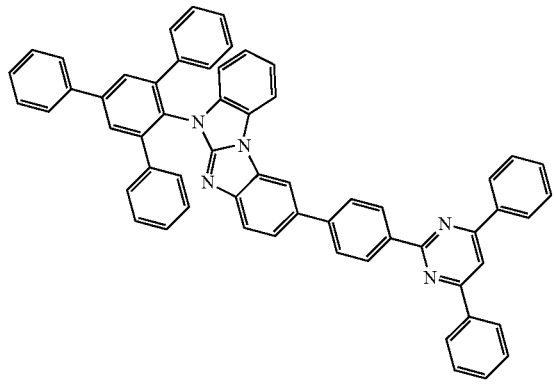
102
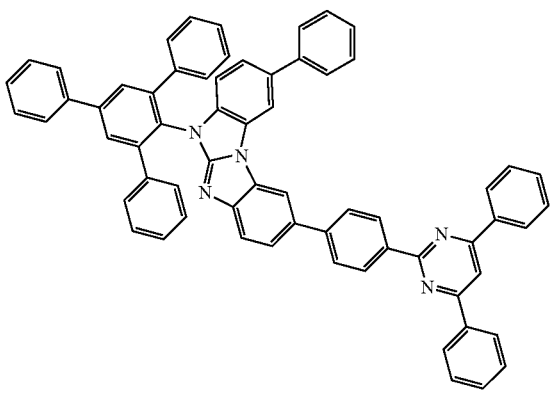
103
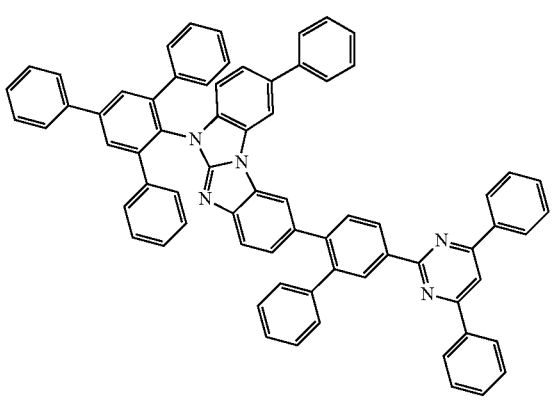
104
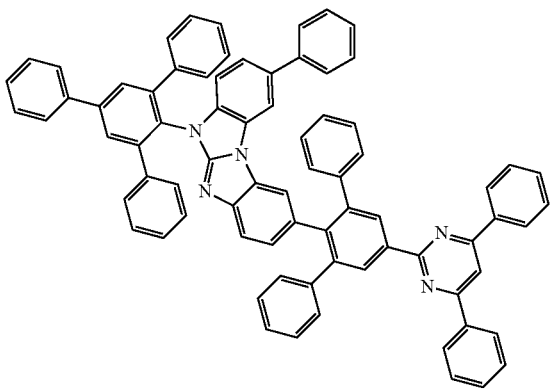
105
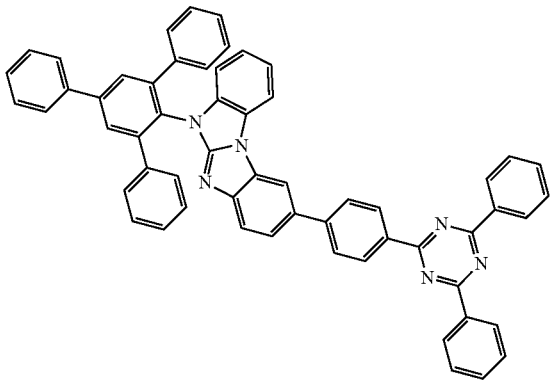

106
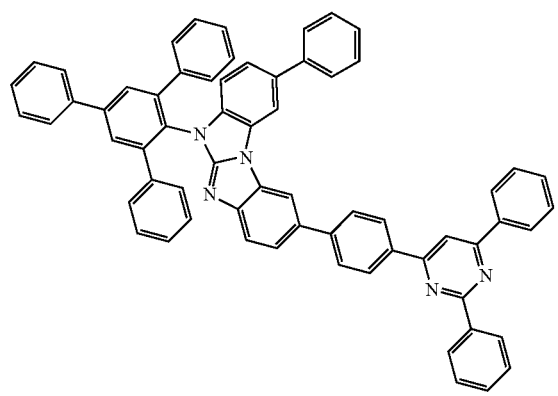
107
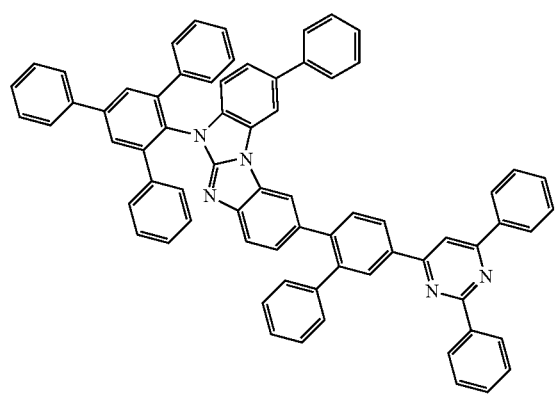
108
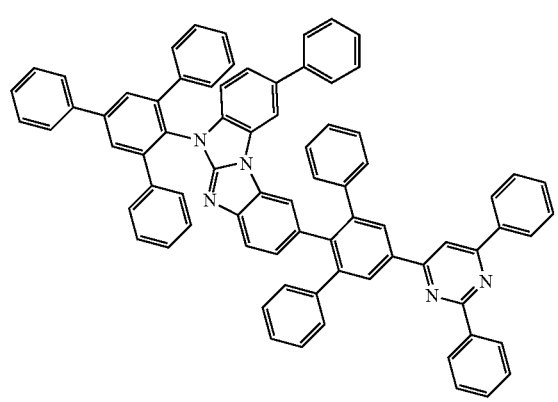
109
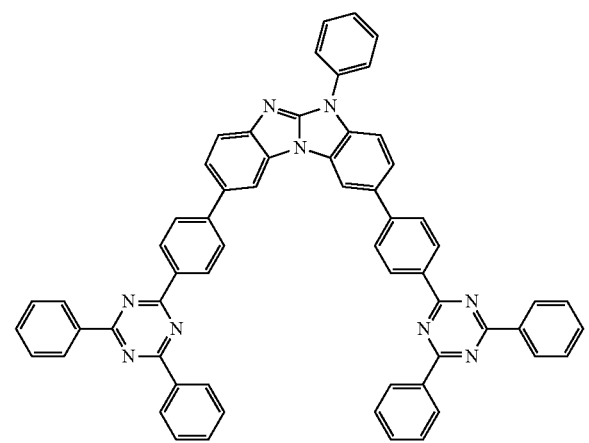
110
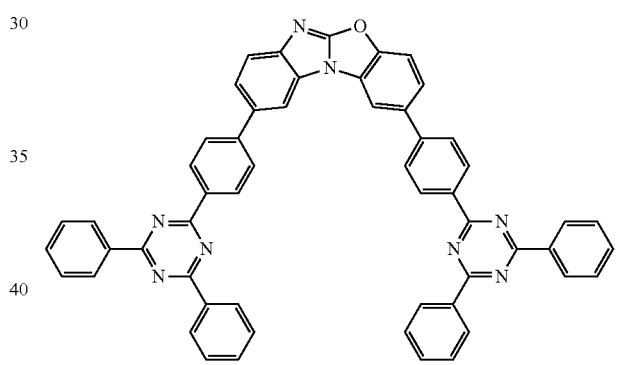
111
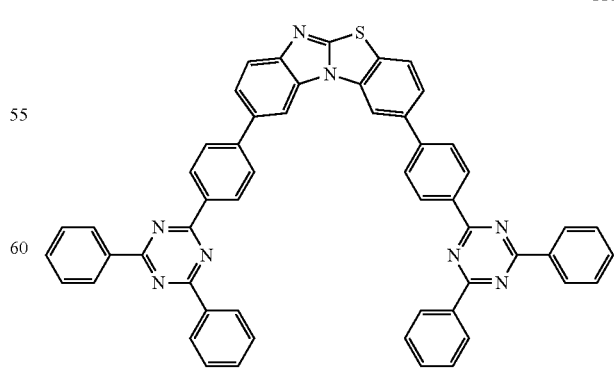

112

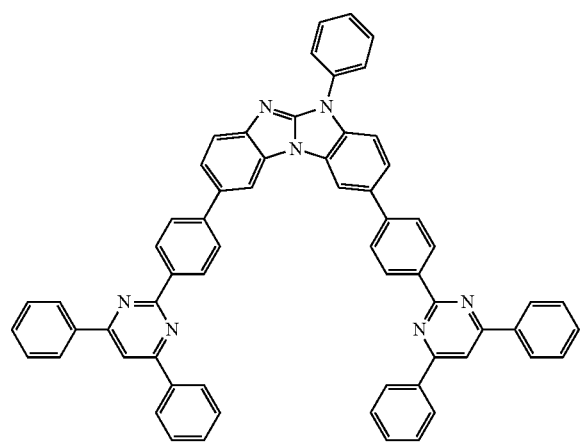

113

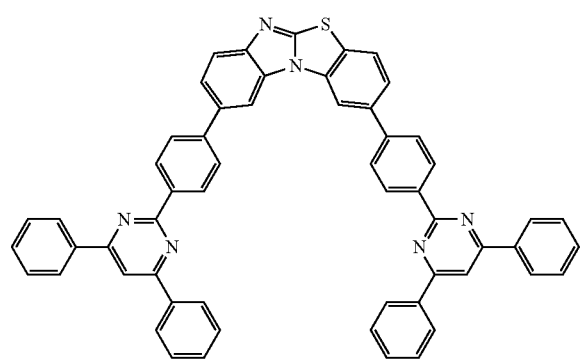

114

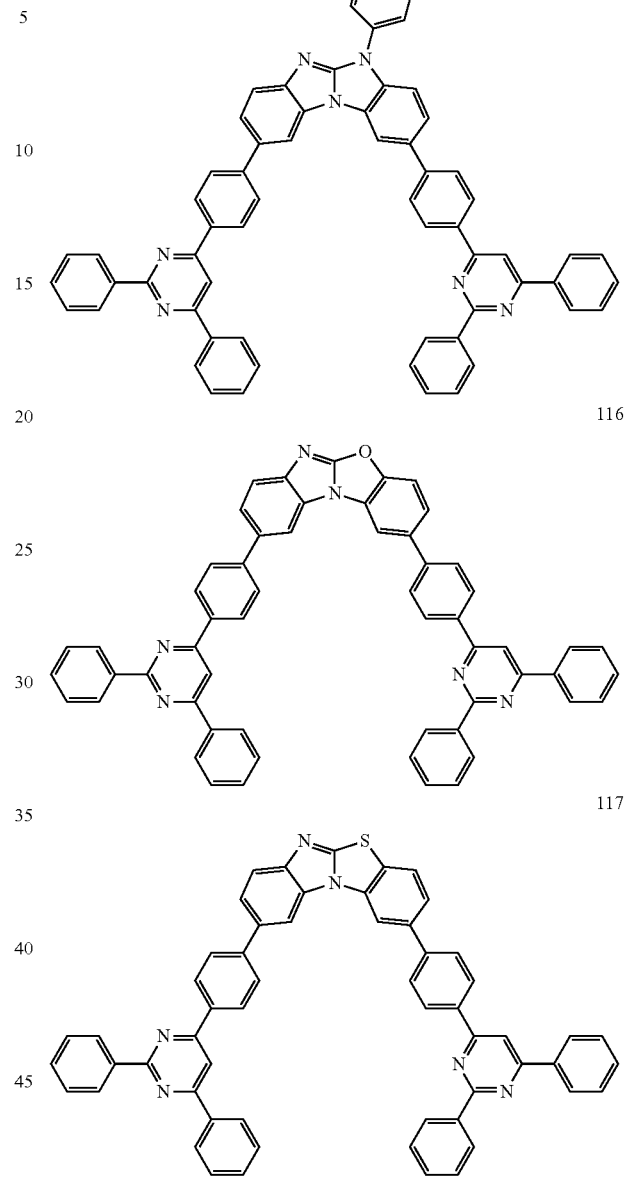

115

116

117

The condensed cyclic compound of Formula 1 may include an electron accepting group and an electron donating group. Accordingly, in the condensed cyclic compound of Formula 1, a highest occupied molecular orbital (HOMO) and a lowest unoccupied molecular orbital (LUMO) may be spatially separated from each other, resulting in an effect of reducing $\Delta E_{ST}$ (where $\Delta E_{ST}$ indicates a difference between a lowest excitation singlet energy level ($E_{S1}$) and a lowest excitation triplet energy level ($E_{T1}$)). Therefore, the condensed cyclic compound of Formula 1 may undergo reverse intersystem crossing.

In the condensed cyclic compound of Formula 1, $Y_{11}$ and $Y_{12}$, which may respectively serve as an electron transport group and/or a hole transport group, may be combined at a "para position" with respect to a phenylene group. In this regard, the condensed cyclic compound of Formula 1 may have a high oscillator strength, and thus an electronic device, for example, an organic light-emitting device, including the condensed cyclic compound of Formula 1 may have high luminescence efficiency.

The condensed cyclic compound of Formula 1 does not include a cyano group at the $R_{11}$ to $R_{14}$ positions. In this regard, the energy level may be adjusted easily, and accordingly, an organic light-emitting device having high luminescence efficiency and being capable of exhibiting red, green, and blue (RGB) may be provided.

The condensed cyclic compound Formula 1 may include a core in which two 5-membered rings share one nitrogen atom. As the number of nitrogens increase, it can become difficult to synthesize the condensed cyclic compound of Formula 1 while the electron-donating characteristics of the condensed cyclic compound of Formula 1 are improved, thereby improving the electron mobility characteristics of the condensed cyclic compound of Formula 1. Therefore, an organic light-emitting device including the condensed cyclic compound may have improved efficiency.

The condensed cyclic compound of Formula 1 may satisfy Equation 1:

$$0 \text{ eV} < \Delta E_{ST} \leq 0.5 \text{ eV} \qquad \text{Equation 1}$$

In Equation 1, $\Delta E_{ST}$ indicates a different between a lowest excitation singlet energy level ($E_{S1}$) of the condensed cyclic compound of Formula 1 and a lowest excitation triplet energy level ($E_{T1}$) of the condensed cyclic compound of Formula 1. The lowest excitation triplet energy level $E_{T1}$ and the lowest excitation singlet energy level $E_{S1}$ are evaluated by a DFT method of Gaussian program structurally optimized at a level of B3LYP, 6-31G(d,p).

In a specific embodiment, the condensed cyclic compound of Formula 1 may satisfy Equation 1-1, but embodiments of the present disclosure are not limited thereto:

$$0.01 \text{ eV} < \Delta E_{ST} \leq 0.3 \text{ eV} \qquad \text{Equation 1-1}$$

The lowest excitation singlet energy level of the condensed cyclic compound of Formula 1 may be greater than 2.5 eV and less than 3.0 eV, but embodiments of the present disclosure are not limited thereto.

For example, a highest occupied molecular orbital (HOMO) energy level, a lowest unoccupied molecular orbital (LUMO) energy level, a triplet ($T_1$) energy level, a singlet ($S_1$) energy level, and an oscillator strength of the condensed cyclic compound of Formula 1 are evaluated by the DFT method of Gaussian program structurally optimized at a level of B3LYP, 6-31G(d,p), and results thereof are shown in Table 1:

TABLE 1

| Compound No. | HOMO (eV) | LUMO (eV) | S1 (eV) | T1 (eV) | S1 – T1 (eV) | Oscillator strength (f) |
|---|---|---|---|---|---|---|
| 4 | −5.147 | −2.041 | 2.691 | 2.648 | 0.043 | 0.0420 |
| A | −5.484 | −1.837 | 3.041 | 2.831 | 0.210 | 0.0687 |
| B | −5.372 | −1.733 | 3.314 | 2.961 | 0.353 | 0.0005 |
| C | −4.942 | −2.055 | 2.475 | 2.386 | 0.089 | 0.0761 |

Table 1 shows that the condensed cyclic compound of Formula 1 has a relatively small $\Delta E_{ST}$ and a relatively high oscillator strength. Accordingly, it is confirmed that an electronic device, for example, an organic light-emitting device, including the condensed cyclic compound of Formula 1 has high luminescence efficiency.

A synthesis method for the condensed cyclic compound represented of Formula 1 would be apparent to those of ordinary skill in the art by referring to the following synthesis examples.

The condensed cyclic compound of Formula 1 may be used as, for example, a material for forming an organic light-emitting device. Therefore, another aspect of the present disclosure provides a light-emitting device including: a first electrode, a second electrode, and an organic layer between the first electrode and the second electrode, the organic layer including an emission layer and a condensed cyclic compound of Formula 1 described above.

The organic light-emitting device may have, due to the inclusion of an organic layer including the condensed cyclic compound of Formula 1, low driving voltage, high efficiency, high brightness, high quantum emission efficiency, and/or a long lifespan.

The condensed cyclic compound of Formula 1 may be used between a pair of electrodes of an organic light-emitting device. For example, the condensed cyclic compound of Formula 1 may be included in an emission layer, a hole transport region (including, for example, a hole injection layer, a hole transport layer, a buffer layer, an electron blocking layer, or any combination thereof), or any combination thereof, that is disposed between the first electrode and the emission layer, and an electron transport region (including, for example, a hole blocking layer, an electron transport layer, an electron injection layer, or any combination thereof) that is disposed between the emission layer and the second electrode.

First Embodiment

The first embodiment provides an embodiment in which the condensed cyclic compound included in the emission layer is used as a fluorescence emitter. That is, the first embodiment is an embodiment in which the condensed cyclic compound is a fluorescence emitter.

According to the first embodiment, the emission layer may consist of the condensed cyclic compound of Formula 1 only, or the emission layer may further include a host (hereinafter, referred to as 'Host A', and Host A is not identical to the condensed cyclic compound of Formula 1).

Therefore, according to the first embodiment, a proportion of emission components emitted from the condensed cyclic compound among the total emission components emitted from the emission layer may be 80% or more, for example, 90% or more. For example, a proportion of emission components emitted from the condensed cyclic compound among the total emission components emitted from the emission layer may be 95% or more. Here, the condensed cyclic compound of Formula 1 emits fluorescence and/or delayed fluorescence, and emission components emitted from the condensed cyclic compound is the sum of prompt emission components emitted from the condensed cyclic compound and delayed fluorescence components of reverse intersystem crossing in the condensed cyclic compound.

In the first embodiment, when the emission layer further includes Host A in addition to the condensed cyclic compound of Formula 1, an amount of the condensed cyclic compound may be 50 parts by weight or less, for example, 30 parts by weight or less, based on 100 parts by weight of the emission layer, and an amount of Host A included in the emission layer may be 50 parts by weight, for example, 70 parts by weight or more, based on 100 parts by weight of the emission layer, but embodiments of the present disclosure are not limited thereto.

In the first embodiment, when the emission layer further includes Host A in addition to the condensed cyclic compound of Formula 1, Host A and the condensed cyclic compound of Formula 1 may respectively satisfy Equation 2:

$$E(H_A)_{S1} > E_{S1}. \qquad \text{Equation 2}$$

In Equation 2, $E(H_A)_{S1}$ indicates a lowest excitation singlet energy level of Host A, and $E_{S1}$ indicates a lowest excitation singlet energy level of the condensed cyclic compound of Formula 1, wherein $E(H_A)_{S1}$ and $E_{S1}$ are evaluated by a DFT method of Gaussian program structurally optimized at a level of B3LYP, 6-31G(d,p).

When the condensed cyclic compound of Formula 1 satisfies Equation 1, and the condensed cyclic compound of Formula 1 and Host A respectively satisfy Equation 2, the condensed cyclic compound of Formula 1 may emit fluorescence and/or delayed fluorescence. Therefore, an organic light-emitting device including the condensed cyclic compound of Formula 1 and Host A may have improved luminescence efficiency.

For example, Host A may be a host material which will be described below, but embodiments of the present disclosure are not limited thereto.

Second Embodiment

According to the second embodiment, the emission layer may include a host and a dopant, and the host may include the condensed cyclic compound of Formula 1. That is, the host may consist of the condensed cyclic compound of Formula only, or may further include other hosts known in the art. The dopant may be, for example, a fluorescence dopant, a phosphorescence dopant, or a thermally delayed fluorescence dopant.

Therefore, a proportion of the dopant among the total emission components emitted from the emission layer may be 80% or more, for example, about 90% or more (for example, 95% or more).

In the second embodiment, an amount of the dopant in the emission layer may be 50 parts by weight or less, for example, 30 parts by weight or less, based on 100 parts by weight of the emission layer, and an amount of the host in the emission layer may be 50 parts by weight or more, for example, 70 parts by weight or more, based on 100 parts by weight of the emission layer. However, embodiments of the present disclosure are not limited thereto.

For example, in the second embodiment, when the dopant is a fluorescence dopant (hereinafter, referred to as 'Fluorescence Dopant A'), the condensed cyclic compound of Formula 1 and Fluorescence Dopant A may respectively satisfy Equation 3:

$$E_{S1} > E(F_A)_{S1}. \qquad \text{Equation 3}$$

In Equation 3, $E_{S1}$ indicates a lowest excitation singlet energy level of the condensed cyclic compound of Formula 1, and $E(F_A)_{S1}$ indicates a lowest excitation singlet energy level of Fluorescence Dopant A.

wherein $E_{S1}$ and $E(F_A)_{S1}$ are evaluated by a DFT method of Gaussian program structurally optimized at a level of B3LYP, 6-31G(d,p).

When the condensed cyclic compound of Formula 1 and Fluorescence Dopant A respectively satisfy Equation 3, the foster energy transfer from the condensed cyclic compound of Formula 1 to Fluorescence Dopant A may be promoted. Therefore, an organic light-emitting device including the condensed cyclic compound of Formula 1 and Fluorescence Dopant A may have improved luminescence efficiency.

For example, the dopant may be a dopant material which will be described below, but embodiments of the present disclosure are not limited thereto.

When the host includes other hosts known in the art, the other hosts known in the art may be host materials which will be described above, but embodiments of the present disclosure are not limited thereto.

Third Embodiment

The third embodiment provides an embodiment in which the condensed cyclic compound of Formula included in the emission layer is used as an auxiliary dopant.

According to the third embodiment, the emission layer may include a host, an auxiliary dopant, and a dopant, wherein the auxiliary dopant may include the condensed cyclic compound of Formula 1. The dopant may be, for example, a fluorescence dopant, a phosphorescence dopant, or a thermally delayed fluorescence dopant.

Therefore, according to the third embodiment, a proportion of emission components emitted from the dopant among the total emission components emitted from the emission layer may be 80% or more, for example, 90% or more (for example, 95%).

In the third embodiment, an amount of the dopant in the emission layer may be 50 parts by weight or less, for example, 30 parts by weight or less, based on 100 parts by weight of the emission layer, an amount of the host in the emission layer may be 50 parts by weight or more, for example, 70 parts by weight or more, based on 100 parts by weight of the host, an amount of the auxiliary dopant in the emission layer may be 30 parts by weight or less, for example, 20 parts by weight or less, based on 100 parts by weight based on 100 parts by weight of the emission layer. However, embodiments of the present disclosure are not limited thereto.

For example, in the third embodiment, when the dopant is a fluorescence dopant (hereinafter, referred to as 'Fluorescence Dopant B'), the host (hereinafter, referred to as 'Host B'), the condensed cyclic compound of Formula 1, and Fluorescence Dopant B may respectively satisfy Equation 4:

$$E(H_B)_{S1} > E_{S1} > E(F_B)_{S1}.$$ Equation 4

In Equation 4,
$E(H_B)_{S1}$ indicates a lowest excitation singlet energy level of Host B, and
$E_{S1}$ indicates a lowest excitation singlet energy level of the condensed cyclic compound of Formula 1, and
$E(F_B)_{S1}$ indicates a lowest excitation singlet energy level of Fluorescence Dopant B,
wherein $E(H_B)_{S1}$, $E_{S1}$, and $E(F_B)_{S1}$ are evaluated by a DFT method of Gaussian program structurally optimized at a level of B3LYP, 6-31G(d,p).

When Host B, the condensed cyclic compound of Formula 1, and Fluorescence Dopant B respectively satisfy Equation 4, the foster energy transfer from the condensed cyclic compound of Formula 1 to Fluorescence Dopant B may be promoted. Therefore, an organic light-emitting device including Host B, the condensed cyclic compound of Formula 1, and Fluorescence Dopant B may have improved luminescence efficiency.

Host B and the condensed cyclic compound of Formula 1 may respectively further satisfy Equation 5:

$$E(H_B)_{T1} - E_{T1} > 0.05 \text{ eV}.$$ Equation 5

In Equation 5,
$E(H_B)_{T1}$ indicates a lowest excitation triplet energy level of Host B,
$E_{T1}$ indicates a lowest excitation triplet energy level of the condensed cyclic compound of Formula 1,
wherein $E(H_B)_{T1}$ and $E_{T1}$ are evaluated by a DFT method of Gaussian program structurally optimized at a level of B3LYP, 6-31G(d,p).

In the third embodiment, when Equation 5 is satisfied (for example, when $E(H_B)_{T1} - E_{T1}$ is 0.10 eV or more and 0.65 eV or less), the triplet exciton energy generated by the auxiliary dopant in the emission layer is not transferred to Host B included in the emission layer so that the probability that the triplet exciton is lost in a path other than light emission is reduced. Accordingly, an organic light-emitting device may have high efficiency.

The condensed cyclic compound of Formula 1 and Fluorescence Dopant B may respectively further satisfy Equation 6:

$$E(F_B)_{S1} - E_{S1} < 0 \text{ eV}.$$ Equation 6

In Equation 6,
$E(F_B)_{S1}$ indicates a lowest excitation singlet energy level of Fluorescence Dopant B, and
$E_{S1}$ indicates a lowest excitation singlet energy level of the condensed cyclic compound of Formula 1,
wherein $E(F_B)_{S1}$ and $E_{S1}$ are evaluated by a DFT method of Gaussian program structurally optimized at a level of B3LYP, 6-31G(d,p).

In the third embodiment, when Equation 6 is satisfied (for example, when $E_{S1(FD)} - E_{S1(AD)}$ is −0.4 eV or more and −0.05 eV or less), the singlet exciton energy generated by the auxiliary dopant in the emission layer is rapidly transferred to Fluorescence Dopant B. In this regard, substantially only Fluorescence Dopant B in the emission layer of the organic light-emitting device emits light, thereby realizing a fluorescence emission spectrum with excellent color purity based on Fluorescence Dopant B. In addition, fluorescence emission having a relatively short exciton lifespan may be achieved, and accordingly, efficiency transfer phenomenon at high luminance (i.e. roll-off phenomenon) which may be caused by an interaction between a plurality of excitons (an exciton-exciton interaction) or an interaction between excitons and charges (e.g., holes or electrons) an exciton-proton interaction may be suppressed, thereby realizing an organic light-emitting device having high efficiency. Furthermore, the auxiliary dopant has a short exciton lifespan so that the probability of chemical or physical degradation that may occur in the exciton state of the auxiliary dopant may be reduced. In this regard, the organic light-emitting device satisfying Equation 6 may have improved durability.

In the third embodiment, the host may be a host material which will be described below, but embodiments of the present disclosure are not limited thereto.

In the third embodiment, the dopant may be a dopant material which will be described below, but embodiments of the present disclosure are not limited thereto.

For example, the host may have a triplet energy level of 2.9 eV or more, for example, greater than 2.9 eV and less than or equal to 4.5 eV. In this regard, the energy transfer from the host to a fluorescence dopant, a phosphorescence dopant, and/or a delayed fluorescence dopant may be efficiently achieved. Accordingly, the organic light-emitting device may have high efficiency.

For example, the host may include a fluorene-containing compound, a carbazole-containing compound, a dibenzofuran-containing compound, a dibenzothiophene-containing compound, an indenocarbazole-containing compound, an indolocarbazole-containing compound, a benzofurocarbazole-containing compound, a benzothienocarbazole-containing compound, an acridine-containing compound, a dihydroacridine-containing compound, a triindolobenzene-containing compound, a pyridine-containing compound, a pyrimidine-containing compound, a triazine-containing compound, a silicon-containing compound, a cyano group-containing compound, a phosphine oxide-containing compound, a sulfoxide-containing compound, or any combination thereof, but embodiments of the present disclosure are not limited thereto.

In one embodiment, the host may include a compound including a carbazole ring and a cyano group.

For example, the host may be a compound represented by Formulae 11-1 to 11-3, but embodiments of the present disclosure are not limited thereto:

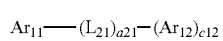

Formula 11-1

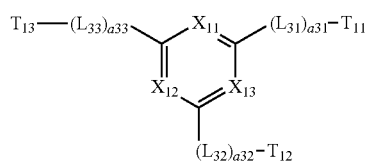

Formula 11-2

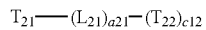

Formula 11-3

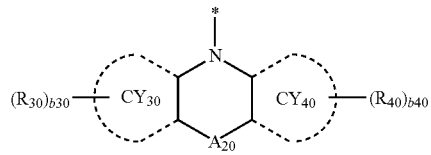

Formula 13

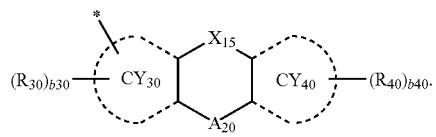

Formula 14

In Formulae 11-1 to 11-3, 13, and 14, $Ar_{11}$ and $Ar_{12}$ may each independently be groups represented by Formulae 13 or 14, $X_{15}$ may be $N(R_{200})$, O, or S, $X_{11}$ may be N or $C(T_{14})$, $X_{12}$ may be N or $C(T_{15})$, and $X_{13}$ may be N or $C(T_{16})$, wherein $X_{11}$ to $X_{13}$ may be N, $T_{21}$ and $T_{22}$ may each independently be *-$(L_{21})_{a21}$-Si$(Q_{41})(Q_{42})(Q_{43})$ or *-$(L_{21})_{a21}$-P(=O)$(Q_{51})(Q_{52})$, $L_{21}$ and $L_{31}$ to $L_{33}$ may each independently be:

a single bond, O, S, Si$(Q_{61})(Q_{62})$, a phenylene group, a pyridinylene group, a pyrimidinylene group, a pyrazinylene group, a pyridazinylene group, a triazinylene group, a naphthylene group, a fluorenylene group, a carbazolylene group, a dibenzofuranylene group, or a dibenzothiophenylene group; or a phenylene group, a pyridinylene group, a pyrimidinylene group, a pyrazinylene group, a pyridazinylene group, a triazinylene group, a naphthylene group, a fluorenylene group, a carbazolylene group, a dibenzofuranylene group, or a dibenzothiophenylene group, each substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, —$CF_3$, —$CF_2H$, —$CFH_2$, a phenyl group, a phenyl group substituted with a cyano group, a biphenyl group, a terphenyl group, a naphthyl group, a pyridinyl group, a pyrimidinyl group, a pyrazinyl group, a pyridazinyl group, a triazinyl group, a fluorenyl group, a carbazolyl group, a dibenzofuranyl group, a dibenzothiophenyl group, —Si$(Q_{71})(Q_{72})(Q_{73})$, or any combination thereof, a21 and a31 to a33 may each independently be an integer from 0 to 5, wherein, when a11 is two or more, two or more $L_{11}$(s) may be identical to or different from each other, when a21 is two or more, two or more $L_{21}$(s) may be identical to or different from each other, when a31 is two or more, two or more $L_{31}$(s) may be identical to or different from each other, when a32 is two or more, two or more $L_{32}$(s) may be identical to or different from each other, and when a33 is two or more, two or more $L_{33}$(s) may be identical to or different from each other, ring $CY_{30}$ and ring $CY_{40}$ may each independently be a benzene group, a naphthalene group, a fluorene group, a carbazole group, a benzocarbazole group, an indolocarbazole group, a dibenzofuran group, or a dibenzothiophene group, $A_{20}$ may be:

a single bond, a $C_1$-$C_4$ alkylene group, or a $C_2$-$C_4$ alkenylene group; or a $C_1$-$C_4$ alkylene group or a $C_2$-$C_4$ alkenylene group, each substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, a pyrazinyl group, a pyridazinyl group, a triazinyl group, a fluorenyl group, a carbazolyl group, a dibenzofuranyl group, a dibenzothiophenyl group, —Si$(Q_{81})(Q_{82})(Q_{83})$, or any combination thereof, $T_{11}$ to $T_{16}$, $R_{30}$, $R_{40}$, and $R_{200}$ may each independently be hydrogen, deuterium, —F, —Cl, —Br, —I, a hydroxyl group, a cyano group (CN), a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, or —Si($Q_{91}$)($Q_{92}$)($Q_{93}$), b30 and b40 may each independently be an integer from 0 to 10, c12 may be 0, 1, 2, or 3,

* indicates a binding site to a neighboring atom, a substituent of the substituted $C_1$-$C_{60}$ alkyl group, the substituted $C_2$-$C_{60}$ alkenyl group, the substituted $C_2$-$C_{60}$ alkynyl group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, or the substituted monovalent non-aromatic condensed heteropolycyclic group may be deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{101}$)($Q_{102}$)($Q_{103}$), or any combination thereof, and $Q_{41}$ to $Q_{43}$, $Q_{51}$ to $Q_{52}$, $Q_{61}$ to $Q_{62}$, $Q_{71}$ to $Q_{73}$, $Q_{81}$ to $Q_{83}$, $Q_{91}$ to $Q_{93}$, and $Q_{101}$ to $Q_{103}$ may each independently be hydrogen, deuterium, a $C_1$-$C_{60}$ alkyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, or a monovalent non-aromatic condensed heteropolycyclic group.

For example, the host may include Compounds H-1 to H-27, but embodiments of the present disclosure are not limited thereto:

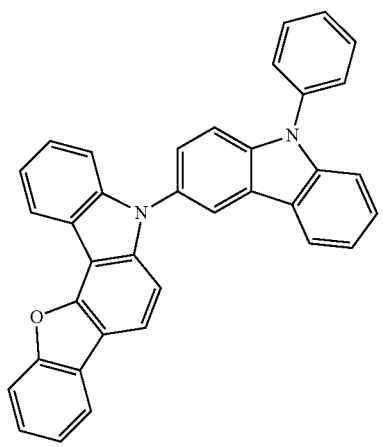

H-1

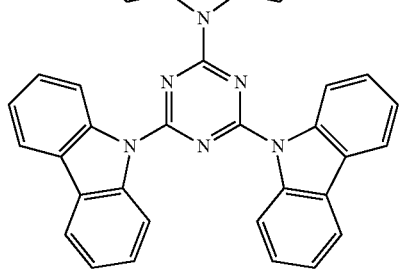

H-2

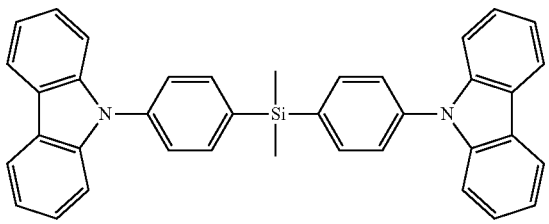

H-3

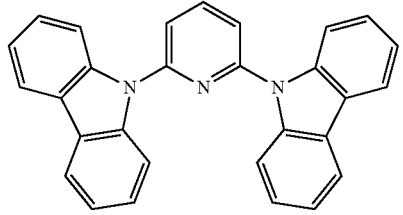

H-4

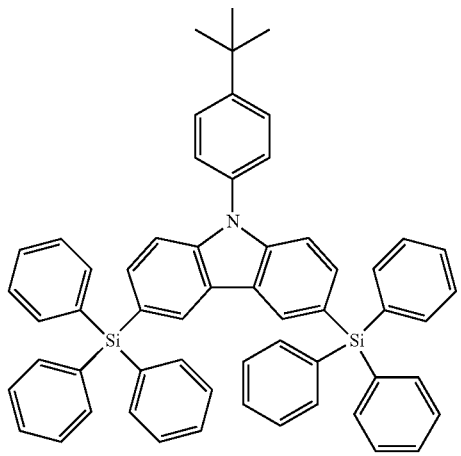

H-5

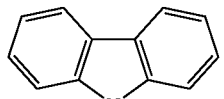

H-6

H-7
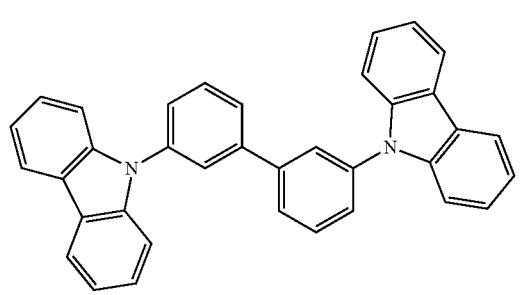
H-8
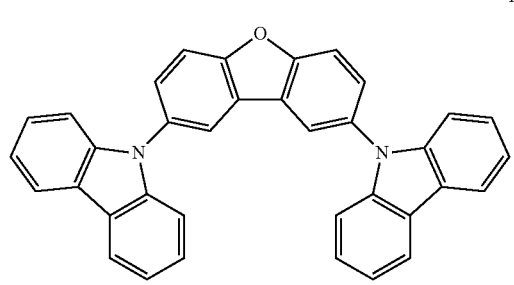
H-9
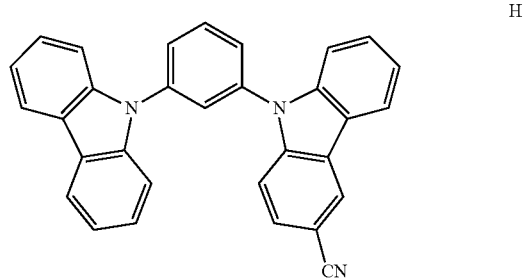
H-10
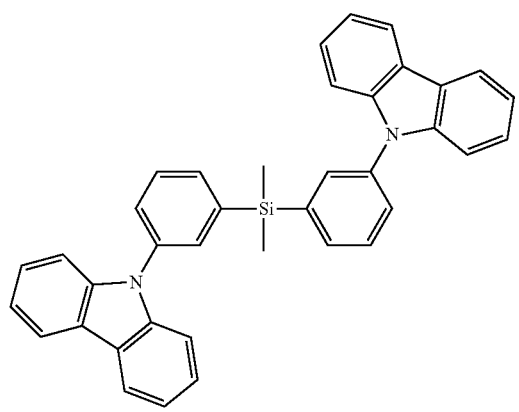
H-11
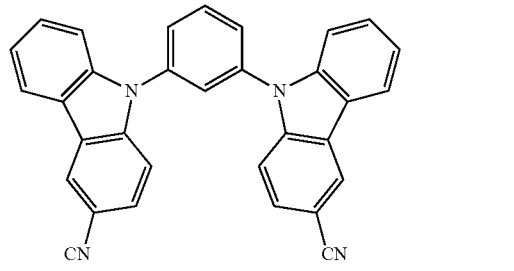
H-12
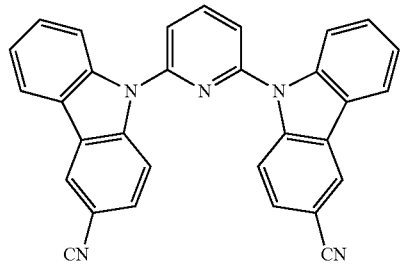
H-13
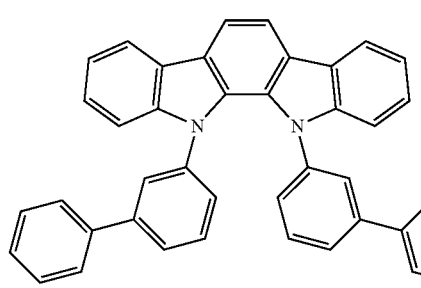
H-14
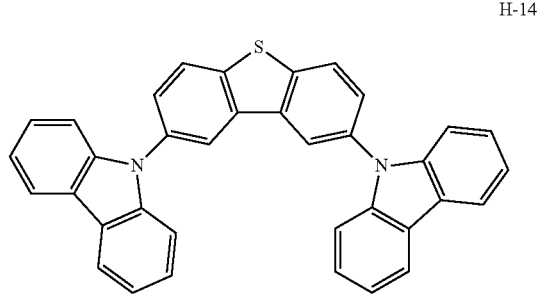
H-15
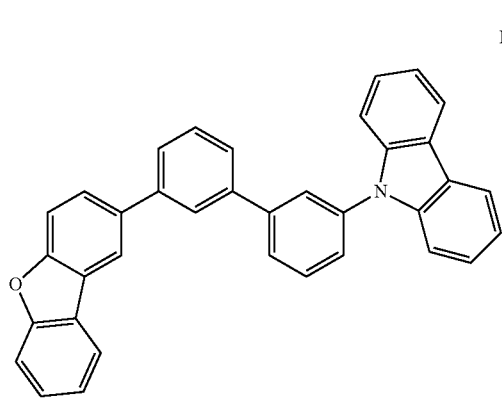
H-16
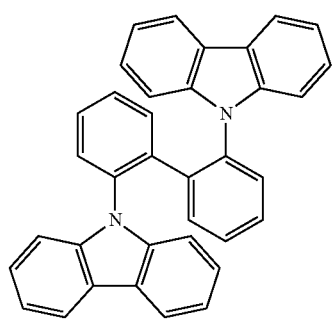

-continued
H-17
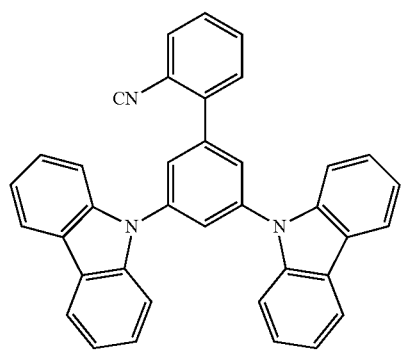
H-18
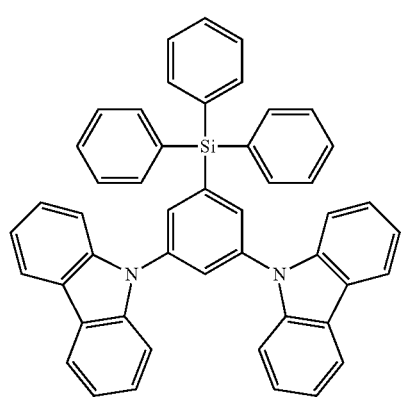
H-19
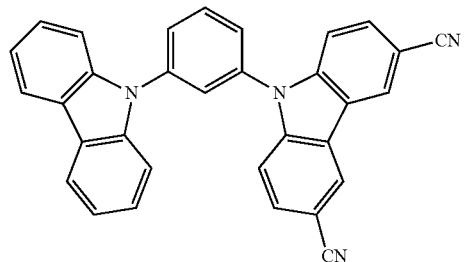
H-20
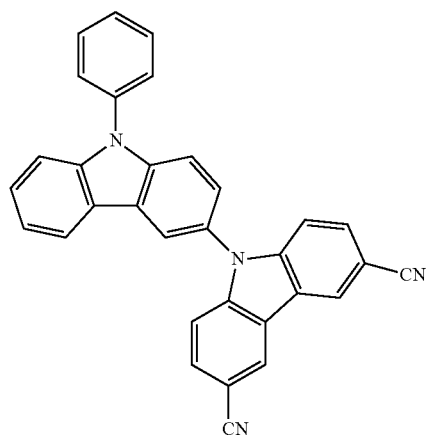
H-21
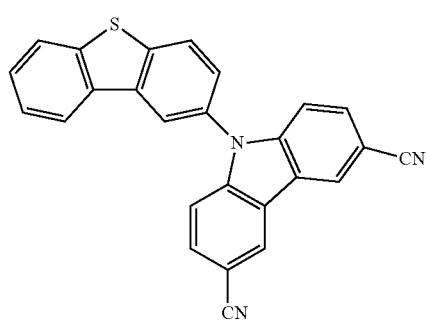
H-22
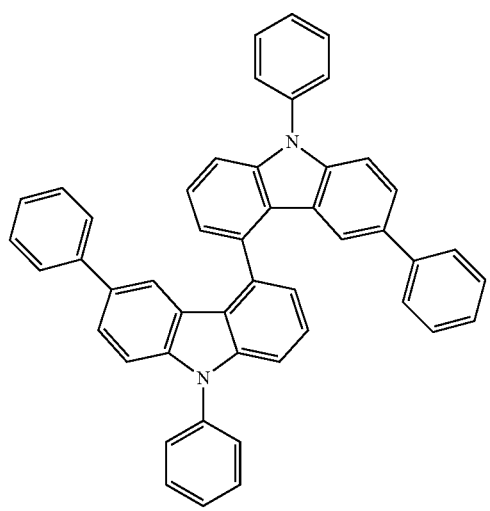
H-23
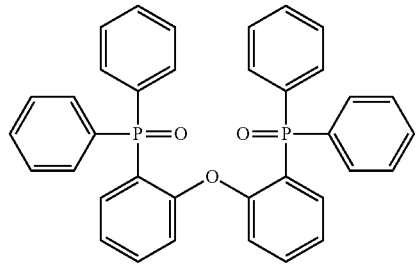
H-24
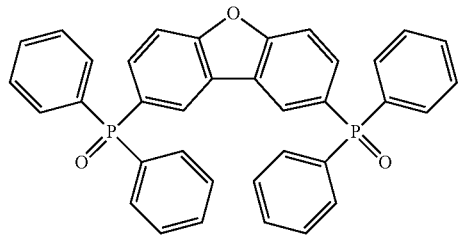
H-25
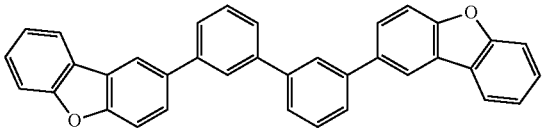

H-26

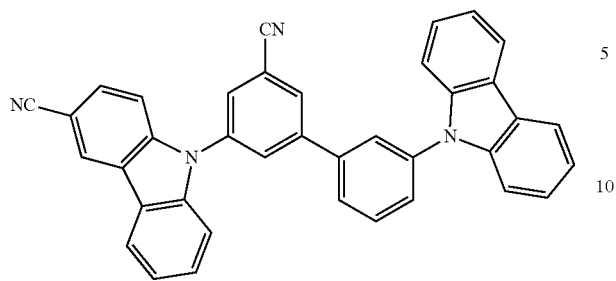

H-27

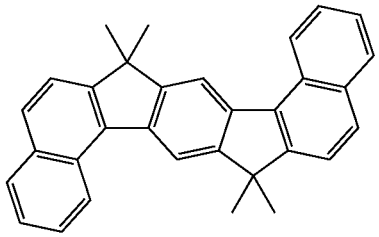

The fluorescence dopant may be a condensed polycyclic compound or a styryl-based compound.

For example, the fluorescence dopant may include a naphthalene-containing core, a fluorene-containing core, a spiro-bifluorene-containing core, a benzofluorene-containing core, a dibenzofluorene-containing core, a phenanthrene-containing core, an anthracene-containing core, a fluoranthene-containing core, a triphenylene-containing core, a pyrene-containing core, a chrysene-containing core, a naphthacene-containing core, a picene-containing core, a perylene-containing core, a pentaphene-containing core, an indenoanthracene-containing core, a tetracene-containing core, a bisanthracene-containing core, or cores represented by Formulae 501-1 to 501-18, but embodiments of the present disclosure are not limited thereto:

501-1

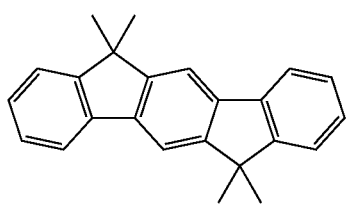

501-2

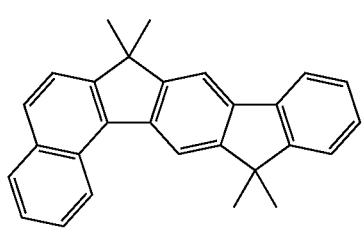

501-3

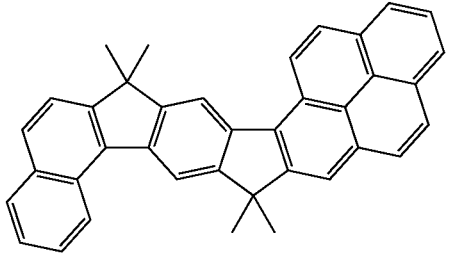

501-4

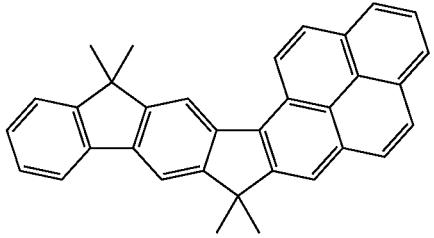

501-5

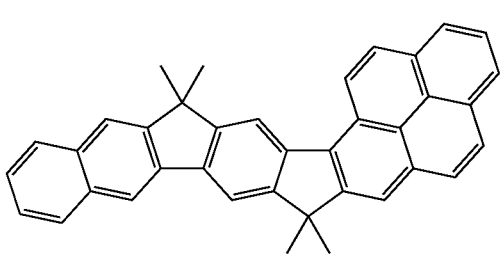

501-6

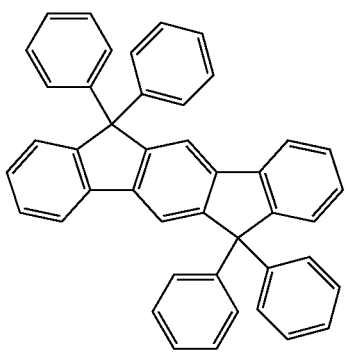

501-7

-continued
501-8
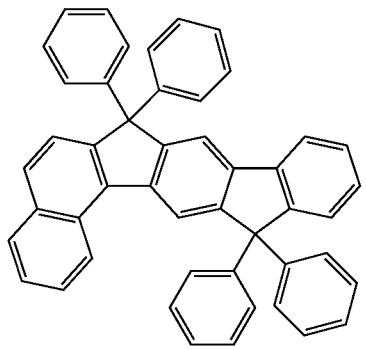
501-9
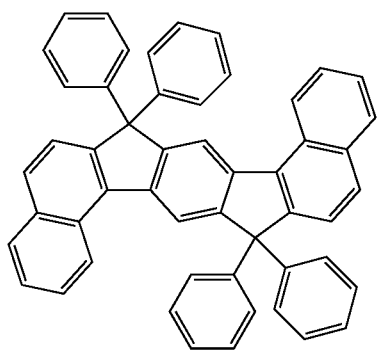
501-10
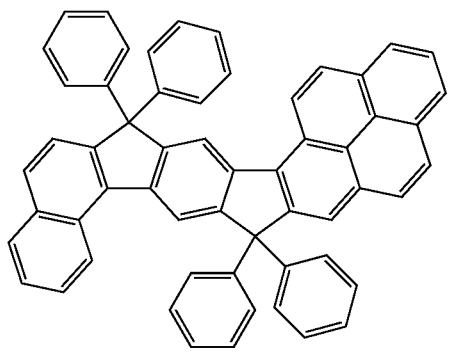
501-11
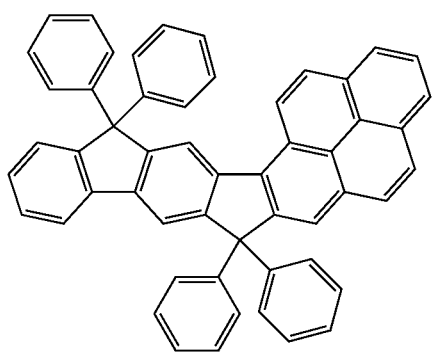
-continued
501-12
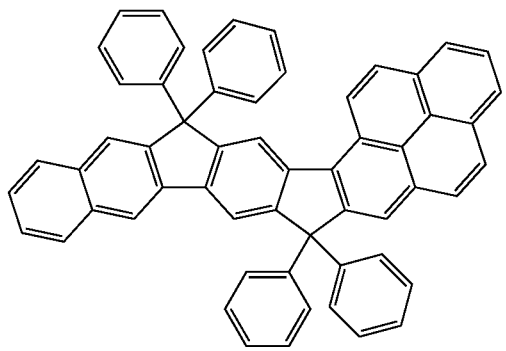
501-13
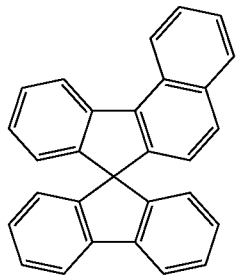
501-14
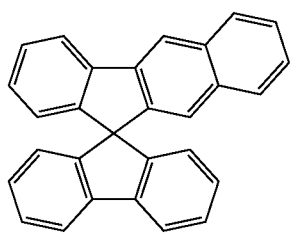
501-15
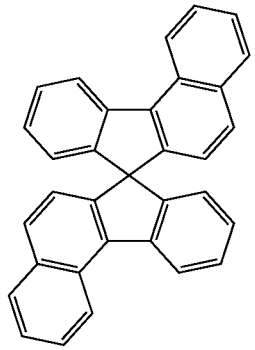
501-16
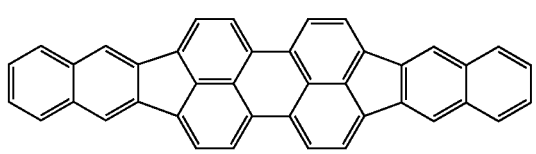
501-17
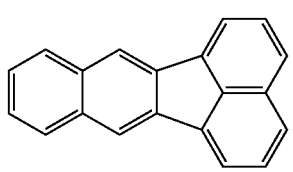

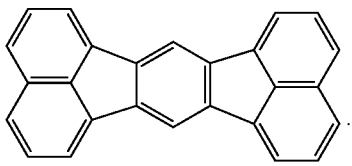

501-18

In one embodiment, the fluorescence dopant may be a styryl-amine-based compound or a styryl-carbazole-based compound, but embodiments of the present disclosure are not limited thereto.

In one embodiment, the fluorescence dopant may be a group represented by Formula 501:

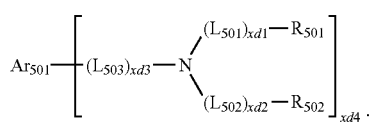

Formula 501

In Formula 501, $Ar_{501}$ may be:

a naphthalene group, a fluorene group, a spiro-bifluorene group, a benzofluorene group, a dibenzofluorene group, a phenanthrene group, an anthracene group, a fluoranthene group, a triphenylene group, a pyrene group, a chrysene group, a naphthacene group, a picene group, a perylene group, a pentaphene group, an indenoanthracene group, a tetracene group, a bisanthracene group, or groups represented by Formulae 501-1 to 501-18; or a naphthalene group, a fluorene group, a spiro-bifluorene group, a benzofluorene group, a dibenzofluorene group, a phenanthrene group, an anthracene group, a fluoranthene group, a triphenylene group, a pyrene group, a chrysene group, a naphthacene group, a picene group, a perylene group, a pentaphene group, an indenoanthracene group, a tetracene, a bisanthracene group, or groups represented by Formulae 501-1 to 501-18, each substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{501}$)($Q_{502}$)($Q_{503}$) (wherein $Q_{501}$ to $Q_{503}$ may each independently be hydrogen, a $C_1$-$C_{60}$ alkyl group, a $C_1$-$C_{60}$ alkoxy group, a $C_6$-$C_{60}$ aryl group, a $C_1$-$C_{60}$ heteroaryl group, a monovalent non-aromatic condensed polycyclic group, a monovalent non-aromatic condensed heteropolycyclic group), or any combination thereof, $L_{501}$ to $L_{503}$ may each independently be a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, or a substituted or unsubstituted divalent non-aromatic condensed heteropolycyclic group, $R_{501}$ and $R_{502}$ may each independently be:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, a triazinyl group, a dibenzofuranyl group, or a dibenzothiophenyl group; or a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, or a dibenzothiophenyl group, each substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, a dibenzothiophenyl group, or a combination thereof, xd1 to xd3 may each independently be 0, 1, 2, or 3, and xd4 may be 0, 1, 2, 3, 4, 5, or 6.

For example, in Formula 50, $Ar_{501}$ may be:

a naphthalene group, a fluorene group, a spiro-bifluorene group, a benzofluorene group, a dibenzofluorene group, a phenanthrene group, an anthracene group, a fluoranthene group, a triphenylene group, a pyrene group, a chrysene group, a naphthacene group, a picene group, a perylene group, a pentaphene group, an indenoanthracene group, a tetracene group, a bisanthracene group, or groups represented by Formulae 501-1 to 501-18; or a naphthalene group, a fluorene group, a spiro-bifluorene group, a benzofluorene group, a dibenzofluorene group, a phenanthrene group, an anthracene group, a fluoranthene group, a triphenylene group, a pyrene group, a chrysene group, a naphthacene group, a picene group, a perylene group, a pentaphene group, an indenoanthracene group, a tetracene group, a bisanthracene group, or groups represented by Formulae 501-1 to 501-18, each substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a dibenzofuranyl group, a dibenzothiophenyl group, a carbazolyl group, a pyridinyl group, a pyrimidinyl group, a triazinyl group, a quinolinyl group, an isoquinolinyl group, —Si($Q_{501}$)($Q_{502}$)($Q_{503}$) (wherein $Q_{500}$ to $Q_{503}$ may each independently be hydrogen, a $C_1$-$C_{20}$ alkyl group, a $C_1$-$C_{20}$ alkoxy group, a phenyl group, a biphenyl group, a terphenyl group, or a naphthyl group), or any combination thereof, $L_{501}$ to $L_{503}$ may each independently be the same as defined in connection with $L_{21}$, xd1 to xd3 may each independently be 0, 1, or 2, and xd4 may be 0, 1, 2, or 3, but embodiments of the present disclosure are not limited thereto.

In one or more embodiments, the fluorescence dopant may include a compound represented by Formulae 502-1 to 502-5:

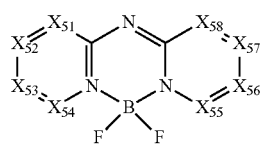

Formula 502-1

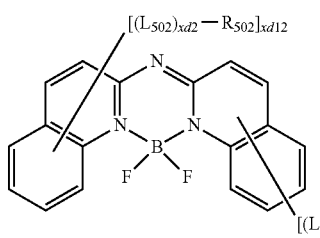

Formula 502-2

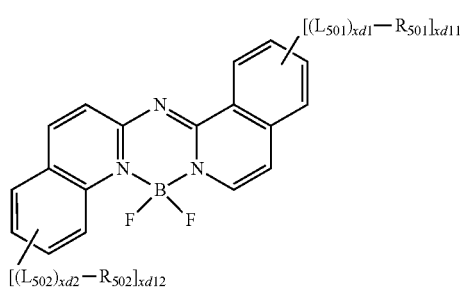

Formula 502-3

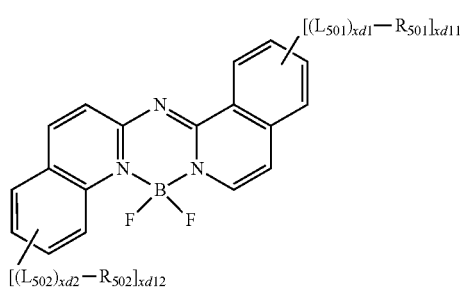

Formula 502-4

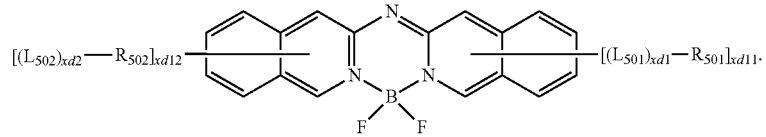

Formula 502-5

In Formulae 502-1 to 502-5, $X_{51}$ may be N or C-[($L_{501}$)$_{xd1}$-$R_{501}$], $X_{52}$ may be N or C-[($L_{502}$)$_{xd2}$-$R_{502}$], $X_{53}$ may be N or C-[($L_{503}$)$_{xd3}$-$R_{503}$], $X_{54}$ may be N or C-[($L_{504}$)$_{xd4}$-$R_{504}$], $X_{55}$ may be N or C-[($L_{505}$)$_{xd5}$-$R_{505}$], $X_{56}$ may be N or C-[($L_{506}$)$_{xd6}$-$R_{506}$], $X_{57}$ may be N or C-[($L_{507}$)$_{xd7}$-$R_{507}$], and $X_{58}$ may be N or C-[($L_{508}$)$_{xd8}$-$R_{508}$], $L_{501}$ to $L_{508}$ may each independently be the same as defined in connection with $L_{501}$ in Formula 501, xd1 to xd8 may each independently be the same as defined in connection with xd1 in Formula 501, $R_{501}$ to $R_{508}$ may each independently be:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, or a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, a triazinyl group, a dibenzofuranyl group, or a dibenzothiophenyl group; or a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, or a dibenzothiophenyl group, each substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, a dibenzothiophenyl group, or any combination thereof, xd11 and xd12 may each independently be an integer from 0 to 5, two of $R_{501}$ to $R_{504}$ may optionally be linked to form a saturated or unsaturated ring, and two of $R_{505}$ to $R_{508}$ may optionally be linked to form a saturated or unsaturated ring.

The fluorescence dopant may include, for example, Compounds FD(1) to FD(16) or FD1 to FD13:

FD(1)
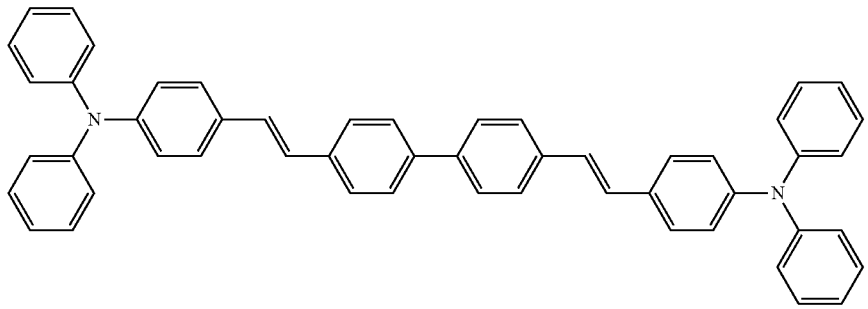
FD(2)
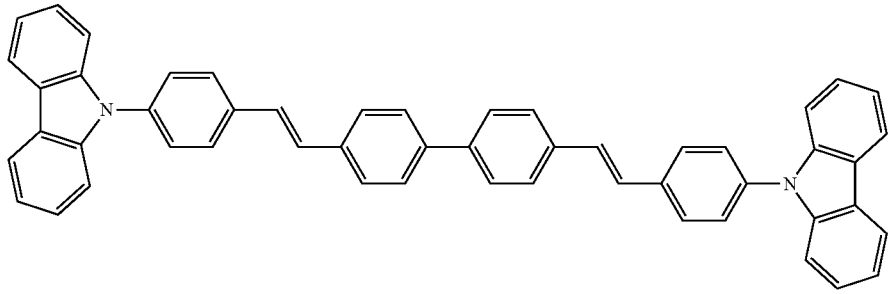
FD(3)
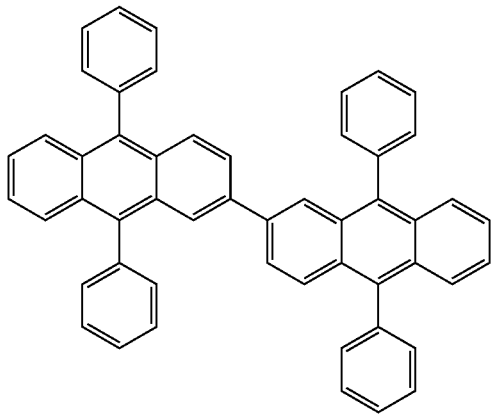
FD(4)
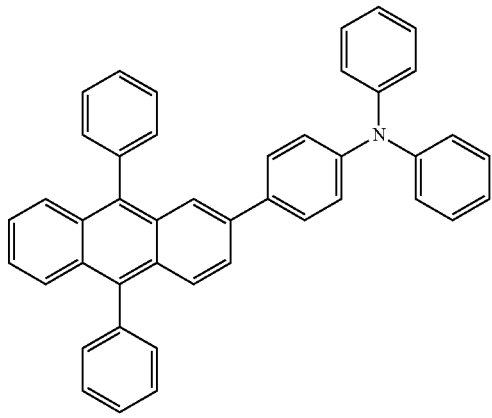
FD(5)
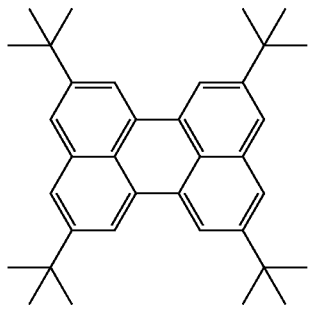
FD(6)
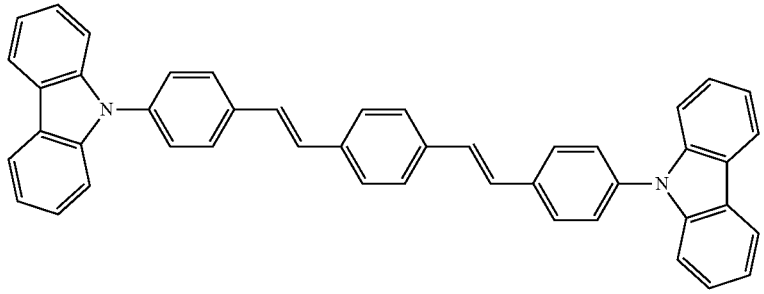

FD(7)
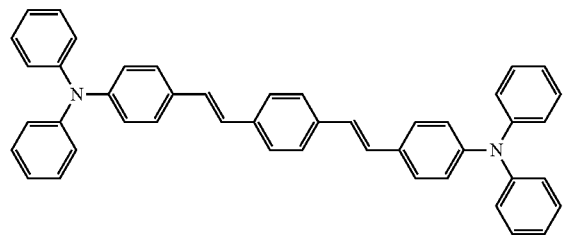
FD(8)
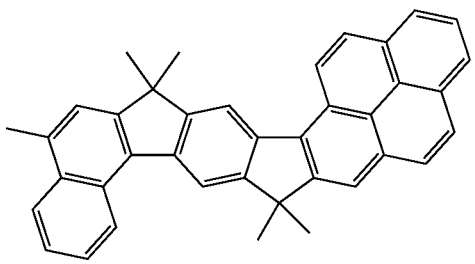
FD(9)
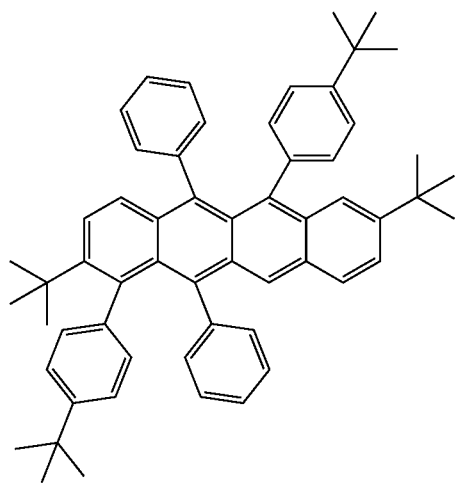
FD(10)
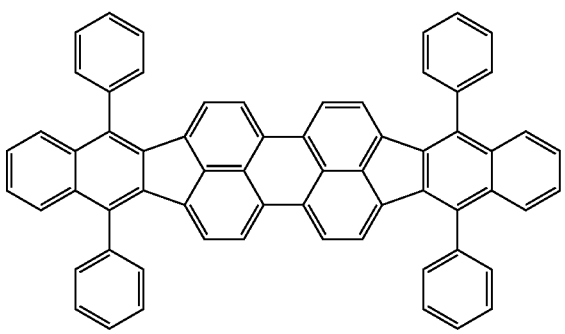
FD(11)
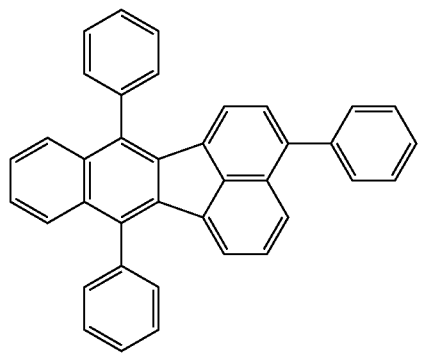
FD(12)
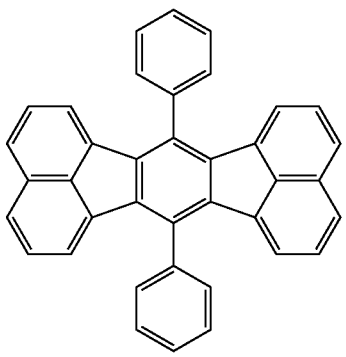
FD(13)
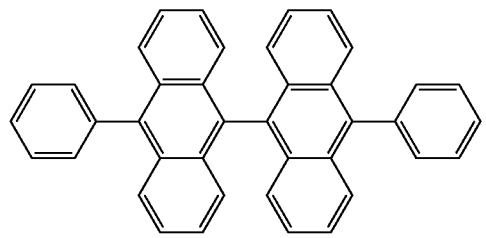
FD(14)
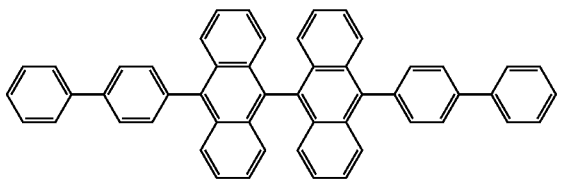

-continued
FD(15)
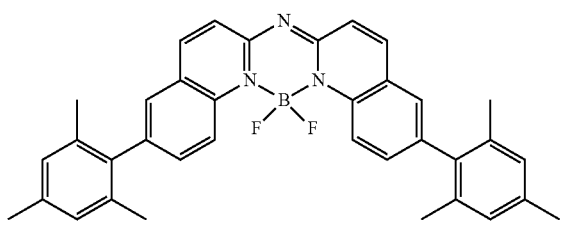
FD(16)
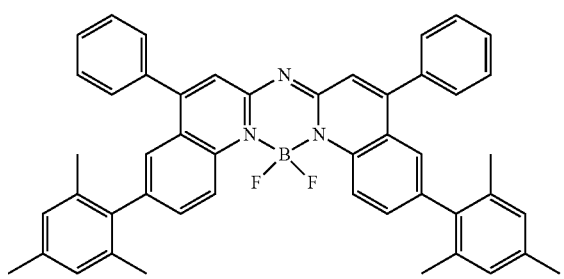
FD1
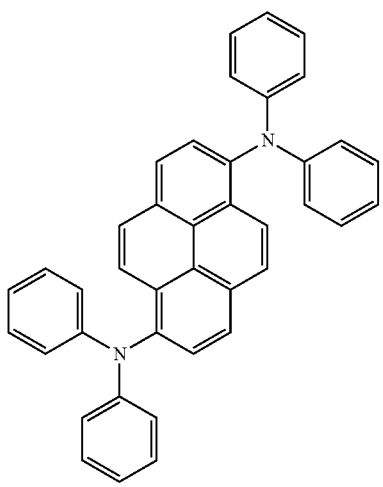
FD2
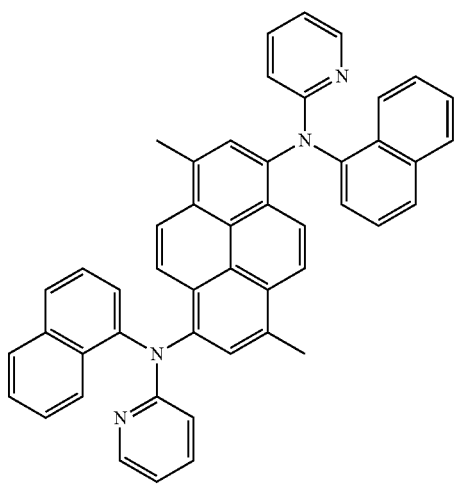
FD3
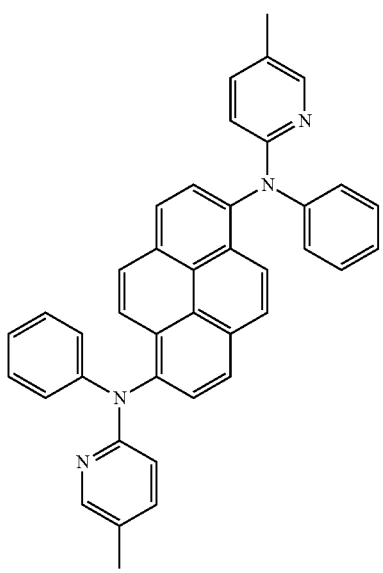
FD4
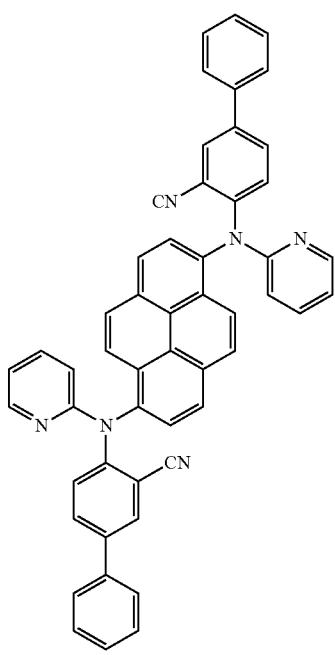

-continued
FD5
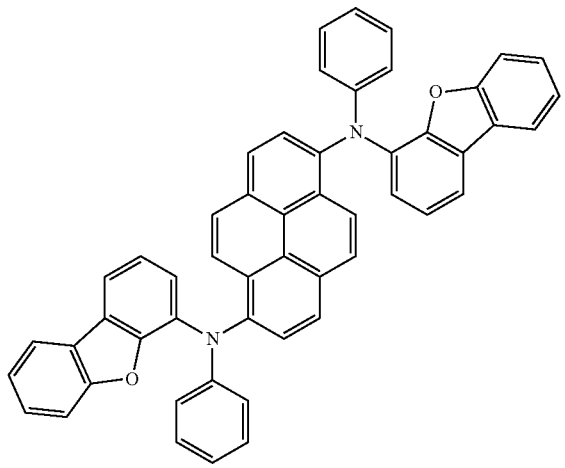
FD6
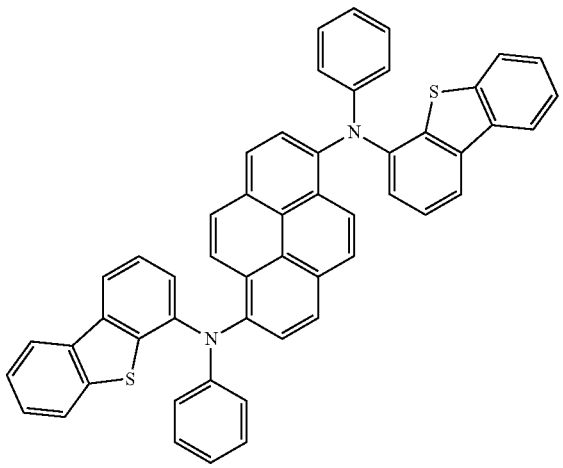
FD7
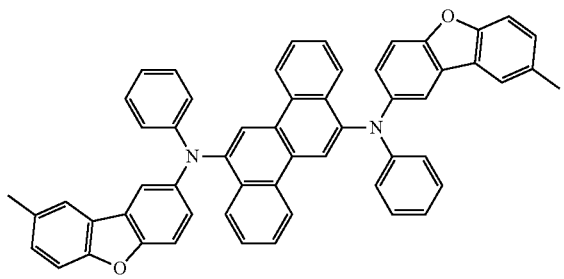
FD8
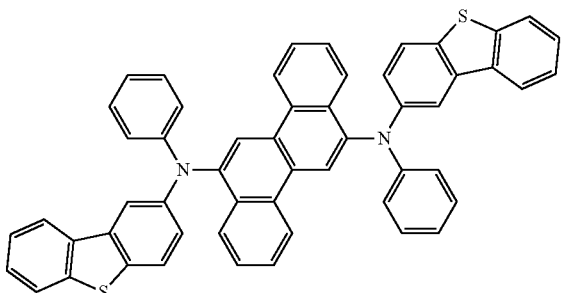
FD9
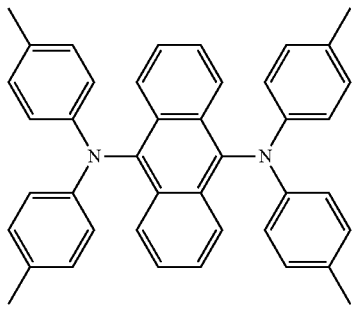
FD10
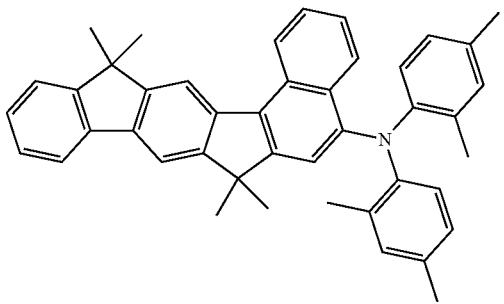
FD11
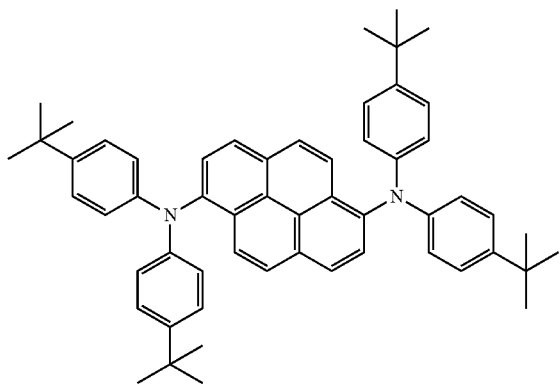
FD12
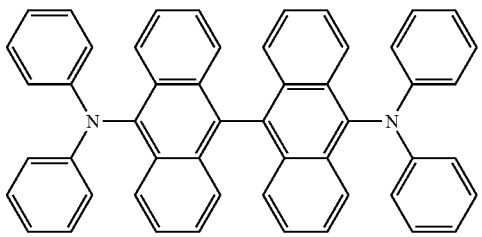

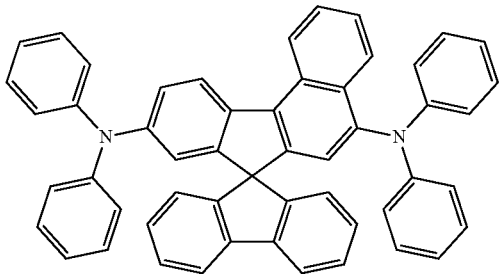

FD13

FIGURE is a schematic cross-sectional view of an organic light-emitting device 10 according to an embodiment. Hereinafter, the structure of an organic light-emitting device according to an embodiment and a method of manufacturing an organic light-emitting device according to an embodiment will be described in connection with the FIGURE. The organic light-emitting device 10 includes a first electrode 11, an organic layer 15, and a second electrode 19, which are sequentially stacked.

A substrate may be additionally disposed under the first electrode 11 or above the second electrode 19. For use as the substrate, any substrate known in the organic light-emitting device art may be used, and the substrate may be a glass substrate or a transparent plastic substrate, each having excellent mechanical strength, thermal stability, transparency, surface smoothness, ease of handling, and water resistance.

The first electrode 11 may be formed by depositing or sputtering a material for forming the first electrode 110 on the substrate. The first electrode 11 may be an anode. The material for forming the first electrode 11 may be a material with a high work function to facilitate hole injection. The first electrode 11 may be a reflective electrode, a semi-reflective electrode, or a transmissive electrode. The material for forming the first electrode may be, for example, indium tin oxide (ITO), indium zinc oxide (IZO), tin oxide (SnO$_2$), or zinc oxide (ZnO). In one or more embodiments, the material for forming the first electrode 11 may be metal or a metal alloy, such as magnesium (Mg), aluminum (Al), aluminum-lithium (Al—Li), calcium (Ca), magnesium-indium (Mg—In), or magnesium-silver (Mg—Ag).

The first electrode 11 may have a single-layered structure or a multi-layered structure including two or more layers. For example, the first electrode 11 may have a three-layered structure of ITO/Ag/ITO, but the structure of the first electrode 110 is not limited thereto.

The organic layer 15 is disposed on the first electrode 11.

The organic layer 15 may include a hole transport region, an emission layer, or an electron transport region.

The hole transport region may be disposed between the first electrode 11 and the emission layer.

The hole transport region may include a hole injection layer, a hole transport layer, an electron blocking layer, a buffer layer, or any combination thereof.

The hole transport region may include only either a hole injection layer or a hole transport layer. In one or more embodiments, the hole transport region may have a hole injection layer/hole transport layer structure or a hole injection layer/hole transport layer/electron blocking layer structure, which are sequentially stacked in this stated order from the first electrode 11.

When the hole transport region includes a hole injection layer (HIL), the hole injection layer may be formed on the first electrode 11 by using one or more suitable methods, for example, vacuum deposition, spin coating, casting, and/or Langmuir-Blodgett (LB) deposition.

When a hole injection layer is formed by vacuum deposition, the deposition conditions may vary according to a material that is used to form the hole injection layer, and the structure and thermal characteristics of the hole injection layer. For example, the deposition conditions may include a deposition temperature of about 100° C. to about 500° C., a vacuum pressure of about $10^{-8}$ to about $10^{-3}$ torr, and a deposition rate of about 0 Å/sec to about 100 Å/sec. However, the deposition conditions are not limited thereto, and embodiments of the present disclosure are not limited thereto.

When the hole injection layer is formed by spin coating, the spin coating may be performed at a coating speed of about 2,000 rpm to about 5,000 rpm and at a heat treatment temperature of about 80° C. to about 200° C. by taking into account a compound used for forming a hole injection layer to be formed and the structure and thermal characteristics of a hole injection layer to be formed. However, embodiments of the present disclosure are not limited thereto.

Conditions for forming the hole transport layer and the electron blocking layer may refer to those for forming the hole injection layer.

The hole transport region may include m-MTDATA, TDATA, 2-TNATA, NPB, β-NPB, TPD, spiro-TPD, spiro-NPB, methylated-NPB, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), a compound represented by Formula 201 below, a compound represented by Formula 202 below, or any combination thereof:

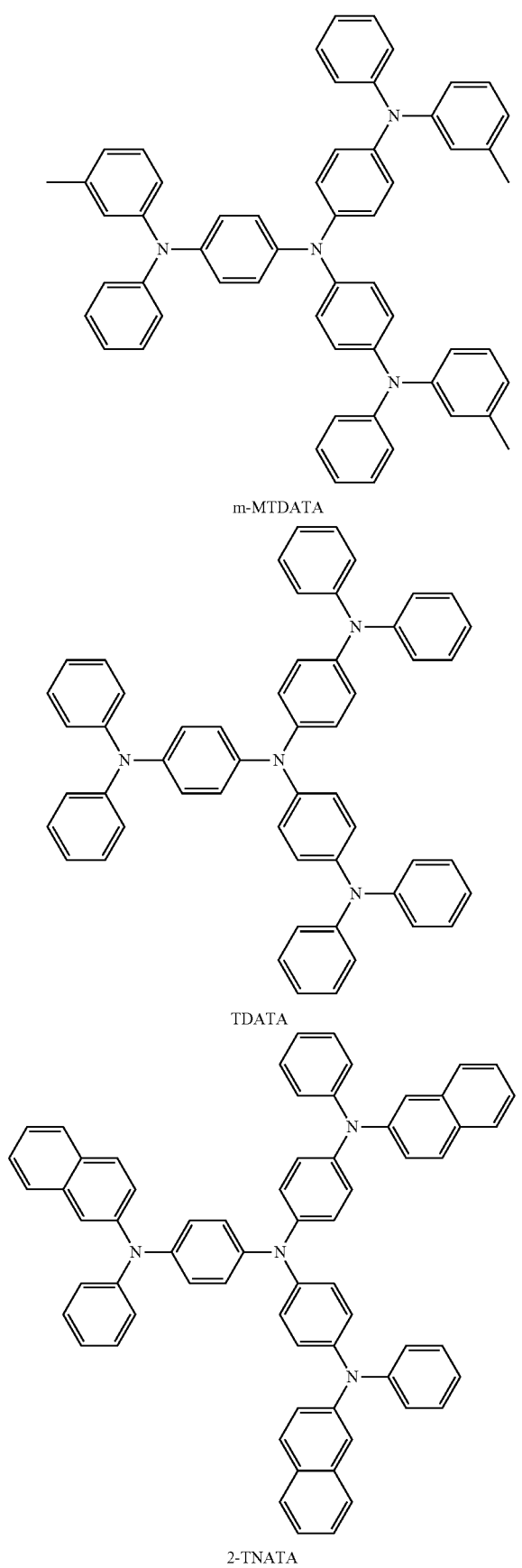
m-MTDATA
TDATA
2-TNATA
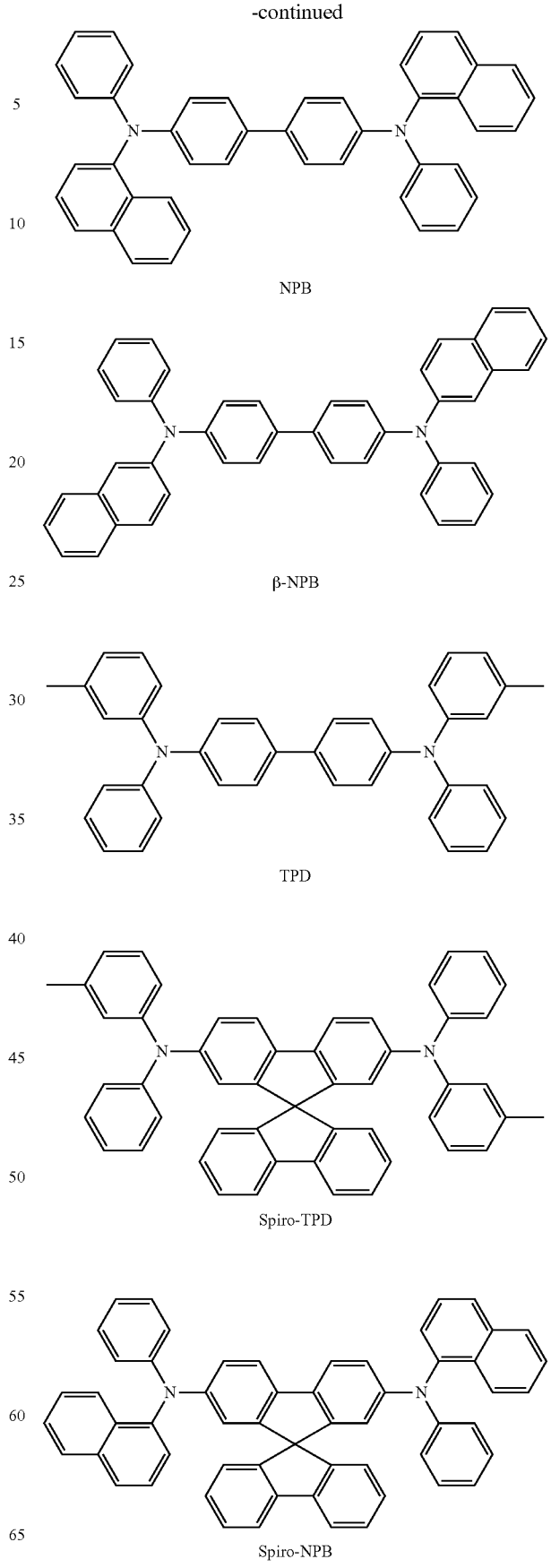
NPB
β-NPB
TPD
Spiro-TPD
Spiro-NPB -continued

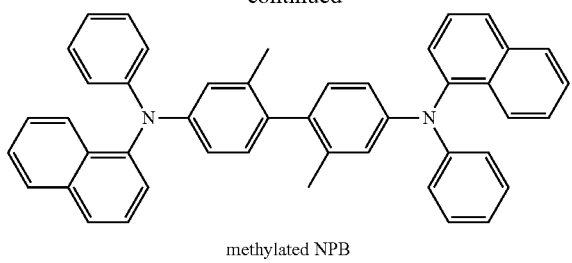
methylated NPB

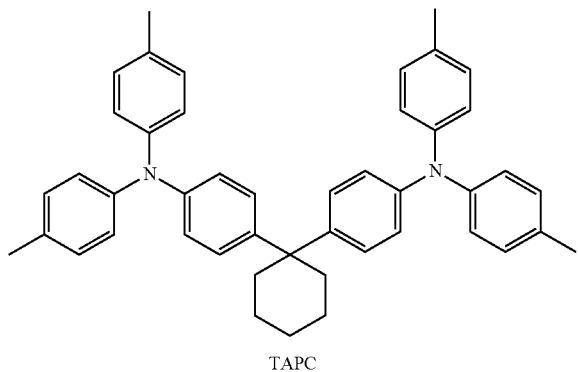
TAPC

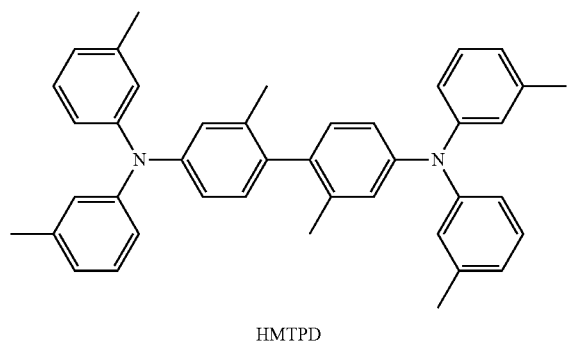
HMTPD

Formula 201

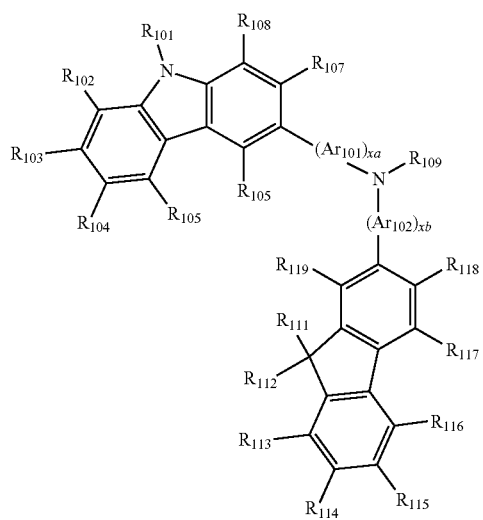

Formula 202

[Formula 202 structure with R121, R122, R123, R124 on carbazole-biphenyl-carbazole framework]

In Formula 201, $Ar_{101}$ and $Ar_{102}$ may each independently be:

a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, or a pentacenylene group; or a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, or a pentacenylene group, each substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, or any combination thereof.

In Formula 201, xa and xb may each independently be an integer from 0 to 5, or may be 0, 1, or 2. For example, xa may be 1, and xb may be 0, but embodiments of the present disclosure are not limited thereto.

In Formulae 201 and 202, $R_{101}$ to $R_{108}$, $R_{111}$ to $R_{119}$, and $R_{121}$ to $R_{124}$ may each independently be:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, pentyl group, a hexyl group, and the like), or a $C_1$-$C_{10}$ alkoxy group (for example, a methoxy group, an ethoxy group, a propoxy group, a butoxy group, a pentoxy group, and the like);

a $C_1$-$C_{10}$ alkyl group or a $C_1$-$C_{10}$ alkoxy group, each substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof a phosphoric acid group or a salt thereof, or any combination thereof;

a phenyl group, a naphthyl group, an anthracenyl group, a fluorenyl group, or a pyrenyl group; or a phenyl group, a naphthyl group, an anthracenyl group, a fluorenyl group, or a pyrenyl group, each substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, or any combination thereof, but embodiments of the present disclosure are not limited thereto.

In Formula 201, $R_{109}$ may be:

a phenyl group, a naphthyl group, an anthracenyl group, or a pyridinyl group; or a phenyl group, a naphthyl group, an anthracenyl group, or a pyridinyl group, each substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, a pyridinyl group, or any combination thereof.

In one embodiment, the compound represented by Formula 201 may be represented by Formula 201A, but embodiments of the present disclosure are not limited thereto:

Formula 201A

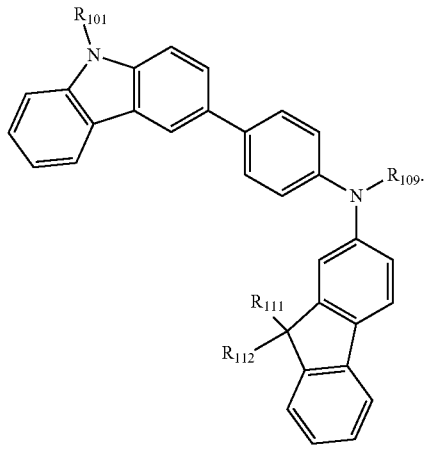

In Formula 201A, $R_{101}$, $R_{111}$, $R_{112}$, and $R_{109}$ may be understood by referring to a detailed description thereof to be provided later.

For example, the compound represented by Formula 201, and the compound represented by Formula 202 may include compounds HT1 to HT20 illustrated below, but are not limited thereto:

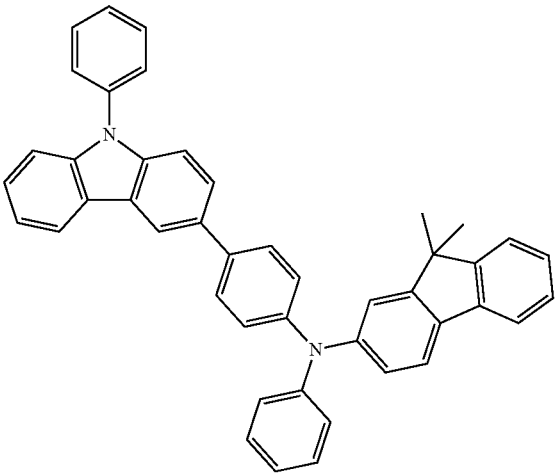

HT1

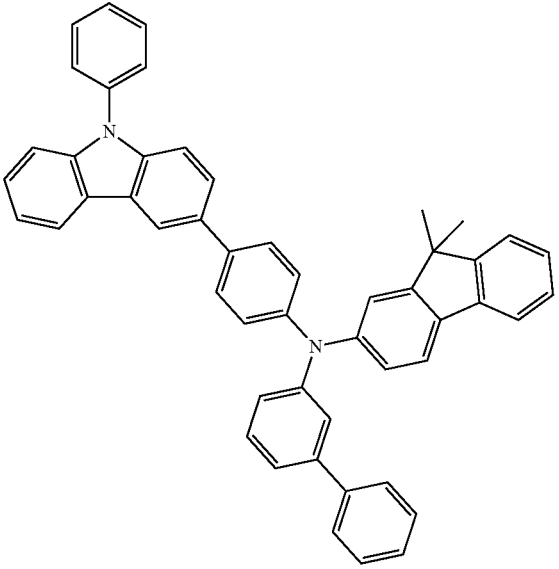

HT2

HT3
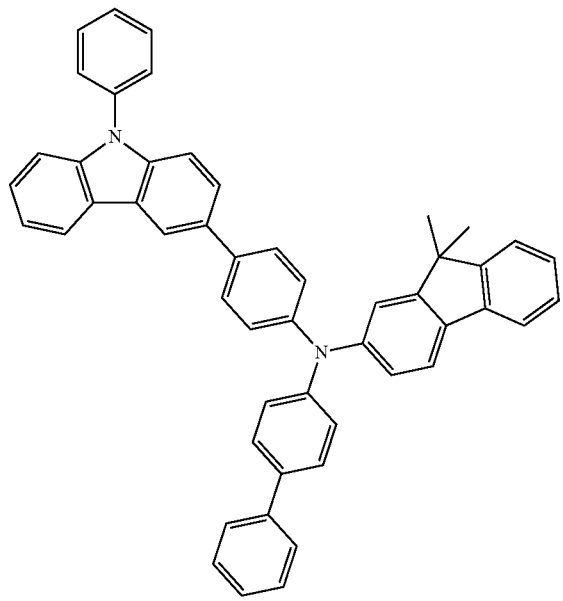
HT5
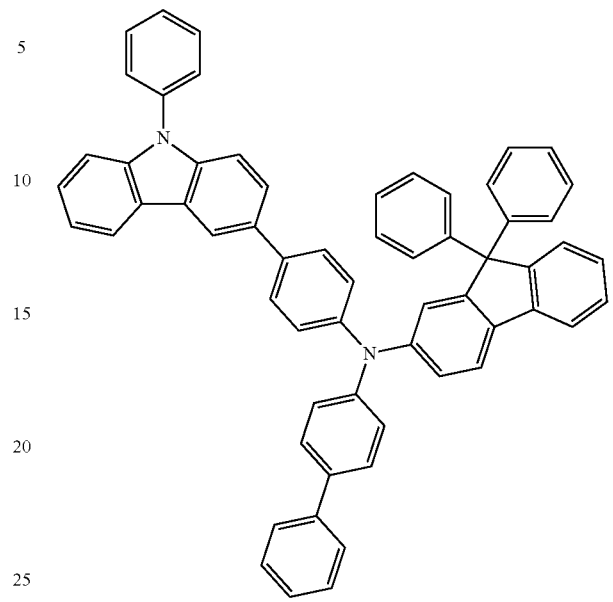
HT4
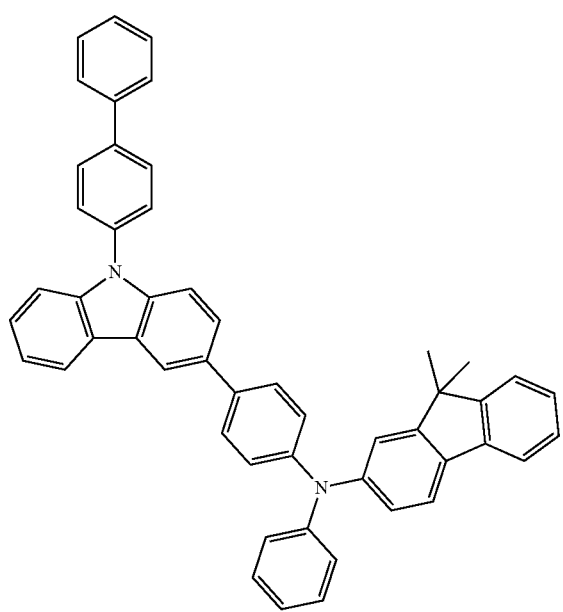
HT6
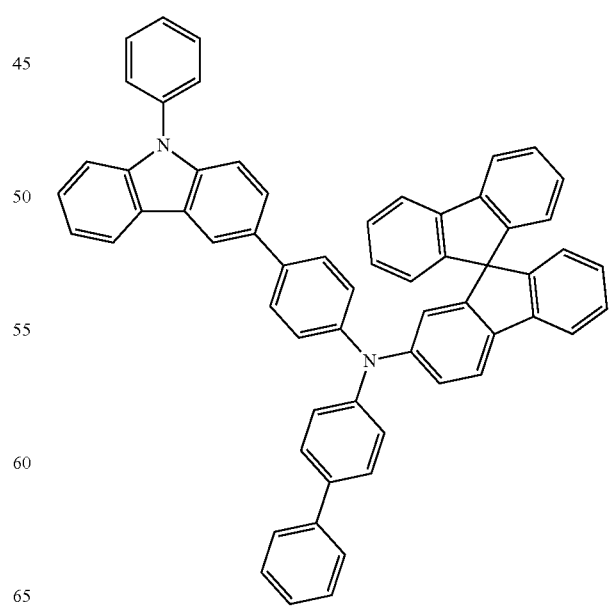

HT7
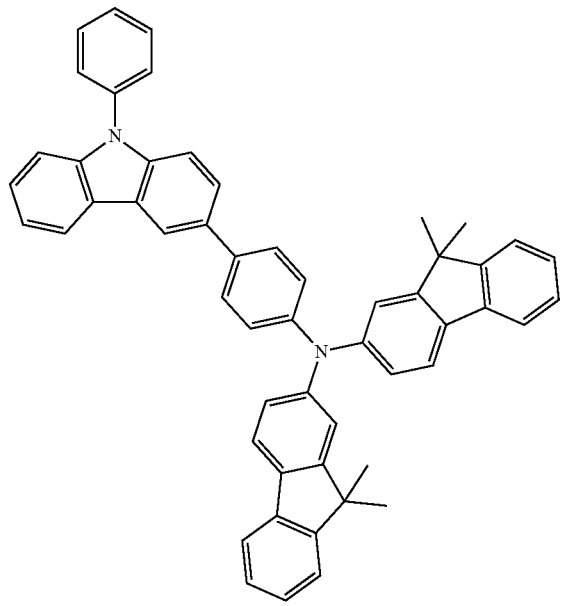
HT8
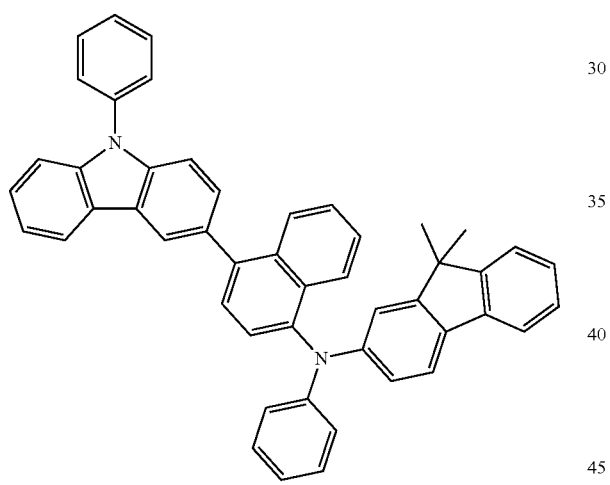
HT10
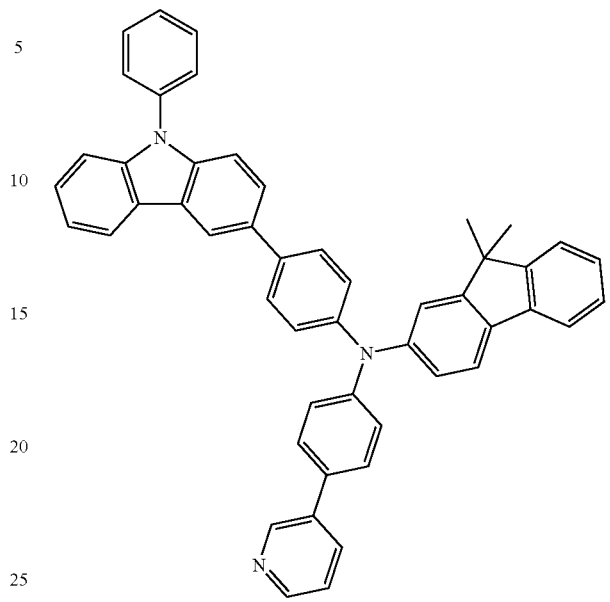
HT9
HT11
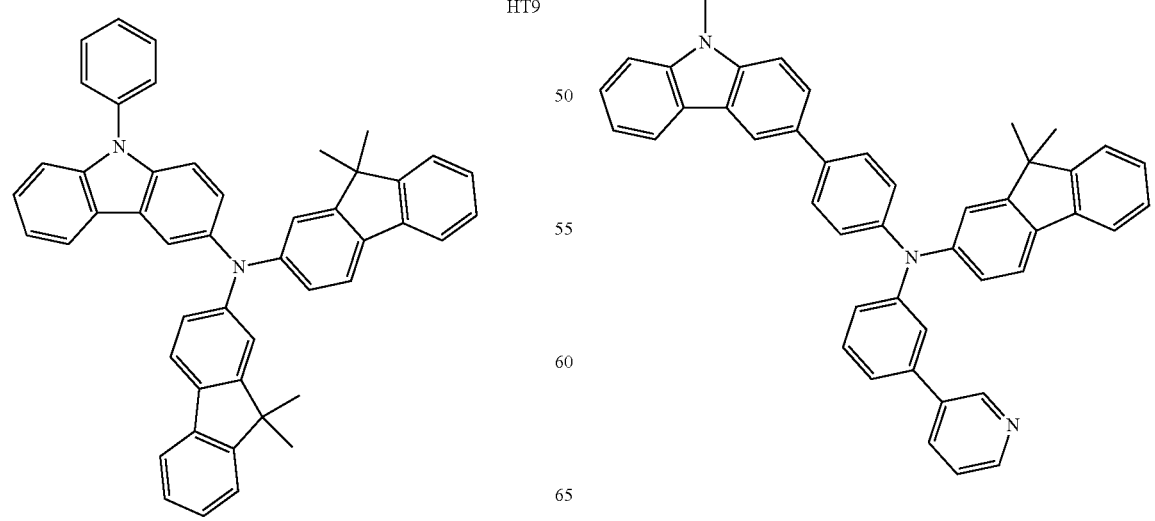

HT12
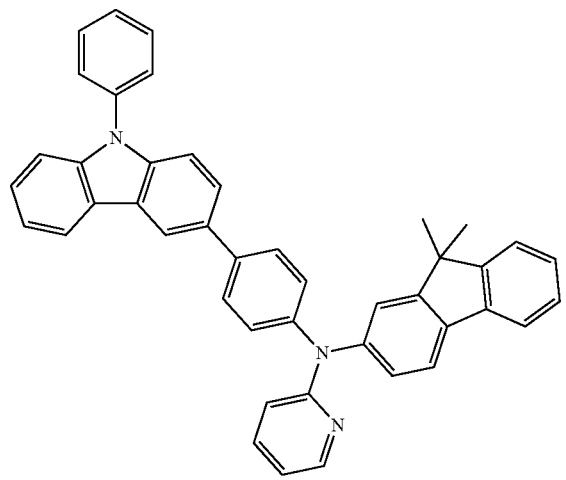
HT16
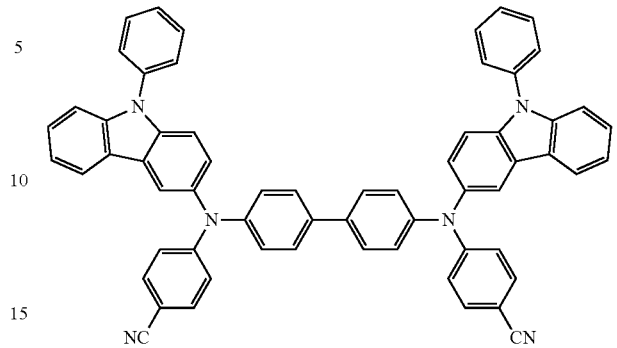
HT13
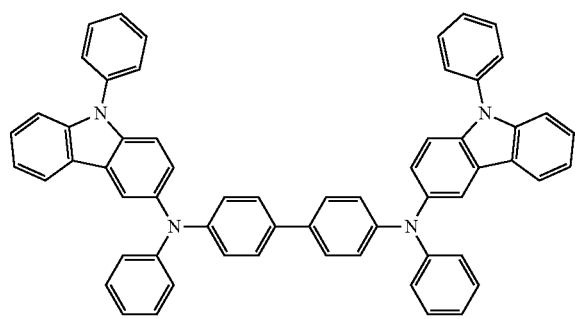
HT17
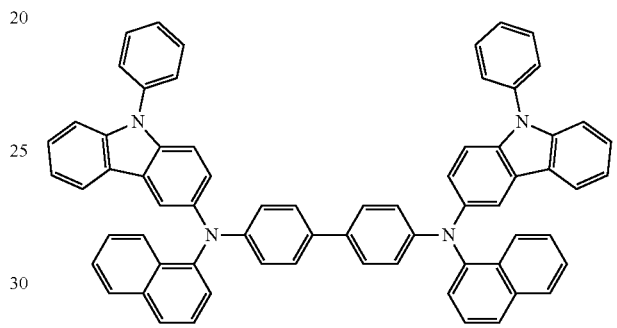
HT14
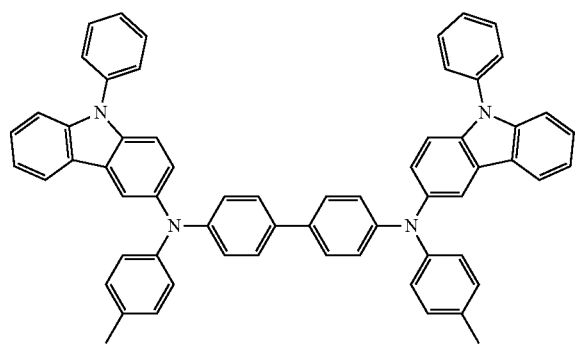
HT18
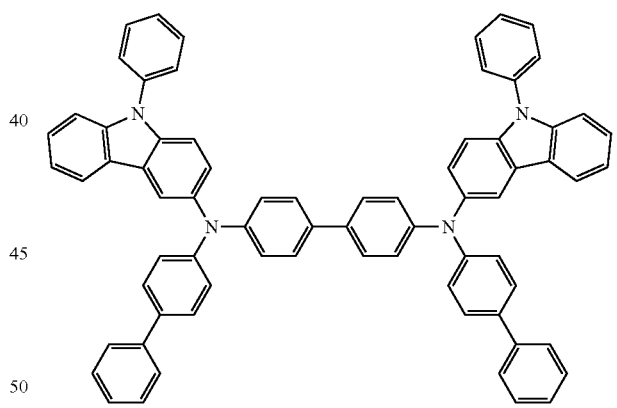
HT15
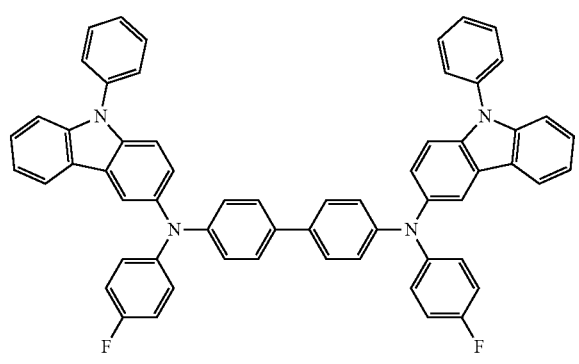
HT19
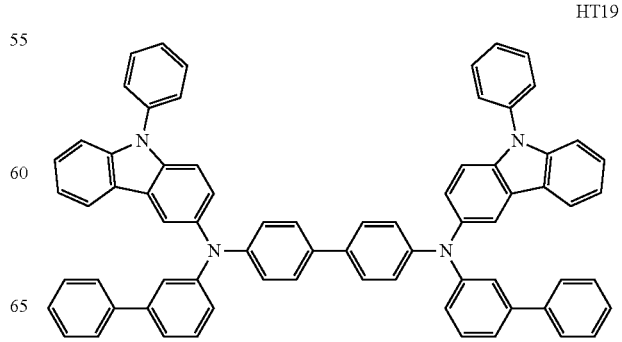

-continued

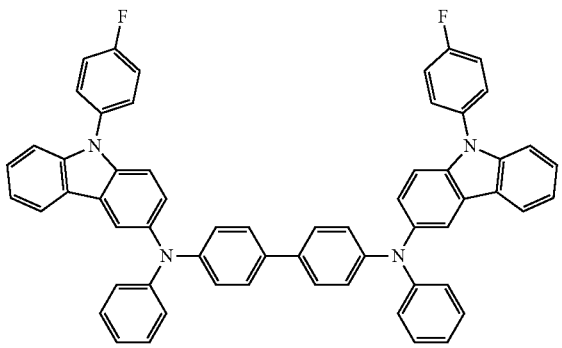

HT20

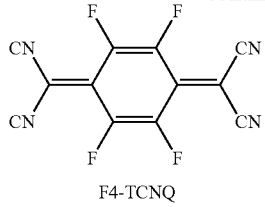

F4-TCNQ

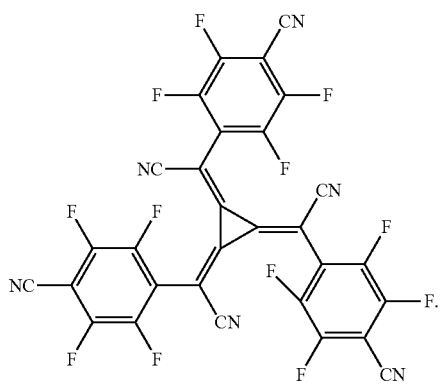

HP-1

A thickness of the hole transport region may be in a range of about 100 Å to about 10,000 Å, for example, about 100 Å to about 1,000 Å. When the hole transport region includes a hole injection layer and a hole transport layer, the thickness of the hole injection layer may be in a range of about 100 Å to about 10,000 Å, and for example, about 100 Å to about 1,000 Å, and the thickness of the hole transport layer may be in a range of about 50 Å to about 2,000 Å, and for example, about 100 Å to about 1,500 Å. When the thicknesses of the hole transport region, the hole injection layer, and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be a quinone derivative, a metal oxide, or a cyano group-containing compound, but embodiments of the present disclosure are not limited thereto. Non-limiting examples of the p-dopant are a quinone derivative, such as tetracyanoquinodimethane (TCNQ) and 2,3,5,6-tetrafluoro-tetracyano-1,4-benzoquinodimethane (F4-TCNQ); a metal oxide, such as a tungsten oxide or a molybdenum oxide; and a cyano group-containing compound, such as Compound HT-D1 or HP-1, but are not limited thereto:

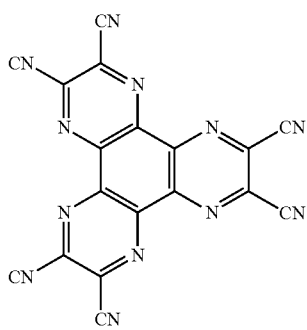

HT-D1

The hole transport region may further include a buffer layer.

Also, the buffer layer may compensate for an optical resonance distance according to a wavelength of light emitted from the emission layer, and thus, the efficiency of a formed organic light-emitting device may be improved.

The electron transport region may further include an electron blocking layer. The electron blocking layer may include, for example, mCP, but a material therefor is not limited thereto:

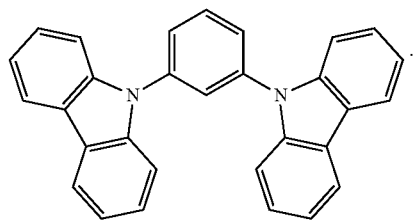

mCP

An emission layer may be formed on the hole transport region by vacuum deposition, spin coating, casting, LB deposition, or the like. When the emission layer is formed by vacuum deposition or spin coating, the deposition or coating conditions may be the same as or similar to those applied in forming the hole injection layer, although the deposition or coating conditions may vary according to a compound that is used to form the emission layer.

When the organic light-emitting device is a full-color organic light-emitting device, the emission layer may be patterned into a red emission layer, a green emission layer, and/or a blue emission layer. In one or more embodiments, due to a stacked structure including a red emission layer, a green emission layer, and/or a blue emission layer, the emission layer may emit white light.

The emission layer is the same as described above.

A thickness of the emission layer may be in a range of about 100 Å to about 1,000 Å, for example, about 200 Å to about 600 Å. When the thickness of the emission layer is within this range, excellent light-emission characteristics may be obtained without a substantial increase in driving voltage.

An electron transport region may be disposed on the emission layer.

The electron transport region may include a hole blocking layer, an electron transport layer, an electron injection layer, or any combination thereof.

For example, the electron transport region may have a hole blocking layer/electron transport layer/electron injection layer structure or an electron transport layer/electron injection layer structure, but the structure of the electron transport region is not limited thereto. The electron transport layer may have a single-layered structure or a multi-layered structure including two or more different materials.

Conditions for forming the hole blocking layer, the electron transport layer, and the electron injection layer which constitute the electron transport region may be understood by referring to the conditions for forming the hole injection layer.

When the electron transport region includes a hole blocking layer, the hole blocking layer may include, for example, BCP, Bphen, or a combination thereof, but may also include other materials:

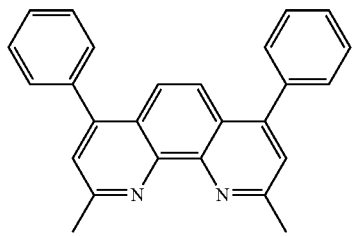

BCP

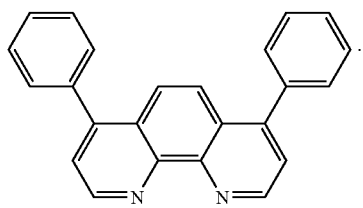

Bphen

The hole blocking layer may include a compound of the hosts described above. For example, the hole blocking layer may include Compound H19, but embodiments of the present disclosure are not limited thereto.

A thickness of the hole blocking layer may be in a range of about 20 Å to about 1,000 Å, for example, about 30 Å to about 300 Å. When the thickness of the hole blocking layer is within these ranges, the hole blocking layer may have excellent hole blocking characteristics without a substantial increase in driving voltage.

The electron transport layer may further include BCP, Bphen, Alq$_3$, BAlq, TAZ, NTAZ, or any combination thereof:

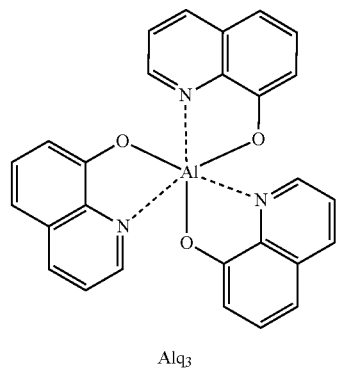

Alq$_3$

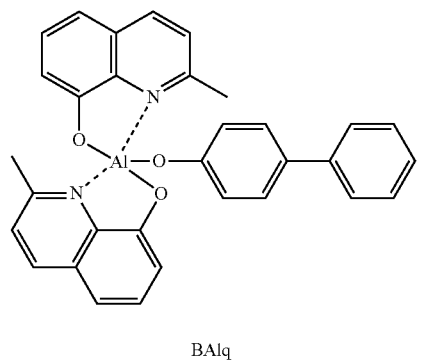

BAlq

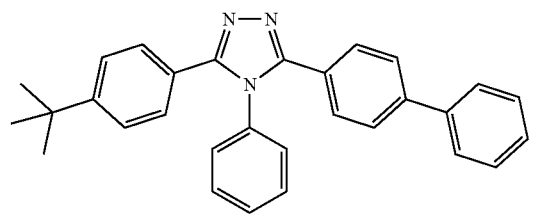

TAZ

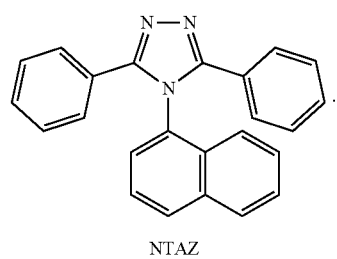

NTAZ

In one or more embodiments, the electron transport layer may include Compounds ET1, ET2, ET3, or any combination thereof, but embodiments of the present disclosure are not limited thereto:

ET1

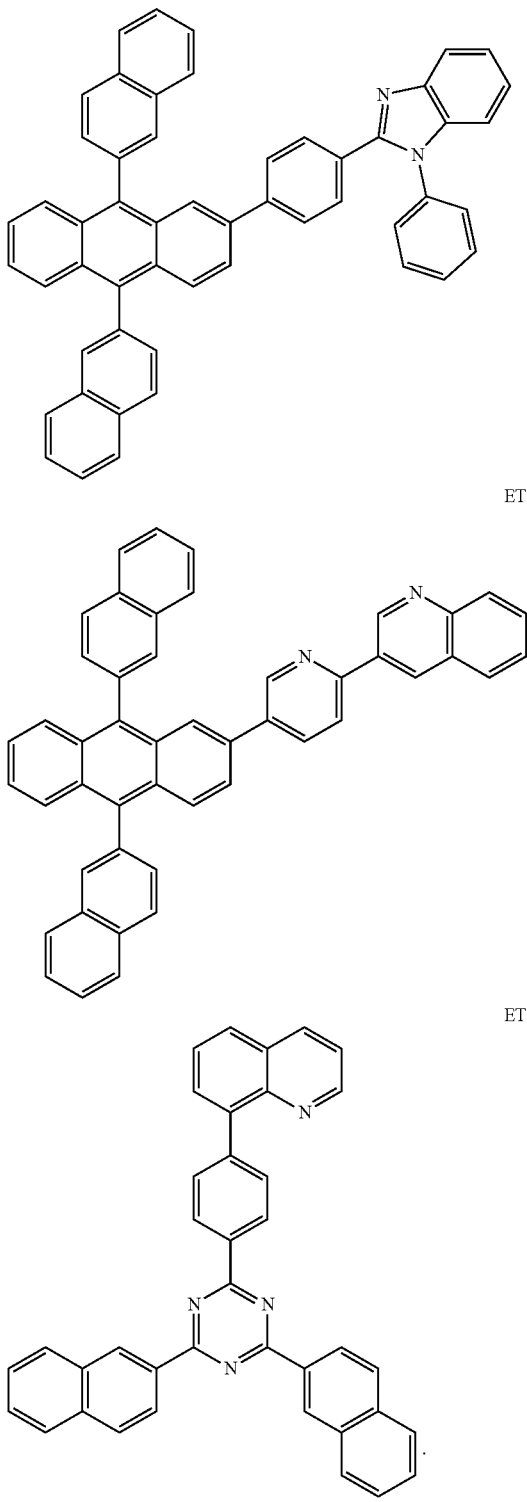

ET2

ET3 electron transport layer may have satisfactory electron transport characteristics without a substantial increase in driving voltage.

Also, the electron transport layer may further include, in addition to the materials described above, a metal-containing material.

The metal-containing material may include a Li complex. The Li complex may include, for example, Compound ET-D1 (lithium quinolate, LiQ) or ET-D2:

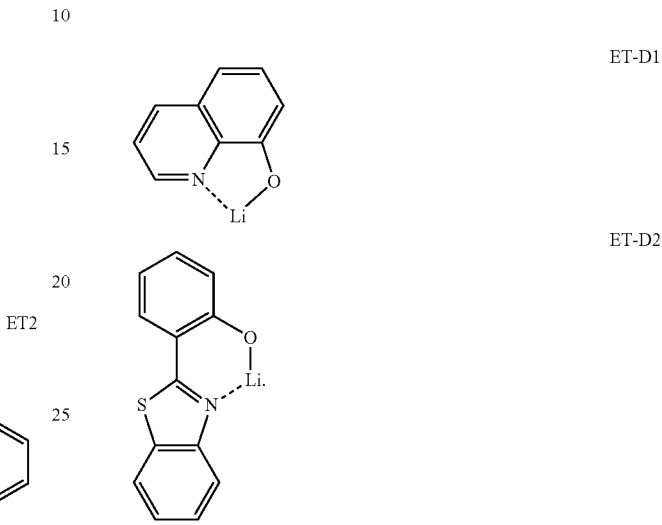

ET-D1

ET-D2

The electron transport region may include an electron injection layer that promotes flow of electrons from the second electrode 19 thereinto.

The electron injection layer may include LiF, NaCl, CsF, $Li_2O$, BaO, or a combination thereof.

A thickness of the electron injection layer may be in a range of about 1 Å to about 100 Å, for example, about 3 Å to about 90 Å. When the thickness of the electron injection layer is within the range described above, the electron injection layer may have satisfactory electron injection characteristics without a substantial increase in driving voltage.

The second electrode 19 may be disposed on the organic layer 15. The second electrode 19 may be a cathode. A material for forming the second electrode 19 may be a metal, an alloy, an electrically conductive compound, or a combination thereof, which have a relatively low work function. For example, lithium (Li), magnesium (Mg), aluminum (Al), aluminum-lithium (Al—Li), calcium (Ca), magnesium-indium (Mg—In), or magnesium-silver (Mg—Ag) may be used as the material for forming the second electrode 19. To manufacture a top-emission type light-emitting device, a transmissive electrode formed using ITO or IZO may be used as the second electrode 19.

Hereinbefore, the organic light-emitting device according to an embodiment has been described in connection with the FIGURE, but embodiments of the present disclosure are not limited thereto.

The term "$C_1$-$C_{60}$ alkyl group" as used herein refers to a linear or branched aliphatic saturated hydrocarbon monovalent group having 1 to 60 carbon atoms, and examples thereof include a methyl group, an ethyl group, a propyl group, an isobutyl group, a sec-butyl group, a tert-butyl group, a pentyl group, an isoamyl group, and a hexyl group. The term "$C_1$-$C_{60}$ alkylene group" as used herein refers to a divalent group having the same structure as the $C_1$-$C_{60}$ alkyl group.

A thickness of the electron transport layer may be in a range of about 100 Å to about 1,000 Å, for example, about 150 Å to about 500 Å. When the thickness of the electron transport layer is within the range described above, the The term "$C_1$-$C_{60}$ alkoxy group" as used herein refers to a monovalent group represented by —$OA_{101}$ (wherein $A_{101}$ is the $C_1$-$C_{60}$ alkyl group), and examples thereof include a methoxy group, an ethoxy group, and an isopropyloxy group.

The term "$C_2$-$C_{60}$ alkenyl group" as used herein refers to a hydrocarbon group having a carbon-carbon double bond in the middle or at the terminus of the $C_2$-$C_{60}$ alkyl group, and examples thereof include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a hydrocarbon group having a carbon-carbon triple bond in the middle or at the terminus of the $C_2$-$C_{60}$ alkyl group, and examples thereof include an ethynyl group, and a propynyl group. The term "$C_2$-$C_{60}$ alkynylene group" as used herein refers to a divalent group having the same structure as the $C_2$-$C_{60}$ alkynyl group.

The term "$C_3$-$C_{10}$ cycloalkyl group" as used herein refers to a monovalent saturated hydrocarbon monocyclic group having 3 to 10 carbon atoms, and non-limiting examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having the same structure as the $C_3$-$O1_0$ cycloalkyl group.

The term "$C_1$-$C_{10}$ heterocycloalkyl group" as used herein refers to a monovalent saturated monocyclic group having N, O, P, Si, Se, S, or a combination thereof and 1 to 10 carbon atoms as ring-forming atoms, and non-limiting examples thereof include a tetrahydrofuranyl group, and a tetrahydrothiophenyl group. The term "$C_1$-$C_{10}$ heterocycloalkylene group" as used herein refers to a divalent group having the same structure as the $C_1$-$C_{10}$ heterocycloalkyl group.

The term "$C_3$-$C_{10}$ cycloalkenyl group" as used herein refers to a monovalent monocyclic group that has 3 to 10 carbon atoms and a carbon-carbon double bond in the ring thereof and no aromaticity, and non-limiting examples thereof include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_1$-$C_{10}$ heterocycloalkenyl group" as used herein refers to a monovalent monocyclic group that has N, O, P, Si, Se S, or a combination thereof and 1 to 10 carbon atoms as ring-forming atoms, and a carbon-carbon double bond in the ring. Examples of the $C_1$-$C_{10}$ heterocycloalkenyl group are a 2,3-dihydrofuranyl group, and a 2,3-dihydrothiophenyl group. The term "$C_1$-$C_{10}$ heterocycloalkenylene group" as used herein refers to a divalent group having the same structure as the $C_1$-$C_{10}$ heterocycloalkenyl group.

The term "$C_6$-$C_{60}$ aryl group" as used herein refers to a monovalent group having a carbocyclic aromatic system having 6 to 60 carbon atoms, and the term "$C_6$-$C_{60}$ arylene group" as used herein refers to a divalent group having a carbocyclic aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

The term "$C_2$-$C_{60}$ heteroaryl group" as used herein refers to a monovalent group having a heterocyclic aromatic system that has N, O, P, Si, Se, S, or a combination thereof and 2 to 60 carbon atoms as ring-forming atoms. The term "$C_2$-$C_{60}$ heteroarylene group" as used herein refers to a divalent group having a heterocyclic aromatic system that has N, O, P, Si, Se, S, or a combination thereof and 2 to 60 carbon atoms as ring-forming atoms. Non-limiting examples of the $C_2$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_2$-$C_{60}$ heteroaryl group and the $C_2$-$C_{60}$ heteroarylene group each include two or more rings, the rings may be fused to each other.

The term "$C_7$-$C_{60}$ alkylaryl group" as used herein refers to an arylene group substituted with an alkyl group. A non-limiting example of a $C_7$-$C_{60}$ alkylaryl group includes a -phenyl-$CH_3$ (i.e., toluyl) group.

The term "$C_2$-$C_{60}$ alkylheteroaryl group" as used herein refers to a heteroarylene group substituted with an alkyl group. A non-limiting example of a $C_2$-$C_{60}$ alkylheteroaryl group includes a -pyridyl-$CH_3$ group.

The term "phenyl($C_1$-$C_{20}$ alkyl) group" as used herein refers to an alkylene group substituted with a phenyl group. Non-limiting examples of a phenyl($C_1$-$C_{20}$ alkyl) group include a —$CH_2$-phenyl (i.e., benzyl) group and a —$(CH_2)_3$-phenyl group.

The term "$C_6$-$C_{60}$ aryloxy group" as used herein refers to —$OA_{102}$ (wherein $A_{102}$ is the $C_6$-$C_{60}$ aryl group), and the term "$C_6$-$C_{60}$ arylthio group" as used herein refers to —$SA_{103}$ (wherein $A_{103}$ is the $C_6$-$C_{60}$ aryl group).

The term "monovalent non-aromatic condensed polycyclic group" as used herein refers to a monovalent group having two or more rings condensed to each other, only carbon atoms (for example, the number of carbon atoms may be in a range of 8 to 60) as a ring-forming atom, and no aromaticity in its entire molecular structure. Non-limiting examples of the monovalent non-aromatic condensed polycyclic group include a fluorenyl group. The term "divalent non-aromatic condensed polycyclic group" as used herein refers to a divalent group having the same structure as the monovalent non-aromatic condensed polycyclic group.

The term "monovalent non-aromatic condensed heteropolycyclic group" as used herein refers to a monovalent group having two or more rings condensed to each other, N, O, P, Si, Se, S, or a combination thereof, other than carbon atoms (for example, the number of carbon atoms may be in a range of 2 to 60), as a ring-forming atom, and no aromaticity in its entire molecular structure. Non-limiting examples of the monovalent non-aromatic condensed heteropolycyclic group include a carbazolyl group. The term "divalent non-aromatic condensed heteropolycyclic group" as used herein refers to a divalent group having the same structure as the monovalent non-aromatic condensed heteropolycyclic group.

The term "$C_5$-$C_{60}$ carbocyclic group" as used herein refers to a saturated or unsaturated cyclic group having 5 to 60 carbon atoms as ring-forming atoms. The term "$C_5$-$C_{60}$ carbocyclic group" as used herein refers to a monocyclic group or a polycyclic group, and, according to its chemical structure, a monovalent, divalent, trivalent, tetravalent, pentavalent, or hexavalent group.

The term "$C_2$-$C_{60}$ heterocyclic group" as used herein refers to a saturated or unsaturated cyclic group having N, O, Si, P, Se, S, of a combination thereof and 2 to 60 carbon atoms as ring-forming atoms. The term "$C_2$-$C_{60}$ heterocyclic group" as used herein refers to a monocyclic group or a polycyclic group, and, according to its chemical structure, a monovalent, divalent, trivalent, tetravalent, pentavalent, or hexavalent group.

A substituent of the substituted $C_5$-$C_{60}$ carbocyclic group, the substituted $C_2$-$C_{60}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, or the substituted monovalent non-aromatic condensed heteropolycyclic group may be:

deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, or a combination thereof;

a $C_1$-$C_{60}$ alkyl group, a $C_2$-$C_{60}$ alkenyl group, a $C_2$-$C_{60}$ alkynyl group, a $C_1$-$C_{60}$ alkoxy group, or a combination thereof, each substituted with deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N(Q$_{11}$)(Q$_{12}$), —Si(Q$_{13}$)(Q$_{14}$)(Q$_{15}$), —B(Q$_{16}$)(Q$_{17}$), —P(=O)(Q$_{18}$)(Q$_{19}$), or a combination thereof;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, or a combination thereof;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, or a combination thereof each substituted deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N(Q$_{21}$)(Q$_{22}$), —Si(Q$_{23}$)(Q$_{24}$)(Q$_{25}$), —B(Q$_{26}$)(Q$_{27}$), —P(=O)(Q$_{28}$)(Q$_{29}$), or a combination thereof; or —N(Q$_{31}$)(Q$_{32}$), —Si(Q$_{33}$)(Q$_{34}$)(Q$_{35}$), —B(Q$_{36}$)(Q$_{37}$), —P(=O)(Q$_{38}$)(Q$_{39}$), or a combination thereof, and $Q_1$ to $Q_9$, $Q_{11}$ to $Q_{19}$, $Q_{21}$ to $Q_{29}$, and $Q_{31}$ to $Q_{39}$ may each independently be hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with a $C_1$-$C_{60}$ alkyl group, a $C_6$-$C_{60}$ aryl group, or a combination thereof, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group.

The term "room temperature" as used herein refers to a temperature of about 25° C.

Hereinafter, a compound and an organic light-emitting device according to embodiments are described in detail with reference to Synthesis Example and Examples. However, the organic light-emitting device is not limited thereto. The wording "'B' was used instead of 'A'" used in describing Synthesis Examples means that a molar equivalent of 'A' was identical to a molar equivalent of 'B'.

EXAMPLES

Synthesis Example 1: Synthesis of Compound 4

Compound 4 was synthesized according to the following reaction scheme:

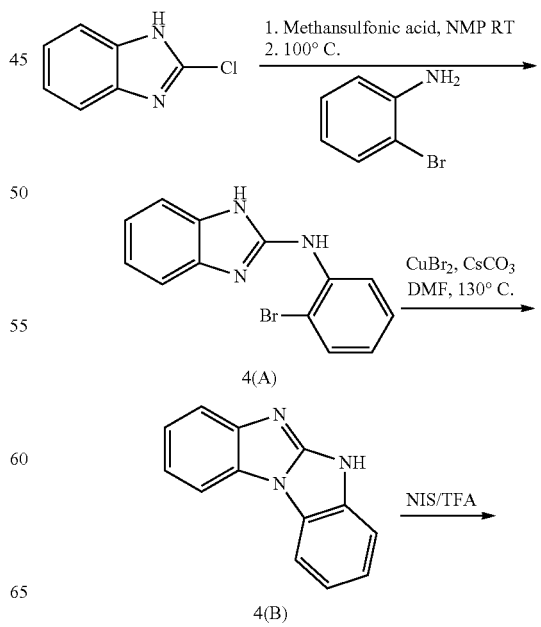

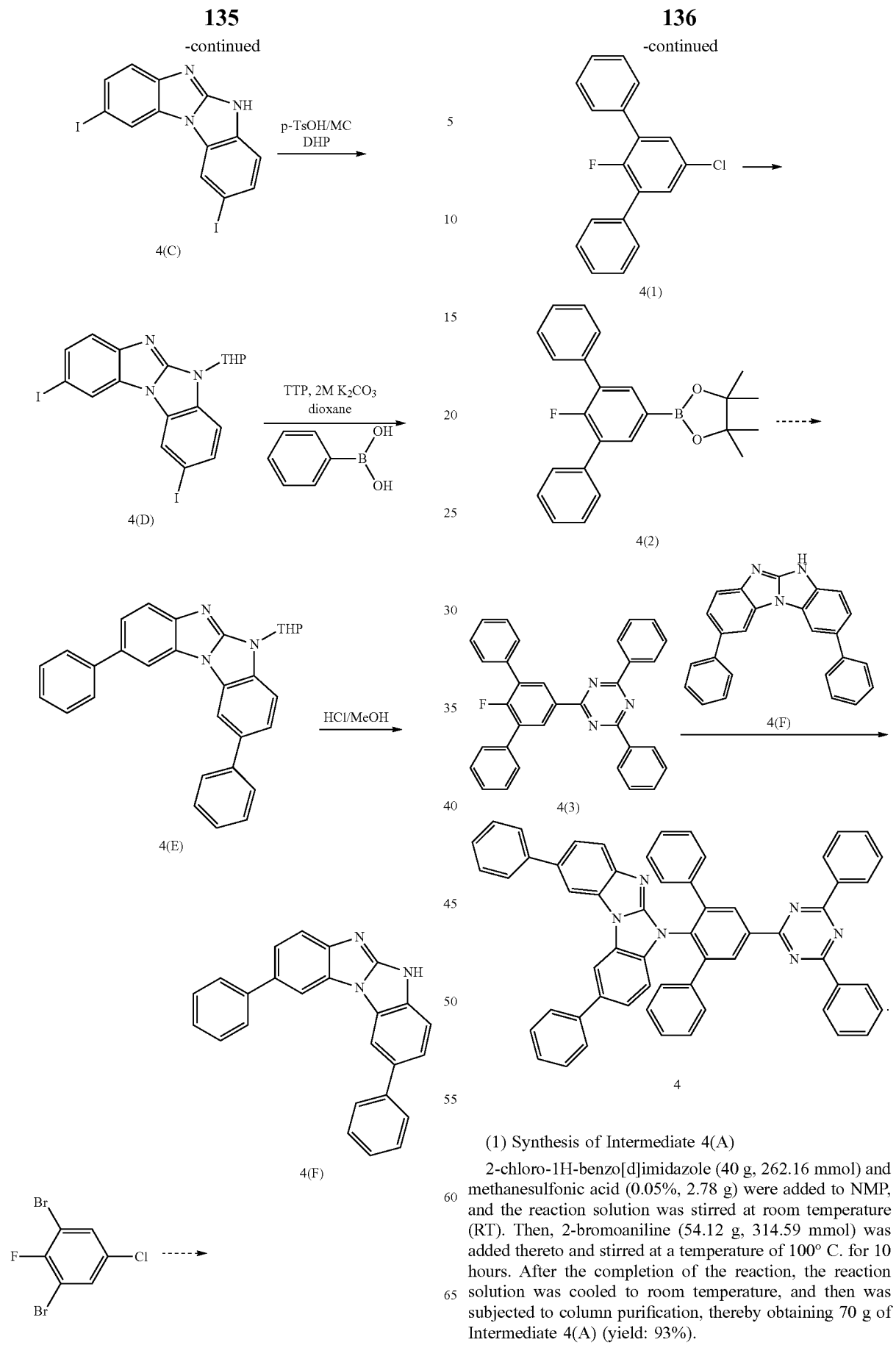

(1) Synthesis of Intermediate 4(A)

2-chloro-1H-benzo[d]imidazole (40 g, 262.16 mmol) and methanesulfonic acid (0.05%, 2.78 g) were added to NMP, and the reaction solution was stirred at room temperature (RT). Then, 2-bromoaniline (54.12 g, 314.59 mmol) was added thereto and stirred at a temperature of 100° C. for 10 hours. After the completion of the reaction, the reaction solution was cooled to room temperature, and then was subjected to column purification, thereby obtaining 70 g of Intermediate 4(A) (yield: 93%).

(2) Synthesis of Intermediate 4(B)

N-2-bromophenyl)-1H-benzo[d]imidazole-1-amine (55 g, 190.87 mmol), Copper(II)bromide ($CuBr_2$) (2.13 g, 9.54 mmol), and cesium carbonate ($Cs_2CO_3$) (93.29 g, 286.31 mmol), were added to 380 mL of N,N-dimethylformamide (DMF), and the reaction solution was stirred at a temperature of 130° C. for 12 hours. After the completion of the reaction, the reaction solution was cooled to room temperature, and methanol was added thereto to obtain a solid product. The solid product obtained was subjected to column purification, thereby obtaining 35 g of light-yellow solid Intermediate 4(B) (yield: 88%).

(3) Synthesis of Intermediate 4(C)

5H-benzo[d]benzo[4,5]imidazole[1,2-a]imidazole (25 g, 120.63 mmol), N-iodosuccinimide (NIS) (59.71 g, 265.39 mmol), and trifluoroacetic acid (TFA) (0.05 mol %) were added to 250 mL of acetonitrile, and the mixed solution was stirred at a temperature of 100° C. for 4 hours. Then, the reaction mixture was stirred at room temperature for 16 hours. After the completion of the reaction, the solvent was removed therefrom, and an extraction process was performed thereon using water and ethyl acetate. An organic layer obtained therefrom was dried using anhydrous sodium sulfate ($Na_2SO_4$), and then concentrated. The resulting product was purified by silica gel column chromatography (dichloromethane/hexane). A solid obtained therefrom was subjected to recrystallization using hexane, thereby obtaining 45 g of Intermediate 4(C).

(4) Synthesis of Intermediate 4(D)

2,9-diiodo-5H-benzo[d]benzo[4,5]imidazo[1,2-a]imidazole (45 g, 98.03 mmol), dihexadecyl phosphate (DHP) (107.218 g, 196.07 mmol), and p-toluenesulfonic acid monohydrate (p-TsOH) (0.466 g, 2.45 mmol) were added to 700 mL of dichloromethane, and the mixed solution was stirred at room temperature for 16 hours. After the completion of the reaction, the organic layer was separated therefrom, dried using anhydrous $Na_2SO_4$, the organic layer obtained therefrom was concentrated, and purified by silica gel column chromatography (ethyl acetate/hexane). A solid obtained therefrom was subjected to recrystallization using hexane, thereby obtaining 41 g of Intermediate 4(D) (yield: 77%).

(5) Synthesis of Intermediate 4(E)

2,9-diiodo-5-(tetrahydro-2H-pyran-2-yl)-5H-benzo[d]benzo[4,5]imidazo[1,2-a]imidazole ((40 g, 73.64 mmol), phenylboronic acid (19.75 g, 162.02 mmol), palladium tetrakis(triphenylphosphine) (TTP, or $Pd(PPh_3)_4$) (4.26 g, 3.68 mmol), and potassium carbonate ($K_2CO_3$) (22.39 g, 162.02 mmol) were added to a mixture of 150 ml of dioxane and 150 ml of distilled water, and the mixed solution was heated under reflux. After the completion of the reaction, the reaction solution was cooled to room temperature, and methanol was added thereto. The resulting solution was then filtered through silica gel. The organic layer obtained therefrom was concentrated, and methanol was added thereto to form a precipitate. The mixture was filtered, thereby obtaining 30.65 g of white solid Intermediate 4(E) (yield: 93%).

(6) Synthesis of Intermediate 4(F)

2,9-diphenyl-5-(tetrahydro-2H-pyran-2-yl)-5H-benzo[d]benzo[4,5]imidazo[1,2-a]imidazole) (30 g, 67.64 mmol) was added to a flask (500 mL) containing hydrochloric acid/methanol (2% HCl/MeOH), and the mixed solution was stirred overnight. After the completion of the reaction, dichloromethane was added thereto to separate an organic layer. The organic layer was dried using anhydrous $Na_2SO_4$, the organic layer obtained therefrom was concentrated, and purified by silica gel column chromatography (ethyl acetate/hexane), thereby obtaining 17.56 g of Intermediate 4(F) (yield: 72%).

(7) Synthesis of Intermediate 4(1)

Phenylboronic acid (63.43 g, 520.22 mmol), 1,3-dibromo-5-chloro-2-fluorobenzene (50 g, 173.41 mmol), $Pd(PPh_3)_4$ (20.04 g, 17.34 mmol), $K_2CO_3$ (95.87 g, 693.63 mmol), and 2-dicyclohexylphosphino-2',6'-dimethoxybiphenyl (S-phos) (14.24 g, 34.68 mmol) were added to a mixture containing 300 ml of tetrahydrofuran and 300 ml of distilled water, and the mixed solution was heated under reflux. After the completion of the reaction, the reaction solution was cooled to room temperature, and an extraction process was performed thereon using ethyl acetate. An organic layer obtained therefrom was dried using anhydrous $Na_2SO_4$, and then, concentrated. The resulting product was purified by silica gel column chromatography (dichloromethane/hexane). A white solid obtained therefrom was subjected to recrystallization using hexane, thereby obtaining 40.7 g of white solid Intermediate 4(1) (143.81 mmol, yield: 83%).

(8) Synthesis of Intermediate 4(2)

Intermediate 4(1) (40.7 g, 143.81 mmol), bis(pinacolato)diboron (54.78 g, 215.71 mmol), potassium acetate (35.29 g, 359.52 mmol), tris(dibenzylideneacetone)dipalladium (0) ($Pd_2(dba)_3$) (13.17 g, 14.38 mmol), and tricyclohexylphosphine (4.03 g, 14.38 mmol) were added to 290 ml of dioxane, and the mixed solution was heated under reflux. After the completion of the reaction, the reaction solution was cooled to room temperature, and an excess of toluene was added thereto. The resulting solution was then filtered through silica gel. The organic layer obtained therefrom was concentrated, and hexane was added thereto to form a precipitate, thereby obtaining 47.0 g of white solid Intermediate 4(2) (125.58 mmol, yield: 87%).

(9) Synthesis of Intermediate 4(3)

2-chloro-4,6-diphenyl-1,3,5-triazine ((18 g, 67.23 mmol), Intermediate 4(2) (30.2 g, 80.68 mmol), $Pd(PPh_3)_4$ (3.89 g, 3.36 mmol), $K_2CO_3$ (18.59 g, 134.47 mmol), and S-phos (5.52 g, 13.45 mmol) were added to a mixture containing 120 ml of tetrahydrofuran and 120 ml of distilled water, and the mixed solution was heated under reflux. After the completion of the reaction, the reaction solution was cooled to room temperature, and methanol was added thereto. The resulting solution was then filtered through silica gel. The organic layer obtained therefrom was concentrated, and methanol was added thereto to form a precipitate, thereby obtaining 30.0 g of white solid Intermediate 4(3) (62.56 mmol, yield: 93%).

(10) Synthesis of Compound 4

Intermediate 4(3) (4.80 g, 10 mmol), Intermediate 4(F) (5.39 g, 15 mmol), and $Cs_2CO_3$ (6.52 g, 20 mmol) were added to 20 ml of DMF, and the mixed solution was stirred at a temperature of 165° C. for 20 hours. After the completion of the reaction, the reaction solution was cooled to room temperature, and methanol was added thereto. The resulting solution was then filtered through silica gel. An organic layer obtained therefrom was concentrated, redissolved in toluene, and filtered through silica gel. The resulting product was concentrated and subjected to recrystallization (using ethyl acetate/ethanol), thereby obtaining 8.75 g of yellow solid Compound 4 (10.68 mmol, yield: 97%).

LC-Mass (calculated: 818.96 g/mol, measured: 818.32 g/mol (M+1)).

Evaluation Example 1

According to the method described in Table 2, emission spectra, HOMO energy levels, LUMO energy levels, singlet ($S_1$) energy levels, triplet ($T_1$) energy levels, and $\Delta E_{ST}$ of Compounds 4 and A to C were evaluated, and results thereof are shown in Table 3:

TABLE 2

| Photoluminescence (PL) spectrum | Each compound was diluted at a concentration of $10^{-5}$ M in toluene, and a F7000 spectrofluorometer equipped with an Xenon lamp (manufactured by HITACHI) was used to measure a PL spectrum of each compound (at 298K). |
|---|---|
| $S_1$ energy level evaluation method | A PL spectrum of a mixture of toluene and each compound (diluted at a concentration of $1 \times 10^{-4}$ M) was measured at room temperature, and peaks observed therefrom were analyzed to calculate on set $S_1$ energy level. |
| $T_1$ energy level evaluation method | A mixture of toluene and each compound (diluted at a concentration of $1 \times 10^{-4}$ M) was put into a quartz cell, and put into liquid nitrogen (77K), and a PL spectrum thereof was measured. The measured spectrum was compared with a PL spectrum measured at room temperature such that peaks observed only at a low temperature were analyzed to calculate the $T_1$ energy level. |
| $\Delta E_{ST}$ | A difference between $S_1$ energy level and $T_1$ energy level was calculated. |

TABLE 3

| Compound No. | HOMO (eV) | LUMO (eV) | $S_1$ energy level (eV) | $T_1$ energy level (eV) | $\Delta E_{ST}$ (eV) | Maximum emission wavelength in PL spectrum (nm) |
|---|---|---|---|---|---|---|
| 4 | −5.606 | −2.597 | 2.725 | 2.719 | 0.006 | 455 |
| A | −5.987 | −2.321 | 2.956 | 2.745 | 0.21 | 420 |
| B | −5.875 | −2.24 | 3.38 | 2.867 | 0.513 | 366 |
| C | −5.32 | −2.55 | 2.421 | 2.405 | 0.016 | 513 |

4

TABLE 3-continued

| Compound No. | HOMO (eV) | LUMO (eV) | $S_1$ energy level (eV) | $T_1$ energy level (eV) | $\Delta E_{ST}$ (eV) | Maximum emission wavelength in PL spectrum (nm) |
|---|---|---|---|---|---|---|

A

B

C

Referring to Table 3, it was confirmed that Compound 4 emitted dark blue light and had a small $\Delta E_{ST}$, but at the same time, was also capable of emitting thermally delayed fluorescence.

Evaluation Example 2

Compound H19 and Compound 4 (15 wt %) were co-deposited on a quartz cell to form Film 1 having a thickness of 100 Å. Likewise, Films A to C were prepared by respectively using Compounds A to C instead of Compound 4. Afterwards, C9920-02 and PMA-11 which are manufactured by Hamamatsu Photonics were used to measure a PL quantum yield of Films 1 and A to C when Films 1 and A to C were respectively excited with excitation light having a wavelength of 340 nm in a nitrogen atmosphere. Results thereof are shown in Table 4.

TABLE 4

| Film No. | Film component | PL quantum yield (%) |
|---|---|---|
| 1 | Compound 4 + H19 | 38 |
| A | Compound A + H19 | <5 |
| B | Compound B + H19 | <5 |
| C | Compound C + H19 | 30 |

Referring to Table 4, it was confirmed that Film 1 had a higher PL quantum yield than that of each of Films A to C.

Example 1

A glass substrate on which an indium tin oxide (ITO) electrode (first electrode or anode) was formed to a thickness of 1,500 Å was cleaned by ultrasonic waves using distilled water. After the distilled water-cleaning was completed, the glass substrate was sequentially sonicated with isopropyl alcohol, acetone, and methanol, and dried and transferred to a plasma cleaner. Then, the glass substrate was cleaned by using oxygen plasma for 5 minutes. Then, the glass substrate was provided to a vacuum deposition apparatus.

Compound HT3 was vacuum-deposited on the ITO electrode of the glass substrate to form a first hole injection layer having a thickness of 100 Å. Then, Compound HT-D1 was vacuum-deposited on the first hole injection layer to form a second hole injection layer having a thickness of 100 Å, and mCP was deposited on the second hole injection layer to form an electron blocking layer having a thickness of 150 Å, thereby forming a hole transport region.

Compound H19 (host) and Compound 4 (dopant) were co-deposited at a volume ratio of 85:15 on the hole transport region to form an emission layer having a thickness of 300 Å.

Compound ET3 was vacuum-deposited on the emission layer to form an electron transport layer having a thickness of 300 Å, and ET-D1 (Liq) was deposited on the electron transport layer to form an electron injection layer having a thickness of 10 Å. In addition, Al was formed on the electron injection layer to form an Al second electrode (cathode) having a thickness of 1,200 Å, thereby completing the manufacture of an organic light-emitting device:

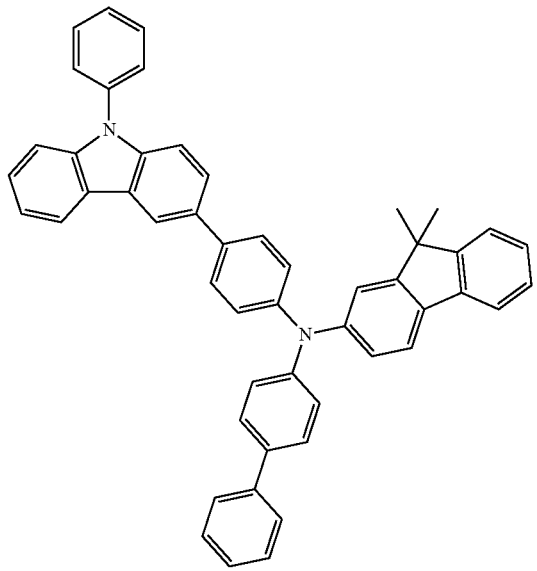

HT3

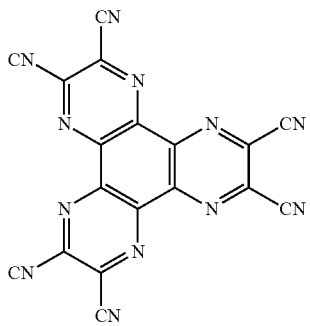

HT-D1 mCP

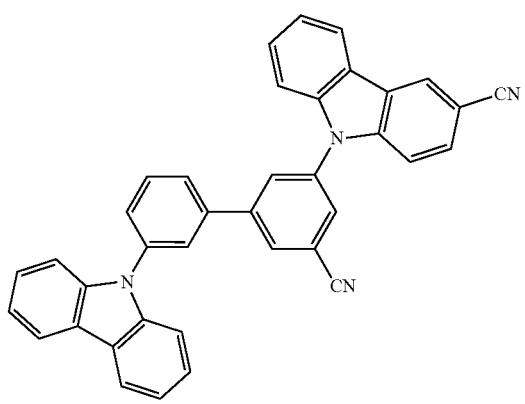

H19

-continued

ET3

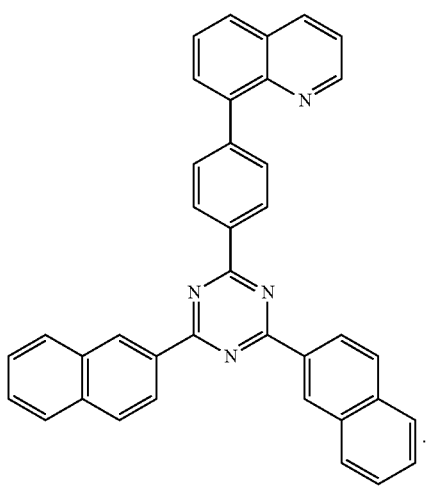

Comparative Examples A to C

Organic light-emitting devices were manufactured in the same manner as in Example 1, except that Compounds shown in Table 5 were each used as a dopant instead of Compound 4 in forming an emission layer.

Evaluation Example 3

Regarding the organic light-emitting devices of Example 1 and Comparative Examples A to C, the driving voltage, external quantum efficiency, and lifespan were measured by using a current-voltage meter (Keithley 2400) and a luminance meter (Minolta Cs-1000A) (at 500 cd/m$^2$), and results thereof are shown in Table 5. In Table 5, the lifespan (T$_{95}$)(at 500 cd/m$^2$)(relative value) data indicate an amount of time (hr) that lapsed when luminance was 95% of initial luminance (100%), and were indicated by the relative value. The driving voltage, external quantum efficiency, and lifespan were each indicated by the relative value of data of Comparative Example A.

TABLE 5

| Example No. | Host | Dopant | Driving voltage (relative value (%)) | External quantum efficiency (relative value (%)) | Roll-off (%) | LT$_{95}$ at 500 cd/m$^2$ (relative value (%)) |
|---|---|---|---|---|---|---|
| Example 1 | Compound H19 | Compound 4 | 90.2 | 103 | 22.1 | 300 |
| Comparative Example A | Compound H19 | Compound A | 100 | 100 | 27.2 | 100 |
| Comparative Example B | Compound H19 | Compound B | 110 | 91.4 | 31.1 | 172 |
| Comparative Example C | Compound H19 | Compound C | 97 | 98.7 | 38 | 48 |

Referring to Table 5, it was confirmed that the organic light-emitting device of Example 1 has excellent driving voltage, external quantum efficiency, roll-off ratio, and/or long lifespan characteristics, as compared with the organic light-emitting devices of Comparative Examples A to C.

According to the one or more embodiments, the condensed cyclic compound has excellent delayed fluorescence characteristics, and an organic light-emitting device including the condensed cyclic compound may accordingly have high efficiency and/or long lifespan.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the FIGURES, it will be understood by those of ordinary skill in the art that various changes in form and details may be made therein without departing from the spirit and scope as defined by the following claims.

What is claimed is:
1. A condensed cyclic compound represented by Formula 1:

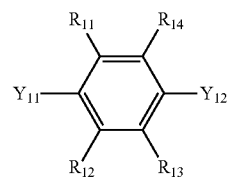

Formula 1

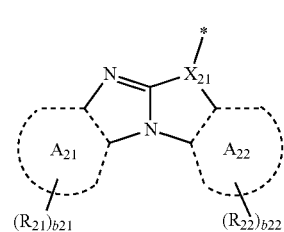

Formula 2-1

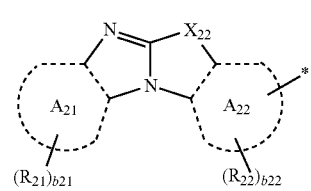

Formula 2-2

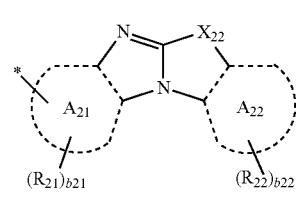

Formula 2-3

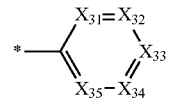

Formula 3-1

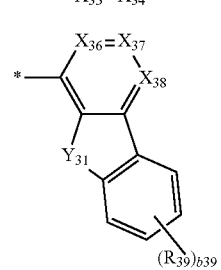

Formula 3-2

-continued

Formula 3-3

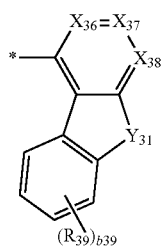

Formula 3-4

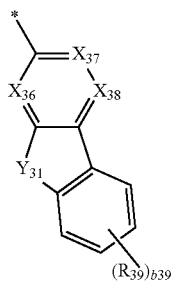

Formula 3-5

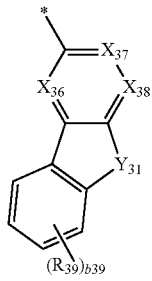

Formula 4-1

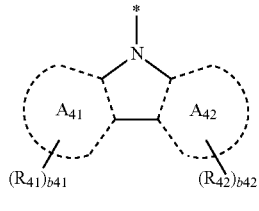

Formula 4-2

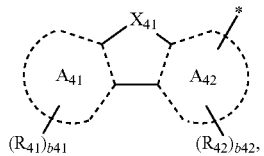

wherein, in Formulae 1, 2-1 to 2-3, 3-1 to 3-5, 4-1, and 4-2, $Y_{11}$ is a group represented by Formulae 2-1 to 2-3, $Y_{12}$ is a group represented by Formulae 3-1 to 3-5, 4-1, or 4-2, $X_{21}$ is N or $C(R_{23})$, $X_{22}$ is $N(R_{24})$, $C(R_{24})(R_{25})$, O, or S, $X_{31}$ is N or $C(R_{31})$, $X_{32}$ is N or $C(R_{32})$, $X_{33}$ is N or $C(R_{33})$, $X_{34}$ is N or $C(R_{34})$, $X_{35}$ is N or $C(R_{35})$, $X_{36}$ is N or $C(R_{36})$, $X_{37}$ is N or $C(R_{37})$, and $X_{38}$ is N or $C(R_{38})$, wherein at least one $X_{31}$ to $X_{35}$ in Formula 3-1 is N, and at least one $X_{36}$ to $X_{38}$ in Formulae 3-2 to 3-5 is N, $Y_{31}$ is O or S, $X_{41}$ is O, S, $N(R_{43})$, or $C(R_{43})(R_{44})$, ring $A_{21}$, ring $A_{22}$, ring $A_{41}$, and ring $A_{42}$ are each independently a $C_5$-$C_{60}$ carbocyclic group or a $C_2$-$C_{60}$ heterocyclic group, $R_{11}$ to $R_{14}$ are each independently hydrogen, deuterium, —F, —Cl, —Br, —I, a hydroxyl group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_7$-$C_{60}$ alkylaryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_2$-$C_{60}$ alkylheteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —B($Q_1$)($Q_2$), —N($Q_1$)($Q_2$), —P($Q_1$)($Q_2$), —C(=O)($Q_1$), —S(=O)($Q_1$), —S(=O)$_2$($Q_1$), —P(=O)($Q_1$)($Q_2$), or —P(=S)($Q_1$)($Q_2$), $R_{21}$ to $R_{25}$, $R_{31}$ to $R_{39}$, and $R_{41}$ to $R_{44}$ are each independently hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_7$-$C_{60}$ alkylaryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_2$-$C_{60}$ alkylheteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —B($Q_1$)($Q_2$), —N($Q_1$)($Q_2$), —P($Q_1$)($Q_2$), —C(=O)($Q_1$), —S(=O)($Q_1$), —S(=O)$_2$($Q_1$), —P(=O)($Q_1$)($Q_2$), or —P(=S)($Q_1$)($Q_2$), b21, b22, b39, b41, and b42 are each independently 1, 2, 3, 4, 5, 6, 7, 8, 9, or 10, $Q_1$ to $Q_3$ are each independently hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_7$-$C_{60}$ alkylaryl group, a $C_6$-$C_{60}$ aryloxy group, a $C_6$-$C_{60}$ arylthio group, a $C_1$-$C_{60}$ heteroaryl group, a $C_2$-$C_{60}$ alkylheteroaryl group, a $C_1$-$C_{60}$ heteroaryloxy group, a $C_1$-$C_{60}$ heteroarylthio group, a monovalent non-aromatic condensed polycyclic group, a monovalent non-aromatic condensed heteropoly cyclic group, a $C_1$-$C_{60}$ alkyl group substituted with deuterium, —F, a cyano group, a $C_1$-$C_{60}$ alkyl group, a $C_6$-$C_{60}$ aryl group, or any combination thereof, or a $C_6$-$C_{60}$ aryl group substituted with deuterium, —F, a cyano group, a $C_1$-$C_{60}$ alkyl group, a $C_6$-$C_{60}$ aryl group, or any combination thereof, and

* indicates a binding site to a neighboring atom, wherein the condensed cyclic compound satisfies Equation 1, $$0 \text{ eV} < \Delta E_{ST} \leq 0.5 \text{ eV}, \qquad \text{Equation 1}$$

in Equation 1, $\Delta E_{ST}$ indicates a different between a lowest excitation singlet energy level ($E_{S1}$) of the condensed cyclic compound of Formula 1 and a lowest excitation triplet energy level ($E_{T1}$) of the condensed cyclic compound of Formula 1; and the lowest excitation triplet energy level $E_{T1}$ and the lowest excitation singlet energy level $E_{S1}$ are evaluated by a DFT method of Gaussian program structurally optimized at a level of B3LYP, 6-31 G(d,p).

2. The condensed cyclic compound of claim 1, wherein
$X_{21}$ is N, and
$X_{22}$ is $N(R_{24})$, O, or S.

3. The condensed cyclic compound of claim 1, wherein two or three of $X_{31}$ to $X_{35}$ in Formula 3-1 are respectively N, and
two of $X_{36}$ to $X_{38}$ in Formulae 3-2 to 3-5 are respectively N.

4. The condensed cyclic compound of claim 1, wherein $X_{41}$ is $N(R_{43})$.

5. The condensed cyclic compound of claim 1, wherein ring $A_{21}$, ring $A_{22}$, ring $A_{41}$, and ring $A_{42}$ are each independently a benzene group, a naphthalene group, an anthracene group, a phenanthrene group, a phenalene group, a triphenylene group, a pyridine group, a pyrimidine group, a pyrazine group, a pyridazine group, a triazine group, a quinoline group, an isoquinoline group, a 2,6-naphthyridine group, a 1,8-naphthyridine group, a 1,5-naphthyridine group, a 1,6-naphthyridine group, a 1,7-naphthyridine group, a 2,7-naphthyridine group, a quinoxaline group, a phthalazine group, a quinazoline group, a phenanthroline group, a benzoquinoline group, a benzoisoquinoline group, a benzoquinoxaline group, a benzoquinazoline group, a furan group, a thiophene group, a silole group, an indene group, a fluorene group, an indole group, a carbazole group, a benzofuran group, a dibenzofuran group, a benzothiophene group, a dibenzothiophene group, a benzosilole group, a dibenzosilole group, an indenopyridine group, an indolopyridine group, a benzofuropyridine group, a benzothienopyridine group, a benzosilolopyridine group, an indenopyrimidine group, an indolopyrimidine group, a benzofuropyrimidine group, a benzothienopyrimidine group, or a benzosilolopyrimidine group.

6. The condensed cyclic compound of claim 1, wherein ring $A_{21}$ and ring $A_{22}$ are each independently a benzene group or a naphthalene group, and
ring $A_{41}$ and ring $A_{42}$ are each independently a benzene group, a naphthalene group, a fluorene group, a carbazole group, a dibenzofuran group, or a dibenzothiophene group.

7. The condensed cyclic compound of claim 1, wherein $R_{11}$ to $R_{14}$, $R_{21}$ to $R_{25}$, $R_{31}$ to $R_{39}$, and $R_{41}$ to $R_{44}$ are each independently:

hydrogen, deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, or a $C_1$-$C_{20}$ alkoxy group;

a $C_1$-$C_{20}$ alkyl group or a $C_1$-$C_{20}$ alkoxy group, each substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a cyclopentyl group, a cyclohexyl group, a cycloheptyl group, a cyclooctyl group, a an adamantyl group, a norbornyl group, a norbornenyl group, a cyclopentenyl group, a cyclohexenyl group, a cycloheptenyl group, a phenyl group, a biphenyl group, a $C_1$-$C_{20}$ alkylphenyl group, a naphthyl group, a pyridinyl group, a pyrimidinyl group, or any combination thereof;

a cyclopentyl group, a cyclohexyl group, a cycloheptyl group, a cyclooctyl group, a an adamantyl group, a norbornyl group, a norbornenyl group, a cyclopentenyl group, a cyclohexenyl group, a cycloheptenyl group, a phenyl group, a biphenyl group, a $C_1$-$C_{20}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, an imidazopyridinyl group, or an imidazopyrimidinyl group;

a cyclopentyl group, a cyclohexyl group, a cycloheptyl group, a cyclooctyl group, an adamantyl group, a norbornyl group, a norbornenyl group, a cyclopentenyl group, a cyclohexenyl group, a cycloheptenyl group, a phenyl group, a biphenyl group, a $C_1$-$C_{20}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, an imidazopyridinyl group, or an imidazopyrimidinyl group, each substituted with deuterium, —F, —Cl, —Br, —I, —CD$_3$, —CD$_2$H, —CDH$_2$, —CF$_3$, —CF$_2$H, —CFH$_2$, a hydroxyl group, a nitro group, a cyano group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclooctyl group, an adamantyl group, a norbornyl group, a norbornenyl group, a cyclopentenyl group, a cyclohexenyl group, a cycloheptenyl group, a phenyl group, a biphenyl group, a phenyl($C_1$-$C_{20}$ alkyl) group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyridinyl group substituted with a phenyl group, a pyrazinyl group, a pyrazinyl group substituted with a phenyl group, a pyrimidinyl group, a pyrimidinyl group substituted with a phenyl group, a pyridazinyl group, a pyridazinyl group substituted with a phenyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a triazinyl group substituted with a phenyl group, a dibenzofuranyl group, a dibenzothiophenyl group, a dibenzosilolyl group, a benzocarbazolyl group, a dibenzocarbazolyl group, an imidazopyridinyl group, an imidazopyrimidinyl group, —Si(Q$_{11}$)(Q$_{12}$)(Q$_{13}$), —B(Q$_{11}$)(Q$_{12}$), —N(Q$_{11}$)(Q$_{12}$), or any combination thereof; and —Si(Q$_1$)(Q$_2$)(Q$_3$), —B(Q$_1$)(Q$_2$), or —N(Q$_1$)(Q$_2$), and Q$_1$ to Q$_3$ and Q$_{11}$ to Q$_{13}$ are each independently:

a methyl group, an ethyl group, an n-propyl group, an isopropyl group, an n-butyl group, an isobutyl group, a sec-butyl group, a tert-butyl group, an n-pentyl group, an isopentyl group, a 2-methylbutyl group, a sec-pentyl group, a tert-pentyl group, a neo-pentyl group, a 3-pentyl group, a 3-methyl-2-butyl group, a phenyl group, a biphenyl group, a phenyl($C_1$-$C_{20}$ alkyl) group, or a naphthyl group; or a methyl group, an ethyl group, an n-propyl group, an isopropyl group, an n-butyl group, an isobutyl group, a sec-butyl group, a tert-butyl group, an n-pentyl group, an isopentyl group, a 2-methylbutyl group, a sec-pentyl group, a tert-pentyl group, a neo-pentyl group, a 3-pentyl group, a 3-methyl-2-butyl group, a phenyl group, or a naphthyl group, each substituted with deuterium, a phenyl group, or a combination thereof.

8. The condensed cyclic compound of claim 1, wherein Y$_{11}$ is a group represented by Formulae 2-11 to 2-13:

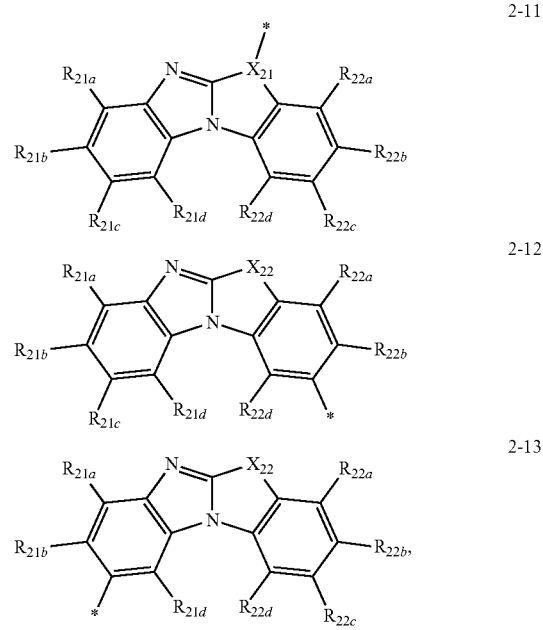

wherein, in Formulae 2-11 to 2-13,

X$_{21}$ and X$_{22}$ are the same as defined in connection with those in Formulae 2-1 to 2-3 of claim 1, R$_{21a}$ to R$_{21d}$ are each independently the same as defined in connection with R$_{21}$ in Formula 2-1 of claim 1, R$_{22a}$ to R$_{22d}$ are each independently the same as defined in connection with R$_{22}$ in Formula 2-1 of claim 1, and

* indicates a binding site to a neighboring atom.

9. The condensed cyclic compound of claim 8, wherein X$_{21}$ is N, and

X$_{22}$ is N(R$_{24}$), O, or S.

10. The condensed cyclic compound of claim 1, wherein Y$_{12}$ is a group represented by Formulae 3-11 to 3-35 or 4-11 to 4-17:

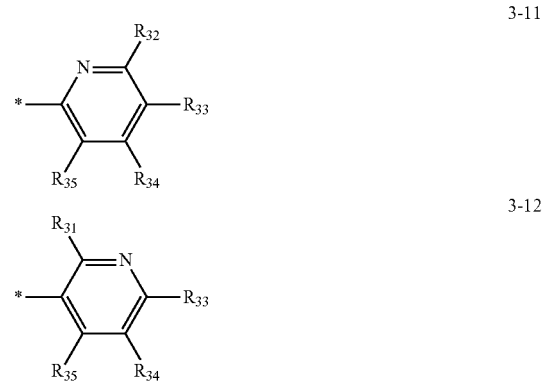

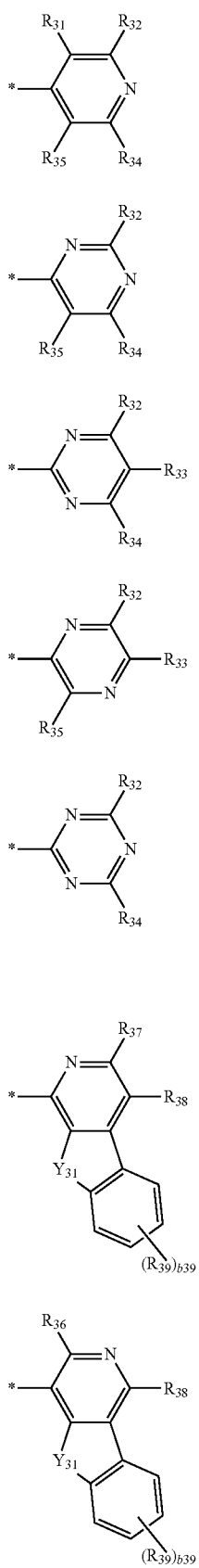
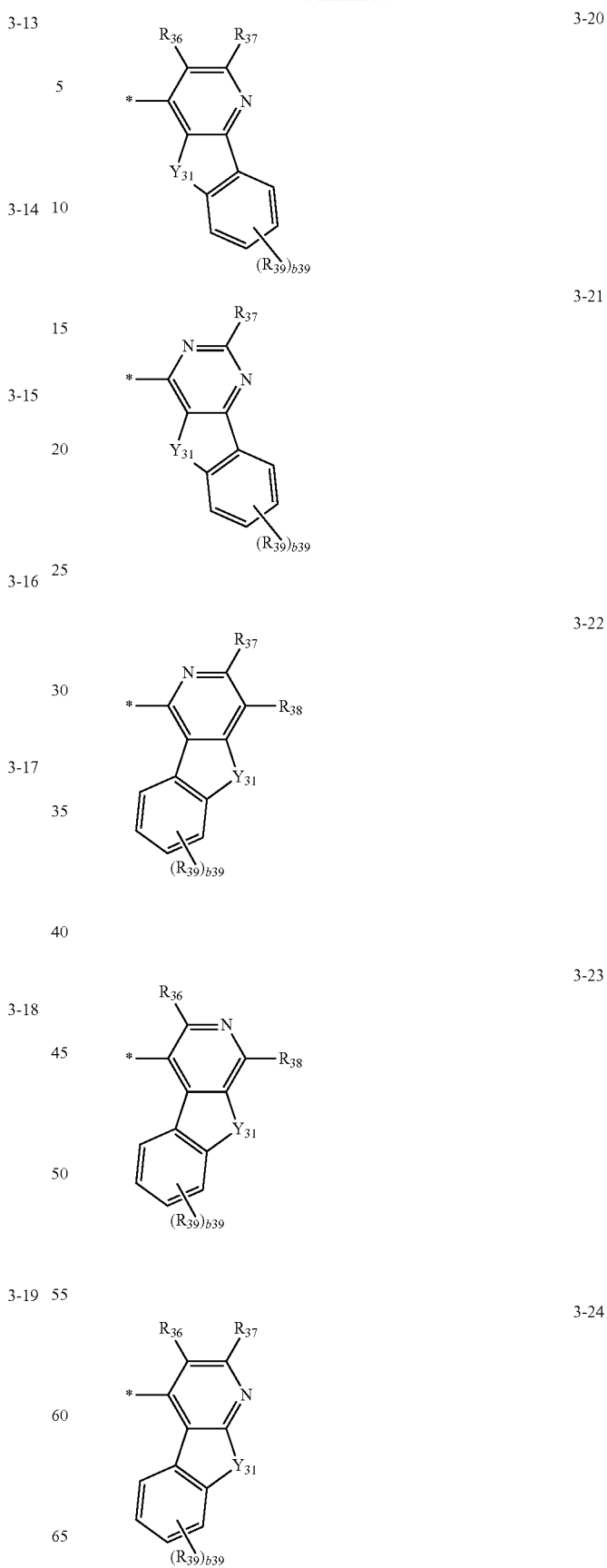

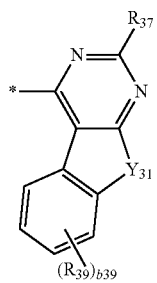 3-25
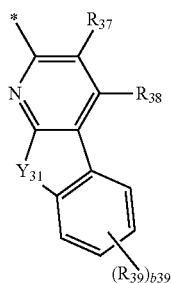 3-26
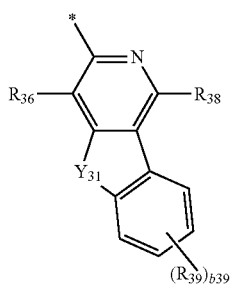 3-27
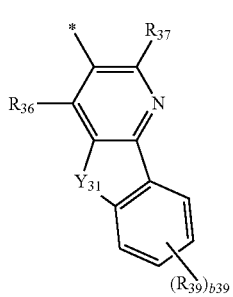 3-28
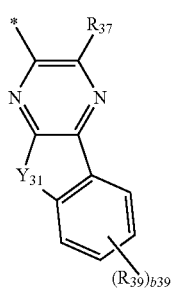 3-29
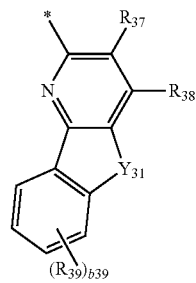 3-30
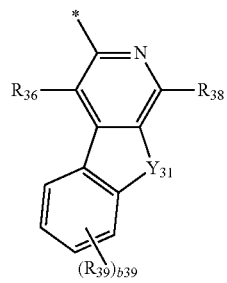 3-31
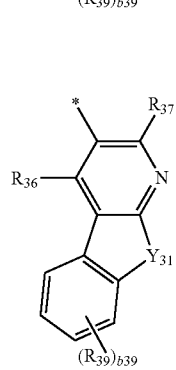 3-32
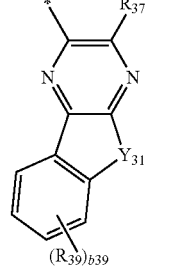 3-33
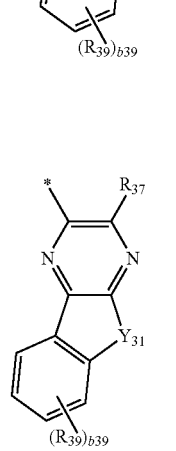 3-34

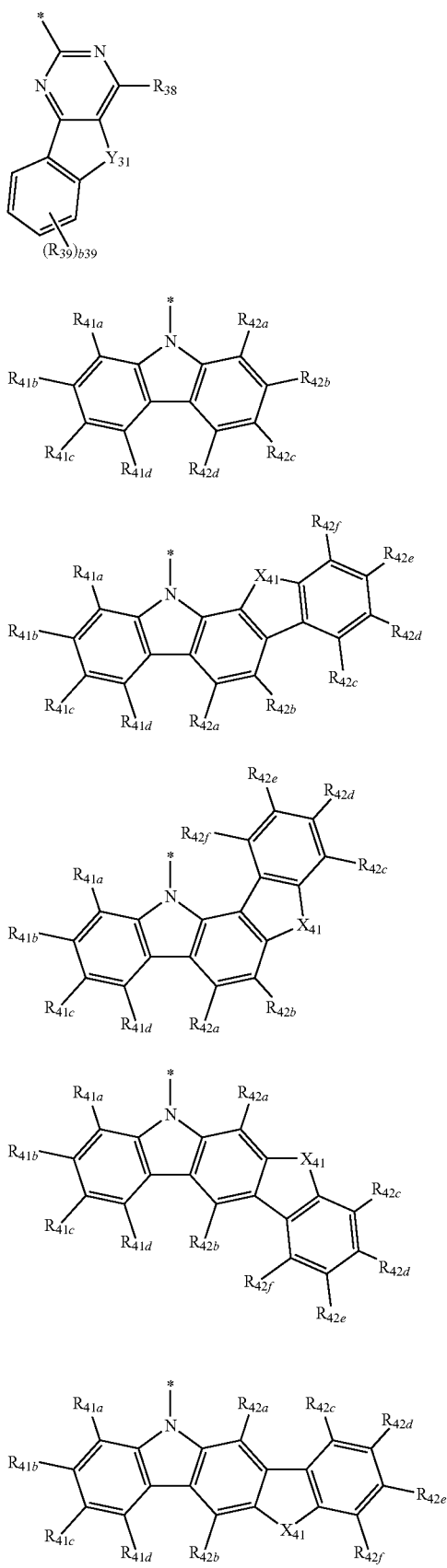
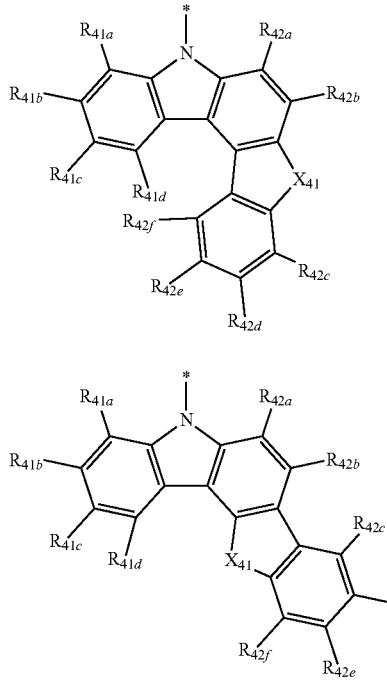

wherein, in Formulae 3-11 to 3-35 and 4-11 to 4-17,

Y$_{31}$, R$_{36}$ to R$_{39}$, and b39 are the same as defined in connection with those of Formulae 3-1 to 3-5 in claim 1, X$_{41}$ is O, S, N(R$_{42g}$), or C(R$_{42g}$)(R$_{42h}$), R$_{41a}$ to R$_{41d}$ are the same as defined in connection with R$_{41}$ in Formula 4-1 in claim 1, R$_{42a}$ to R$_{42h}$ are the same as defined in connection with R$_{42}$ in Formula 4-1 in claim 1, and

* indicates a binding site to a neighboring atom.

11. The condensed cyclic compound of claim 1, wherein Y$_{11}$ is a group represented by Formulae 2-11 to 2-13, and Y$_{12}$ is a group represented by Formulae 3-11 to 3-35 or 4-11 to 4-17:

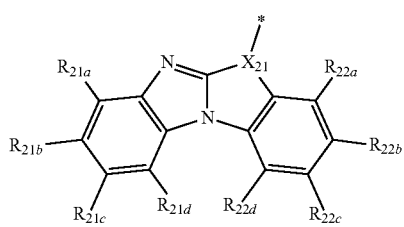
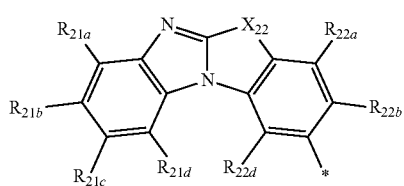

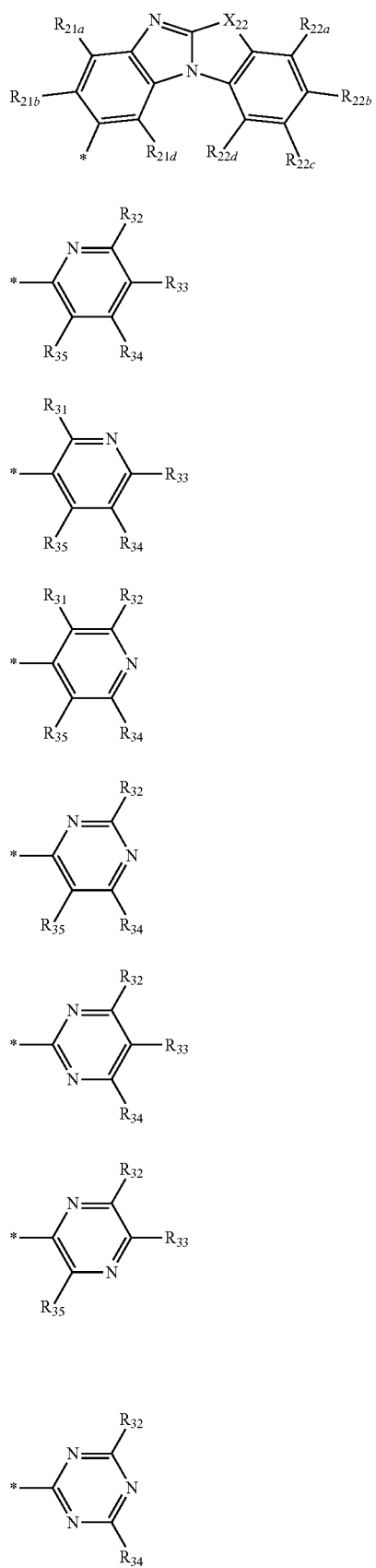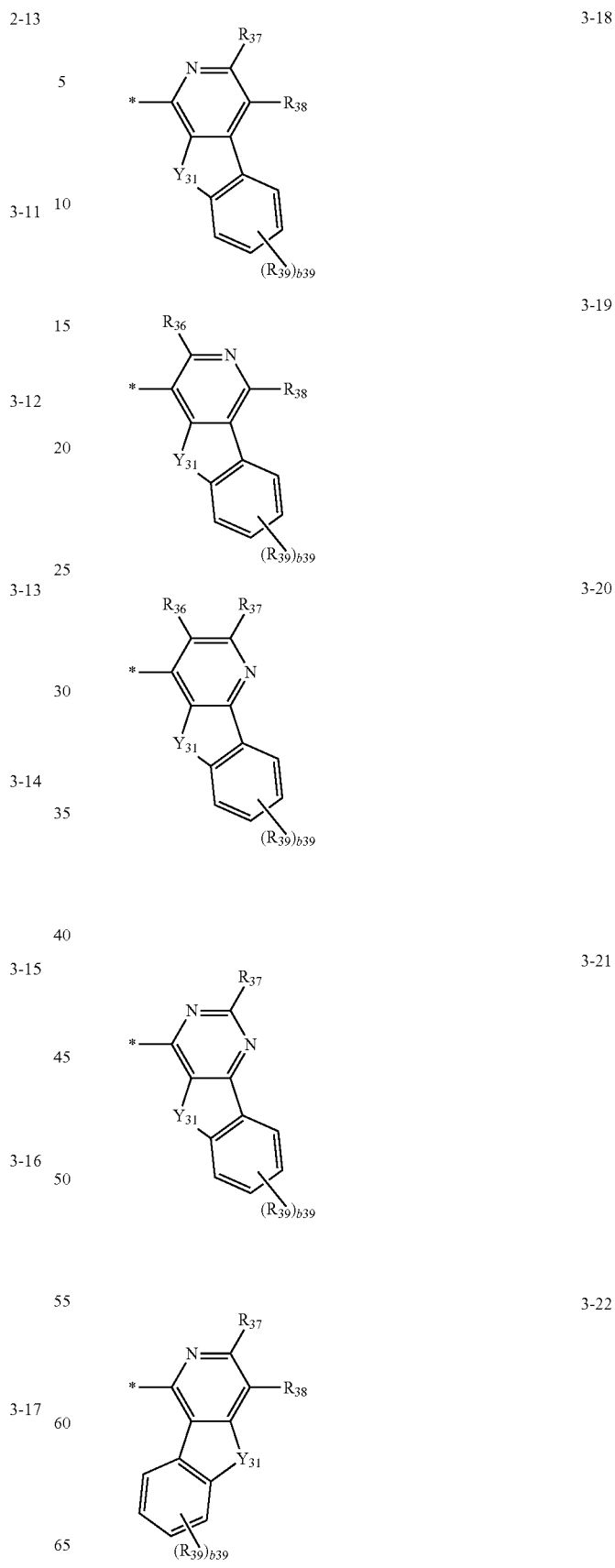

3-23 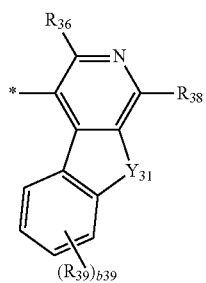
3-24 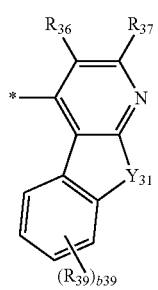
3-25 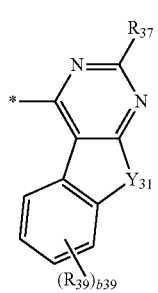
3-26 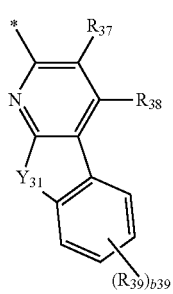
3-37 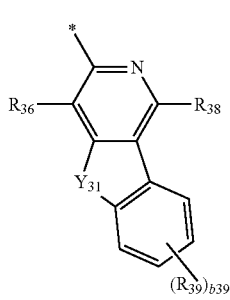
3-28 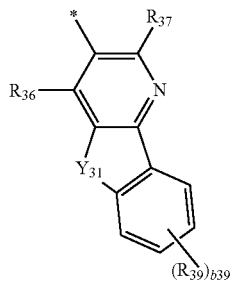
3-29 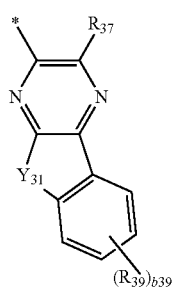
3-30 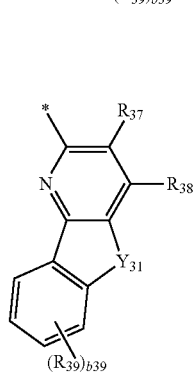
3-31 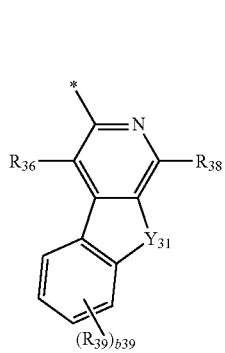
3-32 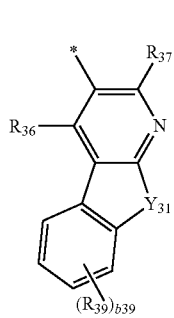

161
-continued 3-33
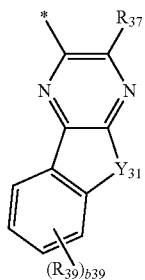

3-34
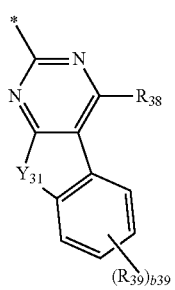

3-35
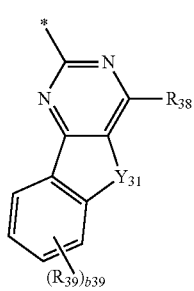

4-11
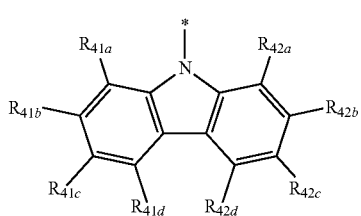

4-12
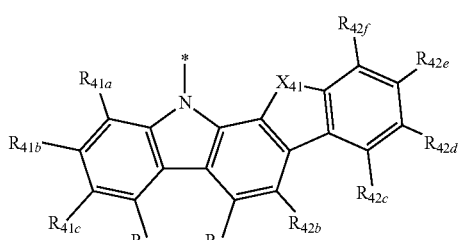

4-13
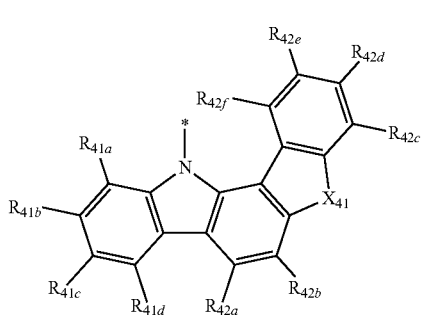

162
-continued 4-14
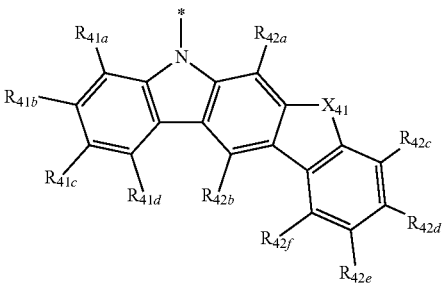

4-15
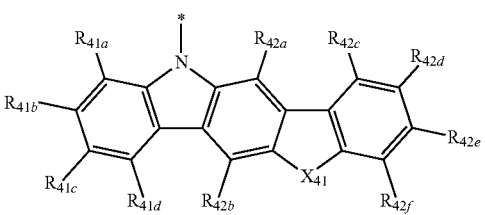

4-16
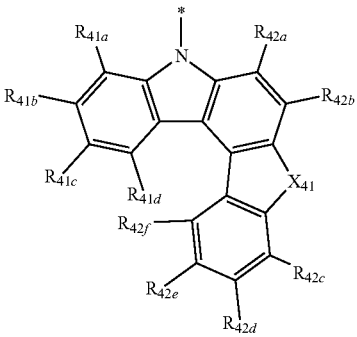

4-17
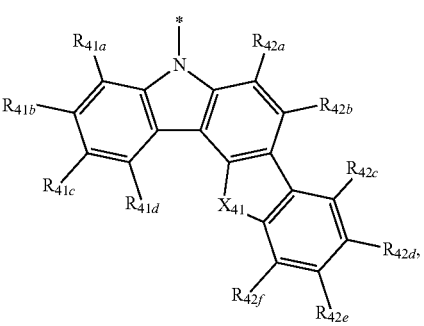

wherein, in Formulae 2-11 to 2-13, 3-11 to 3-35, and 4-11 to 4-17, $X_{21}$ and $X_{22}$ are the same as defined in connection with those in Formulae 2-1 to 2-3 in claim 1, $R_{21a}$ to $R_{21d}$ are the same as defined in connection with $R_{21}$ in Formula 2-1 in claim 1, $R_{22a}$ to $R_{22d}$ are the same as defined in connection with $R_{22}$ in Formula 2-1 in claim 1, $Y_{31}$, $R_{36}$ to $R_{39}$, and b39 are the same as defined in connection with those in Formulae 3-1 to 3-5 in claim 1, $X_{41}$ is O, S, $N(R_{42g})$, or $C(R_{42g})(R_{42h})$, $R_{41a}$ to $R_{41d}$ are the same as defined in connection with Ru in Formula 4-1 in claim 1, $R_{42a}$ to $R_{42h}$ are the same as defined in connection with $R_{42}$ in Formula 4-1 in claim 1, and \* indicates a binding site to a neighboring atom.

12. The condensed cyclic compound of claim 1, wherein the condensed cyclic compound is of Compounds 1 to 117:
1
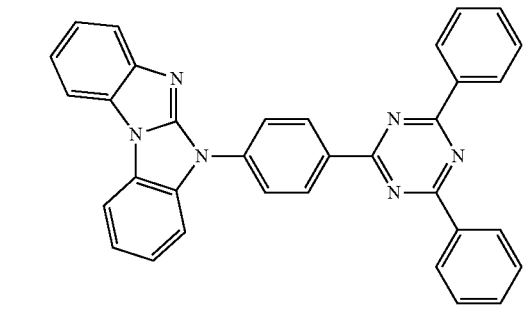
2
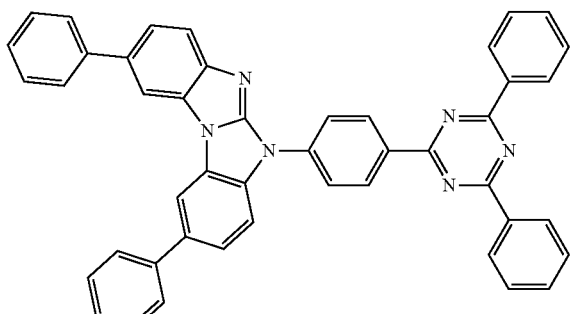
3
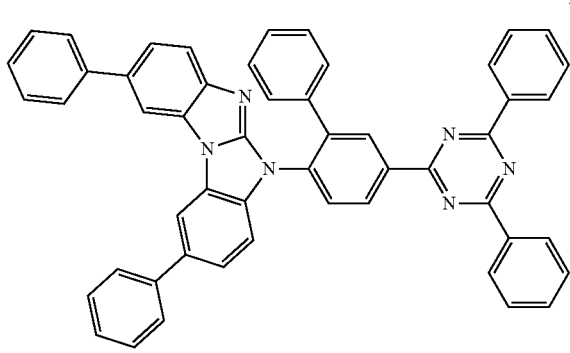
4
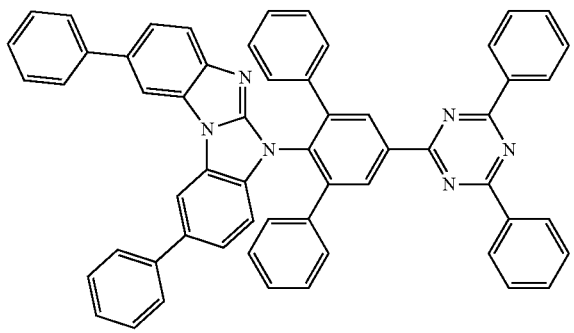
-continued
5
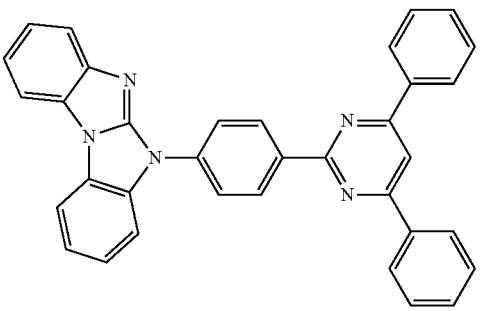
6
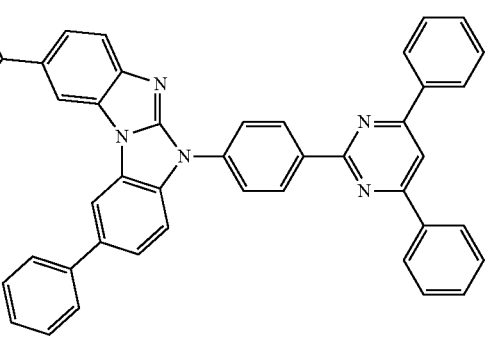
7
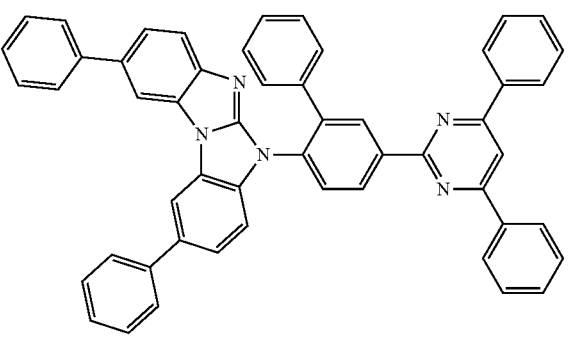
8
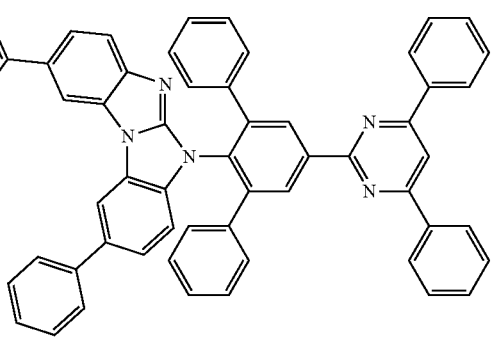

9
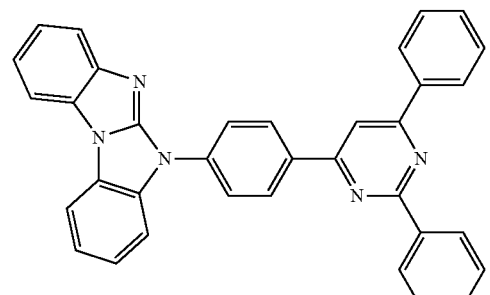
10
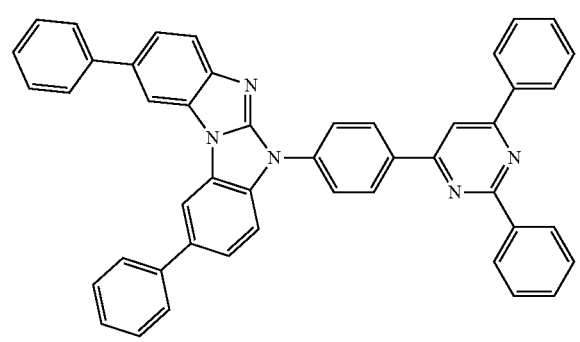
11
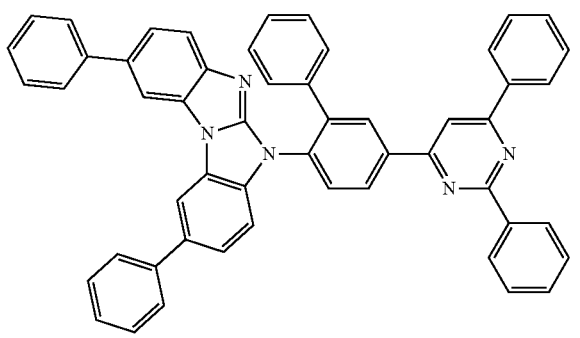
13
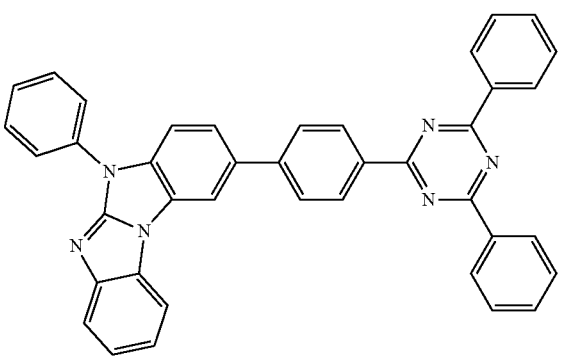
14
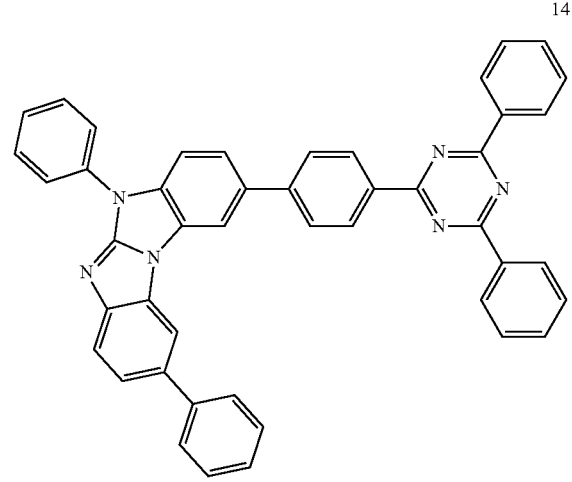
15
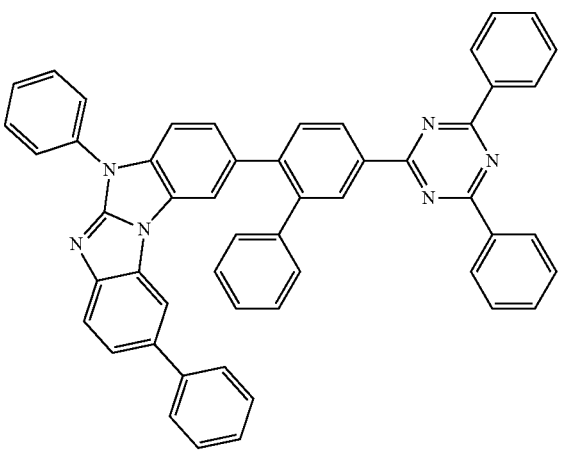

16
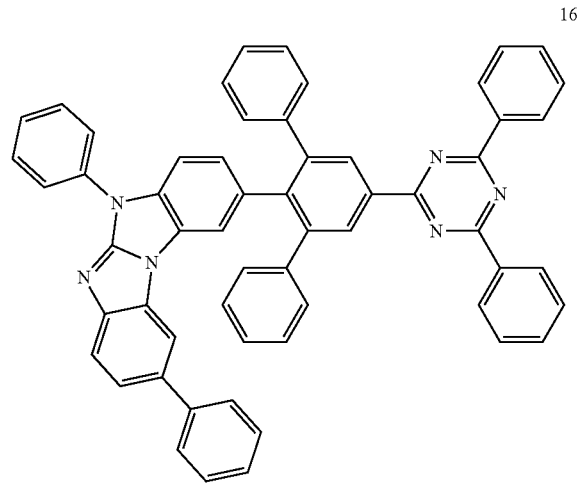
17
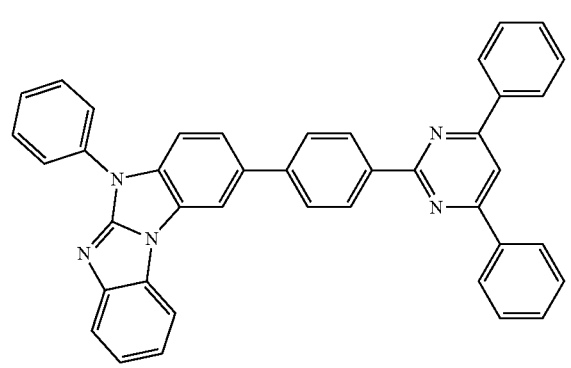
18
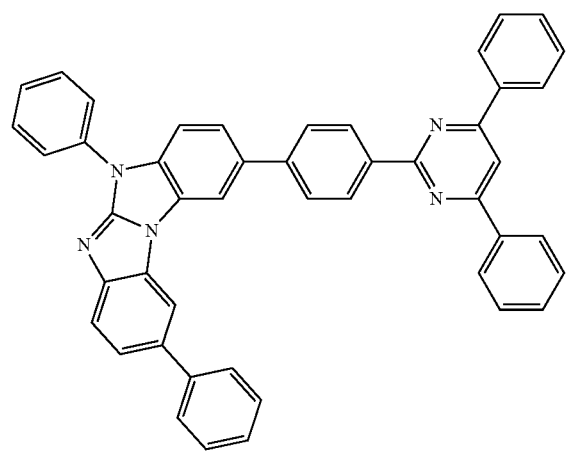
19
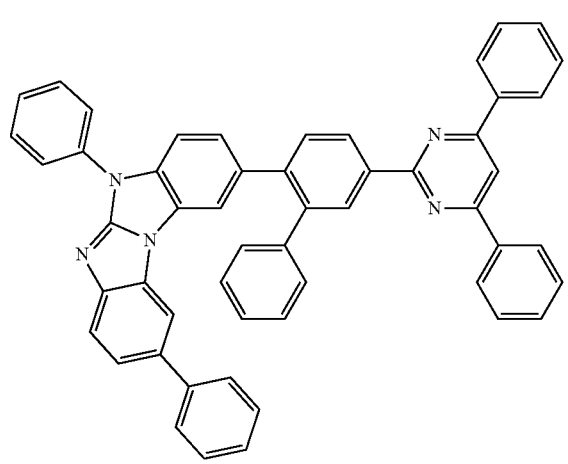
20
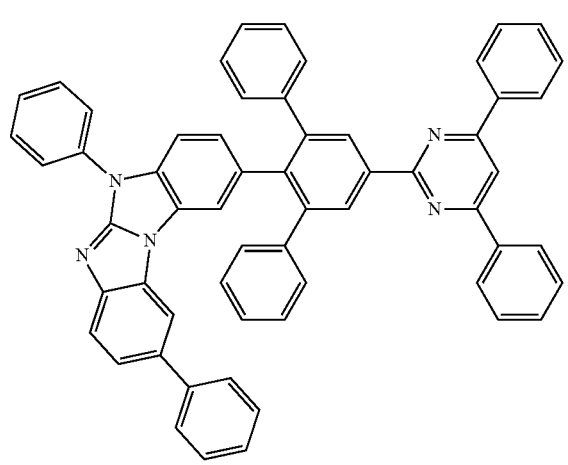
21
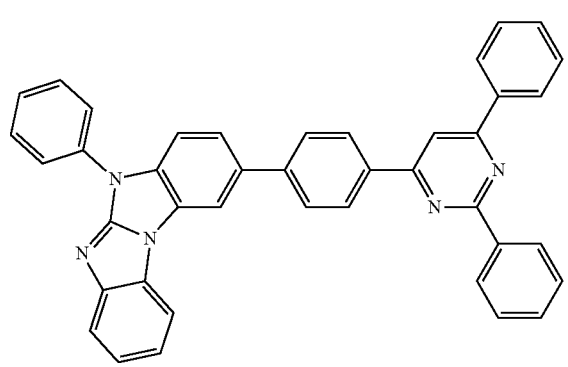

169
-continued
22
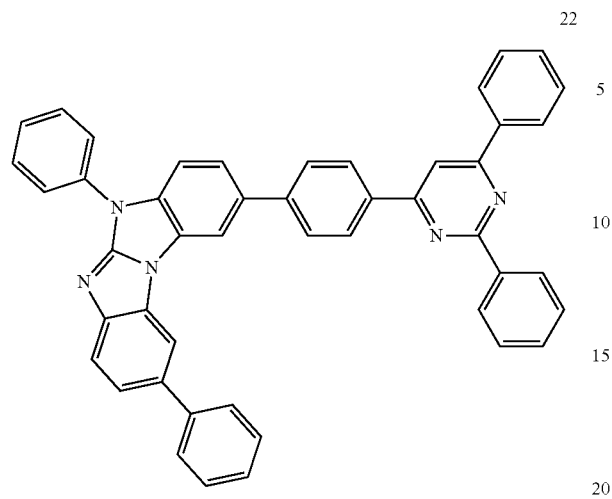
23
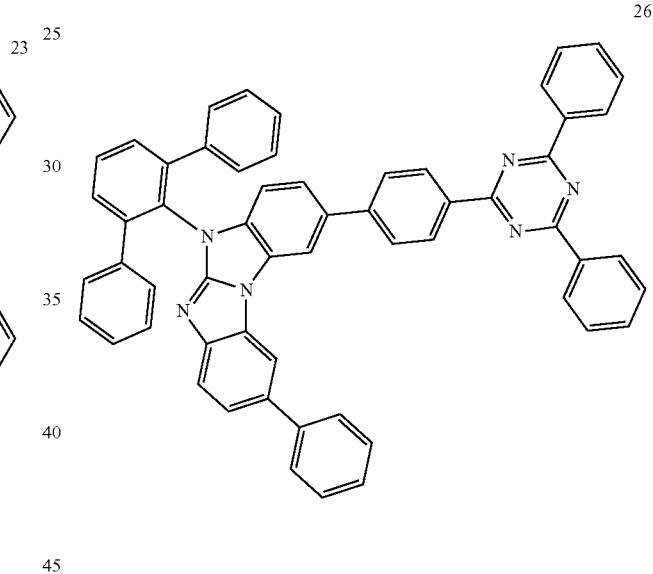
24
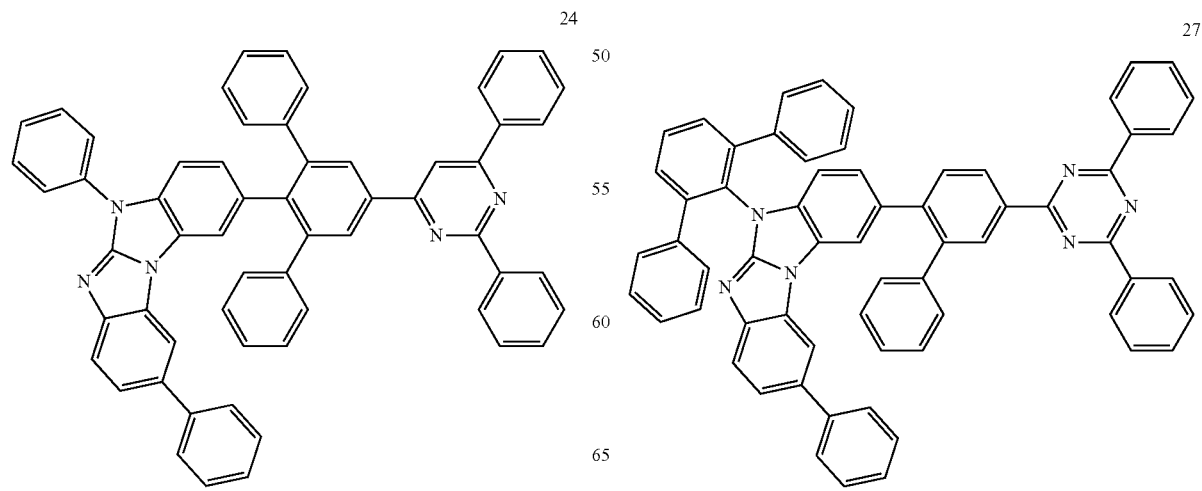
170
-continued
25
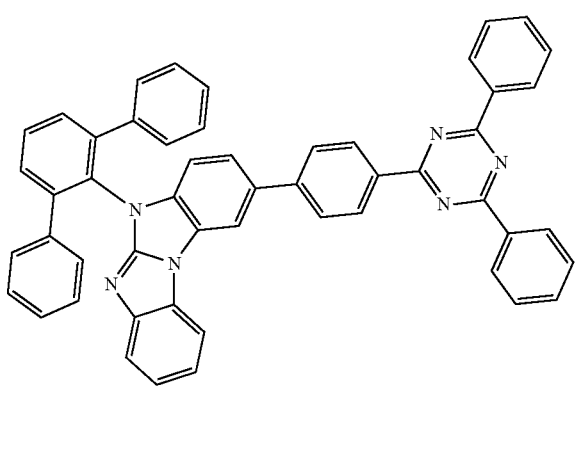
26
27

28
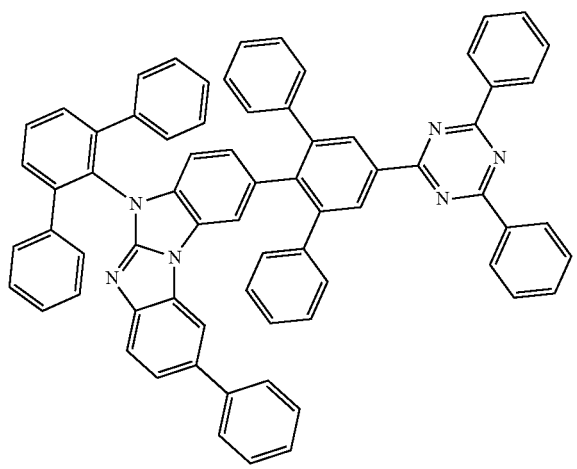
29
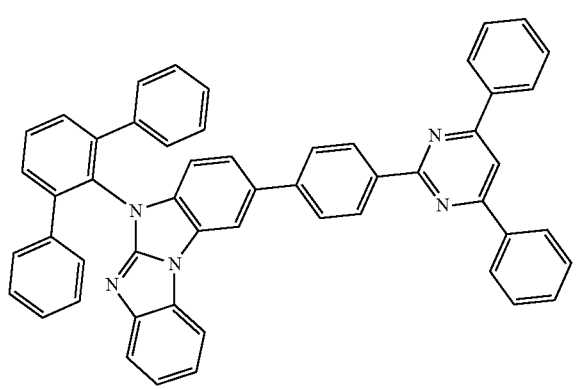
30
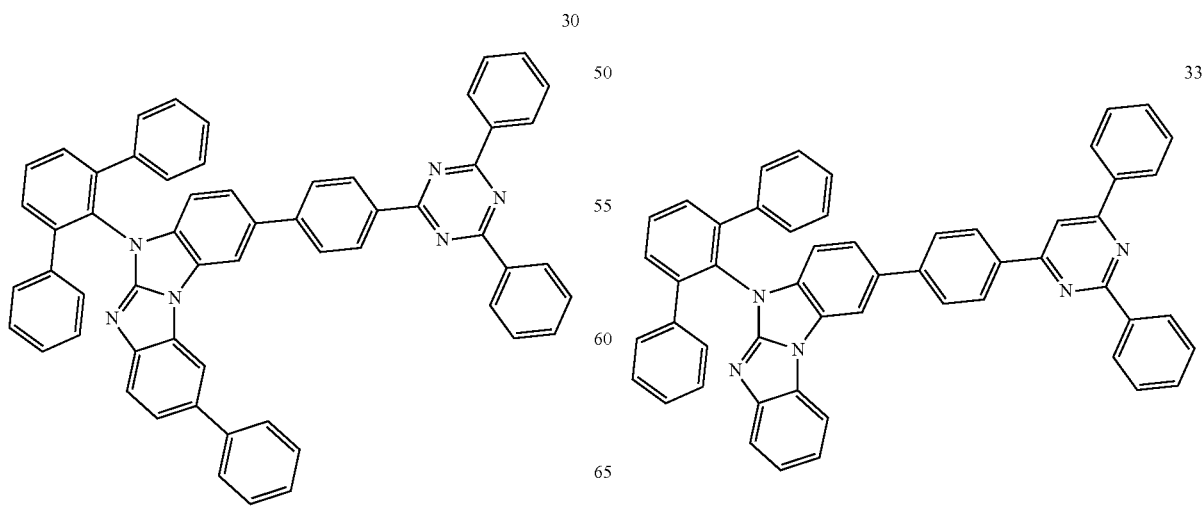
31
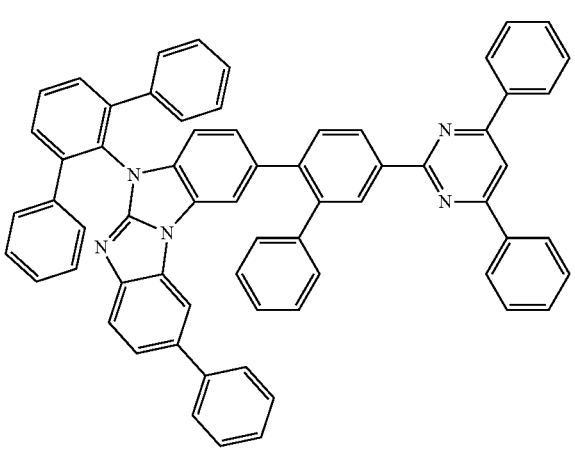
32
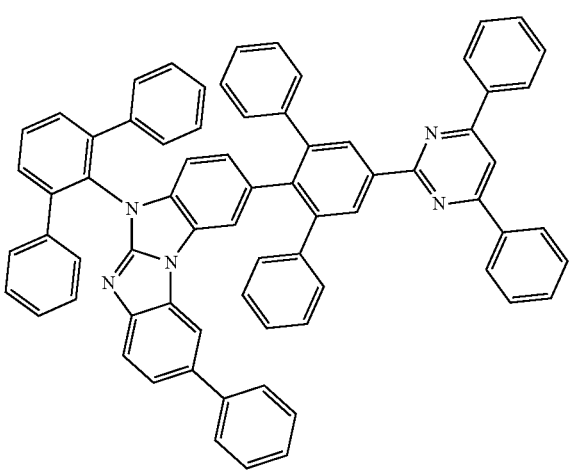

34
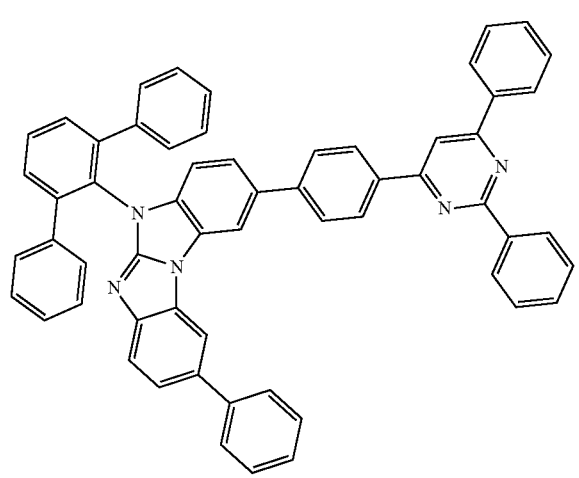
35
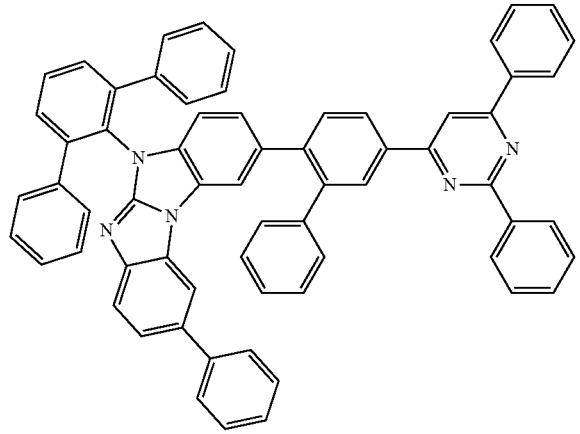
36
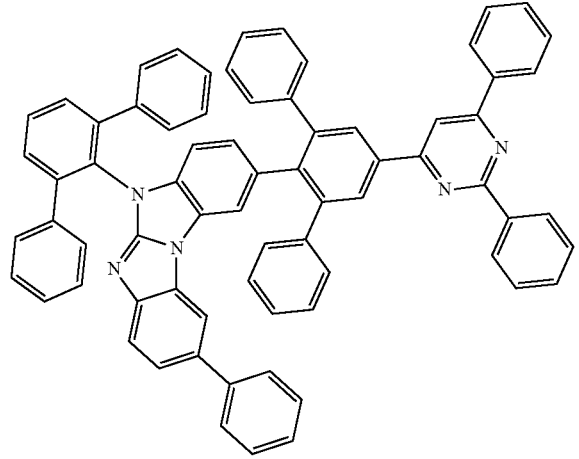
37
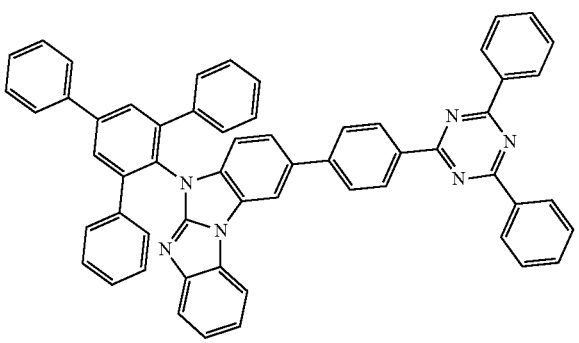
38
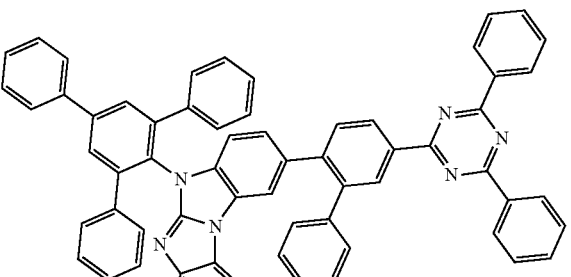
39
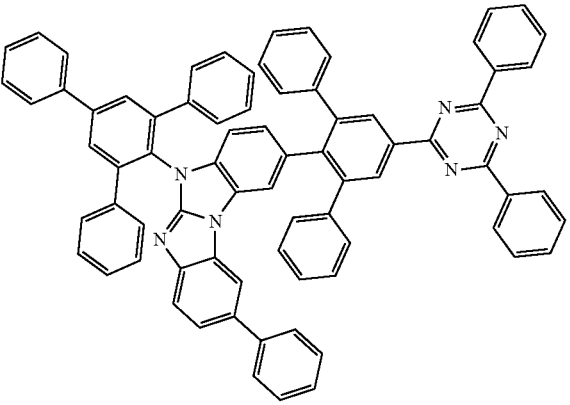
40

-continued
41
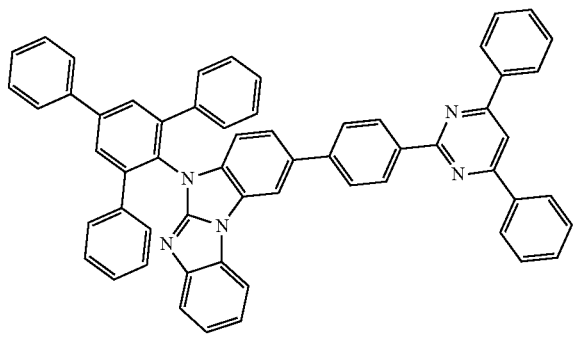
42
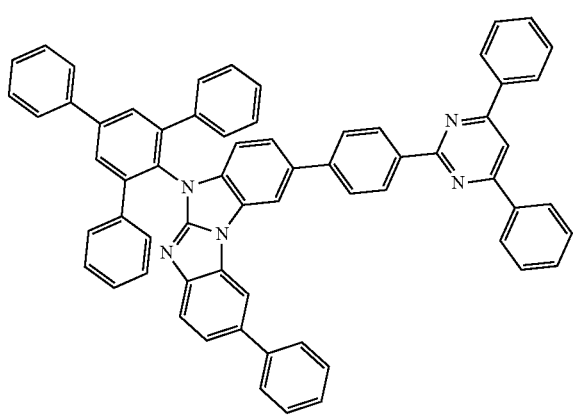
43
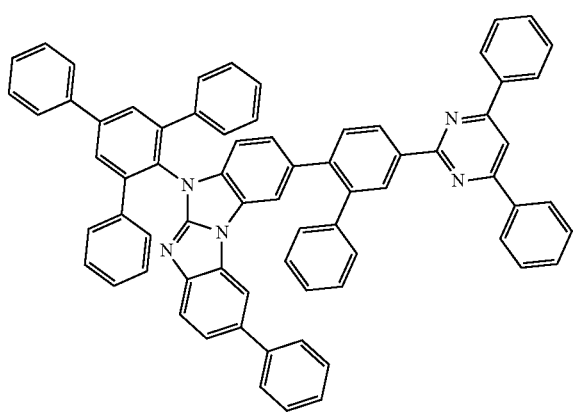
44
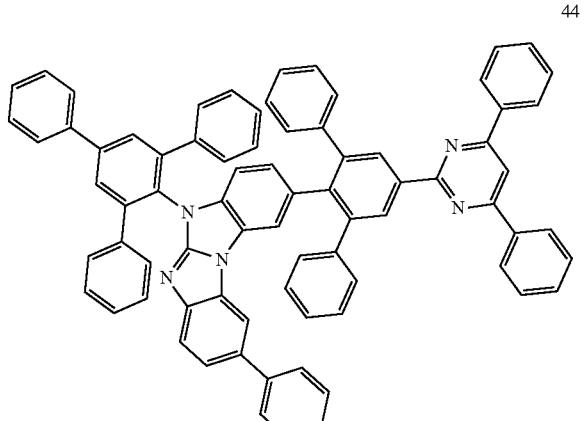
-continued
45
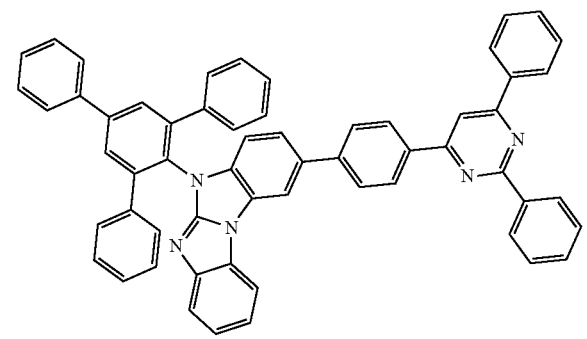
46
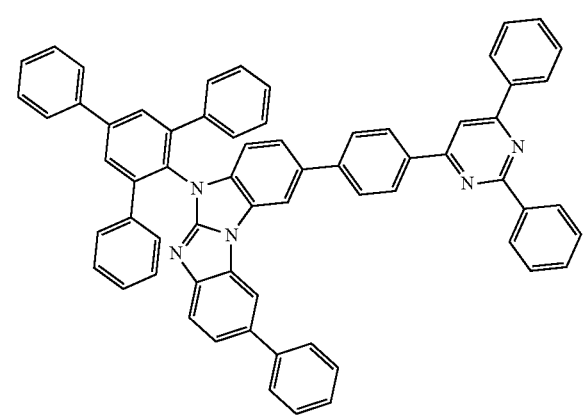
47
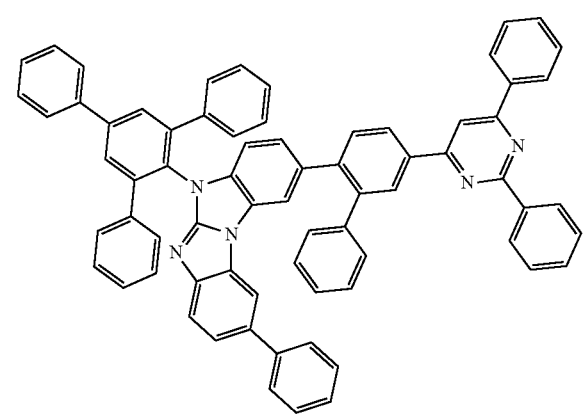
48
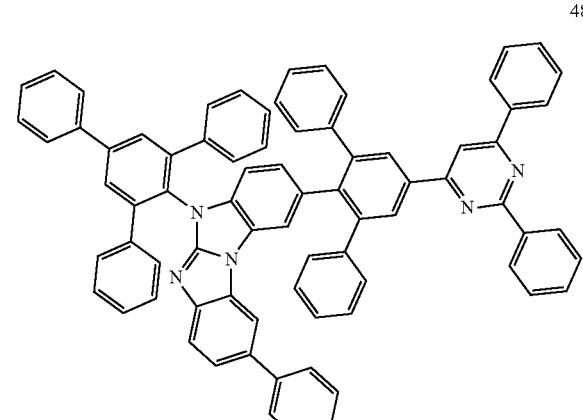

-continued
49
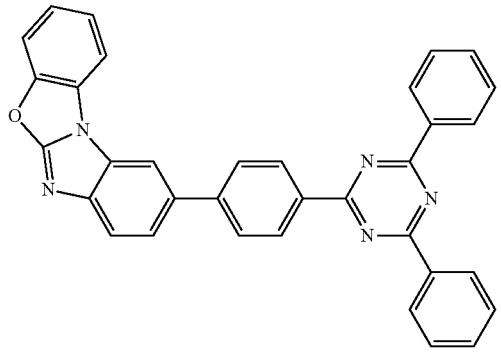
50
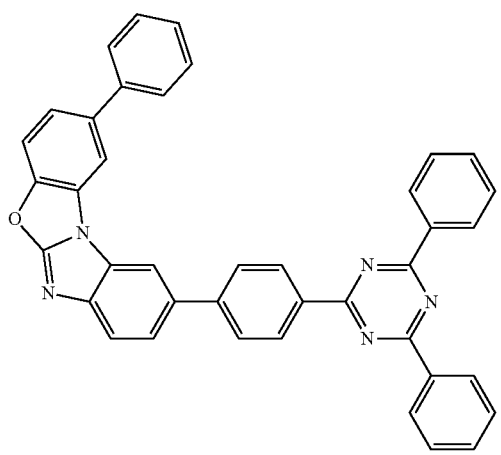
51
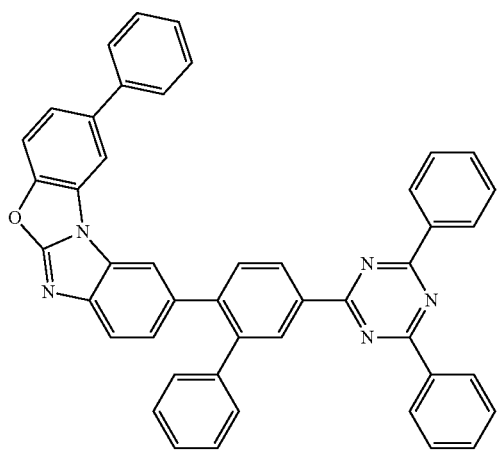
-continued
52
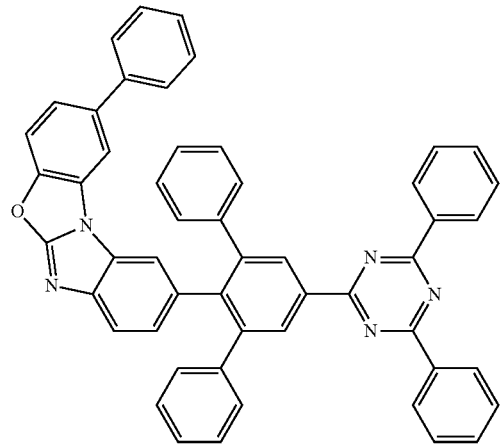
53
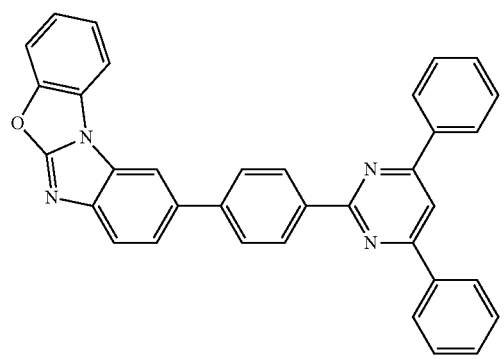
54
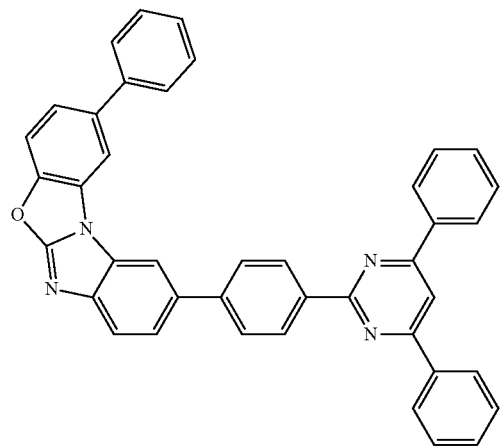

55
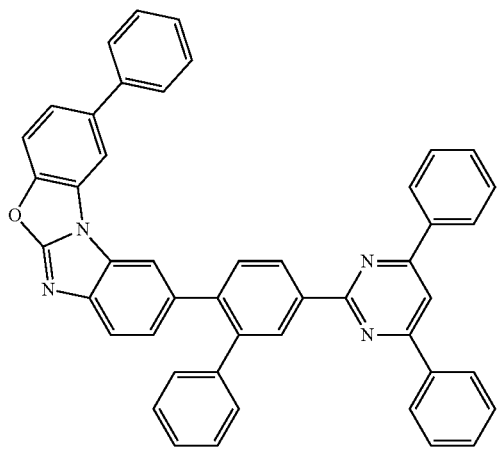
56
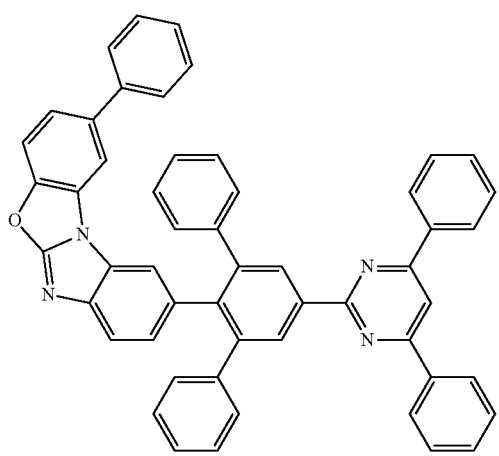
57
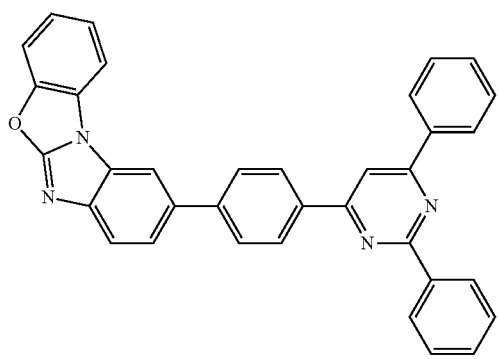
58
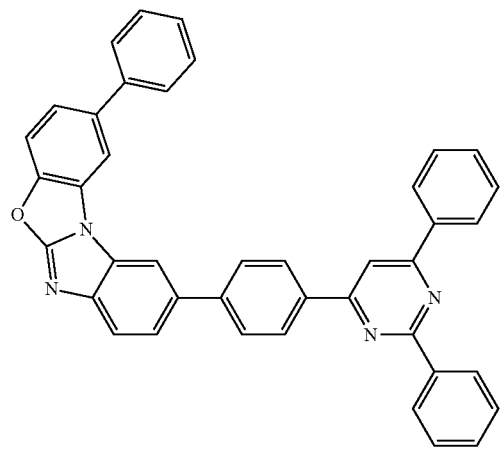
59
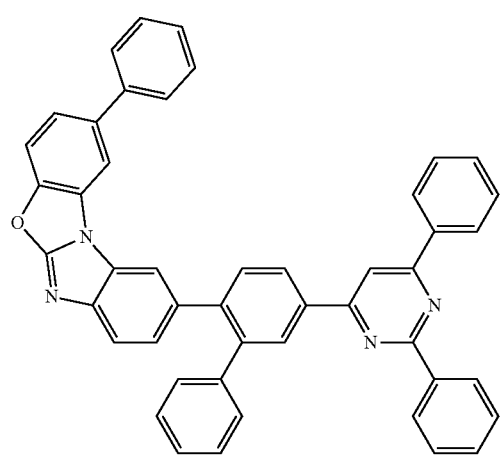
60
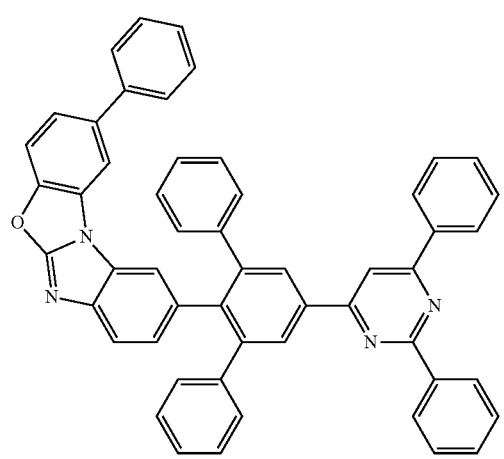

61
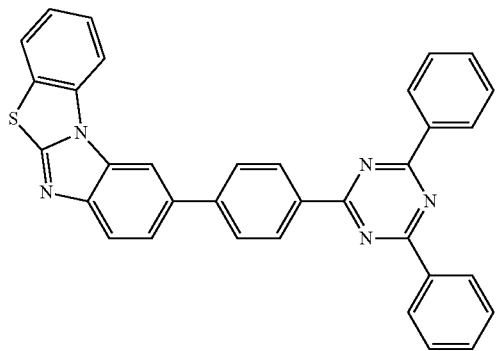
62
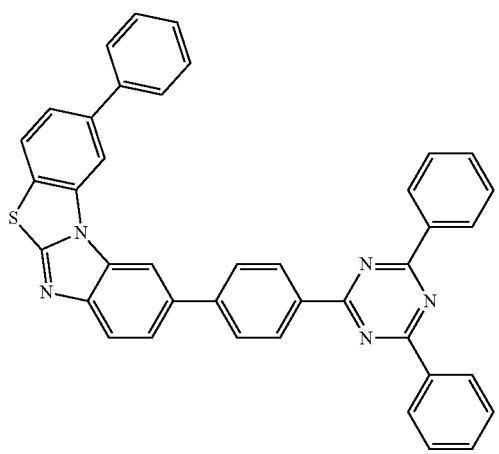
63
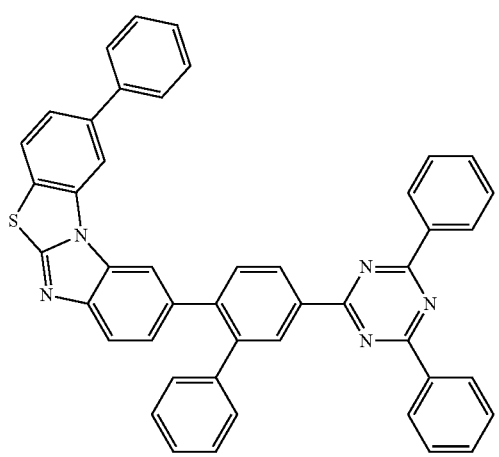
64
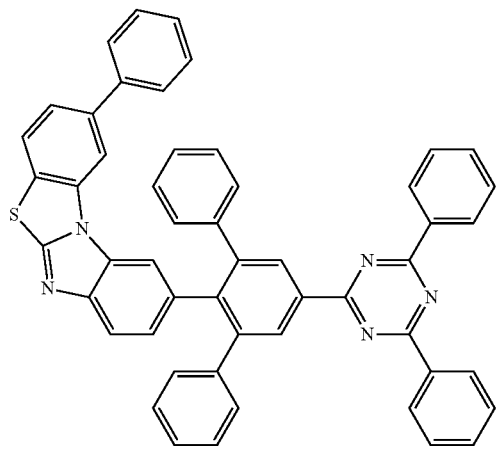
65
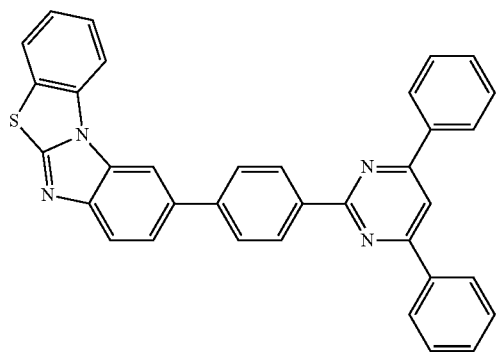
66
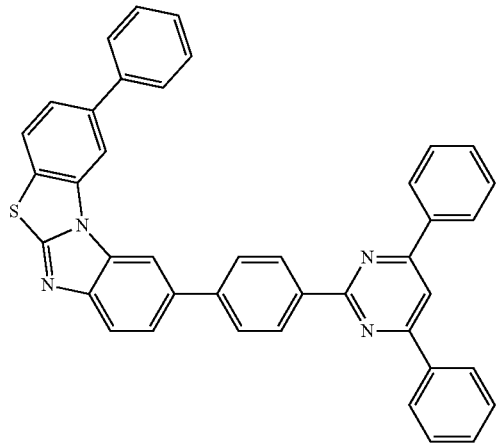

67
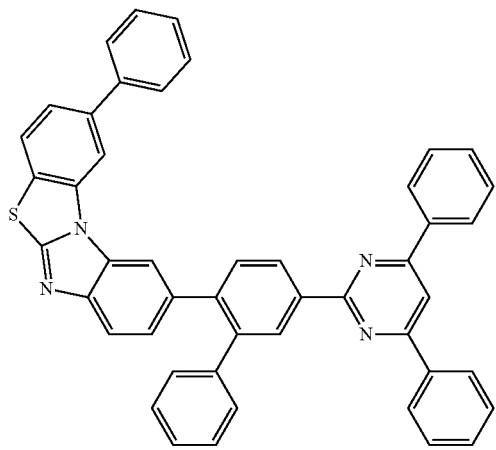
68
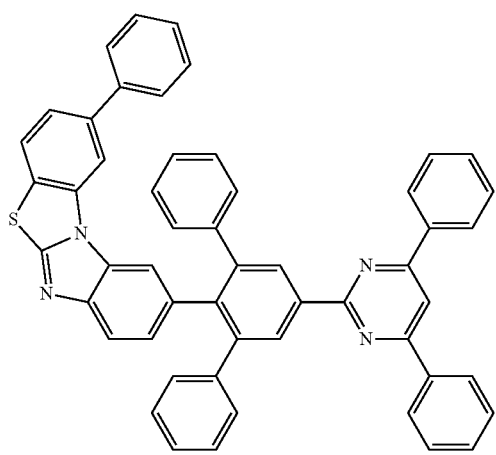
69
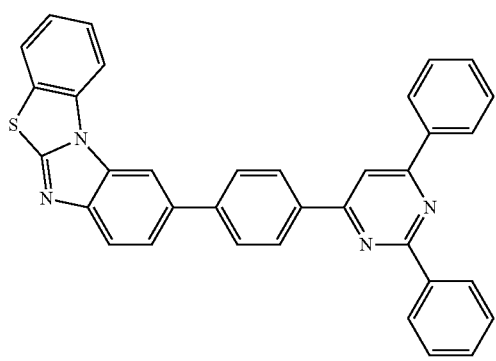
70
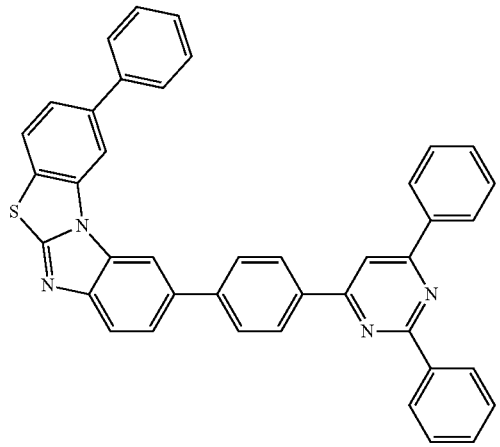
71
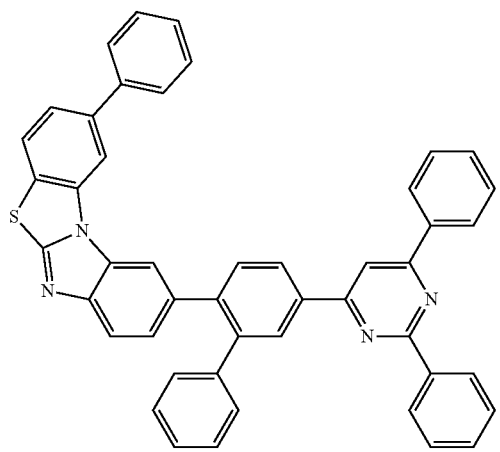
72
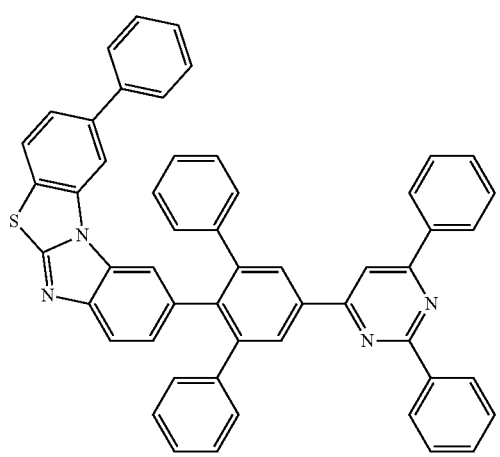

73
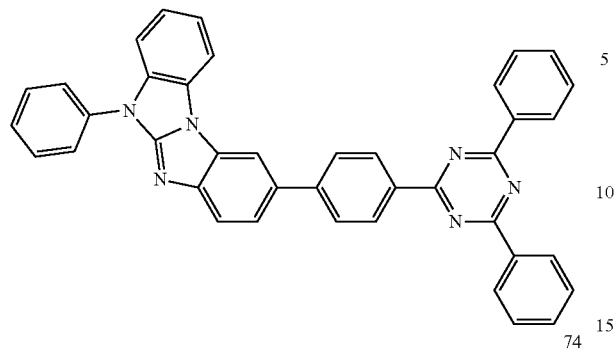
74
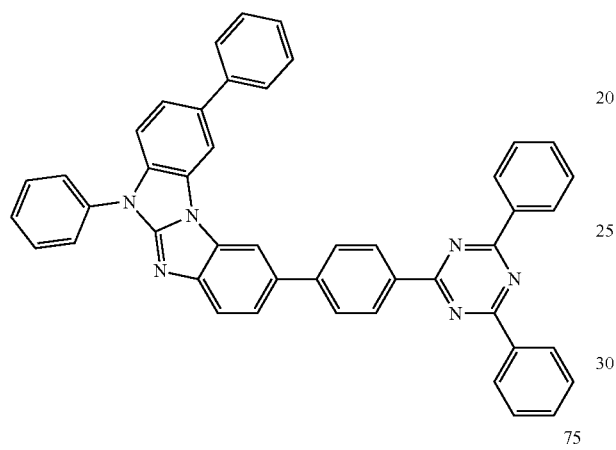
75
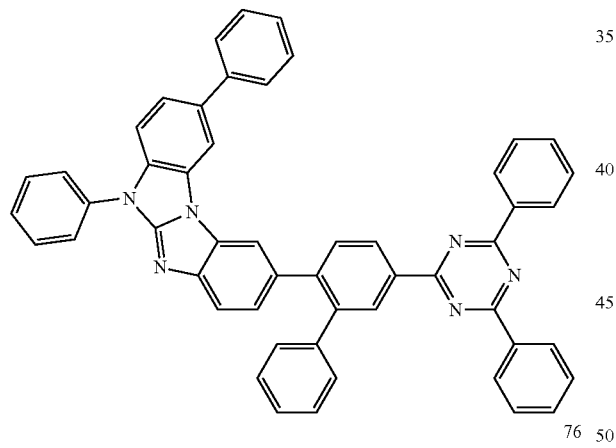
76
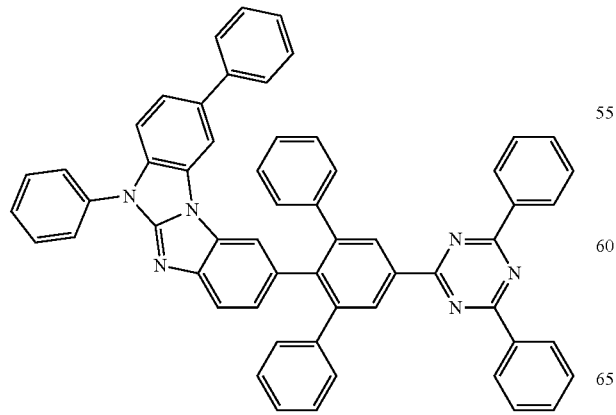
77
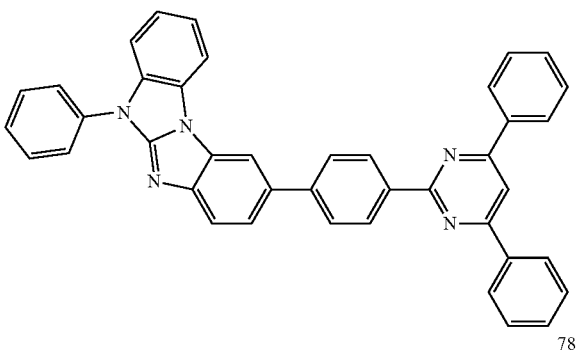
78
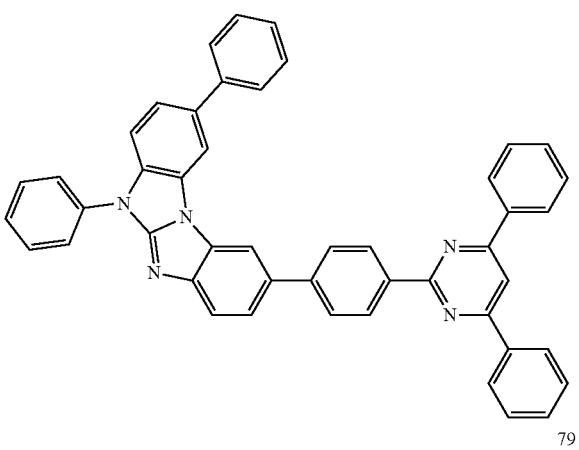
79
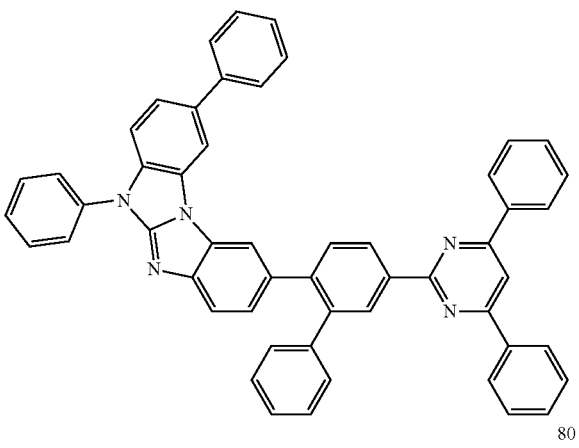
80
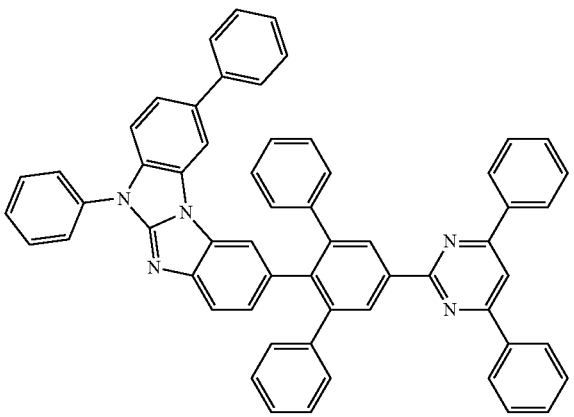

-continued
81
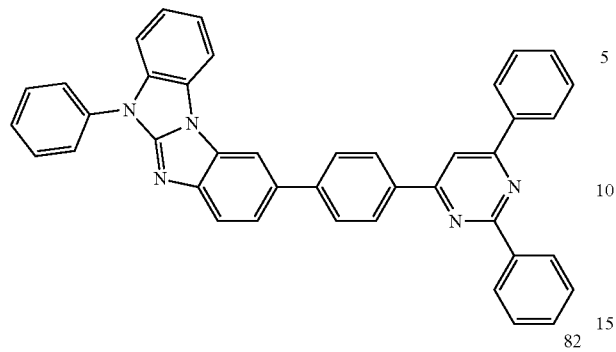
82
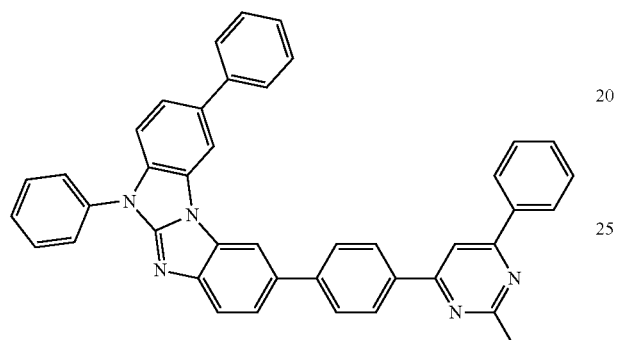
83
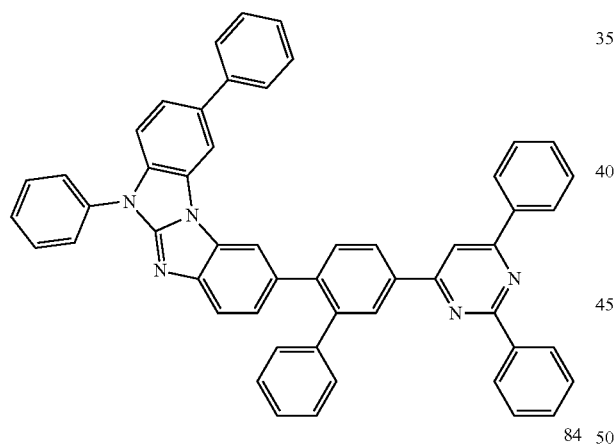
84
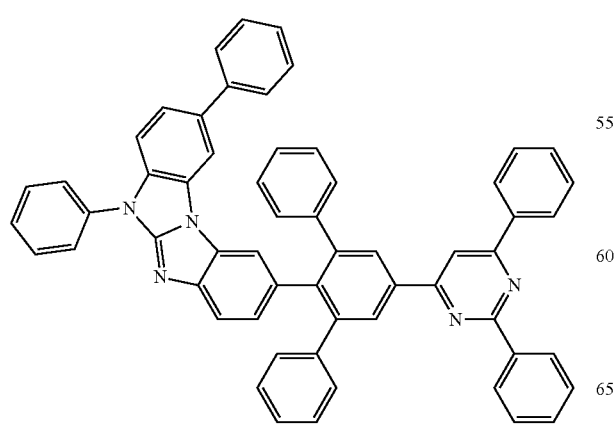
-continued
85
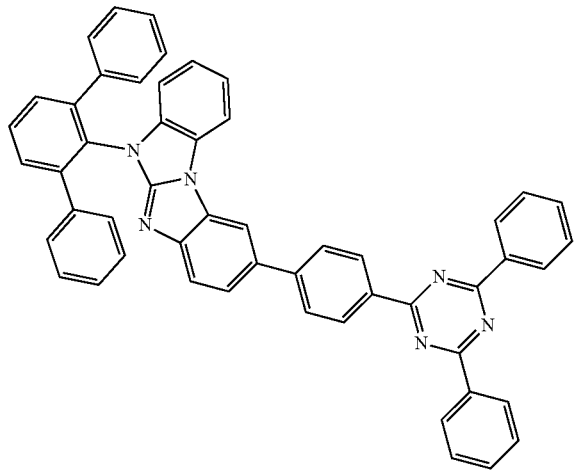
86
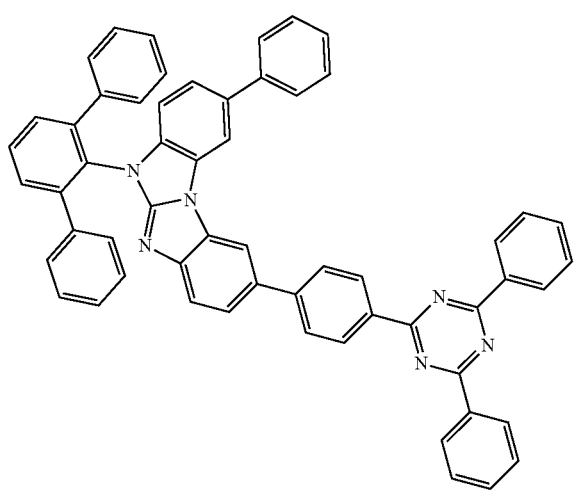
87
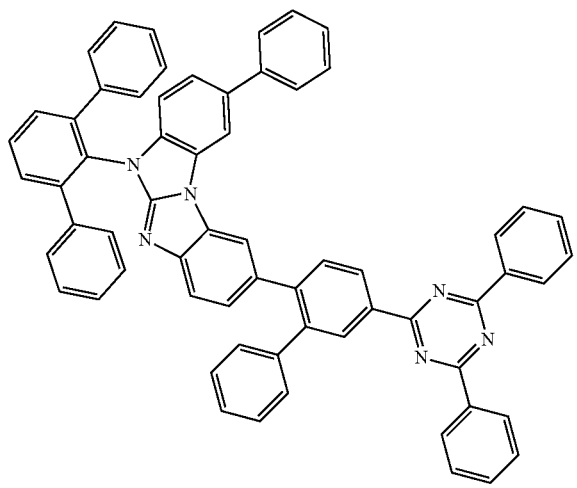

88
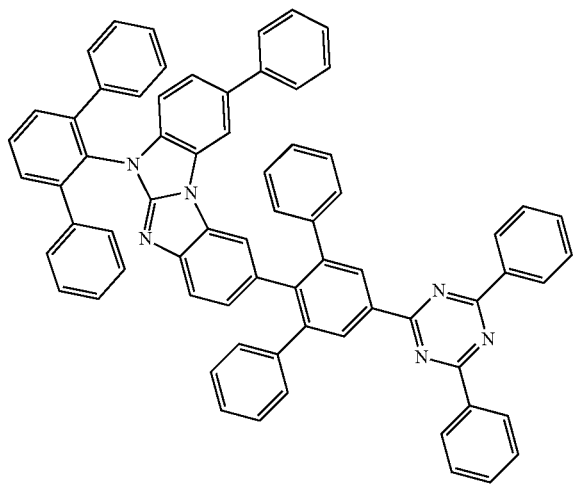
89
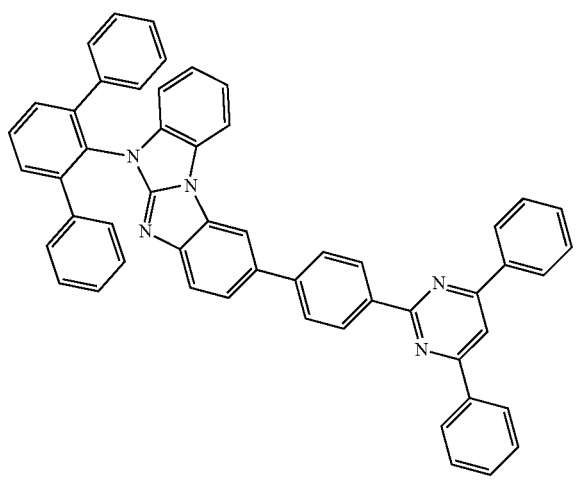
90
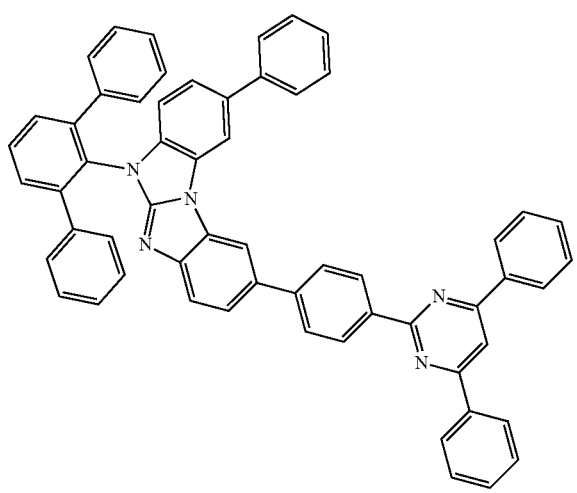
91
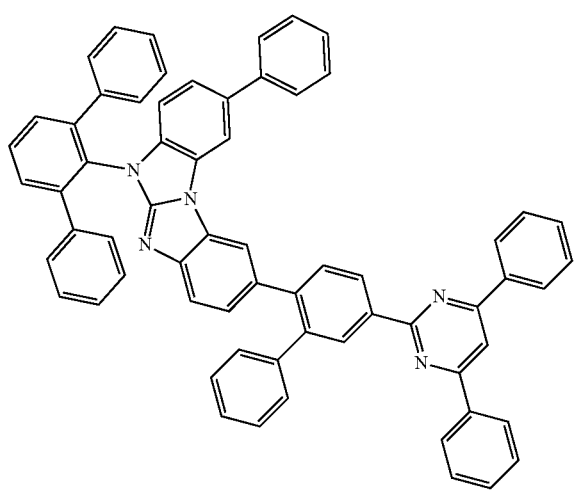
92
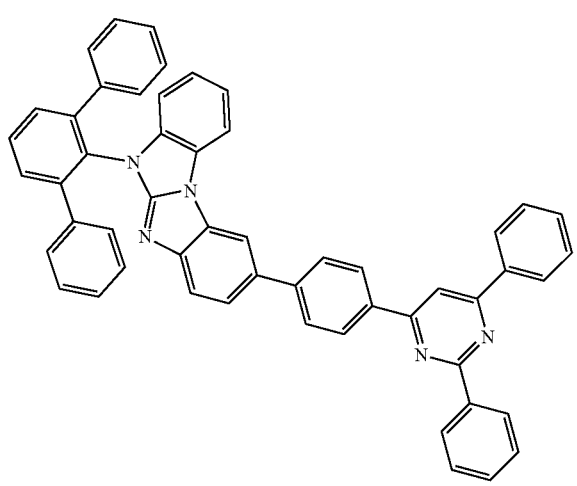
93

94
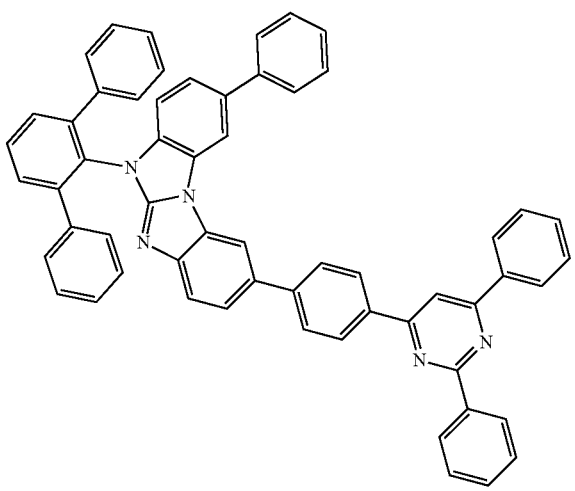
95
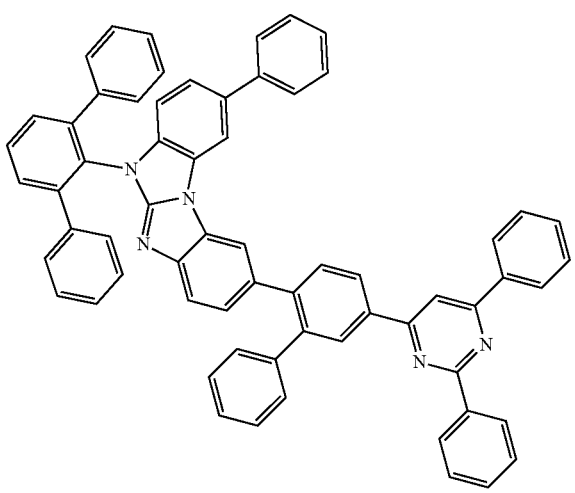
96
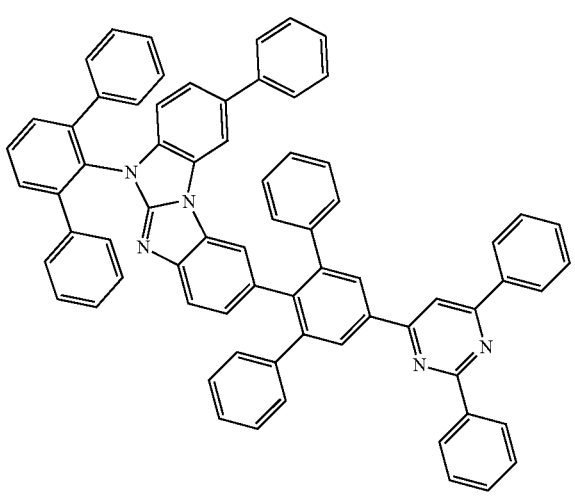
97
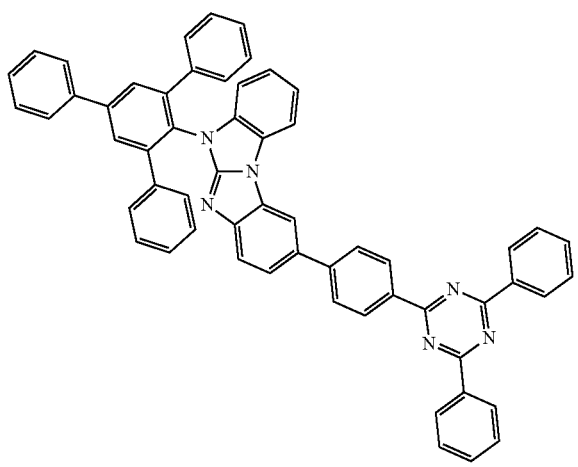
98
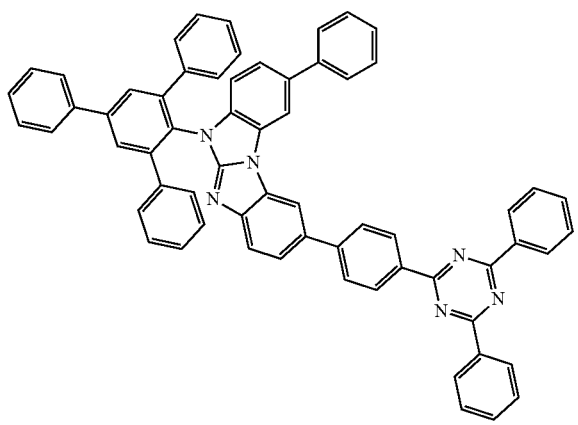
99
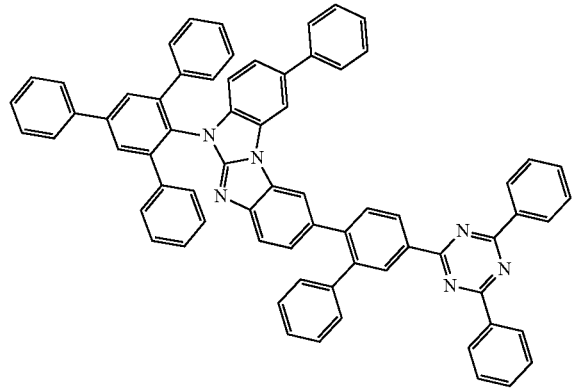

100
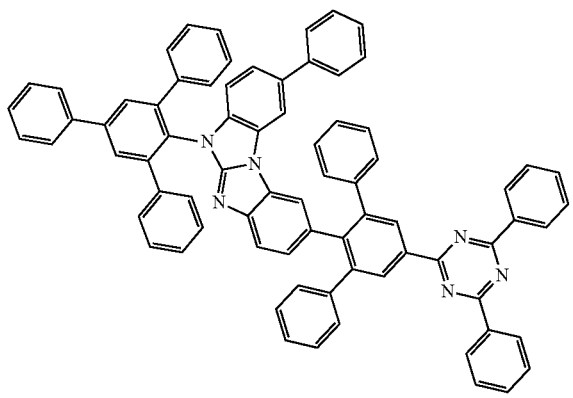
101
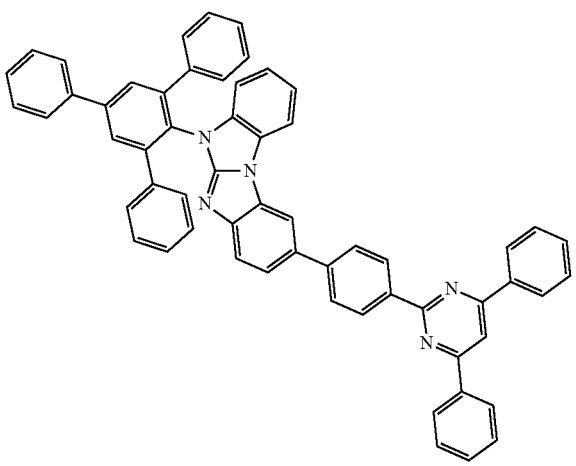
102
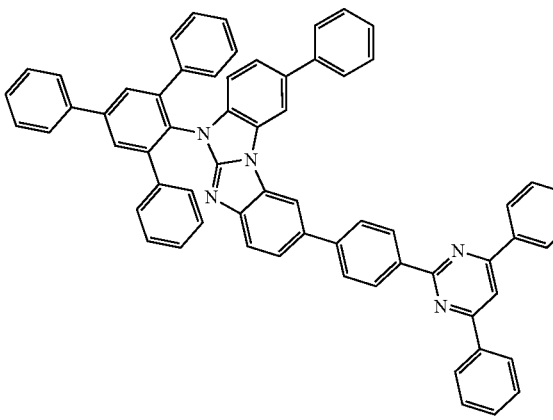
103
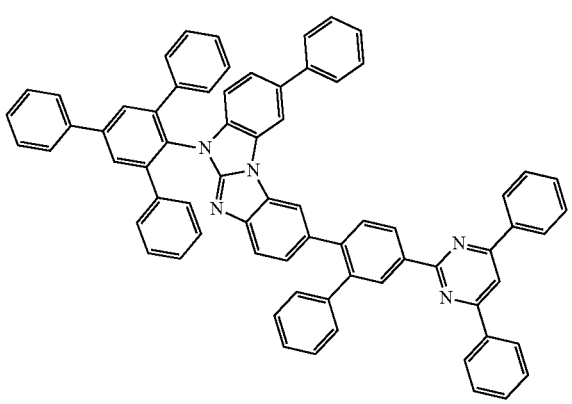
104
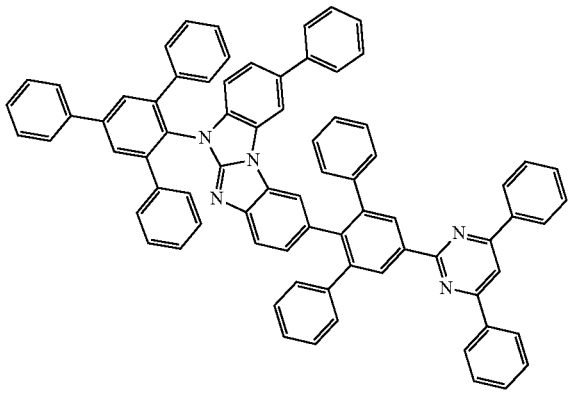
105
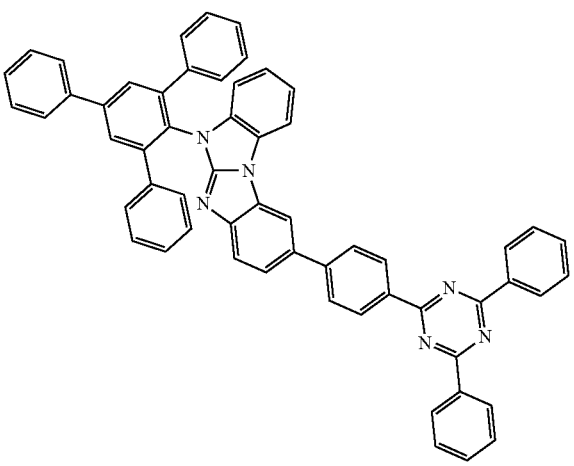

106
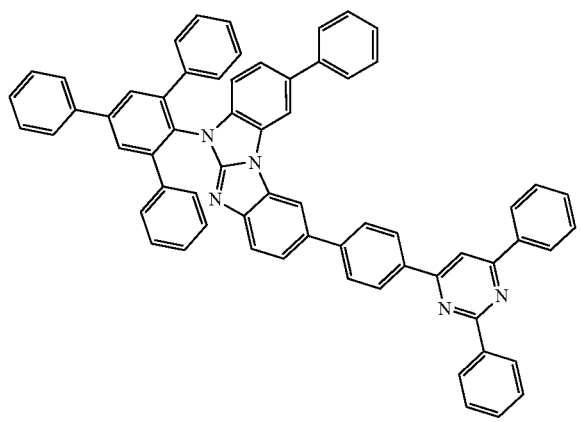
107
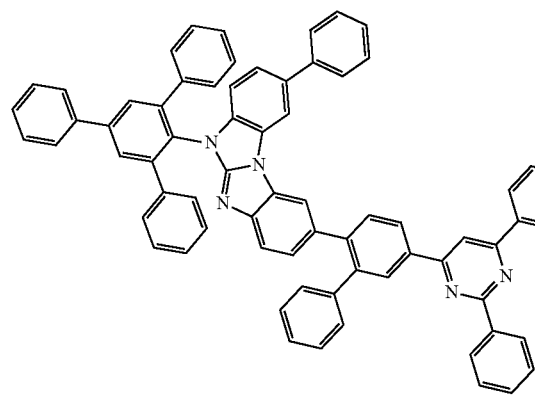
108
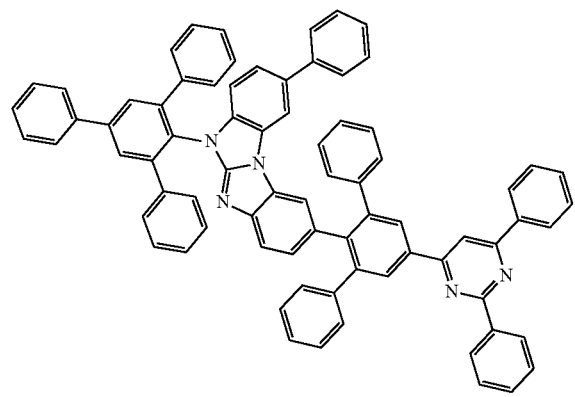
109
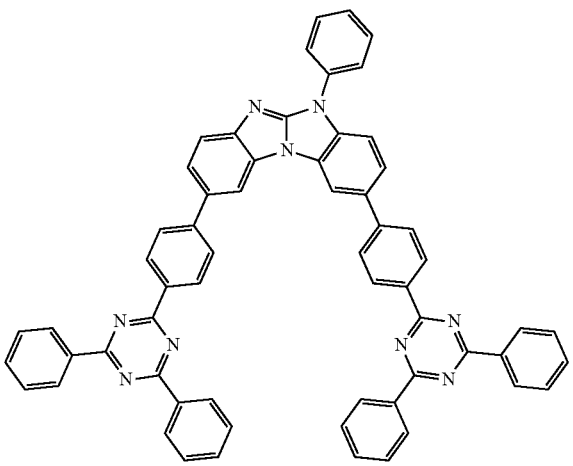
110
111
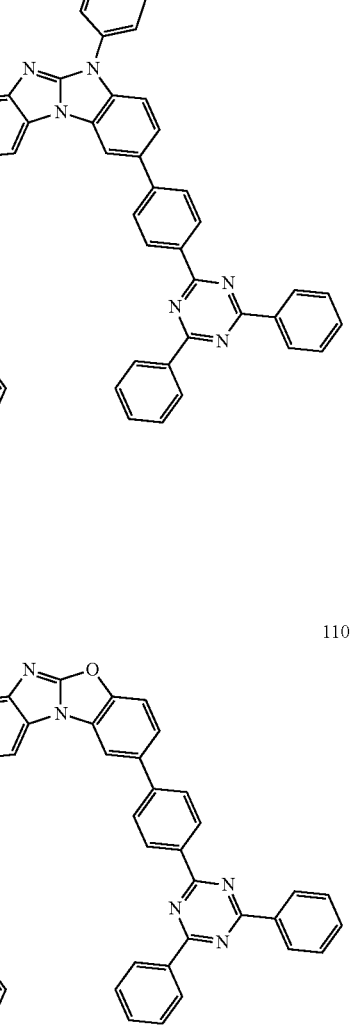

197

-continued

112

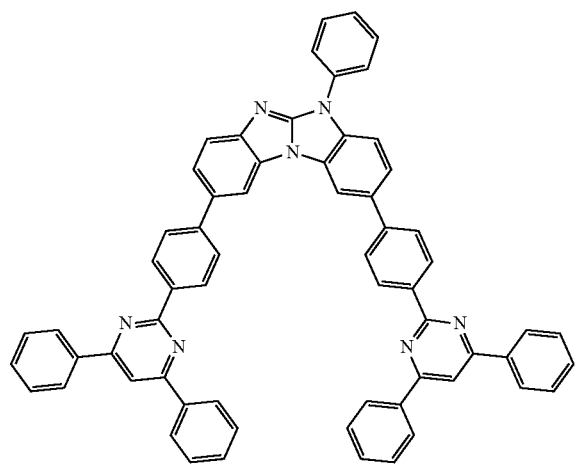

113

114

115

-continued

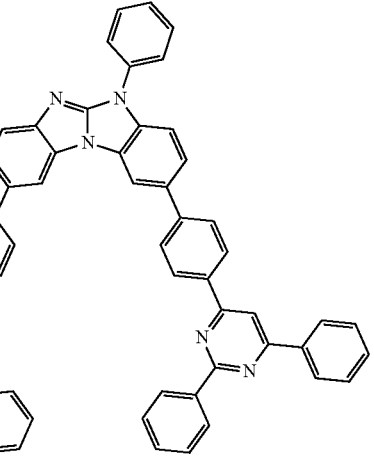

116

117

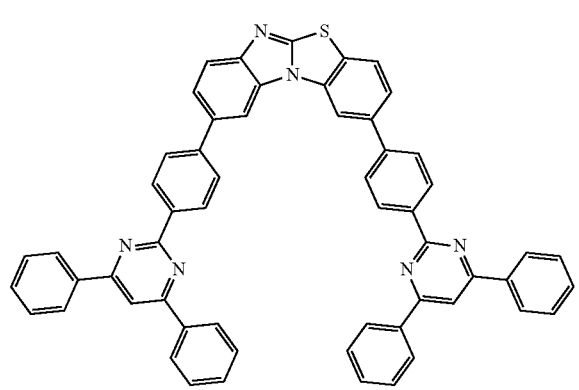

13. An organic light-emitting device comprising:
 a first electrode;
 a second electrode; and
 an organic layer between the first electrode and the second electrode and comprising an emission layer and the condensed cyclic compound of claim 1.

14. The organic light-emitting device of claim 13, wherein
 the first electrode is an anode,
 the second electrode is a cathode,
 the organic layer comprises a hole transport region between the first electrode and the emission layer and an electron transport region between the emission layer and the second electrode, the hole transport region comprises a hole injection layer, a hole transport layer, an electron blocking layer, or any combination thereof, and the electron transport region comprises a hole blocking layer, an electron transport layer, an electron injection layer, or any combination thereof.

15. The organic light-emitting device of claim 13, wherein the emission layer comprises the condensed cyclic compound.

16. The organic light-emitting device of claim 15, wherein a proportion of fluorescence components among the total emission components emitted from the emission layer is 90% or more.

17. The organic light-emitting device of claim 15, wherein the condensed cyclic compound is a fluorescence emitter, and a proportion of emission components emitted from the condensed cyclic compound among the total emission components emitted from the emission layer is 80% or more.

18. The organic light-emitting device of claim 17, wherein the emission layer consists of the condensed cyclic compound only, or the emission layer further comprises a host.

19. The organic light-emitting device of claim 15, wherein the emission layer comprises a host and a dopant, the host comprises the condensed cyclic compound, an amount of the host is greater than that of the dopant, and a proportion of emission components emitted from the dopant among the total emission components emitted from the emission layer is 80% or more.

20. The organic light-emitting device of claim 15, wherein the emission layer comprises a host, an auxiliary dopant, and a dopant, the auxiliary dopant comprises the condensed cyclic compound, and a proportion of emission components emitted from the dopant among the total emission components emitted from the emission layer is 80% or more.

* * * * *